(12) United States Patent
Howard et al.

(10) Patent No.: US 11,370,801 B2
(45) Date of Patent: Jun. 28, 2022

(54) PYRROLOBENZODIAZEPINE CONJUGATES

(71) Applicant: Medimmune Limited, Cambridge (GB)

(72) Inventors: Philip Wilson Howard, Cambridge (GB); Stephen John Gregson, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 16/605,962

(22) PCT Filed: Apr. 18, 2018

(86) PCT No.: PCT/EP2018/059846
§ 371 (c)(1),
(2) Date: Oct. 17, 2019

(87) PCT Pub. No.: WO2018/192944
PCT Pub. Date: Oct. 25, 2018

(65) Prior Publication Data
US 2020/0115390 A1    Apr. 16, 2020

(30) Foreign Application Priority Data

Apr. 18, 2017 (GB) .................................. 1706133
Dec. 19, 2017 (GB) .................................. 1721337

(51) Int. Cl.
A61P 35/00     (2006.01)
C07D 519/00    (2006.01)
A61K 47/68     (2017.01)

(52) U.S. Cl.
CPC ........ C07D 519/00 (2013.01); A61K 47/6851 (2017.08)

(58) Field of Classification Search
CPC ............ A61K 47/6851; A61K 47/6803; A61K 47/6855; A61P 35/00; C07D 519/00
See application file for complete search history.

(56) References Cited

U.S. PATENT DOCUMENTS

| | | | |
|---|---|---|---|
| 3,361,742 A | 1/1968 | Julius et al. | |
| 3,523,941 A | 8/1970 | Leimgruber et al. | |
| 3,524,849 A | 8/1970 | Batcho et al. | |
| 3,794,644 A | 2/1974 | Karlyone et al. | |
| 4,185,016 A | 1/1980 | Takanabe et al. | |
| 4,239,683 A | 12/1980 | Takanabe et al. | |
| 4,309,437 A | 1/1982 | Ueda et al. | |
| 4,353,827 A | 10/1982 | Hunkeler et al. | |
| 4,382,032 A | 5/1983 | Hunkeler et al. | |
| 4,386,028 A | 5/1983 | Hunkeler et al. | |

(Continued)

FOREIGN PATENT DOCUMENTS

| | | |
|---|---|---|
| CN | 101171257 | 4/2008 |
| EP | 0522868 | 1/1993 |

(Continued)

OTHER PUBLICATIONS

Adair et al., "Antibody-drug conjugates—a perfect synergy," Exp. Opin. Biol. Ther. (2012), pp. 1-16.
Adams et al., "Molecular modelling of a sequence-specific DNA-binding agent based on the pyrrolo[2,1-c][1,4]benzodiazepines," Pharm. Pharmacol. Commun. (1999) 5:555-560.
Aird et al., "ABCB1 genetic polymorphism influences the pharmacology of the new pyrrolobenzodiazepine derivative SJG-136," Pharmacogenomics Journal (2008) 8(4):289-296.
Alley et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.
Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

(Continued)

Primary Examiner — Brenda L Coleman
(74) Attorney, Agent, or Firm — Casimir Jones, S.C.; Lisa Mueller

(57) ABSTRACT

A compound of formula I and salts and solvates thereof, wherein: $R^6$ and $R^9$ are independently selected from H, R, OH, OR, SH, SR, $NH_2$, NHR, NRR', nitro, $Me_3Sn$ and halo; where R and R' are independently selected from optionally substituted $C_{1-12}$ alkyl, $C_{3-20}$ heterocyclyl and $C_{5-20}$ aryl groups; $R^7$ is selected from H, R, OH, OR, SH, SR, $NH_2$, NHR, NRR', nitro, $Me_3Sn$ and halo; R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine; Y and Y' are selected from O, S, or NH; $R^6$, $R^7$, $R^9$ are selected from the same groups as $R^6$, $R^7$ and $R^9$ respectively; $R^{11b}$ is selected from OH, $OR^A$, where $R^A$ is $C_{1-4}$ alkyl; and $R^L$ is a linker for connection to a cell binding agent.

23 Claims, No Drawings
Specification includes a Sequence Listing.

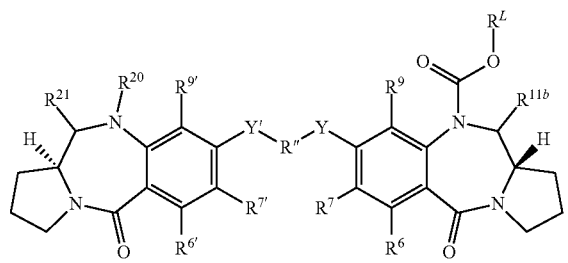

(56) References Cited

U.S. PATENT DOCUMENTS

| | | |
|---|---|---|
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,816,567 A | 3/1989 | Cabilly et al. |
| 4,923,984 A | 5/1990 | Matsumura et al. |
| 5,362,852 A | 11/1994 | Geoghegan |
| 5,418,241 A | 5/1995 | Jegham et al. |
| 5,440,021 A | 8/1995 | Chuntharapai et al. |
| 5,561,119 A | 10/1996 | Jacquesy et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,976,551 A | 11/1999 | Mottez et al. |
| 6,011,146 A | 1/2000 | Mottez et al. |
| 6,153,408 A | 11/2000 | Abastado et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,321,774 B2 | 11/2012 | Barthal et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 9,242,013 B2 | 1/2016 | Howard et al. |
| 9,321,774 B2 | 4/2016 | Howard et al. |
| 9,376,440 B2 | 6/2016 | Howard et al. |
| 9,387,259 B2 | 7/2016 | Jeffrey et al. |
| 9,388,187 B2 | 7/2016 | Howard et al. |
| 9,399,073 B2 | 7/2016 | Howard et al. |
| 9,399,641 B2 | 7/2016 | Howard et al. |
| 9,415,117 B2 | 8/2016 | Howard |
| 9,464,141 B2 | 10/2016 | Asundi et al. |
| 9,526,798 B2 | 12/2016 | Jeffrey et al. |
| 9,562,049 B2 | 2/2017 | Howard |
| 9,592,240 B2 | 3/2017 | Howard et al. |
| 9,624,227 B2 | 4/2017 | Howard et al. |
| 9,649,390 B2 | 5/2017 | Howard et al. |
| 9,707,301 B2 | 7/2017 | Jeffrey et al. |
| 9,713,647 B2 | 7/2017 | Jeffrey et al. |
| 9,732,084 B2 | 8/2017 | Howard et al. |
| 9,745,303 B2 | 8/2017 | Howard et al. |
| 9,889,207 B2 | 2/2018 | Howard |
| 9,956,298 B2 | 5/2018 | Howard et al. |
| 10,799,595 B2 * | 10/2020 | Howard ............... C07H 15/203 |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0175775 A1 | 9/2003 | LePoul et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | DeVaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |

(56) References Cited

U.S. PATENT DOCUMENTS

| | | |
|---|---|---|
| 2005/0271615 A1 | 12/2005 | Shabat et al. |
| 2006/0116422 A1 | 6/2006 | De Groot et al. |
| 2006/0264622 A1 | 11/2006 | Howard et al. |
| 2007/0072846 A1 | 3/2007 | Vishnuvajjala et al. |
| 2007/0154906 A1 | 7/2007 | Martin et al. |
| 2007/0185336 A1 | 8/2007 | Rossen et al. |
| 2007/0191309 A1 | 8/2007 | Howard et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | Mcdonagh et al. |
| 2009/0149449 A1 | 6/2009 | Liu et al. |
| 2009/0274713 A1 | 11/2009 | Chari et al. |
| 2009/0304710 A1 | 12/2009 | Park et al. |
| 2010/0028346 A1 | 2/2010 | Lutz et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2010/0316656 A1 | 12/2010 | Bouchard et al. |
| 2011/0039969 A1 | 2/2011 | Muratoglu et al. |
| 2011/0070227 A1 | 3/2011 | Novotney-Barry et al. |
| 2011/0091372 A1 | 4/2011 | Ghayur et al. |
| 2011/0160192 A1 | 6/2011 | Howard et al. |
| 2011/0195021 A1 | 8/2011 | Deckert et al. |
| 2011/0195022 A1 | 8/2011 | Deckert et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2012/0233172 A1 | 9/2012 | Skillcorn et al. |
| 2012/0238731 A1 | 9/2012 | Fishkin et al. |
| 2013/0028917 A1 | 1/2013 | Howard et al. |
| 2013/0028919 A1 | 1/2013 | Howard et al. |
| 2013/0137659 A1 | 5/2013 | Commercon et al. |
| 2013/0244171 A1 | 9/2013 | Yamasaki et al. |
| 2013/0266595 A1 | 10/2013 | Flygare et al. |
| 2013/0266596 A1 | 10/2013 | Li et al. |
| 2013/0302359 A1 | 11/2013 | Li et al. |
| 2013/0304357 A1 | 11/2013 | Koci et al. |
| 2014/0030279 A1 | 1/2014 | Polakis et al. |
| 2014/0030280 A1 | 1/2014 | Polakis |
| 2014/0066435 A1 | 3/2014 | Howard et al. |
| 2014/0088089 A1 | 3/2014 | Chari |
| 2014/0120118 A1 | 5/2014 | Howard |
| 2014/0127239 A1 | 5/2014 | Howard |
| 2014/0155590 A1 | 6/2014 | Commercon et al. |
| 2014/0234346 A1 | 8/2014 | Howard |
| 2014/0274907 A1 | 9/2014 | Howard et al. |
| 2014/0275522 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0111880 A1 | 4/2015 | Howard et al. |
| 2015/0126495 A1 | 5/2015 | Howard et al. |
| 2015/0133435 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |
| 2016/0075787 A1 | 3/2016 | Zheng et al. |
| 2016/0144052 A1 | 5/2016 | Howard et al. |
| 2016/0074527 A1 | 7/2016 | Flygare et al. |
| 2016/0250344 A1 | 9/2016 | Howard et al. |
| 2016/0250345 A1 | 9/2016 | Howard et al. |
| 2016/0250346 A1 | 9/2016 | Howard et al. |
| 2016/0256561 A1 | 9/2016 | Howard et al. |
| 2016/0263242 A1 | 9/2016 | Howard et al. |
| 2016/0310611 A1 | 10/2016 | Flygare et al. |
| 2017/0239365 A1 | 8/2017 | Howard et al. |
| 2017/0290924 A1 | 10/2017 | Jeffrey et al. |
| 2017/0298137 A1 | 10/2017 | Jeffrey et al. |
| 2017/0340752 A1 | 11/2017 | Howard |
| 2018/0125997 A1 | 5/2018 | Howard et al. |
| 2018/0134717 A1 | 5/2018 | Howard et al. |

FOREIGN PATENT DOCUMENTS

| | | |
|---|---|---|
| EP | 0875569 | 11/1998 |
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| FR | 2027356 | 12/1969 |
| FR | 2586683 | 3/1987 |
| GB | 1299198 | 12/1972 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 2000053216 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |

(56) References Cited

FOREIGN PATENT DOCUMENTS

| | | |
|---|---|---|
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |

(56) References Cited

FOREIGN PATENT DOCUMENTS

| | | |
|---|---|---|
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 A2 | 6/2006 |
| WO | WO 2006111759 | 10/2006 |
| WO | WO 2007039752 | 4/2007 |
| WO | WO 2007044515 | 4/2007 |
| WO | WO 2007085930 | 8/2007 |
| WO | WO 2008010101 | 1/2008 |
| WO | WO 2008022152 | 2/2008 |
| WO | WO 2008047242 | 4/2008 |
| WO | WO 2008050140 | 5/2008 |
| WO | WO 2008070593 | 6/2008 |
| WO | WO 2009/016647 A1 | 2/2009 |
| WO | WO 2009016516 | 2/2009 |
| WO | WO 2009052249 | 4/2009 |
| WO | WO 2009060208 | 5/2009 |
| WO | WO 2009060215 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010095031 | 8/2010 |
| WO | WO 2011023883 | 3/2011 |
| WO | WO 2011038159 | 3/2011 |
| WO | WO 2011100227 | 8/2011 |
| WO | WO 2011128650 | 10/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011133039 | 10/2011 |
| WO | WO 2012014147 | 2/2012 |
| WO | WO 2012064733 | 5/2012 |
| WO | WO 2012112687 | 8/2012 |
| WO | WO 2012112708 | 8/2012 |
| WO | WO 2012128868 | 9/2012 |
| WO | WO 2013041606 | 3/2013 |
| WO | WO 2013053871 | 4/2013 |
| WO | WO 2013053872 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013/165940 A1 | 11/2013 |
| WO | WO 2013164592 | 11/2013 |
| WO | WO 2013164593 | 11/2013 |
| WO | WO 2013177481 | 11/2013 |
| WO | WO 2014011518 | 1/2014 |
| WO | WO 2014011519 | 1/2014 |
| WO | WO 2014022679 | 2/2014 |
| WO | WO 2014031566 | 2/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014080251 | 5/2014 |
| WO | WO 2014096365 | 6/2014 |
| WO | WO 2014096368 | 6/2014 |
| WO | WO 2014130879 | 8/2014 |
| WO | WO 2014140174 | 9/2014 |
| WO | WO 2014140862 | 9/2014 |
| WO | WO 2014159981 | 10/2014 |
| WO | WO 2014174111 | 10/2014 |
| WO | WO 2015031693 | 3/2015 |
| WO | WO 2015052321 | 4/2015 |
| WO | WO 2015052322 | 4/2015 |
| WO | WO 2015052332 | 4/2015 |
| WO | WO 2015052333 | 4/2015 |
| WO | WO 2015052334 | 4/2015 |
| WO | WO 2015052335 | 4/2015 |
| WO | WO 2015052532 | 4/2015 |
| WO | WO 2015052533 | 4/2015 |
| WO | WO 2015052534 | 4/2015 |
| WO | WO 2015052535 | 4/2015 |
| WO | WO 2015095124 | 6/2015 |
| WO | WO 2015112822 | 7/2015 |
| WO | WO 2015159076 | 10/2015 |
| WO | WO 2016037644 | 3/2016 |
| WO | WO 2016040868 | 3/2016 |
| WO | WO 2016044560 | 3/2016 |
| WO | WO 2016053107 | 4/2016 |
| WO | WO 2016166297 | 10/2016 |
| WO | WO 2016166298 | 10/2016 |
| WO | WO 2016166299 | 10/2016 |
| WO | WO 2016166302 | 10/2016 |
| WO | WO 2016166305 | 10/2016 |
| WO | WO 2016166307 | 10/2016 |
| WO | WO 2018/069490 A1 | 4/2018 |

OTHER PUBLICATIONS

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-lmmolative Dendrimers," (2003) Angew. Chem. Int. Ed. 42:4494-4499.

Amsberry, et al., "The Lactonization of 2'-Hydroxyhydrocinnamic Acid Amides: A Potential Prodrug for Amines," (1990) J. Org. Chem. 55:5867-5877.

Antonow, D. et al., "Structure-activity relationships of monomeric C2-aryl pyrrolo[2,1-c][1,4]benzodiazepine (PBD) antitumor agents."J Med Chem. Apr. 8, 2010;53(7):2927-41.

Antonow, D. et al., "Synthesis of DNA-lnteractive Pyrrolo [2,1-c][1,4] benzodiazepines (PBDs)" Chemical Reviews, 2011, 111(4):2815-2864.

Antonow, D. et al.,"Parallel synthesis of a novel C2-aryl pyrrolo[2,1-c][1,4]benzodiazepine (PBD) library," J. Comb. Chem. (2007) 9:437-445.

Arai H., et al., "Molecular cloning of human endothelin receptors and their expressiOn in vascular endothelial cells and smooth muscle cells," Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

Arima et al., "Studies on Tomaymycin, a New Antibiotic. I. Isolation and Properties of Tomaymycin," J. Antibiotics (1972) 25:437-444.

Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.

Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).

Attoe T., et al., "Mutation of the endothelin-receptor B gene in Waardenburg-Hirschsprung disease," Hum. Mol. Genet. 4, 2407-2409, 1995.

(56) References Cited

OTHER PUBLICATIONS

Auricchio A., et al., "Endothelin-B receptor mutations in patients with isolated Hirschsprung disease from a non-inbred population," Hum. Mol. Genet. 5:351-354, 1996.
Axup et al., "Synthesis of site-specific antibody-drug conjugates using unnatural amino acids." Proc Natl Acad Sci U S A. Oct. 2, 2012; 109(40):16101-6.
Bahrenberg et al., "Reduced Expression of PSCA, a Member of the LY-6 Family of Cell Surface Antigens, in Bladder, Esophagus, and Stomach Tumors," Biochem. Biophys. Res. Commun. (2000) 275(3):783-788.
Banker, G.S. et al., "Modern Pharmaceutics", Third edition, Marcel Dekker, New York (1996) 451 and 596.
Barel M., et al., "Evidence for a new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Batisse, et al., "A new delivery system for Auristatin in STxB-drug conjugate therapy." European J. Medicinal Chemistry, 2015, 95: 483-491.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Berry, J.M. et al., "Synthesis and biological evaluation of an N10-Psec substituted pyrrolo[2,1-c][1,4]benzodiazepine prodrug," Bioorg. Med. Chem. Lett. (2002) 12:1413-1416.
Bien & Balcerska, "Serum Soluble Interleukin 2 receptor in human cancer of adults and children: a review," Biomarkers, 2008, 13(1): 1-26.
Blanc et al., "SAR3419: an anti-CD19-Maytansinoid Immunoconjugate for the treatment of B-cell malignancies," Clin Cancer Res., 2011, 17(20):6448-58.
Blumberg H., et al., "Interleukin 20: Discovery, Receptor Identification, and Role in Epidermal Function," Cell 104, 9-19, 2001.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.
Brand et al., Prospect for anti-HER2 receptor therapy in breast cancer. Anticancer Res. Jan.-Feb. 2006;26(1B):463-70.
Brinster et al., "Introits increase transcriptional efficiency in transgenic mice," (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.

Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzyl-amine linker system," Bioorg. Med. Chem. Lett., Apr. 2009, 19(10):2650-2653.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Cancer, 2012, http://wiki.answers.eom/Q/How-many-different-types of cancer are there.
Cancer2, 2012, http://en.wikipedia.org/wiki/Management of cancer.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Chakravarty et al., "Plasmin-Activated Prodrugs for Cancer Chemotherapy. 2. Synthesis and Biological Activity of Peptidyl Derivatives of Doxorubicin," (1983) J. Med. Chem. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chem. 274: 24335-24341.
Cho et al., "Structure of the extracellular region of HER2 alone and in complex with the Herceptin Fab," Nature 421, 756-760, 2003.
Ciccodicola, A, et al., "Molecular characterization of a gene of the 'EGF family' expressed in undifferentiated human NTERA2 teratocarcinoma cells," EMBO J. 8 (7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI), a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.

(56) References Cited

OTHER PUBLICATIONS

Clinical Trial, "Translational research: 4 ways to fix the clinical trial." 2011, http://www.nature.com/news/2011/110928/full/477526a.html.
Collins, "Generation and initial analysis of more than 15,000 full-length human and mouse cDNA sequences," Proc. Natl. Acad. Sci. U.S.A. 99 (26):16899-16903 (2002).
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Corey et al., "LuCap35: a new model of prostate cancer progression to androgen independence." The Prostate 2003;55:239-46.
Courtney, S. M. et al., "A new convenient procedure for the synthesis of pyrrolo[2,1-c][1,4]benzodiazepines", Tetrahedron Letters, vol. 34, No. 33, 5327-28 (1993).
Coussens L., et al., "Tyrosine Kinase Receptor with Extensive Homology to EGF Receptor Shares Chromosomal Location With neu Oncogene," Science (1985) 230(4730):1132-1139.
Cragg et al., "The alternative transcript of CD79b is overexpressed in B-CLL and inhibits signaling for apoptosis," Blood (2002) 100 (9):3068-3076.
Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.
Crouch et al., "The use- of ATP bioluminescence as a measure of cell proliferation and cytotoxicity," (1993) J. Immunol. Meth. 160:81-88.
Dall'acqua, W. F. et al., "Antibody humanization by framework shuffling" Methods, 36, 43-60 (2005).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Davis et al., "Identification of a family of Fe receptor homo logs with preferential B cell expression," (2001) Proc. Natl. Acad. Sci. USA 98(17):9772-9777.
De Groot et al., "Cascade-Release Dendrimers" Liberate All End Groups upon a Single Triggering Event in the Dendritic Core, (2003) Angew. Chern. Int. Ed. 42:4490-4494.
De Groot et al., "Elongated Multiple Electronic Cascade and Cyclization Spacer Systems in Activatible Anticancer Prodrug for Enhanced Drug Release," (2001) J. Org. Chern. 66:8815-8830.
De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Dennis et al., (2002) "Albumin Binding As A General Strategy For Improving The Pharmacokinetics Of Proteins" J Biol Chem. 277:35035-35043.
Duke, P., et al., "Characterization of Type I Receptors for Transforming Growth Factor-beta and Activin," Science 264 (5155):101-104 (1994).
Dobner et al., "Differentiation-specific expression of a novel G protein-coupled receptor from Burkitt's lymphoma," (1992) Eur. J. Immunol. 22:2795-2799.
Dong, Q. et al., "Reductive cleavage of TROC groups under neutral conditions with cadmium-lead couple," Tetrahedron Lett. (1995) 36(32):5681-5682.
Dono et al., "Isolation and Characterization of the CRI PTO Autosomal Gene and Its X-linked Related Sequence," Am. J. Hum. Genet. 49:555-565, 1991.
Dornan et al., "Therapeutic potential of an anti -CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.

Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of staphylococcus aureus to subinhibitory concentrations of a sequence-selective, DNA minor groove cross-linking pyrrolobenzodiazepine dimer," J. Antimicrob. Chemo., Aug. 2009, 64(5):949-959.
Dubowchik et al., "Cathepsin B-sensitive dipeptide prodrugs. 1. A model study of structural requirements for efficient release of doxorubicin." Bioorg Med Chem Lett. Dec. 1, 1998; 8(23):3341-6.
Dubowchik et al., "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dubowchik et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation By IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Ehsani A., et al., "Characterization of a New Allele of the Human ERBB2 Gene by Allele-Specific Competition Hybridization," (1993) Genomics 15, 426-429.
Eliel et al., Stereochemistry of Organic Compounds, John Wiley & Sons, Inc., New York (1994).
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs,", Chemical Abstracts, Abstract No. 239940r, vol. 114, No. 25, 25 899-903 (1991).
Fey, T. et al., "Silica-supported TEMPO catalyst: synthesis and application in the anelli oxidation of alcohols," J. Org. Chem. (2001) 66:8154-8159.
Field, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Flanagan et al., "The ephrins and Eph receptors in neural development," Annu. Rev. Neurosci. 21:309-345 (1998).
Flygare, "Antibody-drug conjugates for the treatment of cancer," Chern. Biol. & Drug Design (2013) 81(1):113-121.
Flynn et al., "Pre-Clinical Activity of Adct-301, a Novel Pyrrolobenzodiazepine (PBD) Dimer-Containing Antibody Drug Conjugate (ADC) Targeting CD25-Expressing Hematological Malignancies," https://www.researchgate.net/publication/275520174.
Foloppe, M.P. et al., "DNA-binding properties of pyrrolo[2,1-c][1,4]benzodiazephine N10-C11 amidines," Eur. J. Med. Chem., 31, 407-410 (1996).

(56) References Cited

OTHER PUBLICATIONS

Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.
Geiser et al. "Automation of solid-phase peptide synthesis" in Macromolecular Sequencing and Synthesis, Alan R. Liss, Inc., 1988, pp. 199-218.
Genbank accession No. 11038674 (2013).
Genbank accession No. 20 NM_006424 (2013).
Genbank accession No. AB040878 (2001).
Genbank accession No. AF116456 (1999).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. NM_000626 (2013).
Genbank accession No. NM_001178098.1 (2012).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. NP 002111.1 (2013).
Genbank accession No. NP_001171569.1 (1992).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "TENB2, a proteogl yean identified in prostate cancer that is associated with disease progression and androgen independence," (2001) Int J Cancer. Oct. 15; 94(2): 178-184.
Gordon et al., "Somatic hypermutation of the B cell receptor genes B29 (Igβ, CD79b) and mb1 (Igα, CD79a)," PNAS, Apr. 11, 2003, vol. 100, No. 7, 4126-4131.
Greene, T.W. and Wuts, P.G.M., Protective Groups in Organic Synthesis, John Wiley & Sons, 2nd ed., Ch 7, 315-345 (1991).
Greene, T.W et al., Protective Groups in Organic Synthesis, John Wiley & Sons (1999) 3rd Edition, 503-549.
Greene, T.W et al., Protective Groups in Organic Synthesis, John Wiley & Sons (1999) 3rd Edition, 23-200.
Greene, T.W et al., Protective Groups in Organic Synthesis, John Wiley & Sons (1999) 3rd Edition, 633-647.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8'ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-lnteractive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.

(56) References Cited

OTHER PUBLICATIONS

Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro- N10-troc protection and Suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "molecular cloning and expression pattern of a human gene homologous to the murine mb-1 gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant staphylococcus aureus," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and Etb," J. Cardiovasc. Pharmacal. 20, s1-S4, 1992.
Haisma et al., "Comparison of two antracycline-based prodrugs for activation by a monoclonal antibody-β-glucuronidase conjugate in the specific treatment of cancer." Cell biophysics, Humana Press Inc. 1994, 24/25: 185-192.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by streptomyces sp.", J. Antibiotics, 41, 702-704 (1988).
Hartley JA: "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "Abstract 2856: pyrrolobenzodiazepine (PBD) dimers—potent next generation warheads in antibody drug conjugates (ADCs) targeted at both solid and haematological tumors," Cancer Res. (2013) 78(8)Supp 1:2856.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (lg-alpha/mb-1) gene," (1994) Immunogenetics 40(4 ):287-295.
Hay et al., "A 2-nitroimidazole carbamate prodrug of 5-amin0-1-(chloromethyl)-3-[(5,6,7-trimethoxyindol-2-yl)carbonyl]-1,2-dihydr0-3h-benz[e]indole (amino-seco-cbi-tmi) for use with adept and gdept," (1999) Bioorg. Med. Chem. Lett. 9:2237-2242.
Herdwijn et al., "Synthesis of trans(+ )6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Surviv Factor for Hippocampal and Mesencephalic Neurons," (2000) Genomics 67: 146-152.
Howard, P.W et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1-c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley, L. and Needham-Vandevanter, D., "Covalent Binding of Antitumor Antibiotics in the Minor Groove of DNA. Mechanism of Action of CC-1065 and the yrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.
International Search Report and Written Opinion for Application No. PCT/EP2012/070233 dated Jan. 28, 2013 (8 pages).
International Search Report and Written Opinion for Application No. PCT/EP2013/071346 dated Feb. 5, 2014 (11 pages).
International Search Report and Written Opinion for Application No. PCT/EP2013/071352 dated Feb. 5, 2014 (14 pages).
International Search Report and Written Opinion for Application No. PCT/EP2014/054958 dated Jul. 2, 2014 (13 pages).
International Search Report and Written Opinion for Application No. PCT/EP2018/053162 dated Apr. 24, 2018 (9 pages).
International Search Report and Written Opinion for Application No. PCT/GB2015/052629 dated Nov. 2, 2015 (12 pages).

(56) References Cited

OTHER PUBLICATIONS

International Search Report and Written Opinion for Application No. PCT/US2011/032664 dated Aug. 19, 2011 (13 pages).
International Search Report and Written Opinion for Application No. PCT/US2011/032668 dated May 26, 2011 (12 pages).
International Search Report and Written Opinion for Application No. PCT/US2015/050634 dated Jan. 29, 2016 (14 pages).
Itoh et al., "Sibanomicin, a new pyrrolo(1,4)benzodiazepine antitumor antibiotic produced by a micromonospora sp." J. Antibiotics, 41, 1281-1284 (1988).
Janjigian, Y.Y., "A phase I trial of SJG-136 (NSC#694501) in advanced solid tumors," Cancer Chemotherapy and Pharmacology, Aug. 2009, 65(5):833-838.
Jeffrey et al., "A Potent Anti-CD70 Antibody-Drug Conjugate Combining a Dimeric Pyrrolobenzodiazepine Drug with Site-Specific Conjugation Technology." Bioconj. Chem. 2013, 24, 1256-1263.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C. et al., "Development of Pyrrolobenzodiazepine-Based Antibody-Drug Conjugates for Cancer," AACR Annual Meeting 2013, Abstract No. 4321.
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.
Jordan, V.C., "Tamoxifen: a most unlikely pioneering medicine," Nature Reviews: Drug Discovery (2003) 2:205-213.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Junutula et al., "Rapid identification of reactive cysteine residues for site-specific labeling of antibody-Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932, 2008.
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22): 3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anticancer activity of pyrrolo[2,1- c][1,4]benzodiazepine-naphthalamide conjugates linked through piperazine side-armed alkane spacers," Bioorg. Med. Chem. (2008) 16(15):7218-7224.

Kamal, A., "Remarkable enhancement in the DNA-binding ability of C2-fluoro substituted pyrrolo[2,1- c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kamal et a., "Pyrrolo[2,1-c][1,4]benzodiazepine-β-glucuronide prodrugs with a potential for selective therapy of solid tumors by PMT and ADEPT strategies" Bioorganic & Medicinal Chemistry Letters 2008, 18:3769-3773.
Kaneko, T. et al., "Bicyclic and tricyclic analogues of anthramycin," J. Med. Chem. (1985) 28:388-392.
Kang, G.-D et al., "Synthesis of a novel C2-aryl substituted 1,2-unsaturated pyrrolobenzodiazepine," Chern. Commun. (2003) 1680-1689.
Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., "A Novel Peptide Delivery System Involving Peptidase Activated Prodrugs as Antimicrobial Agents. Synthesis and Biological Activity of Peptidyl Derivatives of 5 Fluorouracil," (1984) J. Med. Chem. 27:1447-1451.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor eDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kreitman et al., "Phase I Trial of Recombinant Immunotoxin Anti-Tac(Fv)-PE38 (LMB-2) in Patients with Hematologic Malignancies," J. Clin. Oncol., 2000, 18:1622-1636.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kunimoto et al., "Mazethramycin, a new member of anthramycin group antibiotics," J. Antibiotics, 33, 665-667 (1980).
Kurebayashi et al., "Isolation and characterization of a new human breast cancer cell line, KPL-4, expressing the Erb B family receptors and interleukin-6," (1999) Brit. Jour. Cancer 79(5-6):707-717.
Lambert, "Drug-conjugated monoclonal antibodies for the treatment of cancer," (2005) Current Opin. In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.

(56) References Cited

OTHER PUBLICATIONS

Launay et al., "TRPM4 Is a Ca2+ -Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leabman; et al., "Effects of altered FcγR binding on antibody pharmacokinetics in cynomolgus monkeys." MAbs. Nov.-Dec. 2013; 5(6):896-903.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Leonard et al., "Phase I/II trial of epratuzumab (humanized anti-CD22 antibody) in indolent non-Hodgkin's lymphoma," J. Clin. Oncology (2003) 21(16):3051-3059.
Leonard et al., "Preclinical and clinical evaluation of epratuzumab (anti-CD22 IgG) in B-cell malignancies," Oncogene (2007) 26:3704-3713.
Leung et al., "Construction and characterization of a humanized, internalizing, B-cell (CD22)-specific, leukemia/lymphoma antibody, LL2," Mol. Immunol. (1995) 32(17-18):1413-1427.
Levenson et al., "MCF-7: The First Hormone-responsive Breast Cancer Cell Line," (1997) Cancer Res. 57(15):3071-3078.
Lewis Phillips et al., "Targeting HER2-Positive Breast Cancer with Trastuzumab-DM1, an Antibody-Cytotoxic Drug Conjugate," Cancer Res, 2008, 68: (22).
Liang et al., "The Gene for a Novel Transmembrane Protein Containing Epidermal Growth Factor and Follistatin Domains Is Frequently Hypermethylated in Human Tumor Cells," (2000) Cancer Res. 60:4907-4912.
Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase: 4-Methylene-L-, (E)- and (Z)-4 (Fluoromethylene)-L-, cis- and trans-5-Ethynyl-(±)-, and cis- and trans -5-Vinyl-L-proline," J. Org. Chem. 1992, 57, 2060-2065.
Marin, D., "Voltammetric studies of the interaction of pyrrolo[2,1-c][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.

Mastroberardino et al., "Amino-acid transport by heterodimers of 4F2hc/CD98 and members of a permease family," Nature 395 (6699):288-291 (1998).
Matsumoto, K. et al., "Synthesis of polyaminoalkyl substituted conjugates of pyrrolo[2,1-c][1,4]benzodiazepine (PBD)-polyaminoalkyl involving SNA4 reaction of 2-nitro-5-fluorobenzoate precursors," Heterocycles (2000) 52(3):1015-1020.
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," (2002) Cancer Res. 62:5485-5488.
Miller et al., "Design, Construction, and In Vitro Analyses of Multivalent Antibodies," (2003) Jour, of Immunology 170:4854-4861.
Miller et al., "IRTAs: a new family of immunoglobulinlike receptors differentially expressed in B cells," Blood 99 (8):2662-2669 (2002).
Miura et al., "Molecular cloning of a human RP105 homologue and chromosomal localization of the mouse and human RP105 genes (Ly64 and LY64)." Genomics. Dec. 15, 1996; 38(3):299-304.
Miura et al., "RPIOS Is Associated With MD-1 and Transmits an Activation Signal in Human B Cells," (1998) Blood 92:2815-2822.
Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. Immunol. 22 (6): 1621-1625.
Mungall A.J., et al., "The DNA sequence and analysis of human chromosome 6," Nature 425, 805-811, 2003.
Nadler et al., "B4, a human B lymphocyte-associated antigen expressed on normal, mitogen-activated, and malignant B lymphocytes," Journal of Immunology, 1983, 131(1):244-250.
Nagasaka, T. and Koseki, Y, "Stereoselective Synthesis of Tilivalline," Journal of Organic Chemistry, vol. 63, No. 20, 6797-6801 (1998).
Nagasaka, T. et al., "Stereoselective Synthesis of Tilivalline," Tetrahedron Letters, 30:14, 1871-1872(1989).
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2):143-150.
Nakamuta M., et al., "Cloning and sequence analysis of a cDNA encoding human non—selective type of endothelin receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.

(56) References Cited

OTHER PUBLICATIONS

Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.

Naruse et al., "The HLA-DOB gene displays limited polymorphism with only one amino acid substitution," (2002) Tissue Antigens 59:512-519.

Neuberger and Williams, "The intron requirement for immunoglobulin gene expression is dependent upon the promoter," (1988) Nucleic Acids Res. 16:6713-6724.

Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.

Nilius et al., "Voltage Dependence of the Ca2+ -activated Cation Channel TRPM4," The Journal of Biological Chemistry, vol. 278, No. 33, Issue of Aug. 15, p. 30813-30820, 2003.

O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).

O'Neil, I.A., et al., "The Synthesis of Functionalized Pyrrolo-[2,1-c][1,4]-Benzodiazepines," Synlett, 75-78 (1997).

Ogawa Y., et al., "Molecular Cloning of a Non-Isopeptide-Selective Human Endothelin Receptor," Biochem. Biophys. Res. Commun. 178, 248-255, 1991.

Okamoto Y., et al. "Palmitoylation of Human Endothelin B," Biol. Chem. 272, 21589-21596, 1997.

O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).

Parrish-Novak J., et al., "Interleukins 19, 20, and 24 Signal through Two Distinct Receptor Complexes," J. Biol. Chem. 277, 47517-47523, 2002.

Paul, Fundamental Immunology, 3rd Edition, pp. 292-295, 1993.

Payne, G. "Progress in immunoconjugate cancer therapeutics," (2003) Cancer Cell 3:207-212.

PCT/US2012/059864 International Search Report and Written Opinion dated Dec. 21, 2012 (7 pages).

Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.

Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53- independent mechanism of cell kill," Cancer Res. (2004) 64:6750-6755.

Phillips et al., "Targeting HER2-Positive Breast Cancer with Trastuzumab-DM1, an Antibody-Cytotoxic Drug Conjugate," (2008) Cancer Res. 68(22):9280-9290.

Pingault V., et al., "SOX10 mutations in chronic intestinal pseudo-obstruction suggest a complex physiopathological mechanism," (2002) Hum. Genet. 111, 198-206.

Pletnev S., et al., "Characterization of the Recombinant Extracellular Domains of Human Interleukin-20 Receptors and Their Complexe with Interleukin-19 and Interleukin-20," (2003) Biochemistry 42:12617-12624.

Porkaa et al., "Cloning and Characterization of a Novel Six-Transmembrane Protein STEAP2, Expressed in Normal and Malignant Prostate," Lab. Invest. 82 (11):1573-1582 (2002).

Prasad et al., "Human LAT1, a Subunit of System L Amino Acid Transporter: Molecular Cloning and Transport Function," Biochem. Biophys. Res. Commun. 255 (2), 283-288 (1999).

Preud'homme et al., "Structure and expression of the mb-1 transcript in human lymphoid cells," (1992) Clin. Exp. Immunol. 90(1):141-146.

Puffenberger E.G., et al., "A Missense Mutation of the Endothelin-B Receptor Gene in Multigenic Hirschsprung's Disease," Cell 79, 1257-1266, 1994.

Purser, et al., "Fluorine in Medicinal Chemistry." Chem. Soc. Rev., 2008, 37, 320-330.

Puzanov, I., "Phase I and pharmacokinetic trial of SJG-136 administered on a daily x5 schedule," EJC Supplements (Nov. 2006) 4(12):93.

Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.

Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.

Rahman, K.M., "Effect of microwave irradiation on covalent ligand-DNA interactions," Chem. Commun. (Cambridge, UK), Apr. 2009, 20:2875-2877.

Rahman, K.M., "Rules of DNA adduct formation for pyrrolobenzodiazepine (PBD) dimers," Proceedings of the American Association for Cancer Research Annual Meeting (Apr. 2010) 51:851.

Rahman, K.M., "The pyrrolobenzodiazepine dimer SJG-136 forms sequencedependent intrastrand DNA cross- lins and monoalkylated adducts in addition to interstrand cross-links," J. Am. Chem. Soc., Sep. 2009, 131(38):13756-13766.

Rao et al., "Influence of diet on mammary cancer in transgenic mice bearing an oncogene expressed in mammary tissue," (1997) Breast Cancer Res. and Treatment 45:149-158.

Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.

Reiter R.E., et al., "Prostate stem cell antigen: A cell surface marker overexpressed in prostate cancer," Proc. Natl. Acad. Sci. U.S.A. 95, 1735-1740, 1998.

Remmers et al., "Conformations of complexes between pyrrolo[1,4]benzodiazepines and DNA segments," J Med Chem. Dec. 1986;29(12):2492-2503.

Rich, I.N., "Validation and development of a predictive paradigm for hemotoxicology using a multifunctional bioluminescence colony-forming proliferation assay," Toxicological Sci. (2005) 87(2):427-441.

Rodrigues et al., "Synthesis and beta-lactamase-mediated activation of a cephalosporin-taxol prodrug," (1995) Chemistry Biology 2:223-227.

Roguska et al., "A comparison of two murine monoclonal antibodies humanized by CDR-grafting and variable domain resurfacing," Protein Eng, 1996, 9(10):895-904.

Roguska et al., "Humanization of murine monoclonal antibodies through variable domain resurfacing," PNAS, 1994, 91(3):969-973.

Ross et al., "Prostate Stem Cell Antigen as Therapy Target: Tissue Expression and in Vivo Efficacy of an Immunoconjugate," (2002) Cancer Res. 62:2546-2553.

Rudikoff et al., Single amino acid substitution altering antigen-binding specificity. Proc Natl Acad Sci U S A. Mar. 1982; 79(6):1979-83.

Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).

Sakaguchi et al., "8 lymphocyte lineage-restricted expression of mb-1, a gene with CD3-like structural properties," (1988) EMBO J. 7(11):3457-3464.

Sakamoto A, Yanagisawa M., et al., "Cloning and Functional Expression of Human cDNA For the ETB Endothelin Receptor," Biochem. Biophys. Res. Commun. 178, 656-663, 1991.

Sanderson et al., "In vivo Drug-Linker Stability of an Anti-CD30 Dipeptide-Linked Auristatin Immunoconjugate," (2005) Clin. Cancer Res. 11:843-852.

Scholler et al., "Soluble member(s) of the mesothelin/ megakaryocyte potentiating factor family are detectable in sera from patients with ovarian carcinoma," Proc. Natl. Acad. Sci. USA vol. 96, p. 11531-11536, Sep. 1999.

(56) References Cited

OTHER PUBLICATIONS

SCHRODER and Lubke, The Peptides, vol. 1. pp. 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biological Chemistry, vol. 277. No. 22, Issue of May 31, p. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, The DOBeta Gene is a Divergent Member of the Class II P Gene Family," (1987) J. Biol. Chem. 262:8759-8766.
Shamis et al., "Bioactivation of Self-lmmolative Dendritic Prodrugs by Catalytic Antibody 38C2," (2004) J . Am. Chem. Soc. 126:1726-1731.
Sharkey et al., "Epratuzumab-SN-38: a new antibody-drug conjugate for the therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu, K et al., "Prothracarcin, a Novel Antitumor Antibiotic," J. Antibiotics, 35, 972-978 (1982).
Sinha S.K., et al., "Characterization of the EBV /C3d Receptor on the Human Jurkat T Cell Line: Evidence for a Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody- Multidrug Immunoconjugates," (2002) Bioorganic & Medicinal Chemistry Letters 12:2213-2215.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T et al., "Neothramycins A and B, New Antitumor Antibiotics," J. Antibiotics, 29, 93-96 (1976).
Talpur et al., "CD25 Expression is Correlated with Histological Grade and Response to Denileukin Diftitox in Cutaneous T-Cell Lymphoma," J. Investigative Dermatology, 2006, 126: 575-583.
Tawaragi Y., et al., "Primary Structure of Nonspecific Crossreacting Antigen (NCA), a Member of Carcinoembryonic Antigen (CEA) Gene Family, Deduced From cDNA Sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson J.S., et al., "BAFF-R, a Newly Identified TNF Receptor That Specifically Interacts with BAFF," Science 293 (5537), 2108-2111 (2001).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-lnteractive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.

(56) References Cited

OTHER PUBLICATIONS

Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.

Umezawa, H. et al., "Mazethramycins," SciFinder Scholar, 2-3 (2002).

Umezawa, H. et al., Chemical Abstract No. 4427a, "Mazethramycins" Chemical Abstracts, vol. 90, No. 1, 428 (1979).

Van Geel et al., "Chemoenzymatic Conjugation of Toxic Payloads to the Globally Conserved N-Glycan of Native mAbs Provides Homogeneous and Highly Efficacious Antibody-Drug Conjugates," (2015) Bioconjugate Chem. 26: 2233-2242.

Verheij J.B., et al., "ABCD Syndrome Is Caused by a Homozygous Mutation in the EDNRB Gene," Am. J. Med. 15 Genet. 108, 223-225, 2002.

Vippagunta, S.R. et al., "Crystalline solids," Adv. Drug Delivery Rev. (2001) 48:3-26.

Von Hoegen et al., "Identifigation of a human protein homologous to the mouse Lyb-2 B cell differentiation antigen and sequence of the corresponding cDNA," (1990) J. Immunol. 144(12):4870-4877.

Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.

Webster et al., "Mammary tumorigenesis and metastasis in transgenic mice," (1994) Semin. Cancer Biol. 5:69-76.

Weidner-Wells, M.A. et al., "Photochemical approach to the synthesis of the pyrrolo[1,4]benzodiazepine antibiotics," J. Org. Chem. (1989) 54:5746-5758.

Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.

Weis J.J., et al., "Structure of the human b lymphocyte receptor for c3d and the epstein-barr virus and relatedness to other members of the family of C3/C4 binding proteins," J. Exp. Med. 167, 1047-1066, 1988.

Wells, G. et al., "Design, synthesis and biophysical and biological evaluation of a series of pyrrolobenzodiazepine-poly(N-methylpyrrole) conjugates," J. Med. Chem. (2006) 49:5442-5461.

Wilkinson "Eph Receptors and Ephrins: Regulators of Guidance and Assembly," Int. Rev. Cytol. 196:177-244 (2000).

Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.

Wilkinson, G.P., "Pharmacokinetics, metabolism and glutathione reactivity of SJG-136," Br. J. Cancer (2003) 88(Supp. 1):S29.

Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.

Wilson et al., "eDNA Cloning of the B Cell Membrane Protein CD22: A Mediator of B-B Cell Interactions," (1991) J. Exp. Med. 173:137-146.

Wilson, S.C et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).

Wolff, M.E., Burger's Medicinal Chemistry, 4th Edition, Part 1, Wiley: New York (1979) 336-337.

Wolff, M.E., Burger's Medicinal Chemistry, 5th Edition, Part I, John Wiley & Sons (1995) 975-977.

Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.

Wu et al., "Arming antibodies: prospects and challenges for immunoconjugates," (2005) Nature Biotech. 23(9):1137-1145.

Xie et al., "In vivo behaviour of antibody- drug conjugates for the targeted treatment of cancer," (2006) Expert. Opin Biol. Ther. 6(3):281-291.

Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.

Xu et al., "Molecular Cloning, Functional Characterization, Tissue Distribution, and Chromosomal Localization of a Human, Small Intestinal Sodium-Phosphate (Na + -Pi) Transporter (SLC34A2)," Genomics 62 (2):281-284 (1999).

Xu, M.J., et al., "Molecular Cloning and Characterization of SPAP1, an Inhibitory Receptor," (2001) Biochem. Biophys. Res. Commun. 280 (3):768-775.

Xu, X.Z., et al., "Regulation of melastatin, a TRP-related protein, through interaction with a cytoplasmic isoform," Proc. Natl. Acad. Sci. U.S.A. 98 (19):10692-10697 (2001).

Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.

Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.

Yin & Lloyd, "Molecular Cloning of the CA125 Ovarian Cancer Antigen," J. Biol. Chem. 276 (29):27371-27375 (2001).

Younes et al., "Phase 1 multidose-escalation study of the anti-CD19 maytansinoid immunoconjugate SAR3419 administered by intravenous infusion every 3 weeks to patients with relapsed/refractory B-cell lymphoma," J Clin Oncol., 2012, 30(22):2776-82.

Yu et al., "Human mb-1 gene: complete edna sequence and its expression in b cells bearing membrane Ig of various isotypes," (1992) J. Immunol. 148(2) 633-637.

Zammarchi et al., "Pre-Clinical Development of Adct-4O2, a Novel Pyrrolobenzodiazepine (PBD)—Based Antibody Drug Conjugate (ADC) Targeting CD19-Expressing B-Cell Malignancies," Blood, 2015, 126:1564, Abstract.

Zhao et al., "Novel Antibody Therapeutics Targeting Mesothelin In Solid Tumors," (2016) Clin. Cancer Drugs 3: 76-86.

* cited by examiner

SEQUENCE LISTING

```
<160> NUMBER OF SEQ ID NOS: 44

<210> SEQ ID NO 1
<211> LENGTH: 120
<212> TYPE: PRT
<213> ORGANISM: Artificial sequence
<220> FEATURE:
<223> OTHER INFORMATION: Synthetic sequence: Herceptin VH chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 2
<211> LENGTH: 107
<212> TYPE: PRT
<213> ORGANISM: Artificial sequence
<220> FEATURE:
<223> OTHER INFORMATION: Synthetic sequence: Herceptin VL chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 3
<211> LENGTH: 21
<212> TYPE: PRT
<213> ORGANISM: Artificial sequence
<220> FEATURE:
<223> OTHER INFORMATION: Synthetic sequence: A20FMDV-Cys polypeptide

<400> SEQUENCE: 3

Asn Ala Val Pro Asn Leu Arg Gly Asp Leu Gln Val Leu Ala Gln Lys
1               5                   10                  15

Val Ala Arg Thr Cys
            20

<210> SEQ ID NO 4
<211> LENGTH: 21
<212> TYPE: PRT
<213> ORGANISM: Artificial sequence
<220> FEATURE:
<223> OTHER INFORMATION: Synthetic sequence: A20FMDV-Cys polypeptide
<220> FEATURE:
<221> NAME/KEY: VARIANT
<222> LOCATION: (4)..(18)
<223> OTHER INFORMATION: Xaa is any amino acid residue

<400> SEQUENCE: 4

Asn Ala Val Xaa Xaa Xaa Xaa Xaa Xaa Xaa Xaa Xaa Xaa Xaa Xaa Xaa
1               5                   10                  15

Xaa Xaa Arg Thr Cys
            20

<210> SEQ ID NO 5
<211> LENGTH: 137
<212> TYPE: PRT
<213> ORGANISM: Artificial sequence
<220> FEATURE:
<223> OTHER INFORMATION: Synthetic sequence: Anti-Integrin Alpha v Beta
      6, RHAB6.2

<400> SEQUENCE: 5

Gln Val Gln Leu Val Gln Ser Gly Ser Glu Leu Lys Lys Pro Gly Ala
1               5                   10                  15

Ser Val Lys Ile Ser Cys Lys Ala Ser Gly Phe Ala Phe Thr Asp Ser
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Gly Thr Pro Thr Ala Val Pro Asn Leu Arg Gly Asp Leu Gln
            100                 105                 110

Val Leu Ala Gln Lys Val Ala Gly Pro Tyr Pro Phe Asp Tyr Trp Gly
        115                 120                 125

Gln Gly Thr Leu Val Thr Val Ser Ser
    130                 135

<210> SEQ ID NO 6
<211> LENGTH: 137
<212> TYPE: PRT
<213> ORGANISM: Artificial sequence

```
<220> FEATURE:
<223> OTHER INFORMATION: Synthetic sequence: Anti-Integrin Alpha v Beta
      6, RHCB6.2

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asp Ser
            20                  25                  30

Tyr Met His Trp Val Arg Gln Ala Pro Gly Gln Arg Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Thr Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Pro Thr Ala Val Pro Asn Leu Arg Gly Asp Leu Gln
            100                 105                 110

Val Leu Ala Gln Lys Val Ala Gly Pro Tyr Pro Phe Asp Tyr Trp Gly
        115                 120                 125

Gln Gly Thr Leu Val Thr Val Ser Ser
    130                 135

<210> SEQ ID NO 7
<211> LENGTH: 120
<212> TYPE: PRT
<213> ORGANISM: Artificial sequence
<220> FEATURE:
<223> OTHER INFORMATION: Synthetic sequence: Anti-Integrin Alpha v Beta
      6, RHF

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Ile Asp Ser
            20                  25                  30

Tyr Met His Trp Val Arg Gln Ala Pro Gly Gln Arg Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Phe Thr Thr Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Leu Val Thr Val Ser Ser
        115                 120

<210> SEQ ID NO 8
<211> LENGTH: 137
<212> TYPE: PRT
<213> ORGANISM: Artificial sequence
<220> FEATURE:
<223> OTHER INFORMATION: Synthetic sequence: Anti-Integrin Alpha v Beta
      6, RHFB6

<400> SEQUENCE: 8
```

-continued

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Ile Asp Ser
            20                  25                  30

Tyr Met His Trp Val Arg Gln Ala Pro Gly Gln Arg Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Phe Thr Thr Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Asn Glu Gly Thr Pro Thr Ala Val Pro Asn Leu Arg Gly Asp Leu Gln
            100                 105                 110

Val Leu Ala Gln Lys Val Ala Gly Pro Tyr Tyr Phe Asp Tyr Trp Gly
        115                 120                 125

Gln Gly Thr Leu Val Thr Val Ser Ser
    130                 135

<210> SEQ ID NO 9
<211> LENGTH: 120
<212> TYPE: PRT
<213> ORGANISM: Artificial sequence
<220> FEATURE:
<223> OTHER INFORMATION: Synthetic sequence: Anti-Integrin Alpha v Beta
      6, RHAY100bP

<400> SEQUENCE: 9

Gln Val Gln Leu Val Gln Ser Gly Ser Glu Leu Lys Lys Pro Gly Ala
1               5                   10                  15

Ser Val Lys Ile Ser Cys Lys Ala Ser Gly Phe Ala Phe Thr Asp Ser
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Gly Thr Pro Thr Gly Pro Tyr Pro Phe Asp Tyr Trp Gly Gln
            100                 105                 110

Gly Thr Leu Val Thr Val Ser Ser
        115                 120

<210> SEQ ID NO 10
<211> LENGTH: 106
<212> TYPE: PRT
<213> ORGANISM: Artificial sequence
<220> FEATURE:
<223> OTHER INFORMATION: Synthetic sequence: Anti-Integrin Alpha v Beta
      6, RKF

<400> SEQUENCE: 10

Glu Asn Val Leu Thr Gln Ser Pro Gly Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Phe Gln Gln Lys Pro Gly Gln Ala Pro Arg Leu Leu Ile Tyr
          35                  40                  45

Ser Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Arg Ser Ser Tyr Pro Leu Thr
                 85                  90                  95

Phe Gly Gly Gly Thr Lys Val Glu Ile Lys
            100                 105

<210> SEQ ID NO 11
<211> LENGTH: 106
<212> TYPE: PRT
<213> ORGANISM: Artificial sequence
<220> FEATURE:
<223> OTHER INFORMATION: Synthetic sequence: Anti-Integrin Alpha v Beta
      6, RKFL36L50

<400> SEQUENCE: 11

Glu Asn Val Leu Thr Gln Ser Pro Gly Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Leu Gln Gln Lys Pro Gly Gln Ala Pro Arg Leu Leu Ile Tyr
          35                  40                  45

Leu Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Arg Ser Ser Tyr Pro Leu Thr
                 85                  90                  95

Phe Gly Gly Gly Thr Lys Val Glu Ile Lys
            100                 105

<210> SEQ ID NO 12
<211> LENGTH: 106
<212> TYPE: PRT
<213> ORGANISM: Artificial sequence
<220> FEATURE:
<223> OTHER INFORMATION: Synthetic sequence: Anti-Integrin Alpha v Beta
      6, RKC

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Phe Gln Gln Lys Pro Gly Gln Ala Pro Arg Leu Leu Ile Tyr
          35                  40                  45

Ser Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Arg Ser Ser Tyr Pro Leu Thr
                 85                  90                  95

Phe Gly Gly Gly Thr Lys Val Glu Ile Lys
            100                 105

```
<210> SEQ ID NO 13
<211> LENGTH: 116
<212> TYPE: PRT
<213> ORGANISM: Artificial sequence
<220> FEATURE:
<223> OTHER INFORMATION: Synthetic sequence: Anti-CD33, CD33 Hum195 VH

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Ile
            35                  40                  45

Gly Tyr Ile Tyr Pro Tyr Asn Gly Gly Thr Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser
        115

<210> SEQ ID NO 14
<211> LENGTH: 111
<212> TYPE: PRT
<213> ORGANISM: Artificial sequence
<220> FEATURE:
<223> OTHER INFORMATION: Synthetic sequence: Anti-CD33, CD33 Hum195 VK

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
                20                  25                  30

Gly Ile Ser Phe Met Asn Trp Phe Gln Gln Lys Pro Gly Lys Ala Pro
            35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gly Gly Thr Lys Val Glu Ile Lys
            100                 105                 110

<210> SEQ ID NO 15
<211> LENGTH: 120
<212> TYPE: PRT
<213> ORGANISM: Artificial sequence
<220> FEATURE:
<223> OTHER INFORMATION: Synthetic sequence: Anti-CD19, CD19 B4
        resurfaced VH

<400> SEQUENCE: 15

Gln Val Gln Leu Val Gln Pro Gly Ala Glu Val Val Lys Pro Gly Ala
1               5                   10                  15
```

```
Ser Val Lys Leu Ser Cys Lys Thr Ser Gly Tyr Thr Phe Thr Ser Asn
             20                  25                  30

Trp Met His Trp Val Lys Gln Arg Pro Gly Gln Gly Leu Glu Trp Ile
         35                  40                  45

Gly Glu Ile Asp Pro Ser Asp Ser Tyr Thr Asn Tyr Asn Gln Asn Phe
     50                  55                  60

Lys Gly Lys Ala Lys Leu Thr Val Asp Lys Ser Thr Ser Thr Ala Tyr
 65                  70                  75                  80

Met Glu Val Ser Ser Leu Arg Ser Asp Asp Thr Ala Val Tyr Tyr Cys
                 85                  90                  95

Ala Arg Gly Ser Asn Pro Tyr Tyr Tyr Ala Met Asp Tyr Trp Gly Gln
                100                 105                 110

Gly Thr Ser Val Thr Val Ser Ser
            115                 120

<210> SEQ ID NO 16
<211> LENGTH: 104
<212> TYPE: PRT
<213> ORGANISM: Artificial sequence
<220> FEATURE:
<223> OTHER INFORMATION: Synthetic sequence: Anti-CD19, CD19 B4
      resurfaced VK

<400> SEQUENCE: 16

Glu Ile Val Leu Thr Gln Ser Pro Ala Ile Met Ser Ala Ser Pro Gly
 1               5                  10                  15

Glu Arg Val Thr Met Thr Cys Ser Ala Ser Ser Gly Val Asn Tyr Met
             20                  25                  30

His Trp Tyr Gln Gln Lys Pro Gly Thr Ser Pro Arg Arg Trp Ile Tyr
         35                  40                  45

Asp Thr Ser Lys Leu Ala Ser Gly Val Pro Ala Arg Phe Ser Gly Ser
     50                  55                  60

Gly Ser Gly Thr Ser Tyr Ser Leu Thr Ile Ser Ser Met Glu Pro Glu
 65                  70                  75                  80

Asp Ala Ala Thr Tyr Tyr Cys His Gln Arg Gly Ser Tyr Thr Phe Gly
                 85                  90                  95

Gly Gly Thr Lys Leu Glu Ile Lys
            100

<210> SEQ ID NO 17
<211> LENGTH: 104
<212> TYPE: PRT
<213> ORGANISM: Artificial sequence
<220> FEATURE:
<223> OTHER INFORMATION: Synthetic sequence: Anti-CD25, Simulect VK
      (also known as Basiliximab)

<400> SEQUENCE: 17

Gln Ile Val Ser Thr Gln Ser Pro Ala Ile Met Ser Ala Ser Pro Gly
 1               5                  10                  15

Glu Lys Val Thr Met Thr Cys Ser Ala Ser Ser Ser Arg Ser Tyr Met
             20                  25                  30

Gln Trp Tyr Gln Gln Lys Pro Gly Thr Ser Pro Lys Arg Trp Ile Tyr
         35                  40                  45

Asp Thr Ser Lys Leu Ala Ser Gly Val Pro Ala Arg Phe Ser Gly Ser
     50                  55                  60

Gly Ser Gly Thr Ser Tyr Ser Leu Thr Ile Ser Ser Met Glu Ala Glu
 65                  70                  75                  80
```

```
Asp Ala Ala Thr Tyr Tyr Cys His Gln Arg Ser Ser Tyr Thr Phe Gly
                85                  90                  95

Gly Gly Thr Lys Leu Glu Ile Lys
            100

<210> SEQ ID NO 18
<211> LENGTH: 115
<212> TYPE: PRT
<213> ORGANISM: Artificial sequence
<220> FEATURE:
<223> OTHER INFORMATION: Synthetic sequence: Anti-CD25, Simulect VH

<400> SEQUENCE: 18

Gln Leu Gln Gln Ser Gly Thr Val Leu Ala Arg Pro Gly Ala Ser Val
1               5                   10                  15

Lys Met Ser Cys Lys Ala Ser Gly Tyr Ser Phe Thr Arg Tyr Trp Met
            20                  25                  30

His Trp Ile Lys Gln Arg Pro Gly Gln Gly Leu Glu Trp Ile Gly Ala
        35                  40                  45

Ile Tyr Pro Gly Asn Ser Asp Thr Ser Tyr Asn Gln Lys Phe Glu Gly
    50                  55                  60

Lys Ala Lys Leu Thr Ala Val Thr Ser Ala Ser Thr Ala Tyr Met Glu
65                  70                  75                  80

Leu Ser Ser Leu Thr His Glu Asp Ser Ala Val Tyr Tyr Cys Ser Arg
                85                  90                  95

Asp Tyr Gly Tyr Tyr Phe Asp Phe Trp Gly Gln Gly Thr Thr Leu Thr
            100                 105                 110

Val Ser Ser
        115

<210> SEQ ID NO 19
<211> LENGTH: 115
<212> TYPE: PRT
<213> ORGANISM: Artificial sequence
<220> FEATURE:
<223> OTHER INFORMATION: Synthetic sequence: Anti-PSMA, Deimmunised
      VH '1

<400> SEQUENCE: 19

Glu Val Gln Leu Val Gln Ser Gly Pro Glu Val Lys Lys Pro Gly Ala
1               5                   10                  15

Thr Val Lys Ile Ser Cys Lys Thr Ser Gly Tyr Thr Phe Thr Glu Tyr
            20                  25                  30

Thr Ile His Trp Val Lys Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Leu Thr
            100                 105                 110

Val Ser Ser
        115

<210> SEQ ID NO 20
<211> LENGTH: 107
<212> TYPE: PRT
```

```
<213> ORGANISM: Artificial sequence
<220> FEATURE:
<223> OTHER INFORMATION: Synthetic sequence: Anti-PSMA, Deimmunised
      VK '1

<400> SEQUENCE: 20

Asp Ile Gln Met Thr Gln Ser Pro Ser Ser Leu Ser Thr Ser Val Gly
1               5                   10                  15

Asp Arg Val Thr Leu Thr Cys Lys Ala Ser Gln Asp Val Gly Thr Ala
            20                  25                  30

Val Asp Trp Tyr Gln Gln Lys Pro Gly Ser Pro Lys Leu Leu Ile
        35                  40                  45

Tyr Trp Ala Ser Thr Arg His Thr Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Pro Gly Thr Lys Val Asp Ile Lys
            100                 105

<210> SEQ ID NO 21
<211> LENGTH: 116
<212> TYPE: PRT
<213> ORGANISM: Artificial sequence
<220> FEATURE:
<223> OTHER INFORMATION: Synthetic sequence: Anti-PSMA, Deimmunised
      VH1 '5

<400> SEQUENCE: 21

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Ser Gln Ser Asn Asn Phe Ala Thr His Tyr Ala Glu
50                  55                  60

Ser Val Lys Gly Arg Val Thr Ile Ser Arg Asp Asp Ser Lys Ser Ile
65                  70                  75                  80

Val Tyr Leu Gln Met Asn Asn Leu Arg Ala Glu Asp Thr Gly Val Tyr
                85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 22
<211> LENGTH: 116
<212> TYPE: PRT
<213> ORGANISM: Artificial sequence
<220> FEATURE:
<223> OTHER INFORMATION: Synthetic sequence: Anti-PSMA, Deimmunised
      VH2 '5

<400> SEQUENCE: 22

Glu Val Lys Leu Val Glu Ser Gly Gly Gly Leu Val Gln Pro Gly Gly
1               5                   10                  15

Ser Leu Lys Leu Ser Cys Val Ala Ser Gly Phe Thr Phe Ser Asn Tyr
            20                  25                  30
```

```
Trp Met Asn Trp Val Arg Gln Ala Pro Gly Lys Gly Leu Glu Trp Val
            35                  40                  45

Ala Glu Ile Arg Ser Gln Ser Asn Asn Phe Ala Thr His Tyr Ala Glu
     50                  55                  60

Ser Val Lys Gly Arg Val Thr Ile Ser Arg Asp Asp Ser Lys Ser Ile
 65                  70                  75                  80

Val Tyr Leu Gln Met Asn Asn Leu Arg Ala Glu Asp Thr Ala Val Tyr
                 85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 23
<211> LENGTH: 116
<212> TYPE: PRT
<213> ORGANISM: Artificial sequence
<220> FEATURE:
<223> OTHER INFORMATION: Synthetic sequence: Anti-PSMA, Deimmunised
      VH3 '5

<400> SEQUENCE: 23

Glu Val Gln Leu Val Glu Ser Gly Gly Gly Leu Val Gln Pro Gly Gly
 1               5                  10                  15

Ser Leu Lys Leu Ser Cys Val Ala Ser Gly Phe Thr Phe Ser Asn Tyr
             20                  25                  30

Trp Met Asn Trp Val Arg Gln Ala Pro Gly Lys Gly Leu Glu Trp Val
            35                  40                  45

Ala Glu Ile Arg Ser Gln Ser Asn Asn Phe Ala Thr His Tyr Ala Glu
     50                  55                  60

Ser Val Lys Gly Arg Val Thr Ile Ser Arg Asp Asp Ser Lys Ser Ile
 65                  70                  75                  80

Val Tyr Leu Gln Met Asn Asn Leu Arg Ala Glu Asp Thr Ala Val Tyr
                 85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 24
<211> LENGTH: 116
<212> TYPE: PRT
<213> ORGANISM: Artificial sequence
<220> FEATURE:
<223> OTHER INFORMATION: Synthetic sequence: Anti-PSMA, Deimmunised
      VH4 '5

<400> SEQUENCE: 24

Glu Val Gln Leu Val Glu Ser Gly Gly Gly Leu Val Gln Pro Gly Gly
 1               5                  10                  15

Ser Leu Lys Leu Ser Cys Val Ala Ser Gly Phe Thr Phe Ser Asn Tyr
             20                  25                  30

Trp Met Asn Trp Val Arg Gln Ala Pro Gly Lys Gly Leu Glu Trp Val
            35                  40                  45

Ala Glu Ile Arg Ser Gln Ser Asn Asn Phe Ala Thr His Tyr Ala Glu
     50                  55                  60

Ser Val Lys Gly Arg Phe Thr Ile Ser Arg Asp Asp Ser Lys Ser Ile
 65                  70                  75                  80
```

```
Val Tyr Leu Gln Met Asn Asn Leu Arg Ala Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 25
<211> LENGTH: 107
<212> TYPE: PRT
<213> ORGANISM: Artificial sequence
<220> FEATURE:
<223> OTHER INFORMATION: Synthetic sequence: Anti-PSMA, Deimmunised
      VK1 '5

<400> SEQUENCE: 25

Asn Ile Val Met Thr Gln Phe Pro Ser Ser Met Ser Ala Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Asp Gln Ser Pro Lys Met Leu Ile
        35                  40                  45

Tyr Gly Ala Ser Asn Arg Phe Thr Gly Val Pro Asp Arg Phe Thr Gly
    50                  55                  60

Ser Gly Ser Ala Thr Asp Phe Thr Leu Thr Ile Ser Ser Leu Gln Thr
65                  70                  75                  80

Glu Asp Leu Ala Asp Tyr Tyr Cys Gly Gln Ser Tyr Thr Phe Pro Tyr
                85                  90                  95

Thr Phe Gly Gln Gly Thr Lys Leu Glu Met Lys
            100                 105

<210> SEQ ID NO 26
<211> LENGTH: 107
<212> TYPE: PRT
<213> ORGANISM: Artificial sequence
<220> FEATURE:
<223> OTHER INFORMATION: Synthetic sequence: Anti-PSMA, Deimmunised
      VK2 '5

<400> SEQUENCE: 26

Asn Ile Val Met Thr Gln Phe Pro Ser Ser Met Ser Ala Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Asp Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Asp Tyr Tyr Cys Gly Gln Ser Tyr Thr Phe Pro Tyr
                85                  90                  95

Thr Phe Gly Gln Gly Thr Lys Leu Glu Ile Lys
            100                 105

<210> SEQ ID NO 27
<211> LENGTH: 107
<212> TYPE: PRT
<213> ORGANISM: Artificial sequence
```

```
<220> FEATURE:
<223> OTHER INFORMATION: Synthetic sequence: Anti-PSMA, Deimmunised
      VK3 '5

<400> SEQUENCE: 27

Asn Ile Gln Met Thr Gln Phe Pro Ser Ala Met Ser Ala Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Asp Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Asp Tyr Tyr Cys Gly Gln Ser Tyr Thr Phe Pro Tyr
                85                  90                  95

Thr Phe Gly Gln Gly Thr Lys Leu Glu Ile Lys
            100                 105

<210> SEQ ID NO 28
<211> LENGTH: 107
<212> TYPE: PRT
<213> ORGANISM: Artificial sequence
<220> FEATURE:
<223> OTHER INFORMATION: Synthetic sequence: Anti-PSMA, Deimmunised
      VK4 '5

<400> SEQUENCE: 28

Asn Ile Gln Met Thr Gln Phe Pro Ser Ala Met Ser Ala Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Asp Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Glu Ala Asp Tyr Tyr Cys Gly Gln Ser Tyr Thr Phe Pro Tyr
                85                  90                  95

Thr Phe Gly Gln Gly Thr Lys Leu Glu Ile Lys
            100                 105

<210> SEQ ID NO 29
<211> LENGTH: 107
<212> TYPE: PRT
<213> ORGANISM: Artificial sequence
<220> FEATURE:
<223> OTHER INFORMATION: Synthetic sequence: Anti-PSMA, Deimmunised VK
      DI '5

<400> SEQUENCE: 29

Asn Ile Val Met Thr Gln Phe Pro Lys Ser Met Ser Ala Ser Ala Gly
1               5                   10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45
```

```
Tyr Gly Ala Ser Asn Arg Phe Thr Gly Val Pro Asp Arg Phe Ser Gly
        50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
                100                 105
```

<210> SEQ ID NO 30
<211> LENGTH: 116
<212> TYPE: PRT
<213> ORGANISM: Artificial sequence
<220> FEATURE:
<223> OTHER INFORMATION: Synthetic sequence: Anti-PSMA, Deimmunised VH DI '5

<400> SEQUENCE: 30

```
Glu Val Lys Leu Glu Glu Ser Gly Gly Gly Leu Val Gln Pro Gly Gly
 1               5                   10                  15

Ser Met Lys Ile Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Ser Gln Ser Asn Asn Phe Ala Thr His Tyr Ala Glu
        50                  55                  60

Ser Val Lys Gly Arg Val Ile Ile Ser Arg Asp Asp Ser Lys Ser Ser
 65                  70                  75                  80

Val Tyr Leu Gln Met Asn Ser Leu Arg Ala Glu Asp Thr Ala Val Tyr
                 85                  90                  95

Tyr Cys Thr Arg Arg Trp Asn Asn Phe Trp Gly Gln Gly Thr Thr Val
                100                 105                 110

Thr Val Ser Ser
        115
```

<210> SEQ ID NO 31
<211> LENGTH: 116
<212> TYPE: PRT
<213> ORGANISM: Artificial sequence
<220> FEATURE:
<223> OTHER INFORMATION: Synthetic sequence: Anti-PSMA, Humanised RHA '5

<400> SEQUENCE: 31

```
Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Thr Phe Ser Asn Tyr
                20                  25                  30

Trp Met Asn Trp Val Arg Gln Ala Ser Gly Lys Gly Leu Glu Trp Val
            35                  40                  45

Gly Glu Ile Arg Ser Gln Ser Asn Asn Phe Ala Thr His Tyr Ala Glu
        50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg Arg Trp Asn Asn Phe Trp Gly Gln Gly Thr Thr Val
                100                 105                 110

Thr Val Ser Ser
```

-continued

```
                115

<210> SEQ ID NO 32
<211> LENGTH: 116
<212> TYPE: PRT
<213> ORGANISM: Artificial sequence
<220> FEATURE:
<223> OTHER INFORMATION: Synthetic sequence: Anti-PSMA, Humanised RHB '5

<400> SEQUENCE: 32

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Trp Met Asn Trp Val Arg Gln Ala Ser Gly Lys Gly Leu Glu Trp Val
        35                  40                  45

Ala Glu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Asn Thr
65                  70                  75                  80

Val Tyr Leu Gln Met Asn Ser Leu Arg Thr Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 33
<211> LENGTH: 116
<212> TYPE: PRT
<213> ORGANISM: Artificial sequence
<220> FEATURE:
<223> OTHER INFORMATION: Synthetic sequence: Anti-PSMA, Humanised RHC '5

<400> SEQUENCE: 33

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Trp Met Asn Trp Val Arg Gln Ala Ser Gly Lys Gly Leu Glu Trp Val
        35                  40                  45

Ala Glu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Asn Thr
65                  70                  75                  80

Val Tyr Leu Gln Met Asn Ser Leu Arg Thr Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
        115

<210> SEQ ID NO 34
<211> LENGTH: 116
<212> TYPE: PRT
<213> ORGANISM: Artificial sequence
<220> FEATURE:
<223> OTHER INFORMATION: Synthetic sequence: Anti-PSMA, Humanised RHD '5

<400> SEQUENCE: 34
```

```
Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
                20                  25                  30

Trp Met Asn Trp Val Arg Gln Ala Ser Gly Lys Gly Leu Glu Trp Val
            35                  40                  45

Gly Glu Ile Arg Ser Gln Ser Asn Asn Phe Ala Thr His Tyr Ala Glu
        50                  55                  60

Ser Val Lys Gly Arg Val Ile Ile Ser Arg Asp Asp Ser Lys Asn Thr
65                  70                  75                  80

Val Tyr Leu Gln Met Asn Ser Leu Arg Thr Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
            115

<210> SEQ ID NO 35
<211> LENGTH: 116
<212> TYPE: PRT
<213> ORGANISM: Artificial sequence
<220> FEATURE:
<223> OTHER INFORMATION: Synthetic sequence: Anti-PSMA, Humanised RHE '5

<400> SEQUENCE: 35

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
                20                  25                  30

Trp Met Asn Trp Val Arg Gln Ala Ser Gly Lys Gly Leu Glu Trp Val
            35                  40                  45

Ala Glu Ile Arg Ser Gln Ser Asn Asn Phe Ala Thr His Tyr Ala Glu
        50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Thr Glu Asp Thr Ala Val Tyr
                85                  90                  95

Tyr Cys Thr Arg Arg Trp Asn Asn Phe Trp Gly Gln Gly Thr Thr Val
            100                 105                 110

Thr Val Ser Ser
            115

<210> SEQ ID NO 36
<211> LENGTH: 116
<212> TYPE: PRT
<213> ORGANISM: Artificial sequence
<220> FEATURE:
<223> OTHER INFORMATION: Synthetic sequence: Anti-PSMA, Humanised RHF '5

<400> SEQUENCE: 36

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
                20                  25                  30

Trp Met Asn Trp Val Arg Gln Ala Ser Gly Lys Gly Leu Glu Trp Val
            35                  40                  45

Ala Glu Ile Arg Ser Gln Ser Asn Asn Phe Ala Thr His Tyr Ala Glu
```

```
                    50                  55                  60
Ser Val Lys Gly Arg Val Ile Ile Ser Arg Asp Asp Ser Lys Asn Thr
 65                  70                  75                  80

Ala Tyr Leu Gln Met Asn Ser Leu Arg Thr Glu Asp Thr Ala Val Tyr
                     85                  90                  95

Tyr Cys Thr Arg Arg Trp Asn Asn Phe Trp Gly Gln Gly Thr Thr Val
                100                 105                 110

Thr Val Ser Ser
            115

<210> SEQ ID NO 37
<211> LENGTH: 116
<212> TYPE: PRT
<213> ORGANISM: Artificial sequence
<220> FEATURE:
<223> OTHER INFORMATION: Synthetic sequence: Anti-PSMA, Humanised RHG '5

<400> SEQUENCE: 37

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Asn Tyr
                20                  25                  30

Trp Met Asn Trp Val Arg Gln Ala Ser Gly Lys Gly Leu Glu Trp Val
             35                  40                  45

Ala Glu Ile Arg Ser Gln Ser Asn Asn Phe Ala Thr His Tyr Ala Glu
         50                  55                  60

Ser Val Lys Gly Arg Val Ile Ile Ser Arg Asp Asp Ser Lys Asn Thr
 65                  70                  75                  80

Ala Tyr Leu Gln Met Asn Ser Leu Arg Thr Glu Asp Thr Ala Val Tyr
                     85                  90                  95

Tyr Cys Thr Arg Arg Trp Asn Asn Phe Trp Gly Gln Gly Thr Thr Val
                100                 105                 110

Thr Val Ser Ser
            115

<210> SEQ ID NO 38
<211> LENGTH: 107
<212> TYPE: PRT
<213> ORGANISM: Artificial sequence
<220> FEATURE:
<223> OTHER INFORMATION: Synthetic sequence: Anti-PSMA, Humanised RKA '5

<400> SEQUENCE: 38

Asp Ile Gln Met Thr Gln Ser Pro Ser Ser Val Ser Ala Ser Val Gly
 1               5                  10                  15

Asp Arg Val Thr Ile Thr Cys Lys Ala Ser Glu Asn Val Gly Thr Tyr
                20                  25                  30

Val Ser Trp Tyr Gln Gln Lys Pro Gly Thr Ala Pro Lys Leu Leu Ile
             35                  40                  45

Tyr Gly Ala Ser Asn Arg Phe Thr Gly Val Pro Ser Arg Phe Ser Gly
         50                  55                  60

Ser Gly Ser Ala Thr Asp Phe Thr Leu Thr Ile Asn Asn Leu Gln Pro
 65                  70                  75                  80

Glu Asp Phe Ala Thr Tyr Tyr Cys Gly Gln Ser Tyr Thr Phe Pro Tyr
                     85                  90                  95

Thr Phe Gly Gln Gly Thr Lys Val Glu Ile Lys
                100                 105
```

<210> SEQ ID NO 39
<211> LENGTH: 107
<212> TYPE: PRT
<213> ORGANISM: Artificial sequence
<220> FEATURE:
<223> OTHER INFORMATION: Synthetic sequence: Anti-PSMA, Humanised RKB '5

<400> SEQUENCE: 39

```
Asp Ile Gln Met Thr Gln Ser Pro Ser Ser Val Ser Ala Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Gly Thr Ala Pro Lys Leu Leu Ile
        35                  40                  45

Tyr Gly Ala Ser Asn Arg Phe Thr Gly Val Pro Ser Arg Phe Ser Gly
    50                  55                  60

Ser Gly Ser Ala Thr Asp Phe Thr Leu Thr Ile Asn Asn Leu Gln Pro
65                  70                  75                  80

Glu Asp Phe Ala Thr Tyr Tyr Cys Gly Gln Ser Tyr Thr Phe Pro Tyr
                85                  90                  95

Thr Phe Gly Gln Gly Thr Lys Val Glu Ile Lys
            100                 105
```

<210> SEQ ID NO 40
<211> LENGTH: 107
<212> TYPE: PRT
<213> ORGANISM: Artificial sequence
<220> FEATURE:
<223> OTHER INFORMATION: Synthetic sequence: Anti-PSMA, Humanised RKC '5

<400> SEQUENCE: 40

```
Asp Ile Gln Met Thr Gln Ser Pro Ser Ser Val Ser Ala Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Gly Thr Ala Pro Lys Met Leu Ile
        35                  40                  45

Tyr Gly Ala Ser Asn Arg Phe Thr Gly Val Pro Ser Arg Phe Ser Gly
    50                  55                  60

Ser Gly Ser Ala Thr Asp Phe Thr Leu Thr Ile Asn Asn Leu Gln Pro
65                  70                  75                  80

Glu Asp Phe Ala Thr Tyr Tyr Cys Gly Gln Ser Tyr Thr Phe Pro Tyr
                85                  90                  95

Thr Phe Gly Gln Gly Thr Lys Val Glu Ile Lys
            100                 105
```

<210> SEQ ID NO 41
<211> LENGTH: 107
<212> TYPE: PRT
<213> ORGANISM: Artificial sequence
<220> FEATURE:
<223> OTHER INFORMATION: Synthetic sequence: Anti-PSMA, Humanised RKD '5

<400> SEQUENCE: 41

```
Asp Ile Gln Met Thr Gln Ser Pro Ser Ser Val Ser Ala Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Gly Thr Ala Pro Lys Met Leu Ile
```

```
            35                  40                  45
Tyr Gly Ala Ser Asn Arg Phe Thr Gly Val Pro Ser Arg Phe Ser Gly
    50                  55                  60
Ser Gly Ser Ala Thr Asp Phe Thr Leu Thr Ile Asn Asn Leu Gln Pro
65                  70                  75                  80
Glu Asp Phe Ala Thr Tyr Tyr Cys Gly Gln Ser Tyr Thr Phe Pro Tyr
                85                  90                  95
Thr Phe Gly Gln Gly Thr Lys Val Glu Ile Lys
            100                 105
```

<210> SEQ ID NO 42
<211> LENGTH: 107
<212> TYPE: PRT
<213> ORGANISM: Artificial sequence
<220> FEATURE:
<223> OTHER INFORMATION: Synthetic sequence: Anti-PSMA, Humanised RKE '5

<400> SEQUENCE: 42

```
Asn Ile Val Met Thr Gln Ser Pro Ser Ser Val Ser Ala Ser Val Gly
1               5                   10                  15
Asp Arg Val Thr Ile Thr Cys Lys Ala Ser Glu Asn Val Gly Thr Tyr
            20                  25                  30
Val Ser Trp Tyr Gln Gln Lys Pro Gly Thr Ala Pro Lys Leu Leu Ile
            35                  40                  45
Tyr Gly Ala Ser Asn Arg Phe Thr Gly Val Pro Asp Arg Phe Thr Gly
    50                  55                  60
Ser Gly Ser Ala Thr Asp Phe Ile Leu Thr Ile Asn Asn Leu Gln Pro
65                  70                  75                  80
Glu Asp Phe Ala Thr Tyr Tyr Cys Gly Gln Ser Tyr Thr Phe Pro Tyr
                85                  90                  95
Thr Phe Gly Gln Gly Thr Lys Val Glu Ile Lys
            100                 105
```

<210> SEQ ID NO 43
<211> LENGTH: 107
<212> TYPE: PRT
<213> ORGANISM: Artificial sequence
<220> FEATURE:
<223> OTHER INFORMATION: Synthetic sequence: Anti-PSMA, Humanised RKF '5

<400> SEQUENCE: 43

```
Asn Ile Val Met Thr Gln Ser Pro Ser Ser Val Ser Ala Ser Val Gly
1               5                   10                  15
Asp Arg Val Thr Ile Thr Cys Lys Ala Ser Glu Asn Val Gly Thr Tyr
            20                  25                  30
Val Ser Trp Tyr Gln Gln Lys Pro Gly Thr Ala Pro Lys Met Leu Ile
            35                  40                  45
Tyr Gly Ala Ser Asn Arg Phe Thr Gly Val Pro Ser Arg Phe Ser Gly
    50                  55                  60
Ser Gly Ser Ala Thr Asp Phe Ile Leu Thr Ile Asn Asn Leu Gln Pro
65                  70                  75                  80
Glu Asp Phe Ala Thr Tyr Tyr Cys Gly Gln Ser Tyr Thr Phe Pro Tyr
                85                  90                  95
Thr Phe Gly Gln Gly Thr Lys Val Glu Ile Lys
            100                 105
```

<210> SEQ ID NO 44
<211> LENGTH: 107

```
<212> TYPE: PRT
<213> ORGANISM: Artificial sequence
<220> FEATURE:
<223> OTHER INFORMATION: Synthetic sequence: Anti-PSMA, Humanised RKG '5

<400> SEQUENCE: 44

Asn Ile Val Met Thr Gln Ser Pro Ser Ser Val Ser Ala Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Gly Thr Ala Pro Lys Met Leu Ile
        35                  40                  45

Tyr Gly Ala Ser Asn Arg Phe Thr Gly Val Pro Asp Arg Phe Thr Gly
    50                  55                  60

Ser Gly Ser Ala Thr Asp Phe Thr Leu Thr Ile Asn Asn Leu Gln Pro
65                  70                  75                  80

Glu Asp Phe Ala Thr Tyr Tyr Cys Gly Gln Ser Tyr Thr Phe Pro Tyr
                85                  90                  95

Thr Phe Gly Gln Gly Thr Lys Val Glu Ile Lys
            100                 105
```

PYRROLOBENZODIAZEPINE CONJUGATES

CROSS REFERENCE TO RELATED APPLICATIONS

This application is a national phase application under 35 U.S.C. § 371 of International Application No. PCT/EP2018/059846, filed Apr. 18, 2018, which claims the benefit of Great Britain Application No. 1721337.2, filed Dec. 19, 2017, and Great Britain Application No. 1706133.4, filed Apr. 18, 2017, each of which is herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 47,814 Byte ASCII (Text) file named "2020-01-02_38075-251_SQL_ST25," created on Jan. 2, 2020.

The present invention relates to conjugates comprising pyrrolobenzodiazepines and related dimers (PBDs), and the precursor drug linkers used to make such conjugates.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

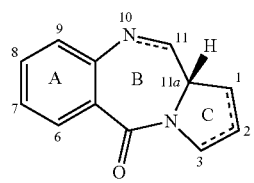

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe))ram at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

It has been previously disclosed that the biological activity of this molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity.

The first dimers (Bose, D. S., et al., *J. Am. Chem. Soc.*, 114, 4939-4941 (1992)) were of the general formula:

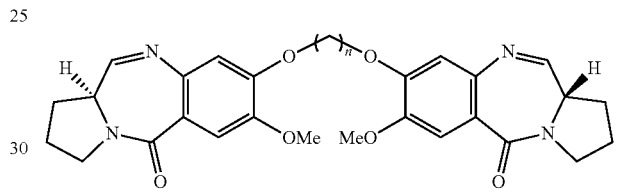

where n is from 3 to 6. The compounds where n were 3 and 5 showed promising cytoxicity in vitro. However when antitumor activity of the the n=3 compound (DSB-120) was studied (Walton, M., et al., *Cancer Chemother Pharmacol* (1996) 38: 431. doi:10.1007/s002800050507), this was found not to be as promising. This lack of promise was thought to be "a consequence of low tumour selectivity and drug uptake as a result of high protein binding and/or extensive drug metabolism in vivo".

In order to improve on these compounds, compounds were investigated (Gregson, S. J., et al., Chem. Commun., 1999, 797-798. doi: 10.1039/A809791G) with the "inclusion of C2/C2' substituents that should follow the contour of the host minor groove". This compound SG2000 (SJG-136):

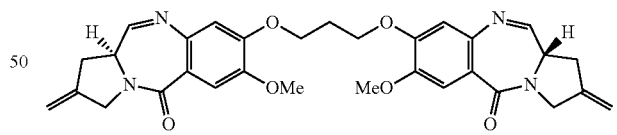

was found to have "exquisite cytotoxicity in the picomolar region . . . some 9000-fold more potent that DSB-120."

This compound (also discussed in Gregson, S., et al., *J. Med. Chem.*, 44, 737-748 (2001); Alley, M. C., et al., *Cancer Research*, 64, 6700-6706 (2004); and Hartley, J. A., et al., *Cancer Research*, 64, 6693-6699 (2004)) has been involved in clinical trials as a standalone agent, for example, NCT02034227 investigating its use in treating Acute Myeloid Leukemia and Chronic Lymphocytic Leukemia (see: https://www.clinicaltrials.gov/ct2/show/NCT02034227).

Dimeric PBD compounds bearing C2 aryl substituents alongside endo-unsaturation, such as SG2202 (ZC-207), are disclosed in WO 2005/085251:

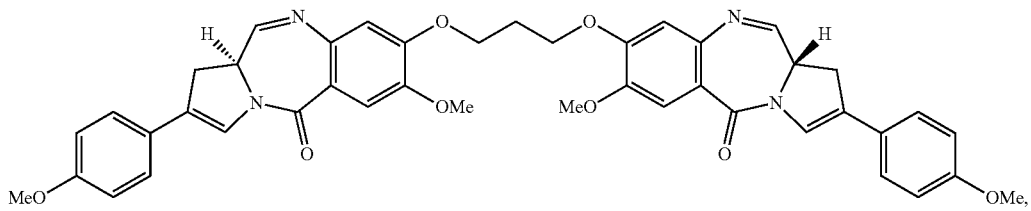

ZC-207 and in WO2006/111759, bisulphites of such PBD compounds, for example SG2285 (ZC-423):

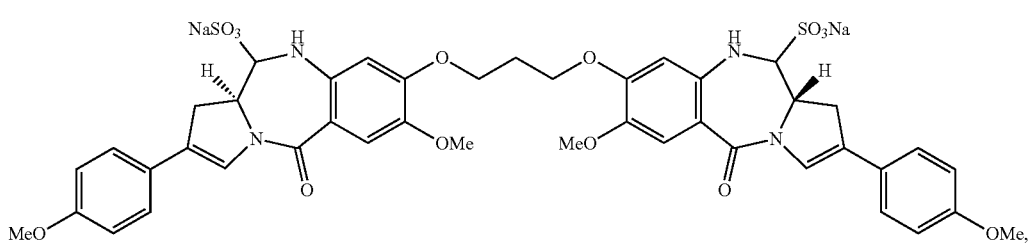

ZC-423

These compounds have been shown to be highly useful cytotoxic agents (Howard, P. W., et al., *Bioorg. Med. Chem.* (2009), doi: 10.1016/j.bmcl.2009.09.012).

In a review of PBD containing ADCs (Mantaj, J., et al., *Angew. Chem. Int. Ed.* (2016), 55, 2-29; DOI: 10.1002/anie.201510610), the SAR of PBD dimers is discussed. The summary of the SAR is presented in FIG. 3-B "C2-exo and C1-C2/C2-C3 unsaturation enhances activity". A more detailed discussion is found at section 2.4 which says:

"DSB-120 has poor activity in vivo, attributed partly to its high reactivity with cellular thiol-containing molecules such as glutathione. However, introduction of C2/C2'-exo unsaturation as in SJG-136 led to an overall increase in DNA-binding affinity and cytotoxicity, and a lower reactivity toward cellular nucleophiles with more of the agent potentially reaching its target DNA."

WO 2007/085930 describes the preparation of dimer PBD compounds having linker groups for connection to a cell binding agent, such as an antibody. The linker is present in the bridge linking the monomer PBD units of the dimer.

Dimer PBD compounds having linker groups for connection to a cell binding agent, such as an antibody, are generally cleaved by action of an enzyme on the linker group. The dimer PBD compounds have either endo or exo unsaturation in the C-ring.

WO 2014/057074 and WO 2015/052322 describes specific PBD dimer conjugates bound via the N10 position on one monomer, and all these compounds have endo unsaturation in the C-ring.

WO2014/096365 discloses the compound:

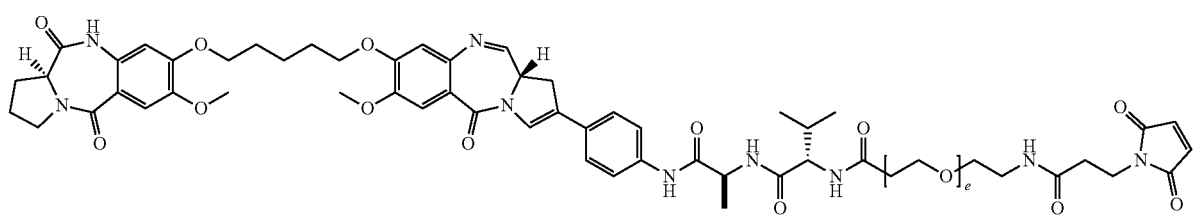

36 where the lack of unsaturation in the C-ring is coupled with the B-ring being a dilactam and therefore not having the ability to covalently bind DNA.

DISCLOSURE OF THE INVENTION

The present invention provides PBD dimer drug linkers and conjugates where neither C-ring has endo- or exo-unsaturation.

A first aspect of the present invention comprises a compound with the formula I:

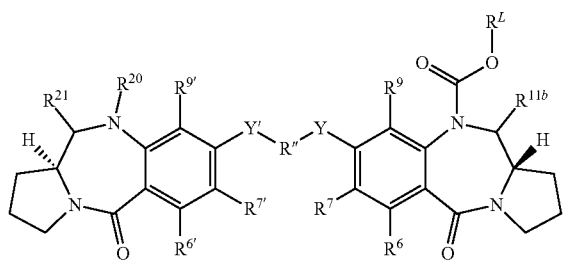

I and salts and solvates thereof, wherein:

$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NRR', nitro, $Me_3Sn$ and halo;
R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;
Y and Y' are selected from O, S, or NH;
$R^{6'}$, $R^{7'}$, $R^{9'}$ are selected from the same groups as $R^6$, $R^7$ and $R^9$ respectively;
$R^{11b}$ is selected from OH, $OR^A$, where $R^A$ is $C_{1-4}$ alkyl; and
$R^L$ is a linker for connection to a cell binding agent, which is selected from:
(iiia):

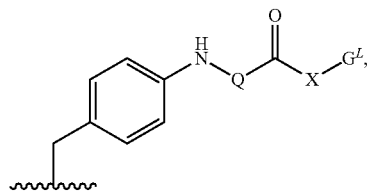

IIIa wherein
Q is:

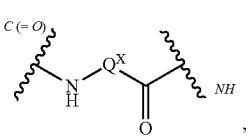

where $Q^X$ is such that Q is an amino-acid residue, a dipeptide residue or a tripeptide residue;
X is:

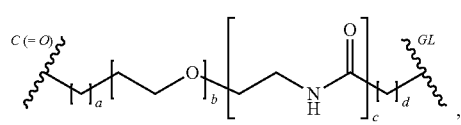

where a=0 to 5, b=0 to 16, c=0 or 1, d=0 to 5;
$G^L$ is a linker for connecting to a Ligand Unit; and (iiib):

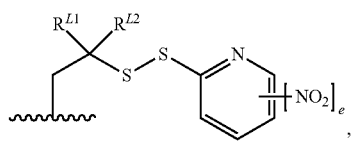

IIIb where $R^{L1}$ and $R^{L2}$ are independently selected from H and methyl, or together with the carbon atom to which they are bound form a cyclopropylene or cyclobutylene group;
and e is 0 or 1;
either
(a) $R^{20}$ is H, and $R^{21}$ is OH or $OR^A$, where $R^A$ is $C_{1-4}$ alkyl; or
(b) $R^{20}$ and $R^{21}$ form a nitrogen-carbon double bond between the nitrogen and carbon atoms to which they are bound; or
(c) $R^{20}$ is H and $R^{21}$ is $SO_zM$, where z is 2 or 3 and M is a monovalent pharmaceutically acceptable cation; or
(d) $R^{20}$ is H and $R^{21}$ is H; or
(e) $R^{21}$ is OH or $OR^A$, where $R^A$ is $C_{1-4}$ alkyl and $R^{20}$ is selected from:
(d-i)

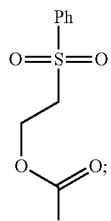

(d-ii)

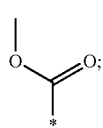 [SMILES: *C(=O)OC]

(d-iii)

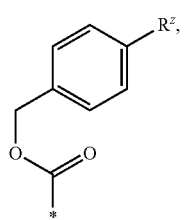

where $R^Z$ is selected from:

(z-i)

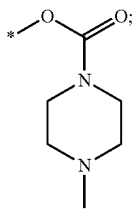 [SMILES: *OC(=O)N1CCN(C)CC1]

(z-ii) $OC(=O)CH_3$;
(z-iii) $NO_2$;
(z-iv) OMe;
(z-v) glucoronide;
(z-vi) —C(=O)—$X_1$—NHC(=O)$X_2$—NH—$R^{ZC}$, where —C(=O)—$X_1$—NH— and —C(=O)—$X_2$—NH— represent natural amino acid residues and $R^{ZC}$ is selected from Me, OMe, $OCH_2CH_2OMe$.

Such drug linkers have been found to undergo ready conjugation to ligand units such as antibodies.

A second aspect of the present invention provides Conjugates of formula II:

  (II)

wherein L is a Ligand unit (i.e., a targeting agent), $D^L$ is a Drug Linker unit of formula I':

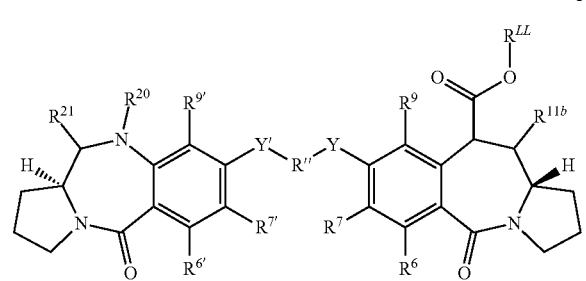

I' wherein $R^6$, $R^7$, $R^9$, $R^{11b}$, Y, R", Y', $R^{6'}$, $R^{7'}$, $R^{9'}$, $R^{20}$ and $R^{21}$ are as defined in the first aspect of the invention;
$R^{LL}$ is a linker for connection to a cell binding agent, which is selected from:
(iiia):

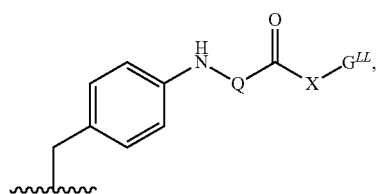

IIIa' where Q and X are as defined in the first aspect and $G^{LL}$ is a linker connected to a Ligand Unit; and (iiib):

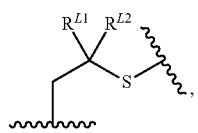

IIIb' where $R^{L1}$ and $R^{L2}$ are as defined in the first aspect;
wherein p is an integer of from 1 to 20.

The Ligand unit, described more fully below, is a targeting agent that binds to a target moiety. The Ligand unit can, for example, specifically bind to a cell component (a Cell Binding Agent) or to other target molecules of interest. The Ligand unit can be, for example, a protein, polypeptide or peptide, such as an antibody, an antigen-binding fragment of an antibody, or other binding agent, such as an Fc fusion protein.

These conjugates have been found to possess a high tolerability which leads to a high therapeutic index, thus making them promising candidates for clinical development.

A third aspect of the present invention provides the use of a conjugate of the second aspect of the invention in the manufacture of a medicament for treating a proliferative disease. The third aspect also provides a conjugate of the second aspect of the invention for use in the treatment of a proliferative disease. The third aspect also provides a method of treating a proliferative disease comprising administering a therapeutically effective amount of a conjugate of the second aspect of the invention to a patient in need thereof.

One of ordinary skill in the art is readily able to determine whether or not a candidate conjugate treats a proliferative condition for any particular cell type. For example, assays which may conveniently be used to assess the activity offered by a particular compound are described in the examples below.

A fourth aspect of the present invention provides the synthesis of a conjugate of the second aspect of the invention comprising conjugating a compound (drug linker) of the first aspect of the invention with a Ligand Unit.

Definitions

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S1$: thiazoline ($C_5$), thiazolidine ($C_5$), thiomorpholine ($C_6$);

$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_5$), indene ($C_5$), isoindene ($C_5$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);

$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{0-7}$alkyl group.
Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).
Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group.
Examples of hemiacetal groups include, but are not limited to, —CH(OH)(OMe) and —CH(OH)(OEt).
Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).
Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).
Oxo (keto, -one): =O.
Thione (thioketone): =S.
Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.
Formyl (carbaldehyde, carboxaldehyde): —C(=O)H.
Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).
Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.
Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group.
Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.
Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.
Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—$NH_2$), secondary (—$NHR^1$), or tertiary (—$NHR^1R^2$), and in cationic form, may be quaternary (—$^+NR^1R^2R^3$). Examples of amino groups include, but are not limited to, —$NH_2$, —$NHCH_3$, —$NHC(CH_3)_2$, —$N(CH_3)_2$, —$N(CH_2CH_3)_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)$N(CH_3)_2$, —C(=O)$NHCH_2CH_3$, and —C(=O)$N(CH_2CH_3)_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)$NR^1R^2$, wherein $R^1$ and $R^2$ are independently amino substituents, as defined for amino groups. Examples of amido groups include, but are not limited to, —C(=S)$NH_2$, —C(=S)$NHCH_3$, —C(=S)$N(CH_3)_2$, and —C(=S)$NHCH_2CH_3$.

Acylamido (acylamino): —$NR^1C$(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group.

Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

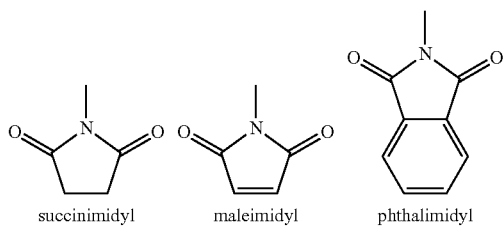

succinimidyl     maleimidyl     phthalimidyl

Aminocarbonyloxy: —OC(=O)$NR^1R^2$, wherein $R^1$ and $R^2$ are independently amino substituents, as defined for amino groups. Examples of aminocarbonyloxy groups include, but are not limited to, —OC(=O)$NH_2$, —OC(=O)NHMe, —OC(=O)$NMe_2$, and —OC(=O)$NEt_2$.

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCON$H_2$, —NHCONHMe, —NHCONHEt, —NHCON$Me_2$, —NHCON$Et_2$, —NMeCON$H_2$, —NMeCONHMe, —NMeCONHEt, —NMeCON$Me_2$, and —NMeCON$Et_2$.

Guanidino: —NH—C(=NH)$NH_2$.

Tetrazolyl: a five membered aromatic ring having four nitrogen atoms and one carbon atom,

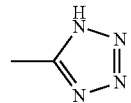

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)$NR_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)$NH_2$, —C(=NH)$NMe_2$, and —C(=NMe)$NMe_2$.

Nitro: —$NO_2$.

Nitroso: —NO.

Azido: —$N_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —$SSCH_3$ and —$SSCH_2CH_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)$CH_3$ and —S(=O)$CH_2CH_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2CH_3$ (methanesulfonyl, mesyl), —S(=O)$_2CF_3$ (triflyl), —S(=O)$_2CH_2CH_3$ (esyl), —S(=O)$_2C_4F_9$ (nonaflyl), —S(=O)$_2CH_2CF_3$ (tresyl), —S(=O)$_2CH_2CH_2NH_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —$SO_2$H.

Sulfonic acid (sulfo): —S(=O)$_2$OH, —$SO_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH-$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{3-12}$ alkylene groups ($C_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated $C_{3-12}$ alkylene groups ($C_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Where the $C_{3-12}$ alkylene group is interrupted by a heteroatom, the subscript refers to the number of atoms in the chain including the heteroatoms. For example, the chain —C$_2$H$_4$—O—C$_2$H$_4$— would be a $C_5$ group.

Where the $C_{3-12}$ alkylene group is interrupted by a heteroatom, the subscript refers to the number of atoms directly in the chain including the aromatic ring. For example, the chain

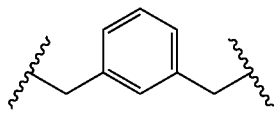 [SMILES: *Cc1cccc(C*)c1]

would be a $C_5$ group.

Ligand Unit

The Ligand Unit may be of any kind, and include a protein, polypeptide, peptide and a non-peptidic agent that specifically binds to a target molecule. In some embodiments, the Ligand unit may be a protein, polypeptide or peptide. In some embodiments, the Ligand unit may be a cyclic polypeptide. These Ligand units can include antibodies or a fragment of an antibody that contains at least one target molecule-binding site, lymphokines, hormones, growth factors, or any other cell binding molecule or substance that can specifically bind to a target.

The terms "specifically binds" and "specific binding" refer to the binding of an antibody or other protein, polypeptide or peptide to a predetermined molecule (e.g., an antigen). Typically, the antibody or other molecule binds with an affinity of at least about $1 \times 10^7$ M$^{-1}$, and binds to the predetermined molecule with an affinity that is at least two-fold greater than its affinity for binding to a non-specific molecule (e.g., BSA, casein) other than the predetermined molecule or a closely-related molecule.

Examples of Ligand units include those agents described for use in WO 2007/085930, which is incorporated herein.

In some embodiments, the Ligand unit is a Cell Binding Agent that binds to an extracellular target on a cell. Such a Cell Binding Agent can be a protein, polypeptide, peptide or a non-peptidic agent. In some embodiments, the Cell Binding Agent may be a protein, polypeptide or peptide. In some embodiments, the Cell Binding Agent may be a cyclic polypeptide. The Cell Binding Agent also may be antibody or an antigen-binding fragment of an antibody. Thus, in one embodiment, the present invention provides an antibody-drug conjugate (ADC).

Cell Binding Agent

A cell binding agent may be of any kind, and include peptides and non-peptides. These can include antibodies or a fragment of an antibody that contains at least one binding site, lymphokines, hormones, hormone mimetics, vitamins, growth factors, nutrient-transport molecules, or any other cell binding molecule or substance.

Peptides

In one embodiment, the cell binding agent is a linear or cyclic peptide comprising 4-30, preferably 6-20, contiguous amino acid residues. In this embodiment, it is preferred that one cell binding agent is linked to one monomer or dimer pyrrolobenzodiazepine compound.

In one embodiment the cell binding agent comprises a peptide that binds integrin $a_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC. Alternatively, a variant of the A20FMDV-Cys sequence may be used wherein one, two, three, four, five, six, seven, eight, nine or ten amino acid residues are substituted with another amino acid residue. Furthermore, the polypeptide may have the sequence NAVXXXXXXXXXXXXXXXXRTC.

Antibodies

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called a, b, E, y, and p, respectively. The subunit structures and three-dimensional configurations of different classes of immunoglobulins are well known.

Humanisation

Techniques to reduce the in vivo immunogenicity of a non-human antibody or antibody fragment include those termed "humanisation".

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins.

There are a range of humanisation techniques, including 'CDR grafting', 'guided selection', 'deimmunization', 'resurfacing' (also known as 'veneering'), 'composite antibodies', 'Human String Content Optimisation' and framework shuffling.

CDR Grafting

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VH×VL combination. The method is described in Nature Biotechnology (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class II-binding motifs by, for example, comparison with databases of MHC-binding motifs (such as the "motifs" database hosted at www.wehi.edu.au). Alternatively, MHC class II-binding motifs may be identified using computational threading methods such as those devised by Altuvia et al. (J. Mol. Biol. 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:
(a) determining the conformational structure of the variable region of the non-human (e.g. rodent) antibody (or fragment thereof) by constructing a three-dimensional model of the non-human antibody variable region;
(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;
(c) defining for the non-human antibody to be humanized, a set of heavy and light chain surface exposed amino acid residues using the set of framework positions generated in step (b);
(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;
(e) substituting, in the amino acid sequence of the non-human antibody to be humanized, the set of heavy and light chain surface exposed amino acid residues defined in step (c) with the set of heavy and light chain surface exposed amino acid residues identified in step (d);
(f) constructing a three-dimensional model of the variable region of the non-human antibody resulting from the substituting specified in step (e);
(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and
(h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in *Methods* 36, 43-60 (2005).

Examples of cell binding agents include those agents described for use in WO 2007/085930, which is incorporated herein.

Tumour-associate antigens and cognate antibodies for use in embodiments of the present invention are listed below.
Tumor-Associated Antigens and Cognate Antibodies
(1) BMPR1B (Bone Morphogenetic Protein Receptor-Type IB)
Nucleotide
  Genbank accession no. NM_001203
  Genbank version no. NM_001203.2 GI: 169790809
  Genbank record update date: Sep. 23, 2012 02:06 PM
Polypeptide
  Genbank accession no. NP_001194
  Genbank version no. NP_001194.1 GI: 4502431
  Genbank record update date: Sep. 23, 2012 02:06 PM
Cross-References
  ten Dijke, P., et al *Science* 264 (5155): 101-104 (1994), *Oncogene* 14 (11):1377-1382 (1997)); WO2004/063362 (Claim 2); WO2003/042661 (Claim 12); US2003/134790-A1 (Page 38-39); WO2002/102235 (Claim 13; Page 296); WO2003/055443
  (Page 91-92); WO2002/99122 (Example 2; Page 528-530); WO2003/029421 (Claim 6); WO2003/024392 (Claim 2; FIG. 112); WO2002/98358 (Claim 1; Page 183); WO2002/54940 (Page 100-101); WO2002/59377 (Page 349-350); WO2002/30268 (Claim 27; Page 376); WO2001/48204 (Example; FIG. 4); NP_001194 bone morphogenetic protein receptor, type IB/pid=NP_001194.1; MIM: 603248; AY065994
(2) E16 (LAT1, SLC7A5)
Nucleotide
  Genbank accession no. NM_003486
  Genbank version no. NM_003486.5 GI: 71979931
  Genbank record update date: Jun. 27, 2012 12:06 PM
Polypeptide
  Genbank accession no. NP_003477
  Genbank version no. NP_003477.4 GI: 71979932
  Genbank record update date: Jun. 27, 2012 12:06 PM
Cross References
  *Biochem. Biophys. Res. Commun.* 255 (2), 283-288 (1999), *Nature* 395 (6699):288-291 (1998), Gaugitsch, H. W., et al (1992) *J. Biol. Chem.* 267 (16):11267-11273); WO2004/048938 (Example 2); WO2004/032842 (Example IV); WO2003/042661 (Claim 12); WO2003/016475 (Claim 1); WO2002/78524 (Example 2); WO2002/99074 (Claim 19; Page 127-129); WO2002/86443 (Claim 27; Pages 222, 393); WO2003/003906 (Claim 10; Page 293); WO2002/64798 (Claim 33; Page 93-95); WO2000/14228 (Claim 5; Page 133-136); US2003/224454 (FIG. 3); WO2003/025138 (Claim 12; Page 150); NP_003477 solute carrier family 7 (cationic amino acid transporter, y+system), member 5/pid=NP_003477.3—*Homo sapiens*; MIM: 600182; NM_015923.
(3) STEAP1 (Six Transmembrane Epithelial Antigen of Prostate)
Nucleotide
  Genbank accession no. NM_012449
  Genbank version no. NM_012449.2 GI: 22027487
  Genbank record update date: Sep. 9, 2012 02:57 PM
Polypeptide
  Genbank accession no. NP_036581
  Genbank version no. NP_036581.1 GI: 9558759
  Genbank record update date: Sep. 9, 2012 02:57 PM
Cross References
  *Cancer Res.* 61 (15), 5857-5860 (2001), Hubert, R. S., et al (1999) *Proc. Natl. Acad. Sci. U.S.A.* 96 (25):14523-14528); WO2004/065577 (Claim 6); WO2004/027049 (FIG. 1L); EP1394274 (Example 11); WO2004/016225 (Claim 2); WO2003/042661 (Claim 12); US2003/157089 (Example 5); US2003/185830 (Example 5); US2003/064397 (FIG. 2); WO2002/89747 (Example 5; Page 618-619); WO2003/022995 (Example 9; FIG. 13A, Example 53; Page 173, Example 2; FIG. 2A); six transmembrane epithelial antigen of the prostate; MIM: 604415.
(4) 0772P (CA125, MUC16)
Nucleotide
  Genbank accession no. AF361486
  Genbank version no. AF361486.3 GI: 34501466
  Genbank record update date: Mar. 11, 2010 07:56 AM
Polypeptide
  Genbank accession no. AAK74120
  Genbank version no. AAK74120.3 GI: 34501467
  Genbank record update date: Mar. 11, 2010 07:56 AM
Cross References
  *J. Biol. Chem.* 276 (29):27371-27375 (2001)); WO2004/045553 (Claim 14); WO2002/92836 (Claim 6; FIG. 12); WO2002/83866 (Claim 15; Page 116-121); US2003/124140 (Example 16); GI: 34501467;
(5) MPF (MPF, MSLN, SMR, Megakaryocyte Potentiating Factor, Mesothelin)
Nucleotide
  Genbank accession no. NM_005823
  Genbank version no. NM_005823.5 GI: 293651528
  Genbank record update date: Sep. 2, 2012 01:47 PM
Polypeptide
  Genbank accession no. NP_005814
  Genbank version no. NP_005814.2 GI: 53988378
  Genbank record update date: Sep. 2, 2012 01:47 PM
Cross References
  Yamaguchi, N., et al *Biol. Chem.* 269 (2), 805-808 (1994), *Proc. Natl. Acad. Sci. U.S.A.* 96 (20):11531-11536 (1999), *Proc. Natl. Acad. Sci. U.S.A.* 93 (1):136-140 (1996), *J. Biol. Chem.* 270 (37):21984-21990 (1995)); WO2003/101283 (Claim 14); (WO2002/102235 (Claim 13; Page 287-288); WO2002/101075 (Claim 4; Page 308-309); WO2002/71928 (Page 320-321); WO94/10312 (Page 52-57); IM: 601051.
(6) Napi3b (NAPI-3B, NPTIIb, SLC34A2, Solute Carrier Family 34 (Sodium Phosphate), Member 2, Type II Sodium-Dependent Phosphate Transporter 3b)
Nucleotide
  Genbank accession no. NM_006424
  Genbank version no. NM_006424.2 GI: 110611905
  Genbank record update date: Jul. 22, 2012 03:39 PM
Polypeptide
  Genbank accession no. NP_006415
  Genbank version no. NP_006415.2 GI: 110611906
  Genbank record update date: Jul. 22, 2012 03:39 PM
Cross References
  *J. Biol. Chem.* 277 (22):19665-19672 (2002), *Genomics* 62 (2):281-284 (1999), Feild, J. A., et al (1999) *Biochem. Biophys. Res. Commun.* 258 (3):578-582); WO2004/022778 (Claim 2); EP1394274 (Example 11); WO2002/102235 (Claim 13; Page 326); EP0875569 (Claim 1; Page 17-19); WO2001/57188 (Claim 20; Page 329); WO2004/032842 (Example IV); WO2001/75177 (Claim 24; Page 139-140); MIM: 604217.
(7) Sema 5b (FLJ10372, KIAA1445, Mm.42015, SEMA5B, SEMAG, Semaphorin 5b Hlog, Sema Domain, Seven Thrombospondin Repeats (Type 1 and Type 1-Like), Transmembrane Domain™ and Short Cytoplasmic Domain, (Semaphorin) 5B)
Nucleotide
  Genbank accession no. AB040878
  Genbank version no. AB040878.1 GI: 7959148
  Genbank record update date: Aug. 2, 2006 05:40 PM Polypeptide
  Genbank accession no. BAA95969
  Genbank version no. BAA95969.1 GI: 7959149
  Genbank record update date: Aug. 2, 2006 05:40 PM
Cross References
  Nagase T., et al (2000) *DNA Res.* 7 (2):143-150); WO2004/000997 (Claim 1); WO2003/003984 (Claim 1); WO2002/06339 (Claim 1; Page 50); WO2001/88133 (Claim 1; Page 41-43, 48-58); WO2003/054152 (Claim 20); WO2003/101400 (Claim 11); Accession: Q9P283; Genew; HGNC: 10737

(8) PSCA hIg (2700050C12Rik, C530008O16Rik, RIKEN cDNA 2700050C12, RIKEN cDNA 2700050C12 gene)
Nucleotide
  Genbank accession no. AY358628
  Genbank version no. AY358628.1 GI: 37182377
  Genbank record update date: Dec. 1, 2009 04:15 AM
Polypeptide
  Genbank accession no. AAQ88991
  Genbank version no. AAQ88991.1 GI: 37182378
  Genbank record update date: Dec. 1, 2009 04:15 AM
Cross References
  Ross et al (2002) *Cancer Res.* 62:2546-2553; US2003/129192 (Claim 2); US2004/044180 (Claim 12); US2004/044179 (Claim 11); US2003/096961 (Claim 11); US2003/232056 (Example 5); WO2003/105758 16 (Claim 12); US2003/206918 (Example 5); EP1347046 (Claim 1); WO2003/025148 (Claim 20); GI: 37182378.

(9) ETBR (Endothelin Type B Receptor)
Nucleotide
  Genbank accession no. AY275463
  Genbank version no. AY275463.1 GI: 30526094
  Genbank record update date: Mar. 11, 2010 02:26 AM
Polypeptide
  Genbank accession no. AAP32295
  Genbank version no. AAP32295.1 GI: 30526095
  Genbank record update date: Mar. 11, 2010 02:26 AM
Cross References
  Nakamuta M., et al *Biochem. Biophys. Res. Commun.* 177, 34-39, 1991; Ogawa Y., et al *Biochem. Biophys. Res. Commun.* 178, 248-255, 1991; Arai H., et al *Jpn. Circ. J.* 56, 1303-1307, 1992; Arai H., et al *J. Biol. Chem.* 268, 3463-3470, 1993; Sakamoto A., Yanagisawa M., et al *Biochem. Biophys. Res. Commun.* 178, 656-663, 1991; Elshourbagy N. A., et al *J. Biol. Chem.* 268, 3873-3879, 1993; Haendler B., et al *J. Cardiovasc. Pharmacol.* 20, s1-S4, 1992; Tsutsumi M., et al *Gene* 228, 43-49, 1999; Strausberg R. L., et al *Proc. Natl. Acad. Sci. U.S.A.* 99, 16899-16903, 2002; Bourgeois C., et al *J. Clin. Endocrinol. Metab.* 82, 3116-3123, 1997; Okamoto Y., et al *Biol. Chem.* 272, 21589-21596, 1997; Verheij J. B., et al *Am. J. Med. Genet.* 108, 223-225, 2002; Hofstra R. M. W., et al *Eur. J. Hum. Genet.* 5, 180-185, 1997; Puffenberger E. G., et al *Cell* 79, 1257-1266, 1994; Attie T., et al, *Hum. Mol. Genet.* 4, 2407-2409, 1995; Auricchio A., et al *Hum. Mol. Genet.* 5:351-354, 1996; Amiel J., et al *Hum. Mol. Genet.* 5, 355-357, 1996; Hofstra R. M. W., et al *Nat. Genet.* 12, 445-447, 1996; Svensson P. J., et al *Hum. Genet.* 103, 145-148, 1998; Fuchs S., et al *Mol. Med.* 7, 115-124, 2001; Pingault V., et al (2002) *Hum. Genet.* 111, 198-206; WO2004/045516 (Claim 1); WO2004/048938 (Example 2); WO2004/040000 (Claim 151); WO2003/087768 (Claim 1); WO2003/016475 (Claim 1); WO2003/016475 (Claim 1); WO2002/61087 (FIG. 1); WO2003/016494 (FIG. 6); WO2003/025138 (Claim 12; Page 144); WO2001/98351 (Claim 1;
  Page 124-125); EP0522868 (Claim 8; FIG. 2); WO2001/77172 (Claim 1; Page 297-299); US2003/109676; U.S. Pat. No. 6,518,404 (FIG. 3); U.S. Pat. No. 5,773,223 (Claim 1a; Col 31-34); WO2004/001004.

(10) MSG783 (RNF124, Hypothetical Protein FLJ20315)
Nucleotide
  Genbank accession no. NM_017763
  Genbank version no. NM_017763.4 GI: 167830482
  Genbank record update date: Jul. 22, 2012 12:34 AM
Polypeptide
  Genbank accession no. NP_060233
  Genbank version no. NP_060233.3 GI: 56711322
  Genbank record update date: Jul. 22, 2012 12:34 AM
Cross References
  WO2003/104275 (Claim 1); WO2004/046342 (Example 2); WO2003/042661 (Claim 12); WO2003/083074 (Claim 14; Page 61); WO2003/018621 (Claim 1); WO2003/024392 (Claim 2; FIG. 93); WO2001/66689 (Example 6); LocusID: 54894.

(11) STEAP2 (HGNC_8639, IPCA-1, PCANAP1, STAMP1, STEAP2, STMP, Prostate Cancer Associated Gene 1, Prostate Cancer Associated Protein 1, Six Transmembrane Epithelial Antigen of Prostate 2, Six Transmembrane Prostate Protein)
Nucleotide
  Genbank accession no. AF455138
  Genbank version no. AF455138.1 GI: 22655487
  Genbank record update date: Mar. 11, 2010 01:54 AM
Polypeptide
  Genbank accession no. AAN04080
  Genbank version no. AAN04080.1 GI: 22655488
  Genbank record update date: Mar. 11, 2010 01:54 AM
Cross References
  *Lab. Invest.* 82 (11):1573-1582 (2002)); WO2003/087306; US2003/064397 (Claim 1; FIG. 1); WO2002/72596 (Claim 13; Page 54-55); WO2001/72962 (Claim 1; FIG. 4B); WO2003/104270 (Claim 11); WO2003/104270 (Claim 16); US2004/005598 (Claim 22); WO2003/042661 (Claim 12); US2003/060612 (Claim 12; FIG. 10); WO2002/26822 (Claim 23; FIG. 2); WO2002/16429 (Claim 12; FIG. 10); GI: 22655488.

(12) TrpM4 (BR22450, FLJ20041, TRPM4, TRPM4B, Transient Receptor Potential Cation Channel, Subfamily M, Member 4)
Nucleotide
  Genbank accession no. NM_017636
  Genbank version no. NM_017636.3 GI: 304766649
  Genbank record update date: Jun. 29, 2012 11:27 AM
Polypeptide
  Genbank accession no. NP_060106
  Genbank version no. NP_060106.2 GI: 21314671
  Genbank record update date: Jun. 29, 2012 11:27 AM
Cross References
  Xu, X. Z., et al *Proc. Natl. Acad. Sci. U.S.A.* 98 (19): 10692-10697 (2001), *Cell* 109 (3):397-407 (2002), *J. Biol. Chem.* 278 (33):30813-30820 (2003)); US2003/143557 (Claim 4); WO2000/40614 (Claim 14; Page 100-103); WO2002/10382 (Claim 1; FIG. 9A); WO2003/042661 (Claim 12); WO2002/30268 (Claim 27; Page 391); US2003/219806 (Claim 4); WO2001/62794 (Claim 14; FIG. 1A-D); MIM: 606936.

(13) CRIPTO (CR, CR1, CRGF, CRIPTO, TDGFI, Teratocarcinoma-Derived Growth Factor)
Nucleotide
  Genbank accession no. NM_003212
  Genbank version no. NM_003212.3 GI: 292494881
  Genbank record update date: Sep. 23, 2012 02:27 PM Polypeptide
  Genbank accession no. NP_003203
  Genbank version no. NP_003203.1 GI: 4507425
  Genbank record update date: Sep. 23, 2012 02:27 PM
Cross References
  Ciccodicola, A., et al *EMBO J.* 8 (7):1987-1991 (1989), *Am. J. Hum. Genet.* 49 (3):555-565 (1991)); US2003/224411 (Claim 1); WO2003/083041 (Example 1); WO2003/034984 (Claim 12); WO2002/88170 (Claim 2; Page 52-53); WO2003/024392 (Claim 2; FIG. 58); WO2002/16413 (Claim 1; Page 94-95, 105); WO2002/22808 (Claim 2; FIG. 1); U.S. Pat. No. 5,854,399 (Example 2; Col 17-18); U.S. Pat. No. 5,792,616 (FIG. 2); MIM: 187395.

(14) CD21 (CR2 (Complement Receptor 2) or C3DR (C3d/Epstein Barr Virus Receptor) or Hs.73792)
Nucleotide
  Genbank accession no M26004
  Genbank version no. M26004.1 GI: 181939
  Genbank record update date: Jun. 23, 2010 08:47 AM
Polypeptide
  Genbank accession no. AAA35786
  Genbank version no. AAA35786.1 GI: 181940
  Genbank record update date: Jun. 23, 2010 08:47 AM
Cross References
  Fujisaku et al (1989) *J. Biol. Chem.* 264 (4):2118-2125); Weis J. J., et al *J. Exp. Med.* 167, 1047-1066, 1988; Moore M., et al *Proc. Natl. Acad. Sci. U.S.A.* 84, 9194-9198, 1987; Barel M., et al *Mol. Immunol.* 35, 1025-1031, 1998; Weis J. J., et al *Proc. Natl. Acad. Sci. U.S.A.* 83, 5639-5643, 1986; Sinha S. K., et al (1993) *J. Immunol.* 150, 5311-5320; WO2004/045520 (Example 4); US2004/005538 (Example 1); WO2003/062401 (Claim 9); WO2004/045520 (Example 4); WO91/02536 (FIGS. 9.1-9.9); WO2004/020595 (Claim 1); Accession: P20023; Q13866; Q14212; EMBL; M26004; AAA35786.1.

(15) CD79b (CD79B, CD793, IGb (Immunoglobulin-Associated Beta), B29)
Nucleotide
  Genbank accession no NM_000626
  Genbank version no. NM_000626.2 GI: 90193589
  Genbank record update date: Jun. 26, 2012 01:53 PM
Polypeptide
  Genbank accession no. NP_000617
  Genbank version no. NP_000617.1 GI: 11038674
  Genbank record update date: Jun. 26, 2012 01:53 PM
Cross References
  *Proc. Natl. Acad. Sci. U.S.A.* (2003) 100 (7):4126-4131, *Blood* (2002) 100 (9):3068-3076, Muller et al (1992) *Eur. J. Immunol.* 22 (6):1621-1625); WO2004/016225 (claim 2, FIG. 140); WO2003/087768, US2004/101874 (claim 1, page 102); WO2003/062401 (claim 9); WO2002/78524 (Example 2); US2002/150573 (claim 5, page 15); U.S. Pat. No. 5,644,033; WO2003/048202 (claim 1, pages 306 and 309); WO 99/58658,
  U.S. Pat. No. 6,534,482 (claim 13, FIG. 17A/B); WO2000/55351 (claim 11, pages 1145-1146); MIM: 147245

(16) FcRH2 (IFGP4, IRTA4, SPAP1A (SH2 Domain Containing Phosphatase Anchor Protein 1a), SPAP1B, SPAP1C)
Nucleotide
  Genbank accession no NM_030764
  Genbank version no. NM_030764.3 GI: 227430280
  Genbank record update date: Jun. 30, 2012 12:30 AM
Polypeptide
  Genbank accession no. NP_110391
  Genbank version no. NP_110391.2 GI: 19923629
  Genbank record update date: Jun. 30, 2012 12:30 AM
Cross References
  AY358130); *Genome Res.* 13 (10):2265-2270 (2003), *Immunogenetics* 54 (2):87-95 (2002), *Blood* 99 (8):2662-2669 (2002), *Proc. Natl. Acad. Sci. U.S.A.* 98 (17):9772-9777 (2001), Xu, M. J., et al (2001) *Biochem. Biophys. Res. Commun.* 280 (3):768-775; WO2004/016225 (Claim 2); WO2003/077836; WO2001/38490 (Claim 5; FIG. 18D-1-18D-2); WO2003/097803 (Claim 12); WO2003/089624 (Claim 25); MIM: 606509.

(17) HER2 (ErbB2)
Nucleotide
  Genbank accession no M11730
  Genbank version no. M11730.1 GI: 183986
  Genbank record update date: Jun. 23, 2010 08:47 AM
Polypeptide
  Genbank accession no. AAA75493
  Genbank version no. AAA75493.1 GI: 306840
  Genbank record update date: Jun. 23, 2010 08:47 AM
Cross References
  Coussens L., et al *Science* (1985) 230(4730):1132-1139); Yamamoto T., et al *Nature* 319, 230-234, 1986; Semba K., et al *Proc. Natl. Acad. Sci. U.S.A.* 82, 6497-6501, 1985; Swiercz J. M., et al *J. Cell Biol.* 165, 869-880, 2004; Kuhns J. J., et al *J. Biol. Chem.* 274, 36422-36427, 1999; Cho H.-S., et al *Nature* 421, 756-760, 2003; Ehsani A., et al (1993) *Genomics* 15, 426-429; WO2004/048938 (Example 2); WO2004/027049 (FIG. 11); WO2004/009622; WO2003/081210;
  WO2003/089904 (Claim 9); WO2003/016475 (Claim 1); US2003/118592; WO2003/008537 (Claim 1); WO2003/055439 (Claim 29; FIG. 1A-B); WO2003/025228 (Claim 37; FIG. 5C); WO2002/22636 (Example 13; Page 95-107); WO2002/12341 (Claim 68; FIG. 7); WO2002/13847 (Page 71-74); WO2002/14503 (Page 114-117); WO2001/53463 (Claim 2; Page 41-46); WO2001/41787 (Page 15); WO2000/44899 (Claim 52; FIG. 7); WO2000/20579
  (Claim 3; FIG. 2); U.S. Pat. No. 5,869,445 (Claim 3; Col 31-38); WO9630514 (Claim 2; Page 56-61); EP1439393 (Claim 7); WO2004/043361 (Claim 7); WO2004/022709; WO2001/00244 (Example 3; FIG. 4); Accession: P04626; EMBL; M11767; AAA35808.1. EMBL; M11761; AAA35808.1

Antibodies
  Abbott: US20110177095
    For example, an antibody comprising CDRs having overall at least 80% sequence identity to CDRs having amino acid sequences of SEQ ID NO:3 (CDR-H1), SEQ ID NO:4 (CDR-H2), SEQ ID NO:5 (CDR-H3), SEQ ID NO:104 and/or SEQ ID NO:6 (CDR-L1), SEQ ID NO:7 (CDR-L2), and SEQ ID NO:8 (CDR-L3), wherein the anti-HER2 antibody or anti-HER2 binding fragment has reduced immunogenicity as compared to an antibody having a VH of SEQ ID NO:1 and a VL of SEQ ID NO:2.
  Biogen: US20100119511
    For example, ATCC accession numbers: PTA-10355, PTA-10356, PTA-10357, PTA-10358
    For example, a purified antibody molecule that binds to HER2 comprising a all six CDR's from an antibody selected from the group consisting of BIIB71F10 (SEQ ID NOs:11, 13), BIIB69A09 (SEQ ID NOs:15, 17); BIIB67F10 (SEQ ID NOs:19, 21); BIIB67F11 (SEQ ID NOs:23, 25), BIIB66A12 (SEQ ID NOs:27, 29), BIIB66C01 (SEQ ID NOs:31, 33), BIIB65C10 (SEQ ID NOs:35, 37), BIIB65H09 (SEQ ID NOs:39, 41) and BIIB65B03 (SEQ ID NOs:43, 45), or CDRs which are identical or which have no more than two alterations from said CDRs.

Herceptin (Genentech)—U.S. Pat. No. 6,054,297; ATCC accession no. CRL-10463 (Genentech)
Pertuzumab (Genentech)
US20110117097
  for example, see SEQ IDs No. 15&16, SEQ IDs No. 17&18, SEQ IDs No. 23&24 & ATCC accession numbers HB-12215, HB-12216, CRL 10463, HB-12697.
US20090285837
US20090202546
  for example, ATCC accession numbers: HB-12215, HB-12216, CRL 10463, HB-12698.
US20060088523
  for example, ATCC accession numbers: HB-12215, HB-12216
  for example, an antibody comprising the variable light and variable heavy amino acid sequences in SEQ ID Nos. 3 and 4, respectively.
  for example, an antibody comprising a light chain amino acid sequence selected from SEQ ID No. 15 and 23, and a heavy chain amino acid sequence selected from SEQ ID No. 16 and 24
US20060018899
  for example, ATCC accession numbers: (7C2) HB-12215, (7F3) HB-12216, (4D5) CRL-10463, (2C4) HB-12697.
  for example, an antibody comprising the amino acid sequence in SEQ ID No. 23, or a deamidated and/or oxidized variant thereof.
US2011/0159014
  for example, an antibody having a light chain variable domain comprising the hypervariable regions of SEQ ID NO: 1".
  For example, an antibody having a heavy chain variable domain comprising the hypervariable regions of SEQ ID NO: 2.
US20090187007
Glycotope: TrasGEX antibody http://www.glycotope.com/pipeline
  For example, see International Joint Cancer Institute and Changhai Hospital Cancer Cent: HMTI-Fc Ab—Gao J., et al *BMB Rep.* 2009 Oct. 31; 42(10):636-41.
Symphogen: US20110217305
Union Stem Cell & Gene Engineering, China—Liu H Q., et al *Xi Bao Yu Fen Zi Mian YiXue Za Zhi*. 2010 May; 26(5):456-8.
(18) NCA (CEACAM6)
Nucleotide
  Genbank accession no M18728
  Genbank version no. M18728.1 GI: 189084
  Genbank record update date: Jun. 23, 2010 08:48 AM
Polypeptide
  Genbank accession no. AAA59907
  Genbank version no. AAA59907.1 GI: 189085
  Genbank record update date: Jun. 23, 2010 08:48 AM
Cross References
  Barnett T., et al *Genomics* 3, 59-66, 1988; Tawaragi Y., et al *Biochem. Biophys. Res. Commun.* 150, 89-96, 1988; Strausberg R. L., et al *Proc. Natl. Acad. Sci. U.S.A.* 99:16899-16903, 2002; WO2004/063709; EP1439393 (Claim 7); WO2004/044178 (Example 4); WO2004/031238; WO2003/042661 (Claim 12); WO2002/78524 (Example 2); WO2002/86443 (Claim 27; Page 427); WO2002/60317 (Claim 2); Accession: P40199; Q14920; EMBL; M29541; AAA59915.1.
  EMBL; M18728.
(19) MDP (DPEP1)
Nucleotide
  Genbank accession no BC017023
  Genbank version no. BC017023.1 GI: 16877538
  Genbank record update date: Mar. 6, 2012 01:00 PM
Polypeptide
  Genbank accession no. AAH17023
  Genbank version no. AAH17023.1 GI: 16877539
  Genbank record update date: Mar. 6, 2012 01:00 PM
Cross References
  *Proc. Natl. Acad. Sci. U.S.A.* 99 (26):16899-16903 (2002)); WO2003/016475 (Claim 1); WO2002/64798 (Claim 33; Page 85-87); JP05003790 (FIG. 6-8); WO99/46284 (FIG. 9); MIM: 179780.
(20) IL20R-Alpha (IL20Ra, ZCYTOR7)
Nucleotide
  Genbank accession no AF184971
  Genbank version no. AF184971.1 GI: 6013324
  Genbank record update date: Mar. 10, 2010 10:00 PM
Polypeptide
  Genbank accession no. AAF01320
  Genbank version no. AAF01320.1 GI: 6013325
  Genbank record update date: Mar. 10, 2010 10:00 PM
Cross References
  Clark H. F., et al *Genome Res.* 13, 2265-2270, 2003; Mungall A. J., et al *Nature* 425, 805-811, 2003; Blumberg H., et al *Cell* 104, 9-19, 2001; Dumoutier L., et al *J. Immunol.* 167, 3545-3549, 2001; Parrish-Novak J., et al *J. Biol. Chem.* 277, 47517-47523, 2002; Pletnev S., et al (2003) *Biochemistry* 42:12617-12624; Sheikh F., et al (2004) *J. Immunol.* 172, 2006-2010; EP1394274 (Example 11); US2004/005320 (Example 5); WO2003/029262 (Page 74-75); WO2003/002717 (Claim 2; Page 63); WO2002/22153 (Page 45-47); US2002/042366 (Page 20-21); WO2001/46261 (Page 57-59); WO2001/46232 (Page 63-65); WO98/37193 (Claim 1; Page 55-59); Accession: Q9UHF4; Q6UWA9; Q96SH8; EMBL; AF184971; AAF01320.1.
(21) Brevican (BCAN, BEHAB)
Nucleotide
  Genbank accession no AF229053
  Genbank version no. AF229053.1 GI: 10798902
  Genbank record update date: Mar. 11, 2010 12:58 AM
Polypeptide
  Genbank accession no. AAG23135
  Genbank version no. AAG23135.1 GI: 10798903
  Genbank record update date: Mar. 11, 2010 12:58 AM
Cross References
  Gary S. C., et al *Gene* 256, 139-147, 2000; Clark H. F., et al *Genome Res.* 13, 2265-2270, 2003; Strausberg R. L., et al *Proc. Natl. Acad. Sci. U.S.A.* 99, 16899-16903, 2002; US2003/186372 (Claim 11); US2003/186373 (Claim 11); US2003/119131 (Claim 1; FIG. 52); US2003/119122 (Claim 1; FIG. 52); US2003/119126 (Claim 1); US2003/119121 (Claim 1; FIG. 52); US2003/119129 (Claim 1); US2003/119130 (Claim 1); US2003/119128 (Claim 1; FIG. 52); US2003/119125 (Claim 1); WO2003/016475 (Claim 1); WO2002/02634 (Claim 1)
(22) EphB2R (DRT, ERK, Hek5, EPHT3, Tyro5)
Nucleotide
  Genbank accession no NM_004442
  Genbank version no. NM_004442.6 GI: 111118979
  Genbank record update date: Sep. 8, 2012 04:43 PM
Polypeptide
  Genbank accession no. NP_004433
  Genbank version no. NP_004433.2 GI: 21396504
  Genbank record update date: Sep. 8, 2012 04:43 PM Cross References Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); MIM: 600997.

(23) ASLG659 (B7h)

Nucleotide

Genbank accession no. AX092328

Genbank version no. AX092328.1 GI: 13444478

Genbank record update date: Jan. 26, 2011 07:37 AM

Cross References

US2004/0101899 (Claim 2); WO2003104399 (Claim 11); WO2004000221 (FIG. 3); US2003/165504 (Claim 1); US2003/124140 (Example 2); US2003/065143 (FIG. 60); WO2002/102235 (Claim 13; Page 299); US2003/091580 (Example 2); WO2002/10187 (Claim 6; FIG. 10); WO2001/94641 (Claim 12; FIG. 7b); WO2002/02624 (Claim 13; FIG. 1A-1B); US2002/034749 (Claim 54; Page 45-46); WO2002/06317 (Example 2; Page 320-321, Claim 34; Page 321-322); WO2002/71928 (Page 468-469); WO2002/02587 (Example 1; FIG. 1); WO2001/40269 (Example 3; Pages 190-192); WO2000/36107 (Example 2; Page 205-207); WO2004/053079 (Claim 12); WO2003/004989 (Claim 1); WO2002/71928 (Page 233-234, 452-453); WO 01/16318.

(24) PSCA (Prostate Stem Cell Antigen Precursor)

Nucleotide

Genbank accession no AJ297436

Genbank version no. AJ297436.1 GI: 9367211

Genbank record update date: Feb. 1, 2011 11:25 AM

Polypeptide

Genbank accession no. CAB97347

Genbank version no. CAB97347.1 GI: 9367212

Genbank record update date: Feb. 1, 2011 11:25 AM

Cross References

Reiter R. E., et al *Proc. Natl. Acad. Sci. U.S.A.* 95, 1735-1740, 1998; Gu Z., et al *Oncogene* 19, 1288-1296, 2000; *Biochem. Biophys. Res. Commun.* (2000) 275(3):783-788; WO2004/022709; EP1394274 (Example 11); US2004/018553 (Claim 17); WO2003/008537 (Claim 1); WO2002/81646 (Claim 1; Page 164); WO2003/003906 (Claim 10; Page 288); WO2001/40309 (Example 1; FIG. 17); US2001/055751 (Example 1; FIG. 1b); WO2000/32752 (Claim 18; FIG. 1); WO98/51805 (Claim 17; Page 97); WO98/51824 (Claim 10; Page 94); WO98/40403 (Claim 2; FIG. 1B); Accession: 043653; EMBL; AF043498; AAC39607.1

(25) GEDA

Nucleotide

Genbank accession no AY260763

Genbank version no. AY260763.1 GI: 30102448

Genbank record update date: Mar. 11, 2010 02:24 AM

Polypeptide

Genbank accession no. AAP14954

Genbank version no. AAP14954.1 GI: 30102449

Genbank record update date: Mar. 11, 2010 02:24 AM

Cross References

AP14954 lipoma HMGIC fusion-partnerlike protein/pid=AAP14954.1—*Homo sapiens* (human); WO2003/054152 (Claim 20); WO2003/000842 (Claim 1); WO2003/023013 (Example 3, Claim 20); US2003/194704 (Claim 45); GI: 30102449;

(26) BAFF-R (B Cell-Activating Factor Receptor, BLyS Receptor 3, BR3)

Nucleotide

Genbank accession no AF116456

Genbank version no. AF116456.1 GI: 4585274

Genbank record update date: Mar. 10, 2010 09:44 PM

Polypeptide

Genbank accession no. AAD25356

Genbank version no. AAD25356.1 GI: 4585275

Genbank record update date: Mar. 10, 2010 09:44 PM

Cross References

BAFF receptor/pid=NP_443177.1—*Homo sapiens*: Thompson, J. S., et al *Science* 293 (5537), 2108-2111 (2001); WO2004/058309; WO2004/011611; WO2003/045422 (Example; Page 32-33); WO2003/014294 (Claim 35; FIG. 6B); WO2003/035846 (Claim 70; Page 615-616); WO2002/94852 (Col 136-137); WO2002/38766 (Claim 3; Page 133); WO2002/24909 (Example 3; FIG. 3); MIM: 606269; NP_443177.1; NM_052945_1; AF132600

(27) CD22 (B-Cell Receptor CD22-B Isoform, BL-CAM, Lyb-8, Lyb8, SIGLEC-2, FLJ22814)

Nucleotide

Genbank accession no AK026467

Genbank version no. AK026467.1 GI: 10439337

Genbank record update date: Sep. 11, 2006 11:24 PM

Polypeptide

Genbank accession no. BAB15489

Genbank version no. BAB15489.1 GI: 10439338

Genbank record update date: Sep. 11, 2006 11:24 PM

Cross References

Wilson et al (1991) *J. Exp. Med.* 173:137-146; WO2003/072036 (Claim 1; FIG. 1); IM: 107266; NP_001762.1; NM_001771_1.

(27a) Cd22 (Cd22 Molecule)

Nucleotide

Genbank accession no X52785

Genbank version no. X52785.1 GI: 29778

Genbank record update date: Feb. 2, 2011 10:09 AM

Polypeptide

Genbank accession no. CAA36988

Genbank version no. CAA36988.1 GI: 29779

Genbank record update date: Feb. 2, 2011 10:09 AM

Cross References

Stamenkovic I. et al., *Nature* 345 (6270), 74-77 (1990)

Other Information

Official Symbol: CD22

Other Aliases: SIGLEC-2, SIGLEC2

Other Designations: B-cell receptor CD22; B-lymphocyte cell adhesion molecule; BL-CAM; CD22 antigen; T-cell surface antigen Leu-14; sialic acid binding Ig-like lectin 2; sialic acid-binding Ig-like lectin 2

Antibodies

G5/44 (Inotuzumab): DiJoseph J F., et al *Cancer Immunol Immunother.* 2005 January; 54(1):11-24.

Epratuzumab—Goldenberg D M., et al *Expert Rev Anticancer Ther.* 6(10): 1341-53, 2006.

(28) CD79a (CD79A, CD79alpha), Immunoglobulin-Associated Alpha, a B Cell-Specific Protein that Covalently Interacts with Ig Beta (CD79B) and Forms a Complex on the Surface with Ig M Molecules, Transduces a Signal Involved in B-Cell Differentiation), pI: 4.84, MW: 25028 TM: 2 [P] Gene Chromosome: 19q13.2).

Nucleotide

Genbank accession no NM_001783

Genbank version no. NM_001783.3 GI: 90193587

Genbank record update date: Jun. 26, 2012 01:48 PM

Polypeptide
    Genbank accession no. NP_001774
    Genbank version no. NP_001774.1 GI: 4502685
    Genbank record update date: Jun. 26, 2012 01:48 PM
Cross References
    WO2003/088808, US2003/0228319; WO2003/062401 (claim 9); US2002/150573 (claim 4, pages 13-14); WO99/58658 (claim 13, FIG. 16); WO92/07574 (FIG. 1); U.S. Pat. No. 5,644,033; Ha et al (1992) *J. Immunol.* 148(5):1526-1531; Müller et al (1992) *Eur. J. Immunol.* 22:1621-1625; Hashimoto et al (1994) *Immunogenetics* 40(4):287-295; Preud'homme et al (1992) *Clin. Exp. Immunol.* 90(1):141-146; Yu et al (1992) *J. Immunol.* 148(2) 633-637; Sakaguchi et al (1988) *EMBO J.* 7(11):3457-3464

(29) CXCR5 (Burkitt's Lymphoma Receptor 1, a G Protein-Coupled Receptor that is Activated by the CXCL13 Chemokine, Functions in Lymphocyte Migration and Humoral Defense, Plays a Role in HIV-2 Infection and Perhaps Development of AIDS, Lymphoma, Myeloma, and Leukemia); 372 aa, pI: 8.54 MW: 41959 TM: 7[P] Gene Chromosome: 11q23.3,
Nucleotide
    Genbank accession no NM_001716
    Genbank version no. NM_001716.4 GI: 342307092
    Genbank record update date: Sep. 30, 2012 01:49 PM
Polypeptide
    Genbank accession no. NP_001707
    Genbank version no. NP_001707.1 GI: 4502415
    Genbank record update date: Sep. 30, 2012 01:49 PM
Cross References
    WO2004/040000; WO2004/015426; US2003/105292 (Example 2); U.S. Pat. No. 6,555,339 (Example 2); WO2002/61087 (FIG. 1); WO2001/57188 (Claim 20, page 269); WO2001/72830 (pages 12-13); WO2000/22129 (Example 1, pages 152-153, Example 2, pages 254-256); WO99/28468 (claim 1, page 38); U.S. Pat. No. 5,440,021 (Example 2, col 49-52); WO94/28931 (pages 56-58); WO92/17497 (claim 7, FIG. 5); Dobner et al (1992) *Eur. J. Immunol.* 22:2795-2799; Barella et al (1995) *Biochem. J.* 309:773-779

(30) HLA-DOB (Beta Subunit of MHC Class II Molecule (Ia Antigen) that Binds Peptides and Presents them to CD4+T Lymphocytes); 273 aa, pI: 6.56, MW: 30820. TM: 1 [P] Gene Chromosome: 6p21.3)
Nucleotide
    Genbank accession no NM_002120
    Genbank version no. NM_002120.3 GI: 118402587
    Genbank record update date: Sep. 8, 2012 04:46 PM
Polypeptide
    Genbank accession no. NP_002111
    Genbank version no. NP_002111.1 GI: 4504403
    Genbank record update date: Sep. 8, 2012 04:46 PM
Cross References
    Tonnelle et al (1985) *EMBO J.* 4(11):2839-2847; Jonsson et al (1989) *Immunogenetics* 29(6):411-413; Beck et al (1992) *J. Mol. Biol.* 228:433-441; Strausberg et al (2002) *Proc. Natl. Acad. Sci USA* 99:16899-16903; Servenius et al (1987) *J. Biol. Chem.* 262:8759-8766; Beck et al (1996) *J. Mol. Biol.* 255:1-13; Naruse et al (2002) *Tissue Antigens* 59:512-519; WO99/58658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) *Immunogenetics* 30(1):66-68; Larhammar et al (1985) *J. Biol. Chem.* 260(26):14111-14119

(31) P2X5 (Purinergic Receptor P2X Ligand-Gated Ion Channel 5, an Ion Channel Gated by Extracellular ATP, May be Involved in Synaptic Transmission and Neurogenesis, Deficiency May Contribute to the Pathophysiology of Idiopathic Detrusor Instability); 422 aa), pI: 7.63, MW: 47206 TM: 1 [P] Gene Chromosome: 17p13.3).
Nucleotide
    Genbank accession no NM_002561
    Genbank version no. NM_002561.3 GI: 325197202
    Genbank record update date: Jun. 27, 2012 12:41 AM
Polypeptide
    Genbank accession no. NP_002552
    Genbank version no. NP_002552.2 GI: 28416933
    Genbank record update date: Jun. 27, 2012 12:41 AM
Cross References
    Le et al (1997) *FEBS Lett.* 418(1-2):195-199; WO2004/047749; WO2003/072035 (claim 10); Touchman et al (2000) *Genome Res.* 10:165-173; WO2002/22660 (claim 20); WO2003/093444 (claim 1); WO2003/087768 (claim 1); WO2003/029277 (page 82)

(32) CD72 (B-Cell Differentiation Antigen CD72, Lyb-2); 359 aa, pI: 8.66, MW: 40225, TM: 1 [P] Gene Chromosome: 9p13.3).
Nucleotide
    Genbank accession no NM_001782
    Genbank version no. NM_001782.2 GI: 194018444
    Genbank record update date: Jun. 26, 2012 01:43 PM
Polypeptide
    Genbank accession no. NP_001773
    Genbank version no. NP_001773.1 GI: 4502683
    Genbank record update date: Jun. 26, 2012 01:43 PM
Cross References
    WO2004042346 (claim 65); WO2003/026493 (pages 51-52, 57-58); WO2000/75655 (pages 105-106); Von Hoegen et al (1990) *J. Immunol.* 144(12):4870-4877; Strausberg et al (2002) *Proc. Natl. Acad. Sci USA* 99:16899-16903.

(33) LY64 (Lymphocyte Antigen 64 (RP105), Type I Membrane Protein of the Leucine Rich Repeat (LRR) Family, Regulates B-Cell Activation and Apoptosis, Loss of Function is Associated with Increased Disease Activity in Patients with Systemic Lupus Erythematosis); 661 aa, pI: 6.20, MW: 74147 TM: 1 [P] Gene Chromosome: 5q12).
Nucleotide
    Genbank accession no NM_005582
    Genbank version no. NM_005582.2 GI: 167555126
    Genbank record update date: Sep. 2, 2012 01:50 PM
Polypeptide
    Genbank accession no. NP_005573
    Genbank version no. NP_005573.2 GI: 167555127
    Genbank record update date: Sep. 2, 2012 01:50 PM
Cross References
    US2002/193567; WO97/07198 (claim 11, pages 39-42); Miura et al (1996) *Genomics* 38(3):299-304; Miura et al (1998) *Blood* 92:2815-2822; WO2003/083047; WO97/44452 (claim 8, pages 57-61); WO2000/12130 (pages 24-26).

(34) FcRH1 (Fc Receptor-Like Protein 1, a Putative Receptor for the Immunoglobulin Fc Domain that Contains C2 Type Ig-Like and ITAM Domains, May have a Role in B-Lymphocyte Differentiation); 429 aa, pI: 5.28, MW: 46925 TM: 1 [P] Gene Chromosome: 1q21-1q22)
Nucleotide
    Genbank accession no NM_052938
    Genbank version no. NM_052938.4 GI: 226958543
    Genbank record update date: Sep. 2, 2012 01:43 PM
Polypeptide
    Genbank accession no. NP_443170
    Genbank version no. NP_443170.1 GI: 16418419
    Genbank record update date: Sep. 2, 2012 01:43 PM Cross References
  WO2003/077836; WO2001/38490 (claim 6, FIG. 18E-1-18-E-2); Davis et al (2001) *Proc. Natl. Acad. Sci USA* 98(17):9772-9777; WO2003/089624 (claim 8); EP1347046 (claim 1); WO2003/089624 (claim 7).
(35) IRTA2 (Immunoglobulin Superfamily Receptor Translocation Associated 2, a Putative Immunoreceptor with Possible Roles in B Cell Development and Lymphomagenesis; Deregulation of the Gene by Translocation Occurs in Some B Cell Malignancies); 977 aa, pI: 6.88, MW: 106468, TM: 1 [P] Gene Chromosome: 1q21)
Nucleotide
  Genbank accession no AF343662
  Genbank version no. AF343662.1 GI: 13591709
  Genbank record update date: Mar. 11, 2010 01:16 AM
Polypeptide
  Genbank accession no. AAK31325
  Genbank version no. AAK31325.1 GI: 13591710
  Genbank record update date: Mar. 11, 2010 01:16 AM
Cross References
  AF343663, AF343664, AF343665, AF369794, AF397453, AK090423, AK090475, AL834187, AY358085; Mouse: AK089756, AY158090, AY506558; NP_112571.1; WO2003/024392 (claim 2, FIG. 97); Nakayama et al (2000) *Biochem. Biophys. Res. Commun.* 277(1):124-127; WO2003/077836; WO2001/38490 (claim 3, FIG. 18B-1-18B-2).
(36) TENB2 (TMEFF2, Tomoregulin, TPEF, HPPI, TR, Putative Transmembrane Proteoglycan, Related to the EGF/Heregulin Family of Growth Factors and Follistatin); 374 aa)
Nucleotide
  Genbank accession no AF179274
  Genbank version no. AF179274.2 GI: 12280939
  Genbank record update date: Mar. 11, 2010 01:05 AM
Polypeptide
  Genbank accession no. AAD55776
  Genbank version no. AAD55776.2 GI: 12280940
  Genbank record update date: Mar. 11, 2010 01:05 AM
Cross References
  NCBI Accession: AAD55776, AAF91397, AAG49451, NCBI RefSeq: NP_057276; NCBI Gene: 23671; OMIM: 605734; SwissProt Q9UIK5; AY358907, CAF85723, CQ782436; WO2004/074320; JP2004113151; WO2003/042661; WO2003/009814; EP1295944 (pages 69-70); WO2002/30268 (page 329); WO2001/90304; US2004/249130; US2004/022727; WO2004/063355; US2004/197325; US2003/232350; US2004/005563; US2003/124579; Horie et al (2000) *Genomics* 67:146-152; Uchida et al (1999) *Biochem. Biophys. Res. Commun.* 266:593-602; Liang et al (2000) *Cancer Res.* 60:4907-12; Glynne-Jones et al (2001) *Int J Cancer.* October 15; 94(2):178-84.
(37) PSMA-FOLH1 (Folate Hydrolase (Prostate-Specific Membrane Antigen) 1)
Nucleotide
  Genbank accession no M99487
  Genbank version no. M99487.1 GI: 190663
  Genbank record update date: Jun. 23, 2010 08:48 AM
Polypeptide
  Genbank accession no. AAA60209
  Genbank version no. AAA60209.1 GI: 190664
  Genbank record update date: Jun. 23, 2010 08:48 AM
Cross References
  Israeli R. S., et al *Cancer Res.* 53 (2), 227-230 (1993)
Other Information
  Official Symbol: FOLH1
  Other Aliases: GIG27, FGCP, FOLH, GCP2, GCPII, NAALAD1, NAALAdase, PSM, PSMA, mGCP
  Other Designations: N-acetylated alpha-linked acidic dipeptidase 1; N-acetylated-alpha-linked acidic dipeptidase I; NAALADase I; cell growth-inhibiting gene 27 protein; folylpoly-gamma-glutamate carboxypeptidase; glutamate carboxylase II; glutamate carboxypeptidase 2; glutamate carboxypeptidase II; membrane glutamate carboxypeptidase; prostate specific membrane antigen variant F; pteroylpoly-gamma-glutamate carboxypeptidase
Antibodies
  U.S. Pat. No. 7,666,425: Antibodies produces by Hybridomas having the following ATCC references: ATCC accession No. HB-12101, ATCC accession No. HB-12109, ATCC accession No. HB-12127 and ATCC accession No. HB-12126.
  Proscan: a monoclonal antibody selected from the group consisting of 8H12, 3E11, 17G1, 29B4, 30C1 and 20F2 (U.S. Pat. No. 7,811,564; Moffett S., et al Hybridoma (Larchmt). 2007 December; 26(6):363-72).
  Cytogen: monoclonal antibodies 7E11-C5 (ATCC accession No. HB 10494) and 9H10-A4 (ATCC accession No. HB11430)—U.S. Pat. No. 5,763,202
  GlycoMimetics: NUH2—ATCC accession No. HB 9762 (U.S. Pat. No. 7,135,301)
  Human Genome Science: HPRAJ70—ATCC accession No. 97131 (U.S. Pat. No. 6,824,993); Amino acid sequence encoded by the cDNA clone (HPRAJ70) deposited as American Type Culture Collection ("ATCC") Deposit No. 97131
  Medarex: Anti-PSMA antibodies that lack fucosyl residues—U.S. Pat. No. 7,875,278
  Mouse anti-PSMA antibodies include the 3F5.4G6, 3D7.1.1, 4E10-1.14, 3E11, 4D8, 3E6, 3C9, 2C7, 1G3, 3C4, 3C6, 4D4, 1G9, 5C8B9, 3G6, 4C8B9, and monoclonal antibodies. Hybridomas secreting 3F5.4G6, 3D7.1.1, 4E10-1.14, 3E11, 4D8, 3E6, 3C9, 2C7, 1G3, 3C4, 3C6, 4D4, 1G9, 5C8B9, 3G6 or 4C8B9 have been publicly deposited and are described in U.S. Pat. No. 6,159,508. Relevant hybridomas have been publicly deposited and are described in U.S. Pat. No. 6,107,090. Moreover, humanized anti-PSMA antibodies, including a humanized version of J591, are described in further detail in PCT Publication WO 02/098897.
  Other mouse anti-human PSMA antibodies have been described in the art, such as mAb 107-1A4 (Wang, S. et al. (2001) *Int. J. Cancer* 92:871-876) and mAb 2C9 (Kato, K. et al. (2003) *Int. J. Urol.* 10:439-444).
  Examples of human anti-PSMA monoclonal antibodies include the 4A3, 7F12, 8C12, 8A11, 16F9, 2A10, 2C6, 2F5 and 1C3 antibodies, isolated and structurally characterized as originally described in PCT Publications WO 01/09192 and WO 03/064606 and in U.S. Provisional Application Ser. No. 60/654,125, entitled "Human Monoclonal Antibodies to Prostate Specific Membrane Antigen (PSMA)", filed on Feb. 18, 2005. The V.sub.H amino acid sequences of 4A3, 7F12, 8C12, 8A11, 16F9, 2A10, 2C6, 2F5 and 1C3 are shown in SEQ ID NOs: 1-9, respectively. The V.sub.L amino acid sequences of 4A3, 7F12, 8C12, 8A11, 16F9, 2A10, 2C6, 2F5 and 1C3 are shown in SEQ ID NOs: 10-18, respectively.
  Other human anti-PSMA antibodies include the antibodies disclosed in PCT Publication WO 03/034903 and US Application No. 2004/0033229.
  NW Biotherapeutics: A hybridoma cell line selected from the group consisting of 3F5.4G6 having ATCC accession number HB12060, 3D7-1.1. having ATCC accession number HB12309, 4E10-1.14 having ATCC accession number HB12310, 3E11 (ATCC HB12488), 4D8 (ATCC HB12487), 3E6 (ATCC HB12486), 3C9 (ATCC HB12484), 2C7 (ATCC HB12490), 1G3 (ATCC HB12489), 3C4 (ATCC HB12494), 3C6 (ATCC HB12491), 4D4 (ATCC HB12493), 1G9 (ATCC HB12495), 5C8B9 (ATCC HB12492) and 3G6 (ATCC HB12485)—see U.S. Pat. No. 6,150,508

PSMA Development Company/Progenics/Cytogen—Seattle Genetics: mAb 3.9, produced by the hybridoma deposited under ATCC Accession No. PTA-3258 or mAb 10.3, produced by the hybridoma deposited under ATCC Accession No. PTA-3347—U.S. Pat. No. 7,850,971

PSMA Development Company—Compositions of PSMA antibodies (US 20080286284, Table 1)

This application is a divisional of U.S. patent application Ser. No. 10/395,894, filed on Mar. 21, 2003 (U.S. Pat. No. 7,850,971)

University Hospital Freiburg, Germany—mAbs 3/A12, 3/E7, and 3/F11 (Wolf P., et al *Prostate*. 2010 Apr. 1; 70(5):562-9).

(38) SST (Somatostatin Receptor; Note that there are 5 Subtypes)

(38.1) SSTR2 (Somatostatin Receptor 2)

Nucleotide
    Genbank accession no NM_001050
    Genbank version no. NM_001050.2 GI: 44890054
    Genbank record update date: Aug. 19, 2012 01:37 PM Polypeptide
    Genbank accession no. NP_001041
    Genbank version no. NP_001041.1 GI: 4557859
    Genbank record update date: Aug. 19, 2012 01:37 PM Cross References
    Yamada Y., et al Proc. Natl. Acad. Sci. U.S.A. 89 (1), 251-255 (1992); Susini C., et al Ann Oncol. 2006 December; 17(12):1733-42

Other Information
    Official Symbol: SSTR2
    Other Designations: SRIF-1; SS2R; somatostatin receptor type 2

(38.2) SSTR5 (Somatostatin Receptor 5)

Nucleotide
    Genbank accession no D16827
    Genbank version no. D16827.1 GI: 487683
    Genbank record update date: Aug. 1, 2006 12:45 PM Polypeptide
    Genbank accession no. BAA04107
    Genbank version no. BAA04107.1 GI: 487684
    Genbank record update date: Aug. 1, 2006 12:45 PM Cross References
    Yamada, Y., et al *Biochem. Biophys. Res. Commun.* 195 (2), 844-852 (1993)

Other Information
    Official Symbol: SSTR5
    Other Aliases: SS-5-R
    Other Designations: Somatostatin receptor subtype 5; somatostatin receptor type 5

(38.3) SSTR1
(38.4) SSTR3
(38.5) SSTR4

AvB6—Both Subunits (39+40)

(39) ITGAV (Integrin, alpha V;

Nucleotide
    Genbank accession no M14648 J02826 M18365
    Genbank version no. M14648.1 GI: 340306
    Genbank record update date: Jun. 23, 2010 08:56 AM Polypeptide
    Genbank accession no. AAA36808
    Genbank version no. AAA36808.1 GI: 340307
    Genbank record update date: Jun. 23, 2010 08:56 AM Cross References
    Suzuki S., et al *Proc. Natl. Acad. Sci. U.S.A.* 83 (22), 8614-8618 (1986)

Other Information
    Official Symbol: ITGAV
    Other Aliases: CD51, MSK8, VNRA, VTNR
    Other Designations: antigen identified by monoclonal antibody L230; integrin alpha-V; integrin alphaVbeta3; integrin, alpha V (vitronectin receptor, alpha polypeptide, antigen CD51); vitronectin receptor subunit alpha

(40) ITGB6 (Integrin, Beta 6)

Nucleotide
    Genbank accession no NM_000888
    Genbank version no. NM_000888.3 GI: 9966771
    Genbank record update date: Jun. 27, 2012 12:46 AM Polypeptide
    Genbank accession no. NP_000879
    Genbank version no. NP_000879.2 GI: 9625002
    Genbank record update date: Jun. 27, 2012 12:46 AM Cross References
    Sheppard D. J., et al *Biol. Chem.* 265 (20), 11502-11507 (1990)

Other Information
    Official Symbol: ITGB6
    Other Designations: integrin beta-6

Antibodies
    Biogen: U.S. Pat. No. 7,943,742—Hybridoma clones 6.3G9 and 6.8G6 were deposited with the ATCC, accession numbers ATCC PTA-3649 and -3645, respectively.
    Biogen: U.S. Pat. No. 7,465,449—In some embodiments, the antibody comprises the same heavy and light chain polypeptide sequences as an antibody produced by hybridoma 6.1A8, 6.3G9, 6.8G6, 6.2B1, 6.2B10, 6.2A1, 6.2E5, 7.1G10, 7.7G5, or 7.1C5.
    Centocor (J&J): U.S. Pat. Nos. 7,550,142; 7,163,681
        For example in U.S. Pat. No. 7,550,142—an antibody having human heavy chain and human light chain variable regions comprising the amino acid sequences shown in SEQ ID NO: 7 and SEQ ID NO: 8.
    Seattle Genetics: 15H3 (Ryan M C., et al *Cancer Res* Apr. 15, 2012; 72(8 Supplement): 4630)

(41) CEACAM5 (Carcinoembryonic Antigen-Related Cell Adhesion Molecule 5)

Nucleotide
    Genbank accession no M17303
    Genbank version no. M17303.1 GI: 178676
    Genbank record update date: Jun. 23, 2010 08:47 AM Polypeptide
    Genbank accession no. AAB59513
    Genbank version no. AAB59513.1 GI: 178677
    Genbank record update date: Jun. 23, 2010 08:47 AM Cross References
    Beauchemin N., et al *Mol. Cell. Biol.* 7 (9), 3221-3230 (1987)

Other Information
    Official Symbol: CEACAM5
    Other Aliases: CD66e, CEA
    Other Designations: meconium antigen 100

Antibodies
    AstraZeneca-MedImmune: US 20100330103; US20080057063; US20020142359
        for example an antibody having complementarity determining regions (CDRs) with the following sequences: heavy chain; CDR1—DNYMH, CDR2—WIDPENGDTE YAPKFRG, CDR3—LI- YAGYLAMD Y; and light chain CDR1—SASSSVTYMH, CDR2—STSNLAS, CDR3—QQRSTYPLT.

Hybridoma 806.077 deposited as European Collection of Cell Cultures (ECACC) deposit no. 96022936.

Research Corporation Technologies, Inc.: U.S. Pat. No. 5,047,507

Bayer Corporation: U.S. Pat. No. 6,013,772

BioAlliance: U.S. Pat. Nos. 7,982,017; 7,674,605

U.S. Pat. No. 7,674,605
- an antibody comprising the heavy chain variable region sequence from the amino acid sequence of SEQ ID NO: 1, and the light chain variable region sequence from the amino acid sequence of SEQ ID NO:2.
- an antibody comprising the heavy chain variable region sequence from the amino acid sequence of SEQ ID NO:5, and the light chain variable region sequence from the amino acid sequence of SEQ ID NO:6.

Celltech Therapeutics Limited: U.S. Pat. No. 5,877,293

The Dow Chemical Company: U.S. Pat. Nos. 5,472,693; 6,417,337; 6,333,405

U.S. Pat. No. 5,472,693—for example, ATCC No. CRL-11215

U.S. Pat. No. 6,417,337—for example, ATCC CRL-12208

U.S. Pat. No. 6,333,405—for example, ATCC CRL-12208

Immunomedics, Inc: U.S. Pat. Nos. 7,534,431; 7,230,084; 7,300,644; 6,730,300;
- US20110189085
  - an antibody having CDRs of the light chain variable region comprise: CDR1 comprises KASQDVGTSVA (SEQ ID NO: 20); CDR2 comprises WTSTRHT (SEQ ID NO: 21); and CDR3 comprises QQYSLYRS (SEQ ID NO: 22);
  - and the CDRs of the heavy chain variable region of said anti-CEA antibody comprise: CDR1 comprises TYWMS (SEQ ID NO: 23); CDR2 comprises EIHPDSSTINYAPSLKD (SEQ ID NO: 24); and CDR3 comprises LYFGFPWFAY (SEQ ID NO: 25).
- US20100221175; US20090092598; US20070202044; US20110064653; US20090185974; US20080069775.

(42) MET (Met Proto-Oncogene; Hepatocyte Growth Factor Receptor)

Nucleotide
- Genbank accession no M35073
- Genbank version no. M35073.1 GI: 187553
- Genbank record update date: Mar. 6, 2012 11:12 AM Polypeptide
- Genbank accession no. AAA59589
- Genbank version no. AAA59589.1 GI: 553531
- Genbank record update date: Mar. 6, 2012 11:12 AM Cross References
- Dean M., et al *Nature* 318 (6044), 385-388 (1985)

Other Information
- Official Symbol: MET
- Other Aliases: AUTS9, HGFR, RCCP2, c-Met
- Other Designations: HGF receptor; HGF/SF receptor; SF receptor; hepatocyte growth factor receptor; met proto-oncogene tyrosine kinase; proto-oncogene c-Met; scatter factor receptor; tyrosine-protein kinase Met Antibodies
- Abgenix/Pfizer: US20100040629
  - for example, the antibody produced by hybridoma 13.3.2 having American Type Culture Collection (ATCC) accession number PTA-5026; the antibody produced by hybridoma 9.1.2 having ATCC accession number PTA-5027; the antibody produced by hybridoma 8.70.2 having ATCC accession number PTA-5028; or the antibody produced by hybridoma 6.90.3 having ATCC accession number PTA-5029.
- Amgen/Pfizer: US20050054019
  - for example, an antibody comprising a heavy chain having the amino acid sequences set forth in SEQ ID NO: 2 where X2 is glutamate and X4 is serine and a light chain having the amino acid sequence set forth in SEQ ID NO: 4 where X8 is alanine, without the signal sequences; an antibody comprising a heavy chain having the amino acid sequences set forth in SEQ ID NO: 6 and a light chain having the amino acid sequence set forth in SEQ ID NO: 8, without the signal sequences; an antibody comprising a heavy chain having the amino acid sequences set forth in SEQ ID NO: 10 and a light chain having the amino acid sequence set forth in SEQ ID NO: 12, without the signal sequences; or an antibody comprising a heavy chain having the amino acid sequences set forth in SEQ ID NO: 14 and a light chain having the amino acid sequence set forth in SEQ ID NO: 16, without the signal sequences.
- Agouron Pharmaceuticals (Now Pfizer): US20060035907
- Eli Lilly: US20100129369
- Genentech: U.S. Pat. No. 5,686,292; US20100028337; US20100016241; US20070129301; US20070098707; US20070092520, US20060270594; US20060134104; US20060035278; US20050233960; US20050037431
  - U.S. Pat. No. 5,686,292—for example, ATCC HB-11894 and ATCC HB-11895
  - US 20100016241—for example, ATCC HB-11894 (hybridoma 1A3.3.13) or HB-11895 (hybridoma 5D5.11.6)
- National Defense Medical Center, Taiwan: Lu R M., et al Biomaterials. 2011 April; 32(12):3265-74.
- Novartis: US20090175860
  - for example, an antibody comprising the sequences of CDR1, CDR2 and CDR3 of heavy chain 4687, wherein the sequences of CDR1, CDR2, and CDR3 of heavy chain 4687 are residues 26-35, 50-65, and 98-102, respectively, of SEQ ID NO: 58; and the sequences of CDR1, CDR2, and CDR3 of light chain 5097, wherein the sequences of CDR1, CDR2, and CDR3 of light chain 5097 are residues 24-39, 55-61, and 94-100 of SEQ ID NO: 37.
- Pharmacia Corporation: US20040166544
- Pierre Fabre: US20110239316, US20110097262, US20100115639
- Sumsung: US 20110129481—for example a monoclonal antibody produced from a hybridoma cell having accession number KCLRF-BP-00219 or accession number of KCLRF-BP-00223.
- Samsung: US 20110104176—for example an antibody produced by a hybridoma cell having Accession Number: KCLRF-BP-00220.
- University of Turin Medical School: DN-30 Pacchiana G., et al *J Biol Chem.* 2010 Nov. 12; 285(46):36149-57
- Van Andel Research Institute: Jiao Y., et al *Mol Biotechnol.* 2005 September; 31(1):41-54.

(43) MUC1 (Mucin 1, Cell Surface Associated)

Nucleotide
- Genbank accession no J05581
- Genbank version no. J05581.1 GI: 188869
- Genbank record update date: Jun. 23, 2010 08:48 AM Polypeptide
  Genbank accession no. AAA59876
  Genbank version no. AAA59876.1 GI: 188870
  Genbank record update date: Jun. 23, 2010 08:48 AM
Cross References
  Gendler S. J., et al *J. Biol. Chem.* 265 (25), 15286-15293 (1990)
Other Information
  Official Symbol: MUC1
  Other Aliases: RP11-263K19.2, CD227, EMA, H23AG, KL-6, MAM6, MUC-1, MUC-1/SEC, MUC-1/X, MUC1/ZD, PEM, PEMT, PUM
  Other Designations: DF3 antigen; H23 antigen; breast carcinoma-associated antigen DF3; carcinoma-associated mucin; episialin; krebs von den Lungen-6; mucin 1, transmembrane; mucin-1; peanut-reactive urinary mucin; polymorphic epithelial mucin; tumor associated epithelial mucin; tumor-associated epithelial membrane antigen; tumor-associated mucin
Antibodies
  AltaRex—Quest Pharma Tech: U.S. Pat. No. 6,716,966—for example an Alt-1 antibody produced by the hybridoma ATCC No PTA-975.
  AltaRex—Quest Pharma Tech: U.S. Pat. No. 7,147,850
  CRT: 5E5—Sørensen A L., et al *Glycobiology* vol. 16 no. 2 pp. 96-107, 2006; HMFG2—Burchell J., et al *Cancer Res.,* 47, 5476-5482 (1987); see WO2015/159076
  Glycotope GT-MAB: GT-MAB 2.5-GEX (Website: http://www.glycotope.com/pipeline/pankomab-gex)
    Immunogen: U.S. Pat. No. 7,202,346
    for example, antibody MJ-170: hybridoma cell line MJ-170 ATCC accession no. PTA-5286Monoclonal antibody MJ-171: hybridoma cell line MJ-171 ATCC accession no. PTA-5287; monoclonal antibody MJ-172: hybridoma cell line MJ-172 ATCC accession no. PTA-5288; or monoclonal antibody MJ-173: hybridoma cell line MJ-173 ATCC accession no. PTA-5302
  Immunomedics: U.S. Pat. No. 6,653,104
  Ramot Tel Aviv Uni: U.S. Pat. No. 7,897,351
  Regents Uni. CA: U.S. Pat. No. 7,183,388; US20040005647; US20030077676.
  Roche GlycArt: U.S. Pat. No. 8,021,856
  Russian National Cancer Research Center: Imuteran-Ivanov P K., et al *Biotechnol J.* 2007 July; 2(7):863-70
  Technische Univ Braunschweig: (1lB6, HT186-B7, HT186-D11, HT186-G2, HT200-3A-C1, HT220-M-D1, HT220-M-G8)—Thie H., et al *PLoS One.* 2011 Jan. 14; 6(1):e15921

(44) CA9 (Carbonic Anhydrase IX)
Nucleotide
  Genbank accession no. X66839
  Genbank version no. X66839.1 GI: 1000701
  Genbank record update date: Feb. 2, 2011 10:15 AM
Polypeptide
  Genbank accession no. CAA47315
  Genbank version no. CAA47315.1 GI: 1000702
  Genbank record update date: Feb. 2, 2011 10:15 AM
Cross References
  Pastorek J., et al *Oncogene* 9 (10), 2877-2888 (1994)
Other Information
  Official Symbol: CA9
  Other Aliases: CAIX, MN
  Other Designations: CA-IX; P54/58N; RCC-associated antigen G250; RCC-associated protein G250; carbonate dehydratase IX; carbonic anhydrase 9; carbonic dehydratase; membrane antigen MN; pMW1; renal cell carcinoma-associated antigen G250
Antibodies
  Abgenix/Amgen: US20040018198
  Affibody: Anti-CAIX Affibody molecules (http://www.affibody.com/en/Product-Portfolio/Pipeline/)
  Bayer: U.S. Pat. No. 7,462,696
  Bayer/Morphosys: 3ee9 mAb—Petrul H M., et al *Mol Cancer Ther.* 2012 February; 11(2):340-9
  Harvard Medical School: Antibodies G10, G36, G37, G39, G45, G57, G106, G119, G6, G27, G40 and G125. Xu C., et al *PLoS One.* 2010 Mar. 10; 5(3):e9625
  Institute of Virology, Slovak Academy of Sciences (Bayer)—U.S. Pat. No. 5,955,075
    for example, M75—ATCC Accession No. HB 11128 or MN12—ATCC Accession No. HB 11647
  Institute of Virology, Slovak Academy of Sciences: U.S. Pat. No. 7,816,493
    for example the M75 monoclonal antibody that is secreted from the hybridoma VU-M75, which was deposited at the American Type Culture Collection under ATCC No. HB 11128; or the V/10 monoclonal antibody secreted from the hybridoma V/10-VU, which was deposited at the International Depository Authority of the Belgian Coordinated Collection of Microorganisms (BCCM) at the Laboratorium voor Moleculaire Bioloqie-Plasmidencollectie (LMBP) at the Universeit Gent in Gent, Belgium, under Accession No. LMBP 6009CB.
  Institute of Virology, Slovak Academy of Sciences US20080177046; US20080176310; US20080176258; US20050031623
  Novartis: US20090252738
  Wilex: U.S. Pat. No. 7,691,375—for example the antibody produced by the hybridoma cell line DSM ASC 2526.
  Wilex: US20110123537; Rencarex: Kennett R H., et al *Curr Opin Mol Ther.* 2003 February; 5(1):70-5
  Xencor: US20090162382

(45) EGFRvIII (Epidermal Growth Factor Receptor (EGFR), Transcript Variant 3,
Nucleotide
  Genbank accession no. NM_201283
  Genbank version no. NM_201283.1 GI: 41327733
  Genbank record update date: Sep. 30, 2012 01:47 PM
Polypeptide
  Genbank accession no. NP_958440
  Genbank version no. NP_958440.1 GI: 41327734
  Genbank record update date: Sep. 30, 2012 01:47 PM
Cross-References
  Batra S K., et al *Cell Growth Differ* 1995; 6:1251-1259.
Antibodies:
  U.S. Pat. Nos. 7,628,986 and 7,736,644 (Amgen)
  For example, a heavy chain variable region amino acid sequence selected from the group consisting of SEQ ID NO: 142 and variants & a light chain variable region amino acid sequence selected from the group consisting of: SEQ ID NO: 144 and variants.
  US20100111979 (Amgen)
  For example, an antibody comprising a heavy chain amino acid sequence comprising:
    CDR1 consisting of a sequence selected from the group consisting of the amino acid sequences for the CDR1 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17);

CDR2 consisting of a sequence selected from the group consisting of the amino acid sequences for the CDR2 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17); and CDR3 consisting of a sequence selected from the group consisting of the amino acid sequences for the CDR3 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).

US20090240038 (Amgen)
For example, an antibody having at least one of the heavy or light chain polypeptides comprises an amino acid sequence that is at least 90% identical to the amino acid sequence selected from the group consisting of: SEQ ID NO: 2, SEQ ID NO: 19, SEQ ID NO: 142, SEQ ID NO: 144, and any combination thereof.

US20090175887 (Amgen)
For example, an antibody having a heavy chain amino acid sequence selected from the group consisting of the heavy chain amino acid sequence of antibody 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).

US20090156790 (Amgen)
For example, antibody having heavy chain polypeptide and a light chain polypeptide, wherein at least one of the heavy or light chain polypeptides comprises an amino acid sequence that is at least 90% identical to the amino acid sequence selected from the group consisting of: SEQ ID NO: 2, SEQ ID NO: 19, SEQ ID NO: 142, SEQ ID NO: 144, and any combination thereof.

US20090155282, US20050059087 and US20050053608 (Amgen)
For example, an antibody heavy chain amino acid sequence selected from the group consisting of the heavy chain amino acid sequence of antibody 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).

MR1-1 (U.S. Pat. No. 7,129,332; Duke)
For example, a variant antibody having the sequence of SEQ ID NO. 18 with the substitutions S98P-T99Y in the CDR3 VH, and F92W in CDR3 VL.

L8A4, H10, Y10 (Wikstrand C J., et al *Cancer Res.* 1995 Jul. 15; 55(14):3140-8; Duke)

US20090311803 (Harvard University)
For example, SEQ ID NO:9 for antibody heavy chain variable region, and SEQ ID NO: 3 for light chain variable region amino acid sequences US20070274991 (EMD72000, also known as matuzumab; Harvard University)
For example, SEQ ID NOs: 3 & 9 for light chain and heavy chain respectively U.S. Pat. No. 6,129,915 (Schering)
For example, SEQ. ID NOs: 1, 2, 3, 4, 5 and 6.

mAb CH12—Wang H., et al *FASEB J.* 2012 January; 26(1):73-80 (Shanghai Cancer Institute).

RAbDMvIII—Gupta P., et al *BMC Biotechnol.* 2010 Oct. 7; 10:72 (Stanford University Medical Center).

mAb Ua30—Ohman L., et al *Tumour Biol.* 2002 March-April; 23(2):61-9 (Uppsala University).

Han D G., et al *Nan Fang Yi Ke Da Xue Xue Bao.* 2010 January; 30(1):25-9 (Xi'an Jiaotong University).

(46) CD33 (CD33 Molecule)
Nucleotide
    Genbank accession no. M_23197
    Genbank version no. NM_23197.1 GI: 180097
    Genbank record update date: Jun. 23, 2010 08:47 AM
Polypeptide
    Genbank accession no. AAA51948
    Genbank version no. AAA51948.1 GI: 188098
    Genbank record update date: Jun. 23, 2010 08:47 AM
Cross-References
    Simmons D., et al *J. Immunol.* 141 (8), 2797-2800 (1988)
Other Information
    Official Symbol: CD33
    Other Aliases: SIGLEC-3, SIGLEC3, p67
    Other Designations: CD33 antigen (gp67); gp67; myeloid cell surface antigen CD33; sialic acid binding Ig-like lectin 3; sialic acid-binding Ig-like lectin
Antibodies
    H195 (Lintuzumab)—Raza A., et al *Leuk Lymphoma.* 2009 August; 50(8):1336-44; U.S. Pat. No. 6,759,045 (Seattle Genetics/Immunomedics)
    mAb OKT9: Sutherland, D. R. et al. *Proc Natl Acad Sci USA* 78(7): 4515-4519 1981, Schneider, C., et al *J Biol Chem* 257, 8516-8522 (1982)
    mAb E6: Hoogenboom, H. R., et al *J Immunol* 144, 3211-3217 (1990)
    U.S. Pat. No. 6,590,088 (Human Genome Sciences)
    For example, SEQ ID NOs: 1 and 2 and ATCC accession no. 97521
    U.S. Pat. No. 7,557,189 (Immunogen)
    For example, an antibody or fragment thereof comprising a heavy chain variable region which comprises three CDRs having the amino acid sequences of SEQ ID NOs:1-3 and a light chain variable region comprising three CDRs having the amino acid sequences of SEQ ID NOs:4-6.

(47) CD19 (CD19 Molecule)
Nucleotide
    Genbank accession no. NM_001178098
    Genbank version no. NM_001178098.1 GI: 296010920
    Genbank record update date: Sep. 10, 2012 12:43 AM
Polypeptide
    Genbank accession no. NP_001171569
    Genbank version no. NP_001171569.1 GI: 296010921
    Genbank record update date: Sep. 10, 2012 12:43 AM
Cross-References
    Tedder T F., et al J. Immunol. 143 (2): 712-7 (1989)
Other Information
    Official Symbol: CD19
    Other Aliases: B4, CVID3
    Other Designations: B-lymphocyte antigen CD19; B-lymphocyte surface antigen B4; T-cell surface antigen Leu-12; differentiation antigen CD19
Antibodies
    Immunogen: HuB4—Al-Katib A M., et al *Clin Cancer Res.* 2009 Jun. 15; 15(12):4038-45.
    4G7: Kügler M., et al *Protein Eng Des Sel.* 2009 March; 22(3):135-47

For example, sequences in FIG. 3 of of Knappik, A. et al. *J Mol Biol* 2000 February; 296(1):57-86

AstraZeneca/MedImmune: MEDI-551—Herbst R., et al *J Pharmacol Exp Ther.* 2010 October; 335(1):213-22

Glenmark Pharmaceuticals: GBR-401—Hou S., et al Mol Cancer Ther November 2011 (Meeting Abstract Supplement) C164

U.S. Pat. No. 7,109,304 (Immunomedics)
For example, an antibody comprising the sequence of hA19Vk (SEQ ID NO:7) and the sequence of hA19VH (SEQ ID NO:10)

U.S. Pat. No. 7,902,338 (Immunomedics)
For example, an antibody or antigen-binding fragment thereof that comprises the light chain complementarity determining region CDR sequences CDR1 of SEQ ID NO: 16 (KASQSVDYDGDSYLN); CDR2 of SEQ ID NO: 17 (DASNLVS); and CDR3 of SEQ ID NO: 18 (QQSTEDPWT) and the heavy chain CDR sequences CDR1 of SEQ ID NO: 19 (SYWMN); CDR2 of SEQ ID NO: 20 (QIWPGDGDTNYNGKFKG) and CDR3 of SEQ ID NO: 21 (RETTTVGRYYYAMDY) and also comprises human antibody framework (FR) and constant region sequences with one or more framework region amino acid residues substituted from the corresponding framework region sequences of the parent murine antibody, and wherein said substituted FR residues comprise the substitution of serine for phenylalanine at Kabat residue 91 of the heavy chain variable region.

Medarex: MDX-1342—Cardarelli P M., et al *Cancer Immunol Immunother.* 2010 February; 59(2):257-65.

MorphoSys/Xencor: MOR-208/XmAb-5574—Zalevsky J., et al *Blood.* 2009 Apr. 16; 113(16):3735-43

U.S. Pat. No. 7,968,687 (Seattle Genetics)
An antibody or antigen-binding fragment comprising a heavy chain variable domain comprising the amino acid sequence of SEQ ID NO:9 and a light chain variable domain comprising the amino acid sequence of SEQ ID NO: 24.

4G7 chim—Lang P., et al Blood. 2004 May 15; 103(10): 3982-5 (University of Tübingen)
For example, FIG. 6 and SEQ ID No: 80 of US20120082664

Zhejiang University School of Medicine: 2E8—Zhang J., et al *J Drug Target.* 2010 November; 18(9):675-8

(48) IL2RA (Interleukin 2 Receptor, Alpha); NCBI Reference Sequence: NM_000417.2);
Nucleotide
Genbank accession no. NM_000417
Genbank version no. NM_000417.2 GI: 269973860
Genbank record update date: Sep. 9, 2012 04:59 PM
Polypeptide
Genbank accession no. NP_000408
Genbank version no. NP_000408.1 GI: 4557667
Genbank record update date: Sep. 9, 2012 04:59 PM
Cross-References
Kuziel W. A., et al *J. Invest. Dermatol.* 94 (6 SUPPL), 27S-32S (1990)
Other Information
Official Symbol: IL2RA
Other Aliases: RP11-536K7.1, CD25, IDDM10, IL2R, TCGFR
Other Designations: FIL-2 receptor subunit alpha; IL-2-RA; IL-2R subunit alpha; IL2-RA; TAC antigen; interleukin-2 receptor subunit alpha; p55

Antibodies
U.S. Pat. No. 6,383,487 (Novartis/UCL: Baxilisimab [Simulect])
U.S. Pat. No. 6,521,230 (Novartis/UCL: Baxilisimab [Simulect])
For example, an antibody having an antigen binding site comprises at least one domain which comprises CDR1 having the amino acid sequence in SEQ. ID. NO: 7, CDR2 having the amino acid sequence in SEQ. ID. NO: 8, and CDR3 having the amino acid sequence in SEQ. ID. NO: 9; or said CDR1, CDR2 and CDR3 taken in sequence as a whole comprise an amino acid sequence which is at least 90% identical to SEQ. ID. NOs: 7, 8 and 9 taken in sequence as a whole.

Daclizumab—Rech A J., et al *Ann N Y Acad Sci.* 2009 September; 1174:99-106 (Roche)

(49) AXL (AXL Receptor Tyrosine Kinase)
Nucleotide
Genbank accession no. M76125
Genbank version no. M76125.1 GI: 292869
Genbank record update date: Jun. 23, 2010 08:53 AM
Polypeptide
Genbank accession no. AAA61243
Genbank version no. AAA61243.1 GI: 29870
Genbank record update date: Jun. 23, 2010 08:53 AM
Cross-References
O'Bryan J. P., et al *Mol. Cell. Biol.* 11 (10), 5016-5031 (1991); Bergsagel P. L., et al *J. Immunol.* 148 (2), 590-596 (1992)
Other Information
Official Symbol: AXL
Other Aliases: JTK11, UFO
Other Designations: AXL oncogene; AXL transforming sequence/gene; oncogene AXL; tyrosine-protein kinase receptor UFO
Antibodies
YW327.6S2—Ye X., et al *Oncogene.* 2010 Sep. 23; 29(38):5254-64. (Genentech)
BergenBio: BGB324 (http://www.bergenbio.com/BGB324)

(50) CD30—TNFRSF8 (Tumor Necrosis Factor Receptor Superfamily, Member 8)
Nucleotide
Genbank accession no. M83554
Genbank version no. M83554.1 GI: 180095
Genbank record update date: Jun. 23, 2010 08:53 AM
Polypeptide
Genbank accession no. AAA51947
Genbank version no. AAA51947.1 GI: 180096
Genbank record update date: Jun. 23, 2010 08:53 AM
Cross-References
Durkop H., et al *Cell* 68 (3), 421-427 (1992)
Other Information
Official Symbol: TNFRSF8
Other Aliases: CD30, D1S166E, Ki-1
Other Designations: CD30L receptor; Ki-1 antigen; cytokine receptor CD30; lymphocyte activation antigen CD30; tumor necrosis factor receptor superfamily member 8

(51) BCMA (B-cell maturation antigen)—TNFRSF17 (Tumor necrosis factor receptor superfamily, member 17)
Nucleotide
Genbank accession no. Z29574
Genbank version no. Z29574.1 GI: 471244
Genbank record update date: Feb. 2, 2011 10:40 AM
Polypeptide
Genbank accession no. CAA82690
Genbank version no. CAA82690.1 GI: 471245
Genbank record update date: Feb. 2, 2011 10:40 AM Cross-References
Laabi Y., et al *Nucleic Acids Res.* 22 (7), 1147-1154 (1994)
Other Information
Official Symbol: TNFRSF17
Other Aliases: BCM, BCMA, CD269
Other Designations: B cell maturation antigen; B-cell maturation factor; B-cell maturation protein; tumor necrosis factor receptor superfamily member 17
(52) CT Ags—CTA (Cancer Testis Antigens)
Cross-References
Fratta E., et al. *Mol Oncol.* 2011 April; 5(2):164-82; Lim S H., at al *Am J Blood Res.* 2012; 2(1):29-35.
(53) CD174 (Lewis Y)—FUT3 (fucosyltransferase 3 (Galactoside 3(4)-L-fucosyltransferase, Lewis Blood Group)
Nucleotide
Genbank accession no. NM000149
Genbank version no. NM000149.3 GI: 148277008
Genbank record update date: Jun. 26, 2012 04:49 PM
Polypeptide
Genbank accession no. NP_000140
Genbank version no. NP_000140.1 GI: 4503809
Genbank record update date: Jun. 26, 2012 04:49 PM
Cross-References
Kukowska-Latallo, J. F., et al *Genes Dev.* 4 (8), 1288-1303 (1990)
Other Information
Official Symbol: FUT3
Other Aliases: CD174, FT3B, FucT-III, LE, Les
Other Designations: Lewis FT; alpha-(1,3/1,4)-fucosyltransferase; blood group Lewis alpha-4-fucosyltransferase; fucosyltransferase III; galactoside 3(4)-L-fucosyltransferase
(54) CLEC14A (C-Type Lectin Domain Family 14, Member a; Genbank Accession No. NM175060)
Nucleotide
Genbank accession no. NM175060
Genbank version no. NM175060.2 GI: 371123930
Genbank record update date: Apr. 1, 2012 03:34 PM
Polypeptide
Genbank accession no. NP_778230
Genbank version no. NP_778230.1 GI: 28269707
Genbank record update date: Apr. 1, 2012 03:34 PM
Other Information
Official Symbol: CLEC14A
Other Aliases: UNQ236/PRO269, C14orf27, CEG1, EGFR-5
Other Designations: C-type lectin domain family 14 member A; CIECT and EGF-like domain containing protein; epidermal growth factor receptor 5
(55) GRP78—HSPA5 (Heat Shock 70 kDa Protein 5 (Glucose-Regulated Protein, 78 kDa)
Nucleotide
Genbank accession no. NM005347
Genbank version no. NM005347.4 GI: 305855105
Genbank record update date: Sep. 30, 2012 01:42 PM
Polypeptide
Genbank accession no. NP_005338
Genbank version no. NP_005338.1 GI: 16507237
Genbank record update date: Sep. 30, 2012 01:42 PM
Cross-References
Ting J., et al *DNA* 7 (4), 275-286 (1988)
Other Information
Official Symbol: HSPA5
Other Aliases: BIP, GRP78, MIF2
Other Designations: 78 kDa glucose-regulated protein; endoplasmic reticulum lumenal Ca(2+)-binding protein grp78; immunoglobulin heavy chain-binding protein

(56) Cd70 (Cd70 Molecule) L08096
Nucleotide
Genbank accession no. L08096
Genbank version no. L08096.1 GI: 307127
Genbank record update date: Jun. 23, 2012 08:54 AM
Polypeptide
Genbank accession no. AAA36175
Genbank version no. AAA36175.1 GI: 307128
Genbank record update date: Jun. 23, 2012 08:54 AM
Cross-References
Goodwin R. G., et al *Cell* 73 (3), 447-456 (1993)
Other Information
Official Symbol: CD70
Other Aliases: CD27L, CD27LG, TNFSF7
Other Designations: CD27 ligand; CD27-L; CD70 antigen; Ki-24 antigen; surface antigen CD70; tumor necrosis factor (ligand) superfamily, member 7; tumor necrosis factor ligand superfamily member 7
Antibodies
MDX-1411 against CD70 (Medarex)
h1F6 (Oflazoglu, E., et al, Clin Cancer Res. 2008 Oct. 1; 14(19):6171-80; Seattle Genetics)
For example, see US20060083736 SEQ ID NOs: 1, 2, 11 and 12 and FIG. 1.
(57) Stem Cell Specific Antigens. For Example:
5T4 (see entry (63) below)
CD25 (see entry (48) above)
CD32
Polypeptide
Genbank accession no. ABK42161
Genbank version no. ABK42161.1 GI: 117616286
Genbank record update date: Jul. 25, 2007 03:00 PM
LGR5/GPR49
Nucleotide
Genbank accession no. NM_003667
Genbank version no. NM_003667.2 GI: 24475886
Genbank record update date: Jul. 22, 2012 03:38 PM
Polypeptide
Genbank accession no. NP_003658
Genbank version no. NP_003658.1 GI: 4504379
Genbank record update date: Jul. 22, 2012 03:38 PM
Prominin/CD133
Nucleotide
Genbank accession no. NM_006017
Genbank version no. NM_006017.2 GI: 224994187
Genbank record update date: Sep. 30, 2012 01:47 PM
Polypeptide
Genbank accession no. NP_006008
Genbank version no. NP_006008.1 GI: 5174387
Genbank record update date: Sep. 30, 2012 01:47 PM
(58) ASG-5
Cross-References
(Smith L. M., et. al *AACR* 2010 *Annual Meeting* (abstract #2590); Gudas J. M., et. al. *AACR* 2010 *Annual Meeting* (abstract #4393)
Antibodies
Anti-AGS-5 Antibody: M6.131 (Smith, L. M., et. al *AACR* 2010 *Annual Meeting* (abstract #2590)
(59) ENPP3 (Ectonucleotide Pyrophosphatase/Phosphodiesterase 3)
Nucleotide
Genbank accession no. AF005632
Genbank version no. AF005632.2 GI: 4432589
Genbank record update date: Mar. 10, 2010 09:41 PM Polypeptide
    Genbank accession no. AAC51813
    Genbank version no. AAC51813.1 GI: 2465540
    Genbank record update date: Mar. 10, 2010 09:41 PM
Cross-References
    Jin-Hua P., et al *Genomics* 45 (2), 412-415 (1997)
Other Information
    Official Symbol: ENPP3
    Other Aliases: RP5-988G15.3, B10, CD203c, NPP3, PD-IBETA, PDNP3
    Other Designations: E-NPP 3; dJ1005H11.3 (phosphodiesterase 1/nucleotide pyrophosphatase 3); dJ914N13.3 (phosphodiesterase 1/nucleotide pyrophosphatase 3); ectonucleotide pyrophosphatase/phosphodiesterase family member 3; gp130RB13-6; phosphodiesterase I beta; phosphodiesterase I/nucleotide pyrophosphatase 3; phosphodiesterase-I beta

(60) PRR4 (Proline Rich 4 (Lacrimal))
Nucleotide
    Genbank accession no. NM_007244
    Genbank version no. NM_007244.2 GI: 154448885
    Genbank record update date: Jun. 28, 2012 12:39 PM
Polypeptide
    Genbank accession no. NP_009175
    Genbank version no. NP_009175.2 GI: 154448886
    Genbank record update date: Jun. 28, 2012 12:39 PM
Cross-References
    Dickinson D. P., et al *Invest. Ophthalmol. Vis. Sci.* 36 (10), 2020-2031 (1995)
Other Information
    Official Symbol: PRR4
    Other Aliases: LPRP, PROL4
    Other Designations: lacrimal proline-rich protein; nasopharyngeal carcinoma-associated proline-rich protein 4; proline-rich polypeptide 4; proline-rich protein 4

(61) GCC—GUCY2C (Guanylate Cyclase 2C (Heat Stable Enterotoxin Receptor)
Nucleotide
    Genbank accession no. NM_004963
    Genbank version no. NM_004963.3 GI: 222080082
    Genbank record update date: Sep. 2, 2012 01:50 PM
Polypeptide
    Genbank accession no. NP_004954
    Genbank version no. NP_004954.2 GI: 222080083
    Genbank record update date: Sep. 2, 2012 01:50 PM
Cross-References
    De Sauvage F. J., et al *J. Biol. Chem.* 266 (27), 17912-17918 (1991); Singh S., et al *Biochem. Biophys. Res. Commun.* 179 (3), 1455-1463 (1991)
Other Information
    Official Symbol: GUCY2C
    Other Aliases: DIAR6, GUC2C, MUCIL, STAR
    Other Designations: GC-C; STA receptor; guanylyl cyclase C; hSTAR; heat-stable enterotoxin receptor; intestinal guanylate cyclase

(62) Liv-1—SLC39A6 (Solute Carrier Family 39 (Zinc Transporter), Member 6)
Nucleotide
    Genbank accession no. U41060
    Genbank version no. U41060.2 GI: 12711792
    Genbank record update date: Nov. 30, 2009 04:35 PM
Polypeptide
    Genbank accession no. AAA96258
    Genbank version no. AAA96258.2 GI: 12711793
    Genbank record update date: Nov. 30, 2009 04:35 PM
Cross-References
    Taylor K M., et al *Biochim Biophys Acta.* 2003 Apr. 1; 1611(1-2):16-30
Other Information
    Official Symbol: SLC39A6
    Other Aliases: LIV-1
    Other Designations: LIV-1 protein, estrogen regulated; ZIP-6; estrogen-regulated protein LIV-1; solute carrier family 39 (metal ion transporter), member 6; solute carrier family 39 member 6; zinc transporter ZIP6; zrt- and lrt-like protein 6

(63) 5T4, Trophoblast Glycoprotein, TPBG—TPBG (Trophoblast Glycoprotein)
Nucleotide
    Genbank accession no. AJ012159
    Genbank version no. AJ012159.1 GI: 3805946
    Genbank record update date: Feb. 1, 2011 10:27 AM
Polypeptide
    Genbank accession no. CAA09930
    Genbank version no. CAA09930.1 GI: 3805947
    Genbank record update date: Feb. 1, 2011 10:27 AM
Cross-References
    King K. W., et al *Biochim. Biophys. Acta* 1445 (3), 257-270 (1999)
Other Information
    Official Symbol: TPBG
    Other Aliases: 5T4, 5T4AG, M6P1
    Other Designations: 5T4 oncofetal antigen; 5T4 oncofetal trophoblast glycoprotein; 5T4 oncotrophoblast glycoprotein
    See WO2015/155345

(64) CD56—NCMA1 (Neural Cell Adhesion Molecule 1)
Nucleotide
    Genbank accession no. NM_000615
    Genbank version no. NM_000615.6 GI: 336285433
    Genbank record update date: Sep. 23, 2012 02:32 PM
Polypeptide
    Genbank accession no. NP_000606
    Genbank version no. NP_000606.3 GI: 94420689
    Genbank record update date: Sep. 23, 2012 02:32 PM
Cross-References
    Dickson, G., et al, *Cell* 50 (7), 1119-1130 (1987)
Other Information
    Official Symbol: NCAM1
    Other Aliases: CD56, MSK39, NCAM
    Other Designations: antigen recognized by monoclonal antibody 5.1H11; neural cell adhesion molecule, NCAM
Antibodies
    Immunogen: HuN901 (Smith S V., et al *Curr Opin Mol Ther.* 2005 August; 7(4):394-401)
    For example, see humanized from murine N901 antibody. See FIGS. 1b and 1e of Roguska, M. A., et al. Proc Natl Acad Sci USA February 1994; 91:969-973.

(65) CanAg (Tumor Associated Antigen CA242)
Cross-References
    Haglund C., et al *Br J Cancer* 60:845-851, 1989; Baeckstrom D., et al *J Biol Chem* 266:21537-21547, 1991
Antibodies
    huC242 (Tolcher A W et al., *J Clin Oncol.* 2003 Jan. 15; 21(2):211-22; Immunogen)
    For example, see US20080138898A1 SEQ ID NO: 1 and 2

(66) FOLR1 (Folate Receptor 1)
Nucleotide
    Genbank accession no. J05013
    Genbank version no. J05013.1 GI: 182417
    Genbank record update date: Jun. 23, 2010 08:47 AM Polypeptide
    Genbank accession no. AAA35823
    Genbank version no. AAA35823.1 GI: 182418
    Genbank record update date: Jun. 23, 2010 08:47 AM
Cross-References
    Elwood P. C., et al *J. Biol. Chem.* 264 (25), 14893-14901 (1989)
Other Information
    Official Symbol: FOLR1
    Other Aliases: FBP, FOLR
    Other Designations: FR-alpha; KB cells FBP; adult folate-binding protein; folate binding protein; folate receptor alpha; folate receptor, adult; ovarian tumor-associated antigen MOv18
Antibodies
    M9346A—Whiteman K R., et al *Cancer Res* Apr. 15, 2012; 72(8 Supplement): 4628 (Immunogen)
(67) GPNMB (Glycoprotein (transmembrane) nmb)
Nucleotide
    Genbank accession no. X76534
    Genbank version no. X76534.1 GI: 666042
    Genbank record update date: Feb. 2, 2011 10:10 AM
Polypeptide
    Genbank accession no. CAA54044
    Genbank version no. CAA54044.1 GI: 666043
    Genbank record update date: Feb. 2, 2011 10:10 AM
Cross-References
    Weterman M. A., et al *Int. J. Cancer* 60 (1), 73-81 (1995)
Other Information
    Official Symbol: GPNMB
    Other Aliases: UNQ1725/PRO9925, HGFIN, NMB
    Other Designations: glycoprotein NMB; glycoprotein nmb-like protein; osteoactivin; transmembrane glycoprotein HGFIN; transmembrane glycoprotein NMB
Antibodies
    Celldex Therapeutics: CR011 (Tse K F., et al *Clin Cancer Res.* 2006 Feb. 15; 12(4):1373-82)
        For example, see EP1827492B1 SEQ ID NO: 22, 24, 26, 31, 33 and 35
(68) TIM-1—HAVCR1 (Hepatitis a Virus Cellular Receptor 1)
Nucleotide
    Genbank accession no. AF043724
    Genbank version no. AF043724.1 GI: 2827453
    Genbank record update date: Mar. 10, 2010 06:24 PM
Polypeptide
    Genbank accession no. AAC39862
    Genbank version no. AAC39862.1 GI: 2827454
    Genbank record update date: Mar. 10, 2010 06:24 PM
Cross-References
    Feigelstock D., et al *J. Virol.* 72 (8), 6621-6628 (1998)
Other Information
    Official Symbol: HAVCR1
    Other Aliases: HAVCR, HAVCR-1, KIM-1, KIM1, TIM, TIM-1, TIM1, TIMD-1, TIMD1
    Other Designations: T cell immunoglobin domain and mucin domain protein 1; T-cell membrane protein 1; kidney injury molecule 1
(69) RG-1/Prostate Tumor Target Mindin—Mindin/RG-1
Cross-References
    Parry R., et al *Cancer Res.* 2005 Sep. 15; 65(18):8397-405

(70) B7-H4—VTCN1 (V-Set Domain Containing T Cell Activation Inhibitor 1
Nucleotide
    Genbank accession no. BX648021
    Genbank version no. BX648021.1 GI: 34367180
    Genbank record update date: Feb. 2, 2011 08:40 AM
Cross-References
    Sica G L., et al *Immunity.* 2003 June; 18(6):849-61
Other Information
    Official Symbol: VTCN1
    Other Aliases: RP11-229A19.4, B7-H4, B7H4, B7S1, B7X, B7h.5, PRO1291, VCTN1
    Other Designations: B7 family member, H4; B7 superfamily member 1; T cell costimulatory molecule B7x; T-cell costimulatory molecule B7x; V-set domain-containing T-cell activation inhibitor 1; immune costimulatory protein B7-H4
(71) PTK7 (PTK7 Protein Tyrosine Kinase 7)
Nucleotide
    Genbank accession no. AF447176
    Genbank version no. AF447176.1 GI: 17432420
    Genbank record update date: Nov. 28, 2008 01:51 PM
Polypeptide
    Genbank accession no. AAL39062
    Genbank version no. AAL39062.1 GI: 17432421
    Genbank record update date: Nov. 28, 2008 01:51 PM
Cross-References
    Park S. K., et al *J. Biochem.* 119 (2), 235-239 (1996)
Other Information
    Official Symbol: PTK7
    Other Aliases: CCK-4, CCK4
    Other Designations: colon carcinoma kinase 4; inactive tyrosine-protein kinase 7; pseudo tyrosine kinase receptor 7; tyrosine-protein kinase-like 7
(72) Cd37 (Cd37 Molecule)
Nucleotide
    Genbank accession no. NM_001040031
    Genbank version no. NM_001040031.1 GI: 91807109
    Genbank record update date: Jul. 29, 2012 02:08 PM
Polypeptide
    Genbank accession no. NP_001035120
    Genbank version no. NP_001035120.1 GI: 91807110
    Genbank record update date: Jul. 29, 2012 02:08 PM
Cross-References
    Schwartz-Albiez R., et al *J. Immunol.* 140 (3), 905-914 (1988)
Other Information
    Official Symbol: CD37
    Other Aliases: GP52-40, TSPAN26
    Other Designations: CD37 antigen; cell differentiation antigen 37; leukocyte antigen CD37; leukocyte surface antigen CD37; tetraspanin-26; tspan-26
Antibodies
    Boehringer Ingelheim: mAb 37.1 (Heider K H., et al *Blood.* 2011 Oct. 13; 118(15):4159-68)
    Trubion: CD37-SMIP (G28-1 scFv-lg) ((Zhao X., et al *Blood.* 2007; 110: 2569-2577)
    For example, see US20110171208A1 SEQ ID NO: 253
    Immunogen: K7153A (Deckert J., et al *Cancer Res* Apr. 15, 2012; 72(8 Supplement): 4625)
(73) CD138—SDC1 (Syndecan 1)
Nucleotide
    Genbank accession no. AJ551176
    Genbank version no. AJ551176.1 GI: 29243141
    Genbank record update date: Feb. 1, 2011 12:09 PM Polypeptide
 Genbank accession no. CAD80245
 Genbank version no. CAD80245.1 GI: 29243142
 Genbank record update date: Feb. 1, 2011 12:09 PM
Cross-References
 O'Connell F P., et al *Am J Clin Pathol.* 2004 February; 121(2):254-63
Other Information
 Official Symbol: SDC1
 Other Aliases: CD138, SDC, SYND1, syndecan
 Other Designations: CD138 antigen; heparan sulfate proteoglycan fibroblast growth factor receptor; syndecan proteoglycan 1; syndecan-1
Antibodies
 Biotest: chimerized MAb (nBT062)—(Jagannath S., et al Poster ASH #3060, 2010; WIPO Patent Application WO/2010/128087)
  For example, see US20090232810 SEQ ID NO: 1 and 2
 Immunogen: B-B4 (Tassone P., et al *Blood* 104_3688-3696)
  For example, see US20090175863A1 SEQ ID NO: 1 and 2

(74) CD74 (CD74 Molecule, Major Histocompatibility Complex, Class II Invariant Chain)
Nucleotide
 Genbank accession no. NM_004355
 Genbank version no. NM_004355.1 GI: 343403784
 Genbank record update date: Sep. 23, 2012 02:30 PM
Polypeptide
 Genbank accession no. NP_004346
 Genbank version no. NP_004346.1 GI: 10835071
 Genbank record update date: Sep. 23, 2012 02:30 PM
Cross-References
 Kudo, J., et al *Nucleic Acids Res.* 13 (24), 8827-8841 (1985)
Other Information
 Official Symbol: CD74
 Other Aliases: DHLAG, HLADG, II, Ia-GAMMA
 Other Designations: CD74 antigen (invariant polypeptide of major histocompatibility complex, class II antigen-associated); HLA class II histocompatibility antigen gamma chain; HLA-DR antigens-associated invariant chain; HLA-DR-gamma; Ia-associated invariant chain; MHC HLA-DR gamma chain; gamma chain of class II antigens; p33
Antibodies
 Immunomedics: hLL1 (Milatuzumab)—Berkova Z., et al *Expert Opin Investig Drugs.* 2010 January; 19(1):141-9)
  For example, see US20040115193 SEQ ID NOs: 19, 20, 21, 22, 23 and 24
 Genmab: HuMax-CD74 (see website)

(75) Claudins—CLs (Claudins)
Cross-References
 Offner S., et al *Cancer Immunol Immunother.* 2005 May; 54(5):431-45, Suzuki H., et al *Ann N Y Acad Sci.* 2012 July; 1258:65-70)
 In humans, 24 members of the family have been described—see literature reference.

(76) EGFR (Epidermal Growth Factor Receptor)
Nucleotide
 Genbank accession no. NM_005228
 Genbank version no. NM_005228.3 GI: 41927737
 Genbank record update date: Sep. 30, 2012 01:47 PM
Polypeptide
 Genbank accession no. NP_005219
 Genbank version no. NP_005219.2 GI: 29725609
 Genbank record update date: Sep. 30, 2012 01:47 PM
Cross-References
 Dhomen N S., et al *Crit Rev Oncog.* 2012; 17(1):31-50
Other Information
 Official Symbol: EGFR
 Other Aliases: ERBB, ERBB1, HER1, PIG61, mENA
 Other Designations: avian erythroblastic leukemia viral (v-erb-b) oncogene homolog; cell growth inhibiting protein 40; cell proliferation-inducing protein 61; proto-oncogene c-ErbB-1; receptor tyrosine-protein kinase erbB-1
Antibodies
 BMS: Cetuximab (Erbitux)—Broadbridge V T., et al *Expert Rev Anticancer Ther.* 2012 May; 12(5):555-65.
  For example, see U.S. Pat. No. 6,217,866—ATTC deposit No. 9764.
 Amgen: Panitumumab (Vectibix)—Argiles G., et al *Future Oncol.* 2012 April; 8(4):373-89
  For example, see U.S. Pat. No. 6,235,883 SEQ ID NOs: 23-38.
 Genmab: Zalutumumab—Rivera F., et al *Expert Opin Biol Ther.* 2009 May; 9(5):667-74.
 YM Biosciences: Nimotuzumab—Ramakrishnan M S., et al MAbs. 2009 January-February; 1(1):41-8.
  For example, see U.S. Pat. No. 5,891,996 SEQ ID NOs: 27-34.

(77) Her3 (ErbB3)—ERBB3 (v-erb-b2 Erythroblastic Leukemia Viral Oncogene Homolog 3 (Avian))
Nucleotide
 Genbank accession no. M34309
 Genbank version no. M34309.1 GI: 183990
 Genbank record update date: Jun. 23, 2010 08:47 PM
Polypeptide
 Genbank accession no. AAA35979
 Genbank version no. AAA35979.1 GI: 306841
 Genbank record update date: Jun. 23, 2010 08:47 PM
Cross-References
 Plowman, G. D., et al., *Proc. Natl. Acad. Sci. U.S.A.* 87 (13), 4905-4909 (1990)
Other Information
 Official Symbol: ERBB3
 Other Aliases: ErbB-3, HER3, LCCS2, MDA-BF-1, c-erbB-3, c-erbB3, erbB3-S, p180-ErbB3, p45-sErbB3, p85-sErbB3
 Other Designations: proto-oncogene-like protein c-ErbB-3; receptor tyrosine-protein kinase erbB-3; tyrosine kinase-type cell surface receptor HER3
Antibodies
 Merimack Pharma: MM-121 (Schoeberl B., et al *Cancer Res.* 2010 Mar. 15; 70(6):2485-2494)
  For example, see US2011028129 SEQ ID NOs: 1, 2, 3, 4, 5, 6, 7 and 8.

(78) RON—MST1R (Macrophage Stimulating I Receptor (c-Met-Related Tyrosine Kinase))
Nucleotide
 Genbank accession no. X70040
 Genbank version no. X70040.1 GI: 36109
 Genbank record update date: Feb. 2, 2011 10:17 PM
Polypeptide
 Genbank accession no. CCA49634
 Genbank version no. CCA49634.1 GI: 36110
 Genbank record update date: Feb. 2, 2011 10:17 PM
Cross-References
 Ronsin C., et al *Oncogene* 8 (5), 1195-1202 (1993)
Other Information
 Official Symbol: MST1R
 Other Aliases: CD136, CDw136, PTK8, RON
 Other Designations: MSP receptor; MST1R variant RON30; MST1R variant RON62; PTK8 protein tyrosine kinase 8; RON variant E2E3; c-met-related tyrosine kinase;

macrophage-stimulating protein receptor; p185-Ron; soluble RON variant 1; soluble RON variant 2; soluble RON variant 3; soluble RONvariant 4

(79) EPHA2 (EPH Receptor A2)
Nucleotide
  Genbank accession no. BC037166
  Genbank version no. BC037166.2 GI: 33879863
  Genbank record update date: Mar. 6, 2012 01:59 PM
Polypeptide
  Genbank accession no. AAH37166
  Genbank version no. AAH37166.1 GI: 22713539
  Genbank record update date: Mar. 6, 2012 01:59 PM
Cross-References
  Strausberg R. L., et al *Proc. Natl. Acad. Sci. U.S.A.* 99 (26), 16899-16903 (2002)
Other Information
  Official Symbol: EPHA2
  Other Aliases: ARCC2, CTPA, CTPP1, ECK
  Other Designations: ephrin type-A receptor 2; epithelial cell receptor protein tyrosine kinase; soluble EPHA2 variant 1; tyrosine-protein kinase receptor ECK
Antibodies
  Medimmune: 1C1 (Lee J W., et al *Clin Cancer Res.* 2010 May 1; 16(9):2562-2570)
    For example, see US20090304721A1 FIGS. 7 and 8.
(80) CD20—MS4A1 (Membrane-Spanning 4-Domains, Subfamily A, Member 1)
Nucleotide
  Genbank accession no. M27394
  Genbank version no. M27394.1 GI: 179307
  Genbank record update date: Nov. 30, 2009 11:16 AM
Polypeptide
  Genbank accession no. AAA35581
  Genbank version no. AAA35581.1 GI: 179308
  Genbank record update date: Nov. 30, 2009 11:16 AM
Cross-References
  Tedder T. F., et al *Proc. Natl. Acad. Sci. U.S.A.* 85 (1), 208-212 (1988)
Other Information
  Official Symbol: MS4A1
  Other Aliases: B1, Bp35, CD20, CVID5, LEU-16, MS4A2, S7
  Other Designations: B-lymphocyte antigen CD20; B-lymphocyte cell-surface antigen B1; CD20 antigen; CD20 receptor; leukocyte surface antigen Leu-16
Antibodies
  Genentech/Roche: Rituximab—Abdulla N E., et al *BioDrugs.* 2012 Apr. 1; 26(2):71-82.
    For example, see U.S. Pat. No. 5,736,137, ATCC deposit No. HB-69119.
  GSK/Genmab: Ofatumumab—Nightingale G., et al Ann Pharmacother. 2011 October; 45(10):1248-55.
    For example, see US20090169550A1 SEQ ID NOs: 2, 4 and 5.
  Immunomedics: Veltuzumab—Goldenberg D M., et al *Leuk Lymphoma.* 2010 May; 51(5):747-55.
    For example, see U.S. Pat. No. 7,919,273B2 SEQ ID NOs: 1, 2, 3, 4, 5 and 6.
(81) Tenascin C—TNC (Tenascin C)
Nucleotide
  Genbank accession no. NM_002160
  Genbank version no. NM_002160.3 GI: 340745336
  Genbank record update date: Sep. 23, 2012 02:33 PM
Polypeptide
  Genbank accession no. NP_002151
  Genbank version no. NP_002151.2 GI: 153946395
  Genbank record update date: Sep. 23, 2012 02:33 PM
Cross-References
  Nies D. E., et al *J. Biol. Chem.* 266 (5), 2818-2823 (1991); Siri A., et al *Nucleic Acids Res.* 19 (3), 525-531 (1991)
Other Information
  Official Symbol: TNC
  Other Aliases: 150-225, GMEM, GP, HXB, JI, TN, TN-C
  Other Designations: GP 150-225; cytotactin; glioma-associated-extracellular matrix antigen; hexabrachion (tenascin); myotendinous antigen; neuronectin; tenascin; tenascin-C isoform 14/AD1/16
Antibodies
  Philogen: G11 (von Lukowicz T., et al *J Nucl Med.* 2007 April; 48(4):582-7) and F16 (Pedretti M., et al *Lung Cancer.* 2009 April; 64(1):28-33)
    For example, see U.S. Pat. No. 7,968,685 SEQ ID NOs: 29, 35, 45 and 47.
(82) FAP (Fibroblast Activation Protein, Alpha)
Nucleotide
  Genbank accession no. U09278
  Genbank version no. U09278.1 GI: 1888315
  Genbank record update date: Jun. 23, 2010 09:22 AM
Polypeptide
  Genbank accession no. AAB49652
  Genbank version no. AAB49652.1 GI: 1888316
  Genbank record update date: Jun. 23, 2010 09:22 AM
Cross-References
  Scanlan, M. J., et al *Proc. Natl. Acad. Sci. U.S.A.* 91 (12), 5657-5661 (1994)
Other Information
  Official Symbol: FAP
  Other Aliases: DPPIV, FAPA
  Other Designations: 170 kDa melanoma membrane-bound gelatinase; integral membrane serine protease; seprase
(83) DKK-1 (Dickkopf 1 Homolog (*Xenopus laevis*)
Nucleotide
  Genbank accession no. NM_012242
  Genbank version no. NM_012242.2 GI: 61676924
  Genbank record update date: Sep. 30, 2012 01:48 PM
Polypeptide
  Genbank accession no. NP_036374
  Genbank version no. NP_036374.1 GI: 7110719
  Genbank record update date: Sep. 30, 2012 01:48 PM
Cross-References
  Fedi P. et al *J. Biol. Chem.* 274 (27), 19465-19472 (1999)
Other Information
  Official Symbol: DKK1
  Other Aliases: UNQ492/PRO1008, DKK-1, SK
  Other Designations: dickkopf related protein-1; dickkopf-1 like; dickkopf-like protein 1; dickkopf-related protein 1; hDkk-1
Antibodies
  Novartis: BHQ880 (Fulciniti M., et al *Blood.* 2009 Jul. 9; 114(2):371-379)
    For example, see US20120052070A1 SEQ ID NOs: 100 and 108.
(84) CD52 (CD52 Molecule)
Nucleotide
  Genbank accession no. NM_001803
  Genbank version no. NM_001803.2 GI: 68342029
  Genbank record update date: Sep. 30, 2012 01:48 PM
Polypeptide
  Genbank accession no. NP_001794
  Genbank version no. NP_001794.2 GI: 68342030
  Genbank record update date: Sep. 30, 2012 01:48 PM Cross-References
Xia M. Q., et al *Eur. J. Immunol.* 21 (7), 1677-1684 (1991)
Other Information
  Official Symbol: CD52
  Other Aliases: CDW52
  Other Designations: CAMPATH-1 antigen; CD52 antigen (CAMPATH-1 antigen); CDW52 antigen (CAMPATH-1 antigen); cambridge pathology 1 antigen; epididymal secretory protein E5; he5; human epididymis-specific protein 5
Antibodies
  Alemtuzumab (Campath)—Skoetz N., et al *Cochrane Database Syst Rev.* 2012 Feb. 15; 2:CD008078.
    For example, see Drugbank Acc. No. DB00087 (BIOD00109, BTD00109)
(85) CS1—SLAMF7 (SLAM Family Member 7)
Nucleotide
  Genbank accession no. NM_021181
  Genbank version no. NM_021181.3 GI: 1993571
  Genbank record update date: Jun. 29, 2012 11:24 AM
Polypeptide
  Genbank accession no. NP_067004
  Genbank version no. NP_067004.3 GI: 19923572
  Genbank record update date: Jun. 29, 2012 11:24 AM
Cross-References
  Boles K. S., et al *Immunogenetics* 52 (3-4), 302-307 (2001)
Other Information
  Official Symbol: SLAMF7
  Other Aliases: UNQ576/PRO1138, 19A, CD319, CRACC, CS1
  Other Designations: 19A24 protein; CD2 subset 1; CD2-like receptor activating cytotoxic cells; CD2-like receptor-activating cytotoxic cells; membrane protein FOAP-12; novel LY9 (lymphocyte antigen 9) like protein; protein 19A
Antibodies
  BMS: elotuzumab/HuLuc63 (Benson D M., et al *J Clin Oncol.* 2012 Jun. 1; 30(16):2013-2015)
    For example, see US20110206701 SEQ ID NOs: 9, 10, 11, 12, 13, 14, 15 and 16.
(86) Endoglin—ENG (Endoglin)
Nucleotide
  Genbank accession no. AF035753
  Genbank version no. AF035753.1 GI: 3452260
  Genbank record update date: Mar. 10, 2010 06:36 PM
Polypeptide
  Genbank accession no. AAC32802
  Genbank version no. AAC32802.1 GI: 3452261
  Genbank record update date: Mar. 10, 2010 06:36 PM
Cross-References
  Rius C., et al *Blood* 92 (12), 4677-4690 (1998)
  Official Symbol: ENG
Other Information
  Other Aliases: RP11-228B15.2, CD105, END, HHT1, ORW, ORW1
  Other Designations: CD105 antigen
(87) Annexin A1—ANXA1 (Annexin A1)
Nucleotide
  Genbank accession no. X05908
  Genbank version no. X05908.1 GI: 34387
  Genbank record update date: Feb. 2, 2011 10:02 AM
Polypeptide
  Genbank accession no. CCA29338
  Genbank version no. CCA29338.1 GI: 34388
  Genbank record update date: Feb. 2, 2011 10:02 AM
Cross-References
  Wallner B. P., et al *Nature* 320 (6057), 77-81 (1986)
Other Information
  Official Symbol: ANXA1
  Other Aliases: RP11-71A24.1, ANX1, LPC1
  Other Designations: annexin I (lipocortin I); annexin-1; calpactin II; calpactin-2; chromobindin-9; lipocortin I; p35; phospholipase A2 inhibitory protein
(88) V-CAM (CD106)—VCAM1 (Vascular Cell Adhesion Molecule 1)
Nucleotide
  Genbank accession no. M60335
  Genbank version no. M60335.1 GI: 340193
  Genbank record update date: Jun. 23, 2010 08:56 AM
Polypeptide
  Genbank accession no. AAA61269
  Genbank version no. AAA61269.1 GI: 340194
  Genbank record update date: Jun. 23, 2010 08:56 AM
Cross-References
  Hession C., et al *J. Biol. Chem.* 266 (11), 6682-6685 (1991)
Other Information
  Official Symbol VCAM1
  Other Aliases: CD106, INCAM-100
  Other Designations: CD106 antigen; vascular cell adhesion protein 1

```
Antibody Sequences
Anti-Integrin αvβ6
RHAB6.2
                                                             (SEQ ID NO: 5)
QVQLVQSGSELKKPGASVKISCKASGFAFTDSYMHWVRQAPGQGLEWMGWIDPENGDT

EYAPKFQGRFVFSLDTSVSTAYLQISSLKAEDTAVYYCTRGTPTAVPNLRGDLQVLAQKVA

GPYPFDYWGQGTLVTVSS

RHCB6.2
                                                             (SEQ ID NO: 6)
QVQLVQSGAEVKKPGASVKVSCKASGYTFIDSYMHWVRQAPGQRLEWMGWIDPENGDT

EYAPKFQGRVTITTDTSASTAYMELSSLRSEDTAVYYCARGTPTAVPNLRGDLQVLAQKV

AGPYPFDYWGQGTLVTVSS

RHF
```

-continued

```
                                                   (SEQ ID NO: 7)
QVQLVQSGAEVKKPGASVKVSCKASGFNFIDSYMHWVRQAPGQRLEWMGWIDPENGD

TEYAPKFQGRVTFTTDTSASTAYMELSSLRSEDTAVYYCNEGTPTGPYYFDYWGQGTLV

TVSS

RHFB6
                                                   (SEQ ID NO: 8)
QVQLVQSGAEVKKPGASVKVSCKASGFNFIDSYMHWVRQAPGQRLEWMGWDPENGD

TEYAPKFQGRVTFTTDTSASTAYMELSSLRSEDTAVYYCNEGTPTAVPNLRGDLQVLAQK

VAGPYYFDYWGQGTLVTVSS

RHAY100bP
                                                   (SEQ ID NO: 9)
QVQLVQSGSELKKPGASVKISCKASGFAFTDSYMHWVRQAPGQGLEWMGWIDPENGDT

EYAPKFQGRFVFSLDTSVSTAYLQISSLKAEDTAVYYCTRGTPTGPYPFDYWGQGTLVTV

SS

RKF
                                                   (SEQ ID NO: 10)
ENVLTQSPGTLSLSPGERATLSCSASSSVSYMHWFQQKPGQAPRLLIYSTSNLASGIPDR

FSGSGSGTDFTLTISRLEPEDFAVYYCQQRSSYPLTFGGGTKVEIK

RKFL36L50
                                                   (SEQ ID NO: 11)
ENVLTQSPGTLSLSPGERATLSCSASSSVSYMHWLQQKPGQAPRLLIYLTSNLASGIPDR

FSGSGSGTDFTLTISRLEPEDFAVYYCQQRSSYPLTFGGGTKVEIK

RKC
                                                   (SEQ ID NO: 12)
EIVLTQSPGTLSLSPGERATLSCSASSSVSYMHWFQQKPGQAPRLLIYSTSNLASGIPDRF

SGSGSGTDFTLTISRLEPEDFAVYYCQQRSSYPLTFGGGTKVEIK

Anti-CD33
CD33 Hum195 VH
                                                   (SEQ ID NO: 13)
QVQLVQSGAEVKKPGSSVKVSCKASGYTFTDYNMHWVRQAPGQGLEWIGYIYPYNGGT

GYNQKFKSKATITADESTNTAYMELSSLRSEDTAVYYCARGRPAMDYWGQGTLVTVSS

CD33 Hum195 VK
                                                   (SEQ ID NO: 14)
DIQMTQSPSSLSASVGDRVTITCRASESVDNYGISFMNWFQQKPGKAPKLLIYAASNQGS

GVPSRFSGSGSGTDFTLTISSLQPDDFATYYCQQSKEVPWTFGQGTKVEIK

Anti-CD19
CD19 B4 resurfaced VH
                                                   (SEQ ID NO: 15)
QVQLVQPGAEVVKPGASVKLSCKTSGYTFTSNWMHWVKQRPGQGLEWIGEIDPSDSYT

NYNQNFKGKAKLTVDKSTSTAYMEVSSLRSDDTAVYYCARGSNPYYYAMDYWGQGTSV

TVSS

CD19 B4 resurfaced VK
                                                   (SEQ ID NO: 16)
EIVLTQSPAIMSASPGERVTMTCSASSGVNYMHWYQQKPGTSPRRWIYDTSKLASGVPA

RFSGSGSGTSYSLTISSMEPEDAATYYCHQRGSYTFGGGTKLEIK

Anti-Her2
Herceptin VH chain
                                                   (SEQ ID NO: 1)
EVQLVESGGGLVQPGGSLRLSCAASGFNIKDTYIHWVRQAPGKGLEWVARIYPTNGYTR

YADSVKGRFTISADTSKNTAYLQMNSLRAEDTAVYYCSRWGGDGFYAMDYWGQGTLVT

VSS
```

-continued

```
Herceptin VL chain
                                                    (SEQ ID NO: 2)
DIQMTQSPSSLSASVGDRVTITCRASQDVNTAVAWYQQKPGKAPKLLIYSASFLYSGVPS

RFSGSRSGTDFTLTISSLQPEDFATYYCQQHYTTPPTFGQGTKVEIK

Anti-CD25
Simulect VK (also known as Basiliximab)
                                                    (SEQ ID NO: 17)
QIVSTQSPAIMSASPGEKVTMTCSASSSRSYMQWYQQKPGTSPKRWIYDTSKLASGVPA

RFSGSGSGTSYSLTISSMEAEDAATYYCHQRSSYTFGGGTKLEIK

Simulect VH
                                                    (SEQ ID NO: 18)
QLQQSGTVLARPGASVKMSCKASGYSFTRYWMHWIKQRPGQGLEWIGAIYPGNSDTSY

NQKFEGKAKLTAVTSASTAYMELSSLTHEDSAVYYCSRDYGYYFDFWGQGTTLTVSS

Anti-PSMA
Deimmunised VH '1
                                                    (SEQ ID NO: 19)
EVQLVQSGPEVKKPGATVKISCKTSGYTFTEYTIHWVKQAPGKGLEWIGNINPNNGGTTY

NQKFEDKATLTVDKSTDTAYMELSSLRSEDTAVYYCAAGWNFDYWGQGTLLTVSS

Deimmunised VK '1
                                                    (SEQ ID NO: 20)
DIQMTQSPSSLSTSVGDRVTLTCKASQDVGTAVDWYQQKPGPSPKLLIYWASTRHTGIPS

RFSGSGSGTDFTLTISSLQPEDFADYYCQQYNSYPLTFGPGTKVDIK

Deimmunised VH1 '5
                                                    (SEQ ID NO: 21)
EVKLVESGGGLVQPGGSMKLSCVASGFTFSNYWMNWVRQAPGKGLEWVAEIRSQSNN

FATHYAESVKGRVTISRDDSKSIVYLQMNNLRAEDTGVYYCTRRWNNFWGQGTTVTVSS

Deimmunised VH2 '5
                                                    (SEQ ID NO: 22)
EVKLVESGGGLVQPGGSLKLSCVASGFTFSNYWMNWVRQAPGKGLEWVAEIRSQSNNF

ATHYAESVKGRVTISRDDSKSIVYLQMNNLRAEDTAVYYCTRRWNNFWGQGTTVTVSS

Deimmunised VH3 '5
                                                    (SEQ ID NO: 23)
EVQLVESGGGLVQPGGSLKLSCVASGFTFSNYWMNWVRQAPGKGLEWVAEIRSQSNNF

ATHYAESVKGRVTISRDDSKSIVYLQMNNLRAEDTAVYYCTRRWNNFWGQGTTVTVSS

Deimmunised VH4 '5
                                                    (SEQ ID NO: 24)
EVQLVESGGGLVQPGGSLKLSCVASGFTFSNYWMNWVRQAPGKGLEWVAEIRSQSNNF

ATHYAESVKGRFTISRDDSKSIVYLQMNNLRAEDTAVYYCTRRWNNFWGQGTTVTVSS

Deimmunised VK1 '5
                                                    (SEQ ID NO: 25)
NIVMTQFPSSMSASVGDRVTITCKASENVGTYVSWYQQKPDQSPKMLIYGASNRFTGVP

DRFTGSGSATDFTLTISSLQTEDLADYYCGQSYTFPYTFGQGTKLEMK

Deimmunised VK2 '5
                                                    (SEQ ID NO: 26)
NIVMTQFPSSMSASVGDRVTITCKASENVGTYVSWYQQKPDQSPKMLIYGASNRFTGVP

DRFSGSGSGTDFTLTISSLQAEDLADYYCGQSYTFPYTFGQGTKLEIK

Deimmunised VK3 '5
                                                    (SEQ ID NO: 27)
NIQMTQFPSAMSASVGDRVTITCKASENVGTYVSWYQQKPDQSPKMLIYGASNRFTGVP

DRFSGSGSGTDFTLTISSLQAEDLADYYCGQSYTFPYTFGQGTKLEIK

Deimmunised VK4 '5
                                                    (SEQ ID NO: 28)
NIQMTQFPSAMSASVGDRVTITCKASENVGTYVSWYQQKPDQSPKMLIYGASNRFTGVP

DRFSGSGSGTDFTLTISSLQAEDEADYYCGQSYTFPYTFGQGTKLEIK
```

-continued

Deimmunised VK DI '5
(SEQ ID NO: 29)
NIVMTQFPKSMSASAGERMTLTCKASENVGTYVSWYQQKPTQSPKMLIYGASNRFTGVP

DRFSGSGSGTDFILTISSVQAEDLVDYYCGQSYTFPYTFGGGTKLEMK

Deimmunised VH DI '5
(SEQ ID NO: 30)
EVKLEESGGGLVQPGGSMKISCVASGFTFSNYWMNWVRQSPEKGLEWVAEIRSQSNNF

ATHYAESVKGRVIISRDDSKSSVYLQMNSLRAEDTAVYYCTRRWNNFWGQGTTVTVSS

Humanised RHA '5
(SEQ ID NO: 31)
EVQLVESGGGLVQPGGSLKLSCAASGFTFSNYWMNWVRQASGKGLEWVGEIRSQSNNF

ATHYAESVKGRFTISRDDSKNTAYLQMNSLKTEDTAVYYCTRRWNNFWGQGTTVTVSS

Humanised RHB '5
(SEQ ID NO: 32)
EVKLVESGGGLVQPGGSLKLSCAASGFTFSNYWMNVVVRQASGKGLEWVAEIRSQSNNF

ATHYAESVKGRVIISRDDSKNTVYLQMNSLRTEDTAVYYCTRRWNNFWGQGTTVTVSS

Humanised RHC '5
(SEQ ID NO: 33)
EVQLVESGGGLVQPGGSLKLSCAASGFTFSNYWMNVWRQASGKGLEVVVAEIRSQSNNF

ATHYAESVKGRVIISRDDSKNTVYLQMNSLRTEDTAVYYCTRRWNNFWGQGTTVTVSS

Humanised RHD '5
(SEQ ID NO: 34)
EVKLVESGGGLVQPGGSLKLSCAASGFTFSNYWMNVWRQASGKGLEWVGEIRSQSNNF

ATHYAESVKGRVIISRDDSKNTVYLQMNSLRTEDTAVYYCTRRWNNFWGQGTTVTVSS

Humanised RHE '5
(SEQ ID NO: 35)
EVKLVESGGGLVQPGGSLKLSCAASGFTFSNYWMNVWRQASGKGLEWVAEIRSQSNNF

ATHYAESVKGRFTISRDDSKNTVYLQMNSLRTEDTAVYYCTRRWNNFWGQGTTVTVSS

Humanised RHF '5
(SEQ ID NO: 36)
EVKLVESGGGLVQPGGSLKLSCAASGFTFSNYWMNVWRQASGKGLEWVAEIRSQSNNF

ATHYAESVKGRVIISRDDSKNTAYLQMNSLRTEDTAVYYCTRRWNNFWGQGTTVTVSS

Humanised RHG '5
(SEQ ID NO: 37)
EVKLVESGGGLVQPGGSLKLSCAASGFTFSNYWMNVWRQASGKGLEWVAEIRSQSNNF

ATHYAESVKGRVIISRDDSKNTAYLQMNSLRTEDTAVYYCTRRWNNFWGQGTTVTVSS

Humanised RKA '5
(SEQ ID NO: 38)
DIQMTQSPSSVSASVGDRVTITCKASENVGTYVSWYQQKPGTAPKLLIYGASNRFTGVPS

RFSGSGSATDFTLTINNLQPEDFATYYCGQSYTFPYTFGQGTKVEIK

Humanised RKB '5
(SEQ ID NO: 39)
DIQMTQSPSSVSASVGDRVTITCKASENVGTYVSWYQQKPGTAPKLLIYGASNRFTGVPS

RFSGSGSATDFTLTINNLQPEDFATYYCGQSYTFPYTFGQGTKVEIK

Humanised RKC '5
(SEQ ID NO: 40)
DIQMTQSPSSVSASVGDRVTITCKASENVGTYVSWYQQKPGTAPKMLIYGASNRFTGVPS

RFSGSGSATDFTLTINNLQPEDFATYYCGQSYTFPYTFGQGTKVEIK

Humanised RKD '5
(SEQ ID NO: 41)
DIQMTQSPSSVSASVGDRVTITCKASENVGTYVSWYQQKPGTAPKMLIYGASNRFTGVPS

RFSGSGSATDFTLTINNLQPEDFATYYCGQSYTFPYTFGQGTKVEIK

-continued

```
Humanised RKE '5
                                                         (SEQ ID NO: 42)
NIVMTQSPSSVSASVGDRVTITCKASENVGTYVSWYQQKPGTAPKLLIYGASNRFTGVPD

RFTGSGSATDFILTINNLQPEDFATYYCGQSYTFPYTFGQGTKVEIK

Humanised RKF '5
                                                         (SEQ ID NO: 43)
NIVMTQSPSSVSASVGDRVTITCKASENVGTYVSWYQQKPGTAPKMLIYGASNRFTGVPS

RFSGSGSATDFILTINNLQPEDFATYYCGQSYTFPYTFGQGTKVEIK

Humanised RKG '5
                                                         (SEQ ID NO: 44)
NIVMTQSPSSVSASVGDRVTITCKASENVGTYVSWYQQKPGTAPKMLIYGASNRFTGVPD

RFTGSGSATDFTLTINNLQPEDFATYYCGQSYTFPYTFGQGTKVEIK
```

The parent antibody may also be a fusion protein comprising an albumin-binding peptide (ABP) sequence (Dennis et al. (2002) "Albumin Binding As A General Strategy For Improving The Pharmacokinetics Of Proteins" *J Biol Chem.* 277:35035-35043; WO 01/45746). Antibodies of the invention include fusion proteins with ABP sequences taught by: (i) Dennis et al (2002) *J Biol Chem.* 277:35035-35043 at Tables III and IV, page 35038; (ii) US 2004/0001827 at [0076]; and (iii) WO 01/45746 at pages 12-13, and all of which are incorporated herein by reference.

In one embodiment, the antibody has been raised to target specific the tumour related antigen $\alpha_v\beta_6$.

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

Connection of Linker Unit to Ligand Unit

The Ligand unit is connected to the Linker unit through a disulfide bond.

In one embodiment, the connection between the Ligand unit and the Drug Linker is formed between a thiol group of a cysteine residue of the Ligand unit and a maleimide group of the Drug Linker unit.

The cysteine residues of the Ligand unit may be available for reaction with the functional group of the Linker unit to form a connection. In other embodiments, for example where the Ligand unit is an antibody, the thiol groups of the antibody may participate in interchain disulfide bonds. These interchain bonds may be converted to free thiol groups by e.g. treatment of the antibody with DTT prior to reaction with the functional group of the Linker unit.

In some embodiments, the cysteine residue is an introduced into the heavy or light chain of an antibody. Positions for cysteine insertion by substitution in antibody heavy or light chains include those described in Published U.S. Application No. 2007-0092940 and International Patent Publication WO2008070593, which are incorporated herein.

Methods of Treatment

The compounds of the present invention may be used in a method of therapy. Also provided is a method of treatment, comprising administering to a subject in need of treatment a therapeutically-effective amount of a conjugate of formula II. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a conjugate of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The Conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, antiphospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmunie disorder is a T cell-mediated immunological disorder.

In some embodiments, the amount of the Conjugate administered ranges from about 0.01 to about 10 mg/kg per dose. In some embodiments, the amount of the Conjugate administered ranges from about 0.01 to about 5 mg/kg per dose. In some embodiments, the amount of the Conjugate administered ranges from about 0.05 to about 5 mg/kg per dose. In some embodiments, the amount of the Conjugate administered ranges from about 0.1 to about 5 mg/kg per dose. In some embodiments, the amount of the Conjugate administered ranges from about 0.1 to about 4 mg/kg per dose. In some embodiments, the amount of the Conjugate administered ranges from about 0.05 to about 3 mg/kg per dose. In some embodiments, the amount of the Conjugate administered ranges from about 0.1 to about 3 mg/kg per dose. In some embodiments, the amount of the Conjugate administered ranges from about 0.1 to about 2 mg/kg per dose.

Drug Loading

The drug loading (p) is the average number of PBD drugs per cell binding agent, e.g. antibody. Where the compounds of the invention are bound to cysteines, drug loading may range from 1 to 8 drugs (D) per cell binding agent, i.e. where 1, 2, 3, 4, 5, 6, 7, and 8 drug moieties are covalently attached to the cell binding agent. Compositions of conjugates include collections of cell binding agents, e.g. antibodies, conjugated with a range of drugs, from 1 to 8. Where the compounds of the invention are bound to lysines, drug loading may range from 1 to 80 drugs (D) per cell binding agent, although an upper limit of 40, 20, 10 or 8 may be preferred. Compositions of conjugates include collections of cell binding agents, e.g. antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the Drug Linker. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of Drug Linker relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per cell binding agent is in the range 1 to 20. In some embodiments the range is selected from 1 to 8, 2 to 8, 2 to 6, 2 to 4, and 4 to 8.

In some embodiments, there is one dimer pyrrolobenzodiazepine group per cell binding agent.

General Synthetic Routes

The synthesis of PBD compounds is extensively discussed in the following references, which discussions are incorporated herein by reference:

a) WO 00/12508 (pages 14 to 30);

b) WO 2005/023814 (pages 3 to 10);

c) WO 2004/043963 (pages 28 to 29); and d) WO 2005/085251 (pages 30 to 39).

Synthesis Route

Compounds of the present invention of formula I where $R^{20}$ and $R^{21}$ form a nitrogen-carbon double bond between the nitrogen and carbon atoms to which they are bound can be synthesised from a compound of Formula II:

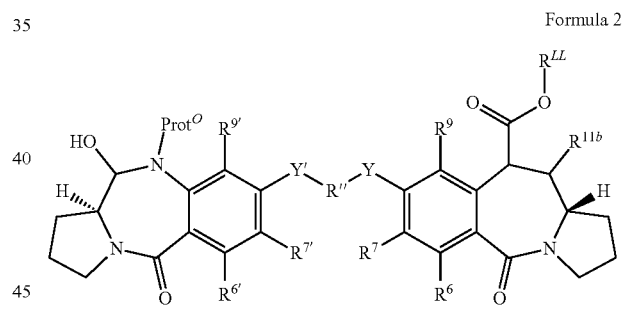

Formula 2 where $R^6$, $R^7$, $R^9$, $R^{6'}$, $R^{7'}$, $R^{9'}$, $R^{11b}$, Y, Y' and R" are as defined for compounds of formula I, and $R^{LL}$ is a precursor of $R^L$—this method is particularly applicable to compounds of formula I where $R^L$ is of formula IIIa. For these compounds, $R^{LL}$ will typically be a portion of $R^L$, such as a group of formula IIIa':

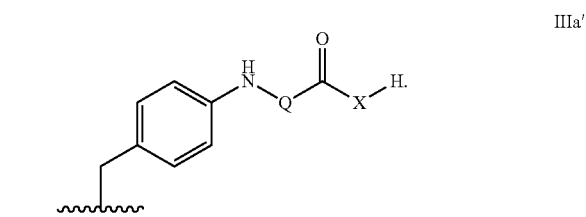

IIIa'

In such as case, the reaction involves adding the group $G^L$. The second required step is removal of the $Prot^O$ group.

The compounds of Formula 2 may be made by deprotecting the $R^{LL}$ group of compounds of Formula 3:

Formula 3

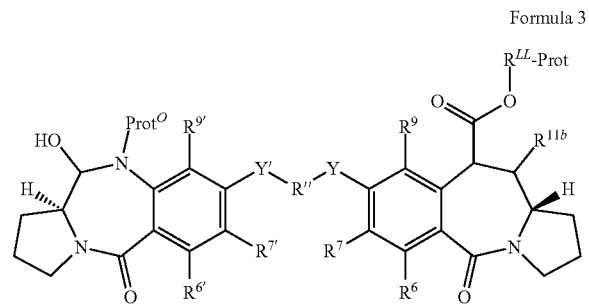

where $R^6$, $R^7$, $R^9$, $R^{6'}$, $R^{7'}$, $R^{9'}$, $R^{11b}$, Y, Y' and R" are as defined for compounds of formula I, $R^{LL-Prot}$ is a protected version of $R^{LL}$, and the $Prot^N$ represents a simple nitrogen protecting group (e.g. Fmoc, Boc) that is orthogonal to the $R^{LL}$ protecting group.

Compounds of formula 3 may be made by ring-closure of compounds of Formula 4:

Formula 4

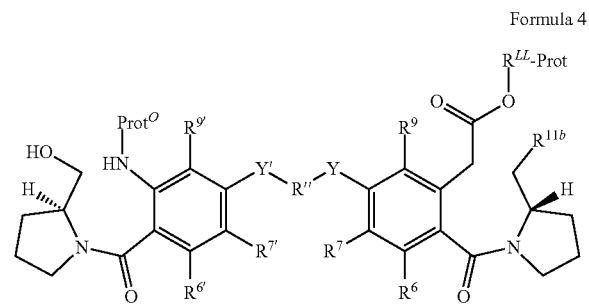

where the ring closure is carried out by oxidation, e.g. Swern.

Compounds of formula 4 can be synthesised from compounds of formula 5:

Formula 5

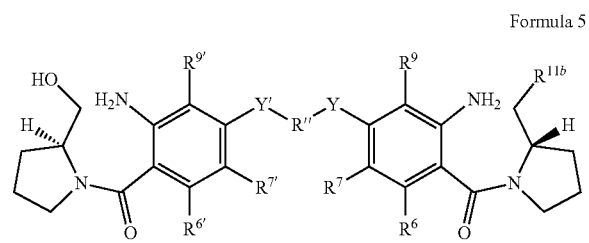

by a step-wise addition of two protecting groups. This can be achieved by simple protection of the amino group which will result in the imino bond in the final compound (e.g. by Fmoc, Boc), followed by installation of a desired protecting group at the other amino group.

Compounds of formula I where $R^L$ is of formula IIIb, may be synthesised in a similar manner, although the complete $R^L$ group may be installed starting from a compound of Formula 5, rather than with the use of a protected precursor.

Compounds of Formula 5 can be synthesised by known methods, such as those disclosed in WO 2011/130598.

Alternatively, compounds of Formula 4 can be synthesised by a monomeric route, as shown in example 3.

Compounds of the present invention of formula I where $R^{20}$ and $R^{21}$ do not form a nitrogen-carbon double bond between the nitrogen and carbon atoms to which they are bound can by made by modifications to the above routes.

Synthesis of Drug Conjugates

Conjugates can be prepared as previously described. Antibodies can be conjugated to the Drug Linker compound as described in Doronina et al., Nature Biotechnology, 2003, 21, 778-784). Briefly, antibodies (4-5 mg/mL) in PBS containing 50 mM sodium borate at pH 7.4 are reduced with tris(carboxyethyl)phosphine hydrochloride (TCEP) at 37° C. The progress of the reaction, which reduces interchain disulfides, is monitored by reaction with 5,5'-dithiobis(2-nitrobenzoic acid) and allowed to proceed until the desired level of thiols/mAb is achieved. The reduced antibody is then cooled to 0° C. and alkylated with 1.5 equivalents of maleimide drug-linker per antibody thiol. After 1 hour, the reaction is quenched by the addition of 5 equivalents of N-acetyl cysteine. Quenched drug-linker is removed by gel filtration over a PD-10 column. The ADC is then sterile-filtered through a 0.22 μm syringe filter. Protein concentration can be determined by spectral analysis at 280 nm and 329 nm, respectively, with correction for the contribution of drug absorbance at 280 nm. Size exclusion chromatography can be used to determine the extent of antibody aggregation, and RP-HPLC can be used to determine the levels of remaining NAC-quenched drug-linker.

Further Preferences

The following preferences may apply to all aspects of the invention as described above, or may relate to a single aspect. The preferences may be combined together in any combination.

In some embodiments, $R^{6'}$, $R^{7'}$, $R^{9'}$, and Y' are selected from the same groups as $R^6$, $R^7$, $R^9$, and Y respectively. In some of these embodiments, $R^{6'}$, $R^{7'}$, $R^{9'}$, and Y' are the same as $R^6$, $R^7$, $R^9$, and Y respectively.

N10'-C11'

In some embodiment, $R^{20}$ is H, and $R^{21}$ is OH, $OR^A$, where $R^A$ is $C_{1-4}$ alkyl. In some of these embodiments, $R^{21}$ is OH. In others of these embodiments, $R^{21}$ is $OR^A$, where $R^A$ is $C_{1-4}$ alkyl. In some of these embodiments, $R^A$ is methyl.

In some embodiments, $R^{20}$ and $R^{21}$ form a nitrogen-carbon double bond between the nitrogen and carbon atoms to which they are bound.

In some embodiments, $R^{20}$ is H and $R^{21}$ is $SO_zM$, where z is 2 or 3 and M is a monovalent pharmaceutically acceptable cation. In some of these embodiments, M is a monovalent pharmaceutically acceptable cation, and may be Na⁺. Furthermore, in some embodiments z is 3.

In some embodiments, $R^{20}$ is H and $R^{21}$ is H.

In some embodiments where $R^{20}$ is (d-iii), there may be an additional nitro group on the benzene ring, e.g. ortho to $R^Z$.

In some embodiments, $R^{21}$ is OH or $OR^A$, where $R^A$ is $C_{1-4}$ alkyl and $R^{20}$ is selected from:

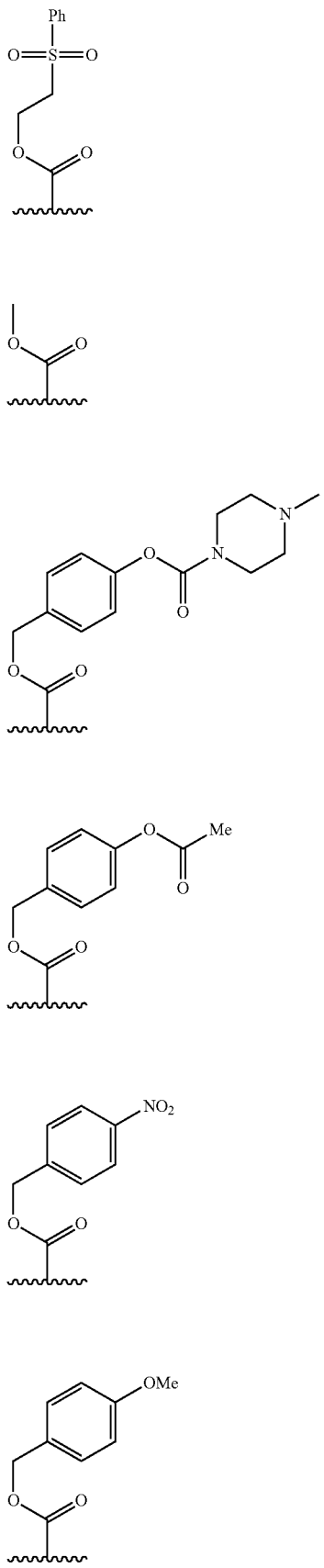

—C(=O)—X₁—NHC(=O)X₂—NH— represent a dipeptide. The amino acids in the dipeptide may be any combination of natural amino acids. The dipeptide may be the site of action for cathepsin-mediated cleavage.

In one embodiment, the dipeptide, —C(=O)—X₁—NHC(=O)X₂—NH—, is selected from:
Phe-Lys-,
Val-Ala-,
Val-Lys-,
Ala-Lys-,
Val-Cit-,
Phe-Cit-,
Leu-Cit-,
Ile-Cit-,
Phe-Arg-,
Trp-Cit-
where Cit is citrulline.

Preferably, the dipeptide, —C(=O)—X₁—NHC(=O)X₂—NH—, is selected from:
Phe-Lys-,
Val-Ala-,
Val-Lys-,
Ala-Lys-,
Val-Cit-.

Most preferably, the dipeptide, —C(=O)—X₁—NHC(=O)X₂—NH—, is -Phe-Lys- or -Val-Ala-.

Other dipeptide combinations may be used, including those described by Dubowchik et al., *Bioconjugate Chemistry*, 2002, 13, 855-869, which is incorporated herein by reference.

In one embodiment, the amino acid side chain is derivatised, where appropriate. For example, an amino group or carboxy group of an amino acid side chain may be derivatised.

In one embodiment, an amino group NH₂ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, CONH₂, CONHR and CONRR'.

In one embodiment, the amino acid side chain is chemically protected, where appropriate. The side chain protecting group may be a group as discussed above. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the invention, the amino acids selected are those having no reactive side chain functionality. For example, the amino acids may be selected from: Ala, Gly, Ile, Leu, Met, Phe, Pro, and Val.

It is particularly preferred in the present invention, that if $L^1$ comprises a dipeptide, then —C(=O)—$X_1$—NHC(=O)—$X_2$—NH— is the same dipeptide.

Other preferred $R^{20}$ groups include:

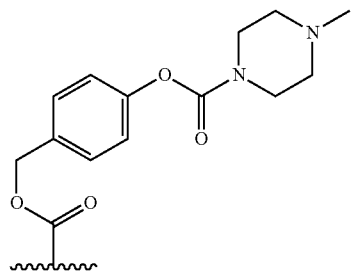

and

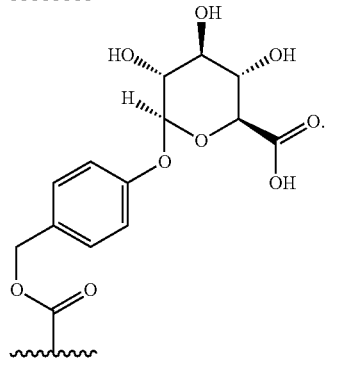

Dimer Link

In some embodiments, Y and Y' are both O.

In some embodiments, R" is a $C_{3-7}$ alkylene group with no substituents. In some of these embodiments, R" is a $C_3$, $C_5$ or $C_7$ alkylene. In particular, R" may be a $C_3$ or $C_5$ alkylene.

In other embodiments, R" is a group of formula:

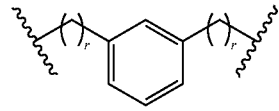

where r is 1 or 2.

The phenylene group may be replaced by a pyridylene group.

$R^6$ to $R^9$

In some embodiments, $R^9$ is H.

In some embodiments, $R^6$ is selected from H, OH, OR, SH, $NH_2$, nitro and halo, and may be selected from H or halo. In some of these embodiments $R^6$ is H.

In some embodiments, $R^7$ is selected from H, OH, OR, SH, SR, $NH_2$, NHR, NRR', and halo. In some of these embodiments $R^7$ is selected from H, OH and OR, where R is selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and $OCH_2Ph$. Other substituents of particular interest are dimethylamino (i.e. —$NMe_2$); —$(OC_2H_4)_q$OMe, where q is from 0 to 2; nitrogen-containing $C_6$ heterocyclyls, including morpholino, piperidinyl and N-methyl-piperazinyl.

These embodiments and preferences apply to $R^{9'}$, $R^{6'}$ and $R^{7'}$ respectively.

$R^{11b}$

In some embodiments, $R^{11b}$ is OH.

In some embodiments, $R^{11b}$ is $OR^A$, where $R^A$ is $C_{1-4}$ alkyl. In some of these embodiments, $R^A$ is methyl.

In some embodiments of the first aspect of the present invention are of formula Ia, Ib or Ic:

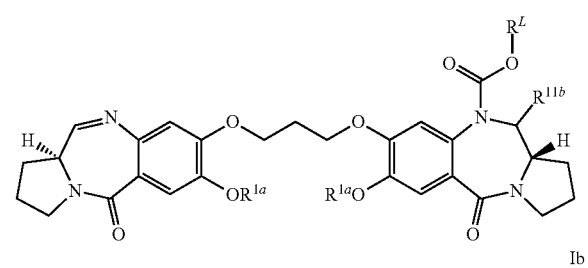

Ia

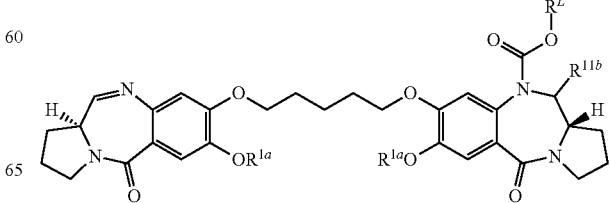

Ib where $R^{1a}$ is selected from methyl and benzyl;

$R^L$ and $R^{11b}$ are as defined above.

These embodiments and preferences also apply to the second aspect of the invention.

Linker ($R^L$)

In some embodiments, $R^L$ is of formula IIIa.

In some embodiments, $R^{LL}$ is of formula IIIa'.

$G^L$ $G^L$ may be selected from ($G^{L1-1}$)

($G^{L1-2}$)

($G^{L2}$)

($G^{L3-1}$)

where the $NO_2$ group is optional ($G^{L3-2}$)

where the $NO_2$ group is optional ($G^{L3-3}$)

where the $NO_2$ group is optional ($G^{L3-4}$)

where the $NO_2$ group is optional ($G^{L4}$)

Where Hal = I, Br, Cl ($G^{L5}$)

($G^{L6}$)

($G^{L7}$)

($G^{L8}$)

($G^{L9}$)

where Ar represents a $C_{5-6}$ arylene group, e.g. phenylene.

In some embodiments, $G^L$ is selected from $G^{L1-1}$ and $G^{L1-2}$. In some of these embodiments, $G^L$ is $G^{L1-1}$.

$G^{LL}$ $G^{LL}$ may be selected from:

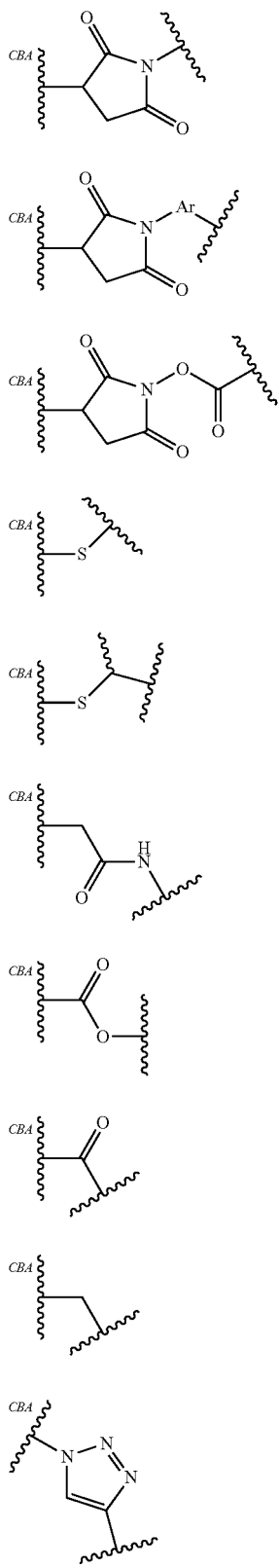

(G^{LL1-1})
(G^{LL1-2})
(G^{LL2})
(G^{LL3-1})
(G^{LL3-2})
(G^{LL4})
(G^{LL5})
(G^{LL6})
(G^{LL7})
(G^{LL8-1})

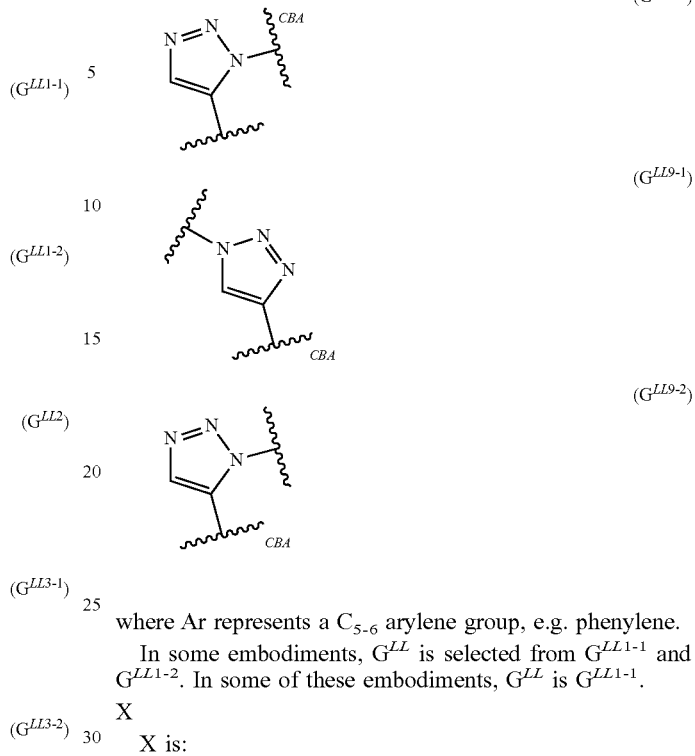

(G^{LL8-2})
(G^{LL9-1})
(G^{LL9-2})

where Ar represents a $C_{5-6}$ arylene group, e.g. phenylene.

In some embodiments, $G^{LL}$ is selected from $G^{LL1-1}$ and $G^{LL1-2}$. In some of these embodiments, $G^{LL}$ is $G^{LL1-1}$.

X

X is:

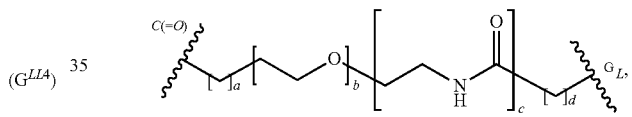

where a=0 to 5, b=0 to 16, c=0 or 1, d=0 to 5.

a may be 0, 1, 2, 3, 4 or 5. In some embodiments, a is 0 to 3. In some of these embodiments, a is 0 or 1. In further embodiments, a is 0.

b may be 0, 1, 2, 3, 4, 5, 6, 7, 8, 9, 10, 11, 12, 13, 14, 15 or 16. In some embodiments, b is 0 to 12. In some of these embodiments, b is 0 to 8, and may be 0, 2, 4 or 8.

c may be 0 or 1.

d may be 0, 1, 2, 3, 4 or 5. In some embodiments, d is 0 to 3. In some of these embodiments, d is 1 or 2. In further embodiments, d is 2.

In some embodiments of X, a is 0, c is 1 and d is 2, and b may be from 0 to 8. In some of these embodiments, b is 0, 4 or 8.

Q

In one embodiment, Q is an amino acid residue. The amino acid may a natural amino acids or a non-natural amino acid.

In one embodiment, Q is selected from: Phe, Lys, Val, Ala, Cit, Leu, lie, Arg, and Trp, where Cit is citrulline.

In one embodiment, Q comprises a dipeptide residue. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, Q is selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$;
where Cit is citrulline.

Preferably, Q is selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$.

Most preferably, Q is selected from $^{CO}$-Phe-Lys-$^{NH}$, $^{CO}$-Val-Cit-$^{NH}$ and $^{CO}$-Val-Ala-$^{NH}$.

Other dipeptide combinations of interest include:
$^{CO}$-Gly-Gly-$^{NH}$
$^{CO}$-Pro-Pro-$^{NH}$, and
$^{CO}$-Val-Glu-$^{NH}$.

Other dipeptide combinations may be used, including those described by Dubowchik et al., *Bioconjugate Chemistry*, 2002, 13, 855-869, which is incorporated herein by reference.

In some embodiments, $Q^X$ is a tripeptide residue. The amino acids in the tripeptide may be any combination of natural amino acids and non-natural amino acids. In some embodiments, the tripeptide comprises natural amino acids. Where the linker is a cathepsin labile linker, the tripeptide is the site of action for cathepsin-mediated cleavage. The tripeptide then is a recognition site for cathepsin.

In one embodiment, the amino acid side chain is chemically protected, where appropriate. The side chain protecting group may be a group as discussed below. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

In some embodiments, $R^L$ is of formula IIIb.

In some embodiments, $R^{LL}$ is formula IIIb'.

$R^{L1}$ and $R^{L2}$ are independently selected from H and methyl, or together with the carbon atom to which they are bound form a cyclopropylene or cyclobutylene group.

In some embodiments, both $R^{L1}$ and $R^{L2}$ are H.

In some embodiments, $R^{L1}$ is H and $R^{L2}$ is methyl.

In some embodiments, both $R^{L1}$ and $R^{L2}$ are methyl.

In some embodiments, $R^{L1}$ and $R^{L2}$ together with the carbon atom to which they are bound form a cyclopropylene group.

In some embodiments, $R^{L1}$ and $R^{L2}$ together with the carbon atom to which they are bound form a cyclobutylene group.

In the group IIIb, in some embodiments, e is 0. In other embodiments, e is 1 and the nitro group may be in any available position of the ring. In some of these embodiments, it is in the ortho position. In others of these embodiments, it is in the para position.

In one particular embodiment, the first aspect of the invention comprises a compound of formula Id:

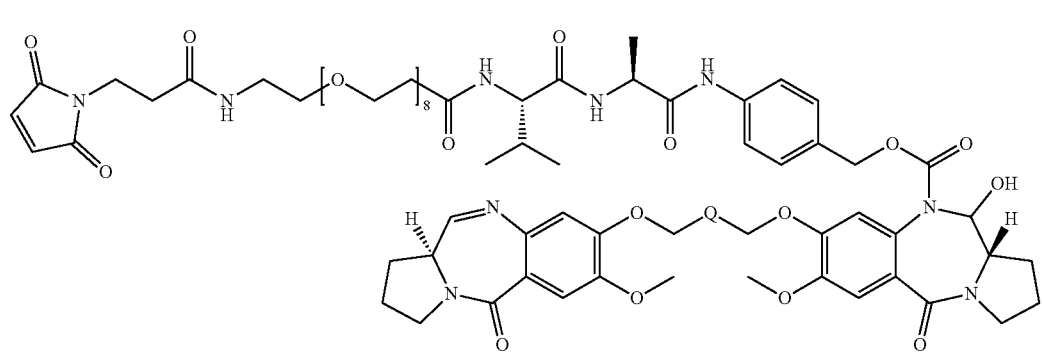

(Id)

where Q is selected from:

(a) —$CH_2$—;

(b) —$C_3H_6$—; and (c)

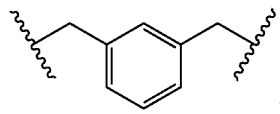

In one particular embodiment, the second aspect of the invention, the Drug linker ($D^L$) is of formula (Id'):

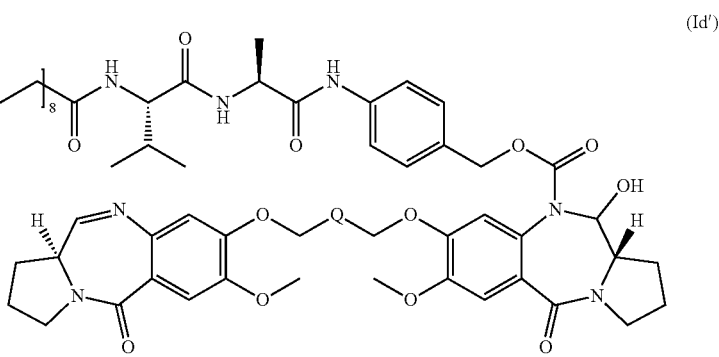

(Id')

where Q is selected from:
(a) —$CH_2$—;
(b) —$C_3H_6$—; and
(c)

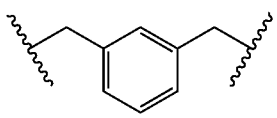

In some embodiments of the present invention, the C11 substituent may be in the following stereochemical arrangement relative to neighbouring groups:

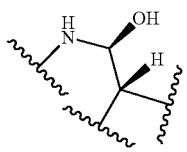

In other embodiments, the C11 substituent may be in the following stereochemical arrangement relative to neighbouring groups:

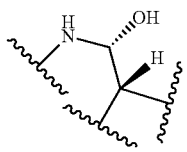

EXAMPLES

General Information

Flash chromatography was performed using a Biotage Isolera 1™ using gradient elution starting from either 88% hexane/EtOAc or 99.9% DCM/MeOH until all UV active components (detection at 214 and 254 nm) eluted from the column. The gradient was manually held whenever substantial elution of UV active material was observed. Fractions were checked for purity using thin-layer chromatography (TLC) using Merck Kieselgel 60 F254 silica gel, with fluorescent indicator on aluminium plates. Visualisation of TLC was achieved with UV light or iodine vapour unless otherwise stated. Extraction and chromatography solvents were bought and used without further purification from VWR U.K. All fine chemicals were purchased from Sigma-Aldrich or TCI Europe unless otherwise stated. Pegylated reagents were obtained from Quanta biodesign US via Stratech UK.

$^1$H and $^{13}$C NMR spectra were obtained on a Bruker Avance® 400 spectrometer. Coupling constants are quoted in hertz (Hz). Chemical shifts are recorded in parts per million (ppm) downfield from tetramethylsilane. Spin multiplicities are described as s (singlet), bs (broad singlet), d (doublet), t (triplet), and m (multiplet).

The analytical LC/MS conditions (for reaction monitoring and purity determination) were as follows: Positive mode electrospray mass spectrometry was performed using a Shimadzu Nexera®/Prominence® LCMS-2020. Mobile phases used were solvent A ($H_2O$ with 0.1% formic acid) and solvent B ($CH_3CN$ with 0.1% formic acid). Gradient for routine 3-minute run: Initial composition 5% B held over 25 seconds, then increased from 5% B to 100% B over a 1 minute 35 second period. The composition was held for 50 seconds at 100% B, then returned to 5% B in 5 seconds and held there for 5 seconds. The total duration of the gradient run was 3.0 minutes. Gradient for 15-minute run: Initial composition 5% B held over 1 minute, then increased from 5% B to 100% B over a 9 minute period. The composition was held for 2 minutes at 100% B, then returned to 5% B in 10 seconds and held there for 2 minutes 50 seconds. The total duration of the gradient run was 15.0 minutes. Flow rate was 0.8 mL/minute (for 3-minute run) and 0.6 mL/minute (for 15-minute run). Detection was at 254 nm. Columns: Waters Acquity UPLC® BEH Shield RP18 1.7 μm 2.1×50 mm at 50° C. fitted with Waters Acquity UPLC® BEH Shield RP18 VanGuard Pre-column, 130A, 1.7 μm, 2.1 mm×5 mm (routine 3-minute run); and ACE Excel 2 C18-AR, 2μ, 3.0×100 mm fitted with Waters Acquity UPLC® BEH Shield RP18 VanGuard Pre-column, 130A, 1.7 μm, 2.1 mm×5 mm (15-minute run).

The preparative HPLC conditions were as follows: Reverse-phase ultra-fast high-performance liquid chromatography (UFLC) was carried out on a Shimazdzu Prominence® machine using a Phenomenex® Gemini NX 5μ C18 column (at 50° C.) 150×21.2 mm. Eluents used were solvent A ($H_2O$ with 0.1% formic acid) and solvent B ($CH_3CN$ with 0.1% formic acid). All UFLC experiments were performed with gradient conditions:

Method A: Initial composition 13% B increased to 60% B over a 15 minute period then increased to 100% B over 2 minutes. The composition was held for 1 minute at 100% B, then returned to 13% B in 0.1 minute and held there for 1.9 minutes. The total duration of the gradient run was 20.0 minutes. Flow was 20.0 mL/minute and detection was at 254 and 280 nm.

Method B: Initial composition 13% B increased to 70% B over a 17 minute period and maintained over 2 minutes, then returned to 13% B in 0.1 minute and held there for 1.9 minutes. The total duration of the gradient run was 20.0 minutes. Flow was 20.0 mL/minute and detection was at 223 nm.

Method C: Initial composition 13% B increased to 75% B over a 15 minute period then increased to 100% B over 2 minutes. The composition was held for 1 minute at 100% B, then returned to 13% B in 0.1 minute and held there for 1.9 minutes. The total duration of the gradient run was 20.0 minutes. Flow rate was 20.0 mL/minute and detection was at 254 and 280 nm.

Example 1

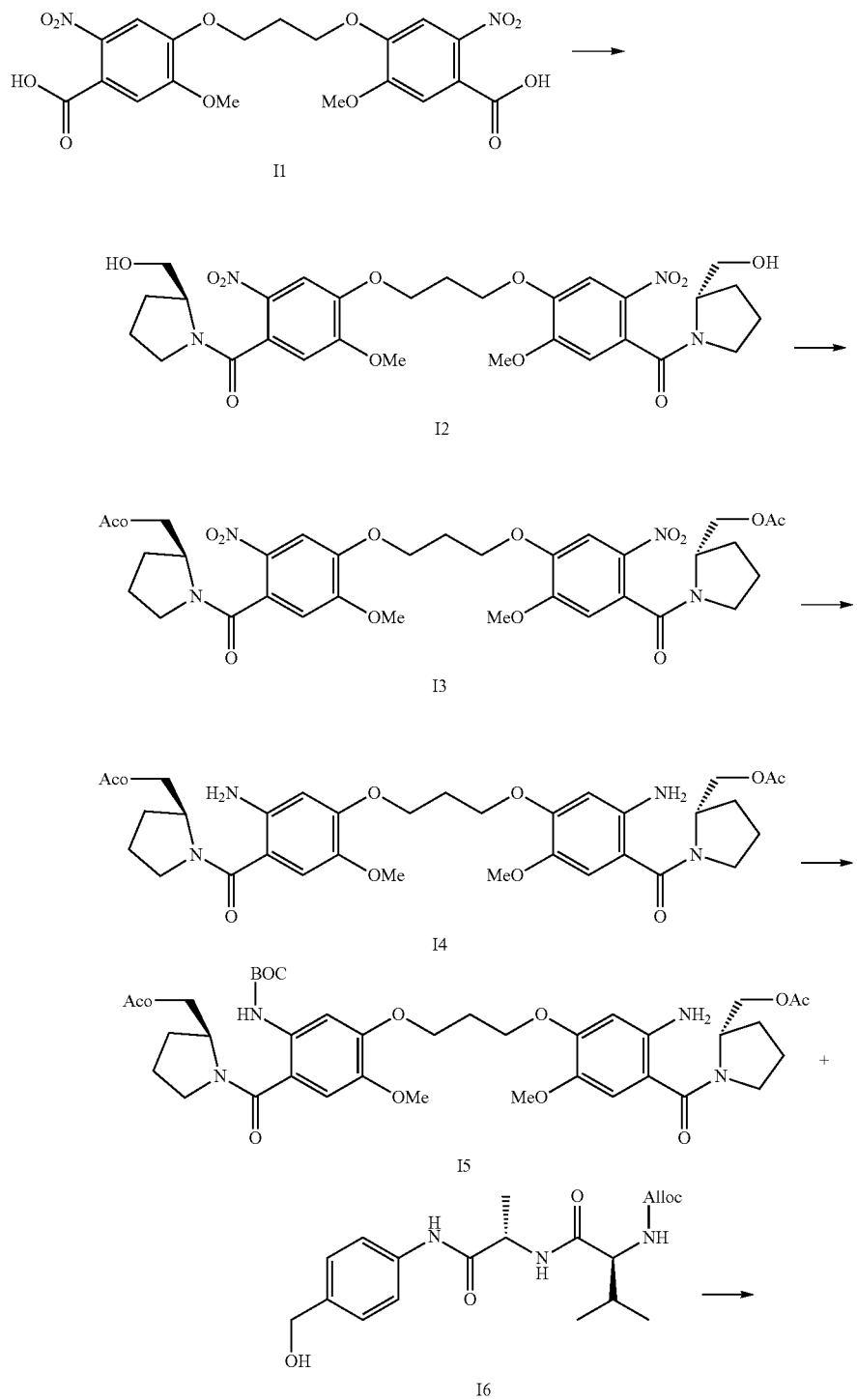

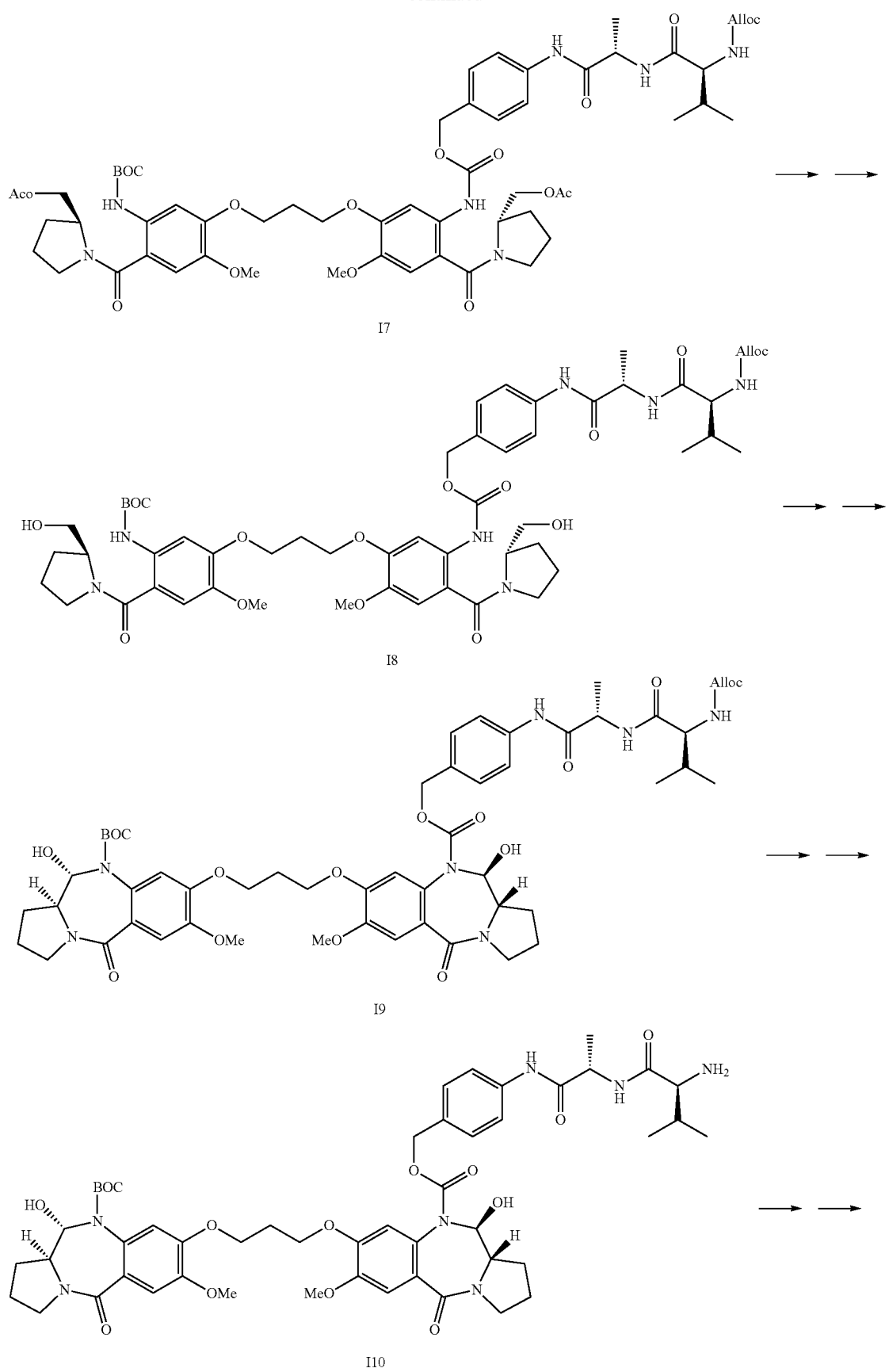

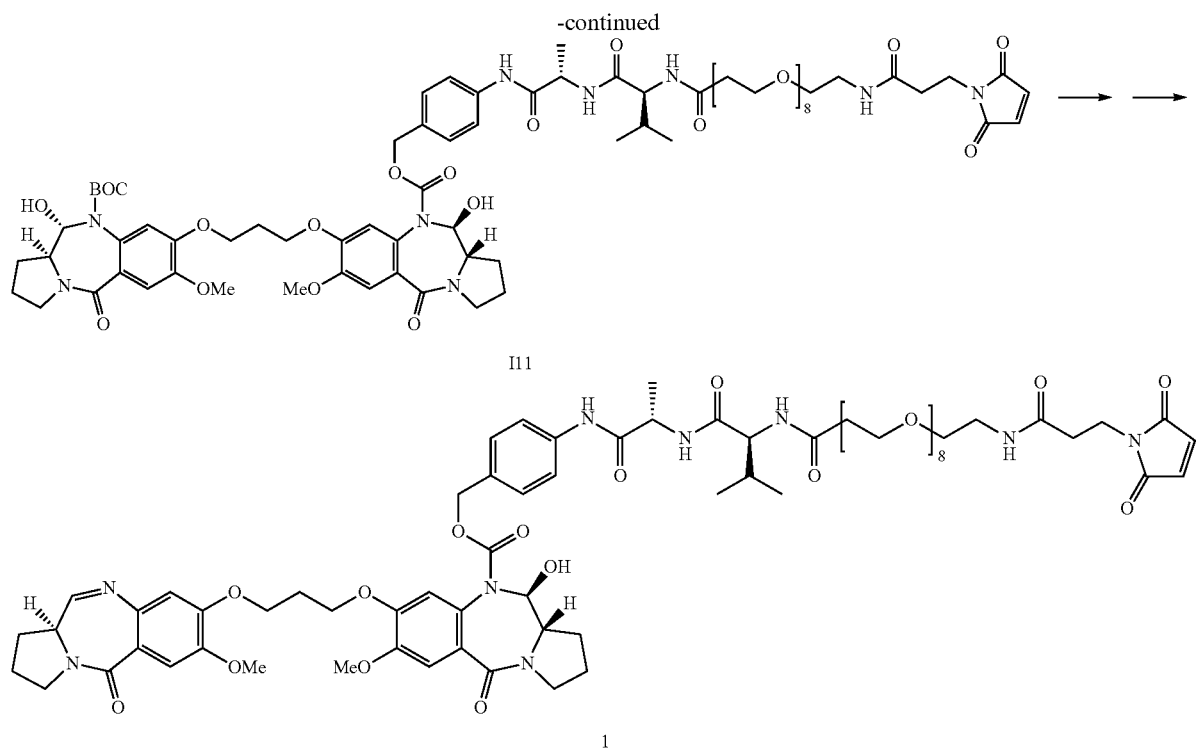

(a) ((Propane-1,3-diylbis(oxy))bis(5-methoxy-2-nitro-4,1-phenylene))bis(((S)-2-(hydroxymethyl)pyrrolidin-1-yl)methanone) (I2)

DMF (12 drops) was added to a stirred suspension of the bis-nitrobenzoic acid 11 (10 g, 21.5 mmol) and oxalyl chloride (5.6 mL, 8.2 g, 64.5 mmol) in anhydrous DCM (150 mL).

Following initial effervescence the reaction suspension became a solution and the mixture was allowed to stir at room temperature for 16 hours. The majority of solvent was removed by evaporation in vacuo and the resulting concentrated solution was re-dissolved in a minimum amount of dry DCM and triturated with diethyl ether. The resulting yellow precipitate was collected by vacuum filtration, washed with cold diethyl ether and dried for 1 hour in a vacuum oven at 40° C. The solid acid chloride was added portion-wise to a stirred suspension of (S)-(+)-2-pyrrolidinemethanol (5.0 g, 4.9 mL, 49.5 mmol) and TEA (15.0 mL, 10.9 g, 108 mmol) in DCM (100 mL) at −40° C. (dry ice/CH$_3$CN). After 1 hour stirring, the reaction was complete as judged by LC/MS with exclusively desired product at retention time 1.33 minutes, ES+ m/z 655 [M+Na]$^+$, 633 [M+H]$^+$. The mixture was diluted with DCM (100 mL) and washed with 1N HCl (2×50 mL), saturated NaHCO$_3$ (3×40 mL), brine (50 mL), dried (MgSO$_4$), filtered and the solvent evaporated in vacuo to give the pure product I2 as a yellow solid (13.6 g, 100% yield).

(b) ((2S,2'S)-(4,4'-(propane-1,3-diylbis(oxy))bis(5-methoxy-2-nitrobenzoyl))bis(pyrrolidine-1,2-diyl)) bis(methylene) diacetate (I3)

A solution of Ac$_2$O (4.47 mL, 4.83 g, 47.3 mmol) in dry DCM (25 mL) was added drop-wise to a stirred solution of the bis-alcohol 12 (13.6 g, 21.5 mmol), DMAP (263 mg, 2.15 mmol) and pyridine (4.17 mL, 4.08 g, 51.6 mmol) in dry DCM (125 mL) at 0° C. (ice/acetone) under an argon atmosphere. The reaction mixture was allowed to warm-up and after 1 hour at room temperature analysis by LC/MS revealed completion of reaction and clean conversion to desired product at retention time 1.55 minutes, ES+ m/z 740 [M+Na]$^+$, 717 [M+H]$^+$. The mixture was diluted with DCM (20 mL) and washed with 1N HCl (2×100 mL), H$_2$O (25 mL), brine (50 mL), dried (MgSO$_4$), filtered and the solvent evaporated in vacuo to give the crude bis-acetate 13 as a yellow solid (14.4 g, 94% yield) which was of satisfactory purity to be carried through to the next step without further purification.

(c) ((2S,2'S)-(4,4'-(propane-1,3-diylbis(oxy))bis(2-amino-5-methoxybenzoyl))bis(pyrrolidine-1,2-diyl)) bis(methylene) diacetate (I4)

A sample of 10% Pd—C (132 mg) was treated carefully with EtOAc (10 mL) to give a slurry which was added to a solution of the nitro compound I3 (1.32 g, 1.84 mmol) in EtOAc (20 mL) and EtOH (30 mL) in a hydrogenation vessel. Using Parr® apparatus, the mixture was treated with hydrogen gas to 10 psi and shaken at room temperature then degassed in vacuo, this process was repeated a further two times. The vessel was filled with hydrogen gas to 45 psi, shaken and the pressure maintained upon consumption of hydrogen. Analysis by LC/MS showed the reaction was incomplete after 3 hours and was left shaking at 45 psi for 3 days (the weekend) after which time satisfactory conversion to product was achieved, retention time=1.32 minutes, ES+ m/z 657 [M+H]$^+$. The reaction mixture was degassed in vacuo and then filtered through a Celite® pad. The filtrate was evaporated in vacuo, the resulting residue re-dissolved in DCM (30 mL), dried (MgSO$_4$), filtered and the solvent evaporated in vacuo to give the crude bis-aniline I4 as a yellowish foam (1.1 g, 91% yield) which contained an 8% impurity but was carried through to the next step without further purification.

(d) ((S)-1-(4-(3-(4-((S)-2-(acetoxymethyl)pyrrolidine-1-carbonyl)-5-((tert-butoxycarbonyl)amino)-2-methoxyphenoxy)propoxy)-2-amino-5-methoxybenzoyl)pyrrolidin-2-yl)methyl acetate (I5)

Boc$_2$O (330 mg, 1.51 mmol) was added to a stirred solution of the bis-aniline 14 (1.1 g, 1.68 mmol) in dry THF (10 mL). The reaction mixture was heated and stirred at 75° C. for 16 hours. Analysis by LC/MS revealed desired mono Boc product I5 at retention time 1.58 minutes, I %=50, ES+ m/z 779 [M+Na]$^+$, 757 [M+H]$^+$ along with unreacted starting material at retention time 1.32 minutes, I %=30, and bis-Boc material at retention time 1.81 minutes, I %=21, ES+ m/z 879 [M+Na]$^+$, 857 [M+H]$^+$. The reaction mixture was allowed to cool to room temperature and the THF removed by evaporation in vacuo. Purification by Isolera™ (DCM/MeOH, SNAP Ultra 50 g, 100 mL per minute) provided the mono Boc product I5 as an orange foam (519 mg, 46% yield based on Boc$_2$O, eluting at 97% DCM/MeOH) unreacted bis-aniline 14 (285 mg, eluting at 95% DCM/MeOH) and bis-Boc (248 mg, eluting at 98% DCM/MeOH).

(e) ((S)-1-(4-(3-(4-((S)-2-(acetoxymethyl)pyrrolidine-1-carbonyl)-5-(((((4-((S)-2-((S)-2-(((allyloxy)carbonyl)amino)-3-methylbutanamido)propanamido)benzyl)oxy)carbonyl)amino)-2-methoxyphenoxy)propoxy)-2-((tert-butoxycarbonyl)amino)-5-methoxybenzoyl)pyrrolidin-2-yl)methyl acetate (I7)

Triphosgene (380 mg, 1.28 mmol) was added to a stirred solution of the mono Boc product I5 (2.69 g, 3.56 mmol) and TEA (1.09 mL, 791 mg, 7.83 mmol) in dry DCM (30 mL) at room temperature. After stirring for 10 minutes under argon, analysis by LC/MS revealed complete conversion to isocyanate (sampled in MeOH to give methyl carbamate, retention time 1.66 minutes, ES+ m/z 837 [M+Na]$^+$, 815 [M+H]$^+$). The mixture was treated with additional TEA (740 µL, 539 mg, 5.34 mmol) followed by the addition of linker 16 (1.34 g, 3.56 mmol). After 2 hours stirring under argon, LC/MS revealed satisfactory conversion to carbamate 17 (retention time 1.74 minutes, (ES+) m/z 1182 [M+Na]$^+$, 1160 [M+H]$^+$). The mixture was diluted with DCM (80 mL) and washed with saturated NH$_4$Cl (2×30 mL), H$_2$O (30 mL), brine (50 mL), dried (MgSO$_4$), filtered and evaporated in vacuo to give the crude product. Purification by Isolera™ (Hexane/EtOAc, SNAP Ultra 100 g, 100 mL per minute) provided the pure carbamate 17 (eluting at 65% Hexane/EtOAc) as a yellow foam (2.95 g, 71% yield).

(f) tert-butyl (5-(3-(5-(((((4-((S)-2-((S)-2-(((allyloxy)carbonyl)amino)-3-methylbutanamido)propanamido)benzyl)oxy)carbonyl)amino)-4-((S)-2-(hydroxymethyl)pyrrolidine-1-carbonyl)-2-methoxyphenoxy)propoxy)-2-((S)-2-(hydroxymethyl)pyrrolidine-1-carbonyl)-4-methoxyphenyl)carbamate (I8)

Solid K$_2$CO$_3$ (1.75 g, 12.7 mmol) was added to a stirred solution of the acetate-protected compound I7 (2.93 g, 2.53 mmol) in MeOH (60 mL) and H$_2$O (12 mL). After 1 hour stirring at room temperature the reaction was deemed to be complete as judged by LC/MS with desired product at retention time 1.57 minutes, ES+ m/z 1098 [M+Na]$^+$, 1076 [M+H]$^+$. The MeOH was removed by evaporation in vacuo and the resulting residue was partitioned between water (75 mL) and DCM (75 mL). The layers were separated and the aqueous phase was extracted with DCM (3×25 mL). The combined organic layers were washed with water (3×50 mL), brine (60 mL), dried (MgSO$_4$), filtered and evaporated in vacuo to provide the crude product. Purification by Isolera™ (DCM/MeOH, SNAP Ultra 100 g, 100 mL per minute) the bis-alcohol 18 (eluting at 97% DCM/MeOH) as a white foam (2.44 g, 90% yield).

(g) 4-((S)-2-((S)-2-(((allyloxy)carbonyl)amino)-3-methylbutanamido)propanamido)benzyl(11S,11aS)-8-(3-(((11S,11aS)-10-(tert-butoxycarbonyl)-11-hydroxy-7-methoxy-5-oxo-2,3,5,10,11,11a-hexahydro-1H-pyrrolo[2,1-c][1,4]benzodiazepin-8-yl)oxy)propoxy)-11-hydroxy-7-methoxy-5-oxo-2,3,11,11a-tetrahydro-1H-pyrrolo[2,1-c][1,4]benzodiazepine-10(5H)-carboxylate (I9)

A solution of anhydrous DMSO (710 µL, 780 mg, 9.99 mmol) in dry DCM (20 mL) was added drop-wise to a stirred solution of oxalyl chloride (2.72 mL of a 2.0M solution in DCM, 5.44 mmol) in dry DCM (20 mL) at −45° C. (dry ice/CH$_3$CN) under an argon atmosphere. After 15 minutes stirring at −45° C., the reaction mixture was treated drop-wise with a solution of the bis-alcohol 18 (2.44 g, 2.27 mmol) in dry DCM (30 mL). After stirring at −45° C. for a further 1 hour, the reaction mixture was treated drop-wise with a solution of TEA (3.16 mL, 2.29 g, 22.7 mmol) in dry DCM (20 mL). The reaction mixture was allowed to warm to room temperature over a period of 1.5 hours and diluted with DCM (100 mL) then washed with saturated NH$_4$Cl (2×50 mL), saturated NaHCO$_3$ (50 mL), water (30 mL), brine (50 mL), dried (MgSO$_4$), filtered and evaporated in vacuo to give the crude product. Purification by Isolera™ (DCM/MeOH, SNAP Ultra 100 g, 100 mL per minute) gave the cyclised compound I9 (eluting at 95.7% DCM/MeOH) as a yellowish foam (1.61 g, 66% yield): LC/MS I9 at retention time 1.46 minutes, ES+ m/z 1072 [M+H]$^+$, 1094 [M+Na]$^+$.

(h) 4-((S)-2-((S)-2-amino-3-methylbutanamido)propanamido)benzyl(11S,11aS)-8-(3-(((11S,11aS)-10-(tert-butoxycarbonyl)-11-hydroxy-7-methoxy-5-oxo-2,3,5,10,11,11a-hexahydro-1H-pyrrolo[2,1-c][1,4]benzodiazepin-8-yl)oxy)propoxy)-11-hydroxy-7-methoxy-5-oxo-2,3,11,11a-tetrahydro-1H-pyrrolo[2,1-c][1,4]benzodiazepine-10(5H)-carboxylate (I10)

Pd(PPh$_3$)$_4$ (6.47 mg, 5.6 µmol) was added to a stirred solution of pyrrolidine (29 µL, 25 mg, 0.35 mmol) and the Alloc compound I9 (300 mg, 0.28 mmol) in dry DCM (10 mL). After stirring for 4 hours under argon at room temperature, analysis by LC/MS revealed reaction completion with desired product observed at retention time 1.10 minutes, ES+, m/z 1010 [M+Na]$^+$, 988 [M+H]$^+$. The reaction mixture was diluted with DCM (30 mL) then washed with saturated NH$_4$Cl (2×20 mL), brine (30 mL), dried (MgSO$_4$), filtered and evaporated in vacuo to give the crude product. Trituration with diethyl ether followed by evaporation in vacuo gave the crude amine I10 (261 mg, 95% yield) which was carried through to the next step without further purification or analysis.

(i) tert-butyl(11S,11aS)-8-(3-(((11S,11aS)-10-(((4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl)oxy)carbonyl)-1-hydroxy-7-methoxy-5-oxo-2,3,5,10,11,11a-hexahydro-1H-pyrrolo[2,1-c][1,4]benzodiazepin-8-yl)oxy)propoxy)-11-hydroxy-7-methoxy-5-oxo-2,3,11,11a-tetrahydro-1H-pyrrolo[2,1-c][1,4]benzodiazepine-10(5H)-carboxylate (I11)

EDCl (56 mg, 0.29 mmol) was added to a stirred solution of MAL-dPEG®₈-acid (172 mg, 0.29 mmol, Stratech Scientific Limited) and the amine I10 (261 mg, 0.26 mmol) in dry DCM (10 mL) at room temperature. The reaction mixture was stirred under an argon atmosphere for 2.5 hours at which point analysis by LC/MS showed complete conversion to desired product at retention time 1.38 minutes, ES+ m/z 1585 [M+Na]⁺, 1563 [M+H]⁺. The reaction mixture was diluted with DCM (30 mL) and washed with H₂O (20 mL), brine (2×20 mL), dried (MgSO₄), filtered and evaporated in vacuo to provide the crude product. Purification by Isolera™ (DCM/MeOH, SNAP Ultra 25 g, 75 mL per minute) gave the amide I11 (eluting at 91% DCM/MeOH) as a white foam (277 mg, 67% yield).

(j) 4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl(11S,11aS)-11-hydroxy-7-methoxy-8-(3-(((S)-7-methoxy-5-oxo-2,3,5,11a-tetrahydro-1H-pyrrolo[2,1-c][1,4]benzodiazepin-8-yl)oxy)propoxy)-5-oxo-2,3,11,11a-tetrahydro-1H-pyrrolo[2,1-c][1,4]benzodiazepine-10(5H)-carboxylate (1)

A solution of 95:5 v/v TFA/H₂O (2 mL) was added to a crude sample of the Boc-protected compound I11 (262 mg, 0.17 mmol) at 0° C. (ice/acetone). After stirring at 0° C. for 3 hours the reaction was deemed complete as judged by LC/MS, desired product peak at retention time 1.30 minutes, ES+ m/z 1445 [M+H]⁺. The reaction mixture was kept cold and added drop-wise to a chilled saturated aqueous solution of NaHCO₃ (100 mL). The mixture was extracted with DCM (3×30 mL) and the combined organic layers washed with brine (30 mL), dried (MgSO₄), filtered and evaporated in vacuo to provide the crude product. Purification by Isolera™ (CHCl₃/MeOH, SNAP Ultra 25 g, 25 mL per minute) gave 1 (eluting at 89.6% CHCl₃/MeOH) as a yellow foam (170 mg, 70% yield). Further purification by preparative HPLC (Method A) gave 1 as a light yellow foam (105 mg, 43% yield): LC/MS (15-minute run), retention time 5.25 minutes, ES+ m/z 1445 [M+H]⁺; ¹H NMR (400 MHz, d6-DMSO) δ 9.92 (s, 1H), 8.16 (d, 1H, J=6.8 Hz), 7.99 (t, 1H, J=5.7 Hz), 7.86 (d, 1H, J=8.6 Hz), 7.80 (d, 1H, J=4.5 Hz), 7.64-7.50 (m, 2H), 7.34 (s, 1H), 7.24-7.13 (m, 2H), 7.06 (s, 1H), 7.00 (s, 2H), 6.88 (s, 1H), 6.75 (s, 1H), 6.53-6.41 (m, 1H), 5.52-5.41 (m, 1H), 5.13 (d, 1H, J=12.2 Hz), 4.93-4.77 (m, 1H), 4.42-4.34 (m, 1H), 4.30-3.90 (m, 6H), 3.80-3.60 (m, 4H), 3.80 (s, 3H), 3.79 (s, 3H), 3.60 (t, 4H, J=7.3 Hz), 3.53-3.46 (m, 28H), 3.41-3.33 (m, 1H), 3.32-3.29 (m, 2H, obscured by H₂O), 3.19-3.12 (m, 2H), 2.48-1.60, m, 15H), 1.35-1.20 (m, 3H), 0.87 (d, 3H, J=6.6 Hz), 0.83 (d, 3H, J=6.8 Hz).

Example 2

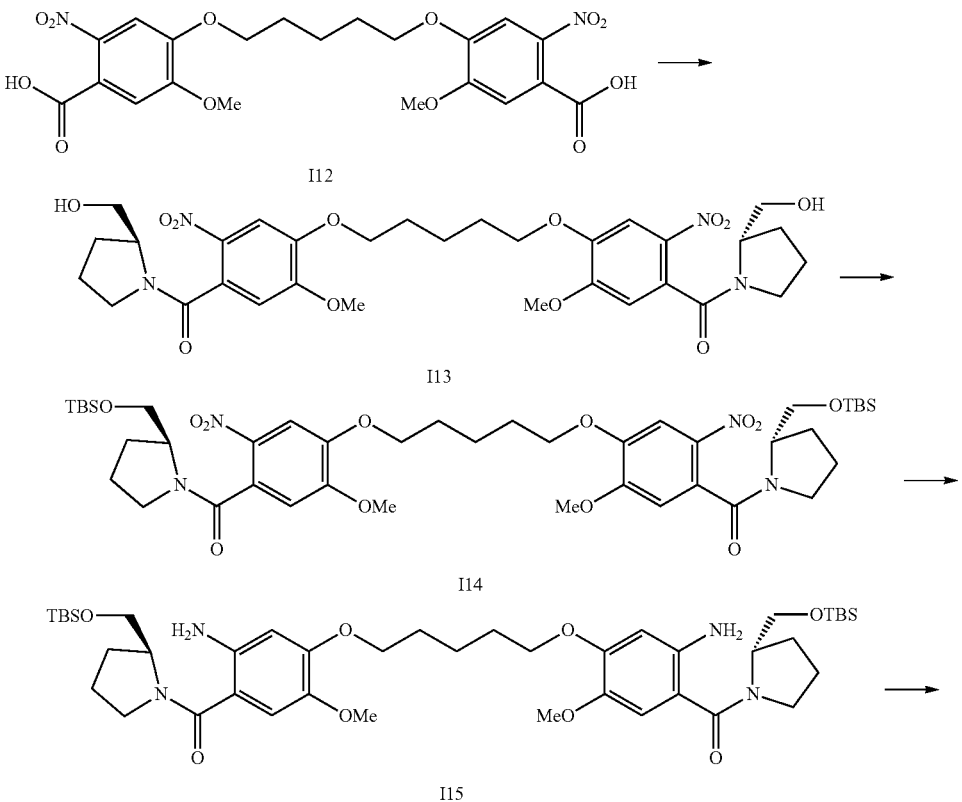

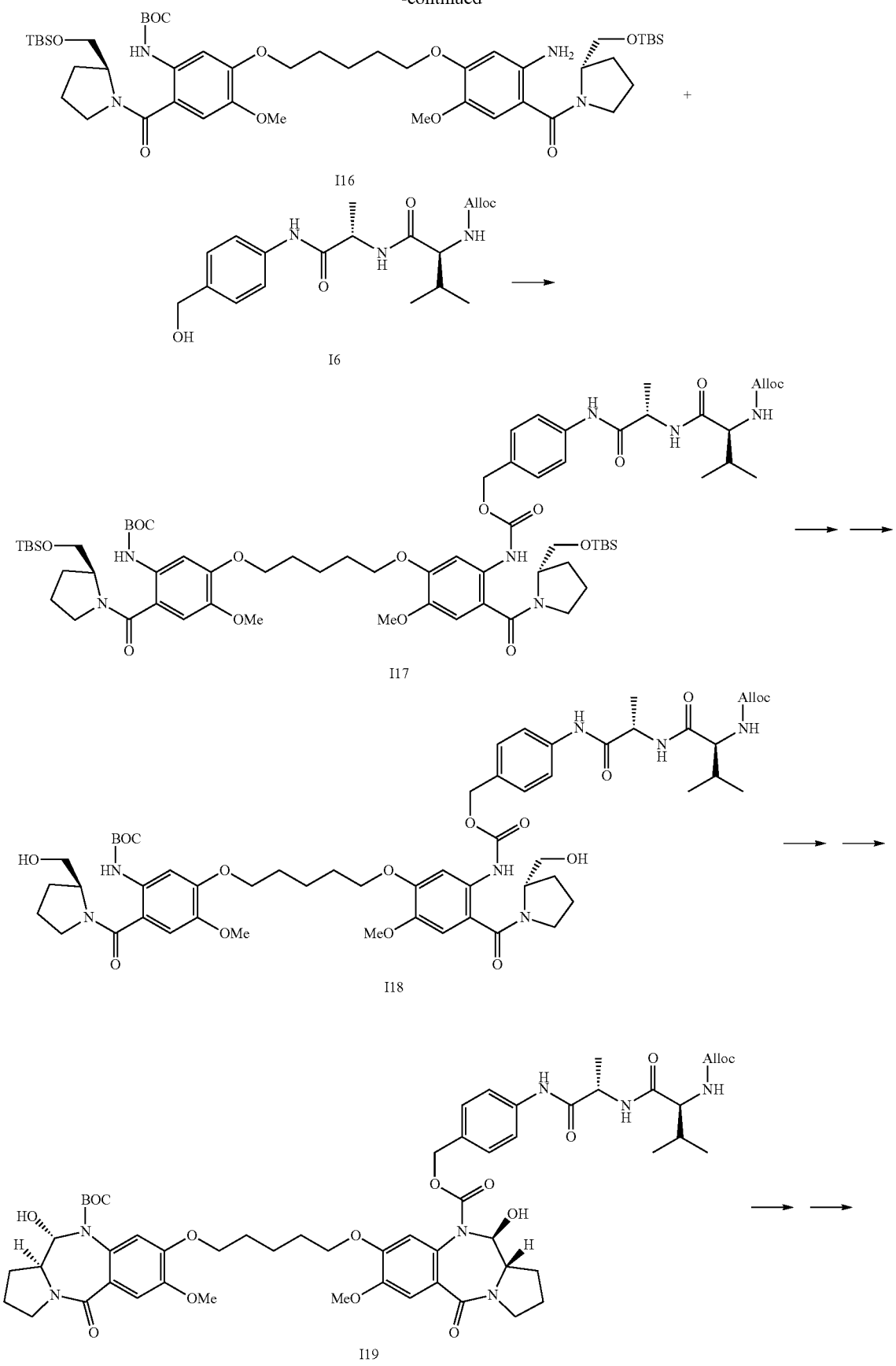

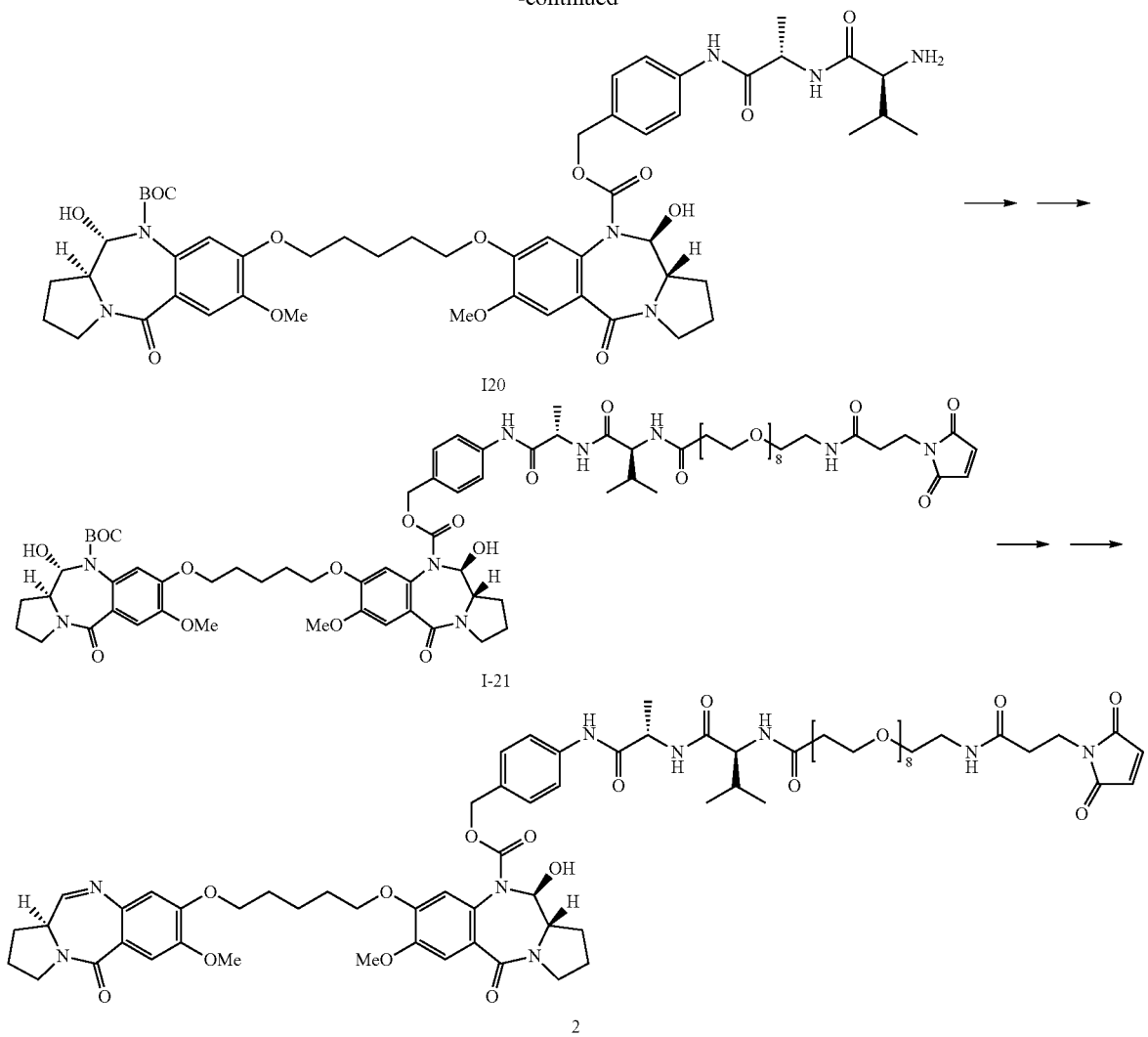

(a) ((pentane-1,5-diylbis(oxy))bis(5-methoxy-2-nitro-4,1-phenylene))bis(((S)-2-(hydroxymethyl)pyrrolidin-1-yl)methanone) (I13)

DMF (5 drops) was added to a stirred suspension of the bis-nitrobenzoic acid I12 (4.05 g, 8.192 mmol, 1.0 eq.) and oxalyl chloride (12.3 mL of 2M solution, 24.57 mmol, 3.0 eq.) in anhydrous CH$_2$Cl$_2$ (65 mL). Following initial effervescence the reaction suspension became a solution and the mixture was allowed to stir at room temperature for 16 hours. The reaction mixture was concentrated in vacuo and the resulting solid was triturated with Et$_2$O and dried in a vacuum oven at 40° C. for 3 hours. The solid acid chloride was added portion-wise to a stirred suspension of (S)-(+)-2-pyrrolidinemethanol (1.78 mL, 18.02 mmol, 2.2 eq.) and i-Pr$_2$NEt (7.13 mL, 40.96 mmol, 5.0 eq.) in CH$_2$Cl$_2$ (65 mL) at −40° C. (dry ice/CH$_3$CN). After 1 hour stirring, the reaction temperature had reached OC, and was complete as judged by LC/MS with exclusively desired product at retention time 1.44 minutes, ES+ m/z 661 [M+H]$^+$, 683 [M+Na]$^+$. The mixture was diluted with CH$_2$Cl$_2$ (100 mL) and washed consecutively with H$_2$O, 1N NaOH and 1M HCl (50 mL), dried (MgSO$_4$), filtered and the solvent evaporated in vacuo to give the pure product I13 as a yellow foam (4.44 g, 82% yield), which was used without further purification.

(b) ((pentane-1,5-diylbis(oxy))bis(5-methoxy-2-nitro-4,1-phenylene))bis(((S)-2-(((tert-butyldimethylsilyl)oxy)methyl)pyrrolidin-1-yl)methanone) (I14)

Imidazole (2.74 g, 40.32 mmol, 6.0 eq.) then TBSCl (3.04 g, 20.16 mmol, 3.0 eq.) were added portion-wise to a stirred solution of bis-alcohol I13 (4.44 g, 6.720 mmol, 1.0 eq.) under an argon atmosphere. After 90 minutes, the reaction mixture was filtered and the filtrated washed with H$_2$O, dried over MgSO$_4$ and concentrated in vacuo. Flash column chromatography (50-80% EtOAc in hexane) afforded the product I14 as a yellow foam (4.84 g, 5.443 mmol, 81% yield). LC/MS retention time=2.18 min, ES+ m/z 889 [M+H]$^+$, 911 [M+Na]$^+$.

(c) ((pentane-1,5-diylbis(oxy))bis(2-amino-5-methoxy-4,1-phenylene))bis(((S)-2-(((tert-butyldimethylsilyl)oxy)methyl)pyrrolidin-1-yl)methanone) (I15)

Zn powder was added to a stirring solution of bis-nitro compound I14 (1.32 g, 1.84 mmol) in MeOH (40 mL) at 0°

C. 5% HCO$_2$H in MeOH was added dropwise at 0° C. and the mixture stirred for 2 hours. The reaction mixture was diluted with EtOAc and washed with sat. NaHCO$_3$ solution, the organic phase dried over MgSO$_4$ and concentrated in vacuo. Flash column chromatography (0-2% MeOH in CHCl$_3$) afforded the product I15 as a pale yellow foam (3.098 mmol, 3.736 mmol, 69% yield). LC/MS retention time=2.09 min, ES+ m/z 415 [M+2H]$^{2+}$, 829 [M+H]$^+$, 851 [M+Na]$^+$.

(d) tert-butyl (5-((5-(5-amino-4-((S)-2-(((tert-butyldimethylsilyl)oxy)methyl)pyrrolidine-1-carbonyl)-2-methoxyphenoxy)pentyl)oxy)-2-((S)-2-(((tert-butyldimethylsilyl)oxy)methyl)pyrrolidine-1-carbonyl)-4-methoxyphenyl)carbamate (I16)

Boc$_2$O (734 mg, 3.362 mmol) was added to a stirred solution of the bis-aniline I15 (3.098 g, 3.736 mmol) in dry THF (20 mL). The reaction mixture was stirred for 16 hours and concentrated in vacuo. Flash column chromatography (30-50% EtOAc in hexane) provided the mono Boc product I16 as a yellow foam (1.474 g, 47% yield based on Boc$_2$O) unreacted bis-aniline I15 (1.043 g, 30% yield) and bis-Boc (419 mg, 15% yield, LC/MS retention time=2.37 min). LC/MS retention time of 116=2.25 min, ES$^+$ m/z 929 [M+H]$^+$, 951 [M+Na]$^+$.

(e) tert-butyl (5-((5-(5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)pyrrolidine-1-carbonyl)-2-hydroxyphenoxy)pentyl)oxy)-2-((S)-2-(((tert-butyldimethylsilyl)oxy)methyl)pyrrolidine-1-carbonyl)-4-methoxyphenyl) carbamate (I17)

Triphosgene (169 mg, 0.5710 mmol, 0.36 eq.) was added to a stirred solution of the mono Boc product I16 (1.474 g, 1.586 mmol, 1.0 eq.) and Et$_3$N (486 µL, 3.489 mmol, 2.2 eq.) in dry CH$_2$Cl$_2$ (9 mL) at −10° C. After stirring for 10 minutes under argon, analysis by LC/MS revealed complete conversion to isocyanate (sampled in MeOH to give methyl carbamate, retention time 2.30 minutes, ES+ m/z 1009 [M+Na]$^+$, 987 [M+H]$^+$). A solution of 16 (898 mg, 2.379 mmol, 1.5 eq.) and Et$_3$N (332 µL, 2.379 mmol, 1.5 eq.) in dry CH$_2$Cl$_2$ (14 mL) was added. The reaction was gradually warmed to rt and stirred for 16 h. 15 minute LC/MS analysis revealed starting material had been consumed. The reaction mixture was filtered through a SiO$_2$ pad (5% MeOH in CH$_2$Cl$_2$ elution) to remove excess 16. Flash column chromatography (20-80% EtOAc in hexane) provided I17 as a yellow foam (1.439 g, 68% yield). LC/MS retention time=2.26 min (3 minute run) and 10.43 min (15 minute run) ES$^+$ m/z 1355 [M+Na]$^+$, 1333 [M+H]$^+$. A negligible amount of urea dimer was observed (LC/MS retention time=12.11 min, ES$^+$ m/z 1906 [M+Na]$^+$) which was removed in subsequent purification steps.

(f) tert-butyl (5-((5-(5-((((4-((S)-2-((S)-2-(((allyloxy)carbonyl)amino)-3-methylbutanamido)propanamido)benzyl)oxy)carbonyl)amino)-2-hydroxy-4-((S)-2-(hydroxymethyl)pyrrolidine-1-carbonyl)phenoxy)pentyl)oxy)-2-((S)-2-(hydroxymethyl)pyrrolidine-1-carbonyl)-4-methoxyphenyl)carbamate (I18)

Acetic acid (124 µL, 2.160 mmol, 2.0 eq.) was added to a 1M solution of TBAF (3.2 mL, 3.200 mmol, 3.0 eq.) and subsequently added to a stirring solution of I17 in THF (67 mL) at 0° C. The reaction mixture was warmed to room temperature and stirred for 16 hours. LC/MS indicated reaction incomplete. TBAF (1.00 mL of 1M solution, 1 mmol, 1.0 eq.) was added and the reaction mixture stirred for a further 24 hours. The reaction mixture was concentrated in vacuo and purified by Isolera™ (0-5% MeOH in CH$_2$Cl$_2$) to afford the product I18 as a pale yellow foam (916 mg, 77% yield). LC/MS retention time=1.62 min, ES$^+$ m/z 1126 [M+Na]$^+$, 1104 [M+H]$^+$.

(g) 4-((S)-2-((S)-2-(((allyloxy)carbonyl)amino)-3-methylbutanamido)propanamido)benzyl (11S,11aS)-8-((5-(((11S,11aS)-10-(tert-butoxycarbonyl)-11-hydroxy-7-methoxy-5-oxo-2,3,5,10,11,11a-hexahydro-1H-benzo[e]pyrrolo[1,2-a][1,4]diazepin-8-yl)oxy)pentyl)oxy)-11-hydroxy-7-methoxy-5-oxo-2,3,11,11a-tetrahydro-1H-benzo[e]pyrrolo[1,2-a][1,4]diazepine-10(5H)-carboxylate (I19)

IBX (1.14 g, 1.825 mmol, 2.2 eq.) was added to a stirring solution of diol I18 (916 mg, 0.8296 mmol, 1.0 eq.) in DMSO. The reaction mixture was warmed to 35° C. and stirred for 60 hours. H$_2$O was added and the aqueous was extracted with CHCl$_3$ several times. The organic extracts were combined, washed with sat. NaHCO$_3$ and dried over MgSO$_4$. Purification by Isolera™ (1-8% MeOH in CH$_2$Cl$_2$) provided I19 as an orange foam (908 mg, 99% yield): LC/MS retention time=1.50 minutes, ES+ m/z 1122 [M+Na]$^+$, 1100 [M+H]$^+$.

(h) 4-((S)-2-((S)-2-amino-3-methylbutanamido)propanamido)benzyl (11S,11aS)-8-((5-(((11S,11aS)-10-(tert-butoxycarbonyl)-11-hydroxy-7-methoxy-5-oxo-2,3,5,10,11,11a-hexahydro-1H-benzo[e]pyrrolo[1,2-a][1,4]diazepin-8-yl)oxy)pentyl)oxy)-11-hydroxy-7-methoxy-5-oxo-2,3,11,11a-tetrahydro-1H-benzo[e]pyrrolo[1,2-a][1,4]diazepine-10(5H)-carboxylate (I20)

Pd(PPh$_3$)$_4$ (15.8 mg, 13.64 µmol, 0.050 eq.) was added to a stirring solution of pyrrolidine (56 µL, 0.6818 mmol, 2.5 eq.) and I19 (300 mg, 0.2727 mmol) in CH$_2$Cl$_2$ (10 mL) under argon. After 30 minutes, sat. NH$_4$Cl solution was added and the mixture vigorously stirred and transferred to an Isolute® Phase Separator. The collected organic phase was concentrated in vacuo to afford an orange foam I20 which was used without further purification.

(i) tert-butyl (11S,11aS)-8-((5-(((11S,11aS)-10-(((4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl)oxy)carbonyl)-11-hydroxy-7-methoxy-5-oxo-2,3,5,10,11,11a-hexahydro-1H-benzo[e]pyrrolo[1,2-a][1,4]diazepin-8-yl)oxy)pentyl)oxy)-11-hydroxy-7-methoxy-5-oxo-2,3,11,11a-tetrahydro-1H-benzo[e]pyrrolo[1,2-a][1,4]diazepine-10(5H)-carboxylate (I21)

EDCl.HCl (117 mg, 0.29 mmol) was added to a stirred solution of MAL-dPEG®$_8$-acid (360 mg, 0.6079 mmol, Stratech Scientific Limited) and amine I20 (608 mg, 0.5526 mmol) in CH$_2$Cl$_2$ (15 mL) at room temperature. The reaction mixture was stirred under an argon atmosphere for 24 hours, at which point analysis by LC/MS showed complete consumption of I20. The reaction mixture was diluted with CH$_2$Cl$_2$ and washed successively with sat. NH$_4$Cl and sat. NaHCO$_3$, dried over MgSO$_4$, and concentrated in vacuo to provide the crude product. Purification by Isolera™ (4-16% MeOH in CH$_2$Cl$_2$) gave amide I21 as a white solid (77 mg, 79% purity (UV integration @ 223 nm) 8.8% crude yield; 107 mg, 88% purity, 12% crude yield; 224 mg, 86% purity, 25% crude yield).

(j) 4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl(11S,11aS)-11-hydroxy-7-methoxy-8-(3-(((S)-7-methoxy-5-oxo-2,3,5,11a-tetrahydro-1H-pyrrolo[2,1-c][1,4]benzodiazepin-8-yl)oxy)propoxy)-5-oxo-2,3,11,11a-tetrahydro-1H-pyrrolo[2,1-c][1,4]benzodiazepine-10(5H)-carboxylate (2)

An ice-cold solution of 95:5 v/v TFA/H$_2$O (3 mL) was added to a crude sample of the Boc-protected compound I21 (107 mg, 67.51 µmol) at 0° C. (ice/brine). After stirring at 0° C. for 30 min, the reaction was deemed complete as judged by LC/MS, desired product peak at retention time 1.38 minutes, ES+ m/z 737 [M+2H]$^{2+}$, 748 [M+H+Na]$^{2}$+; 1472 [M+H]$^{+}$. The reaction mixture was kept cold and added drop-wise to a chilled saturated aqueous solution of NaHCO$_3$. The mixture was extracted with CH$_2$Cl$_2$, then 10% MeOH in CH$_2$Cl$_2$, the combined organic layers dried over MgSO$_4$ and concentrated in vacuo to provide the crude product. This process was repeated for the other batches of I21, the crude products combined and purified by preparative HPLC (Method B) to afford 2 as a white solid after lyophilisation (126 mg, 33% yield, 96% purity by UV @ 223 nm): LC/MS (30 minute run), retention time=10.96 minutes, ES+ m/z 1472 [M+H]$^{+}$.

Example 3

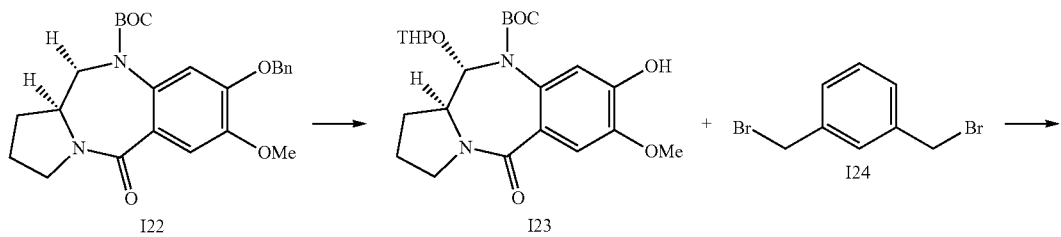

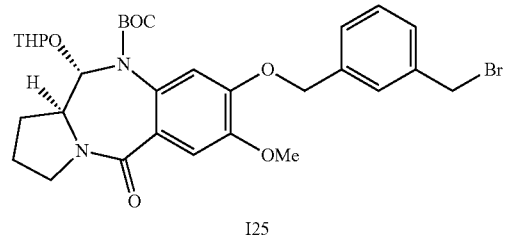

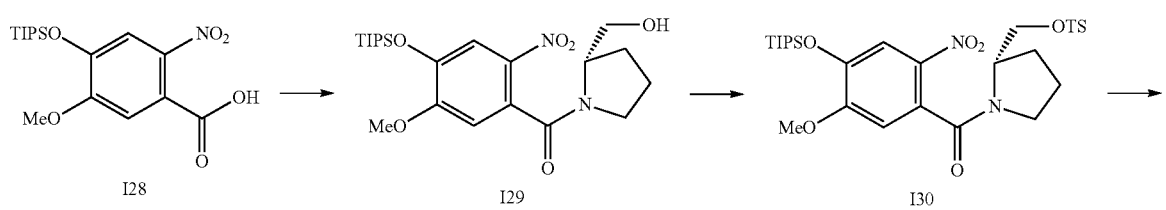

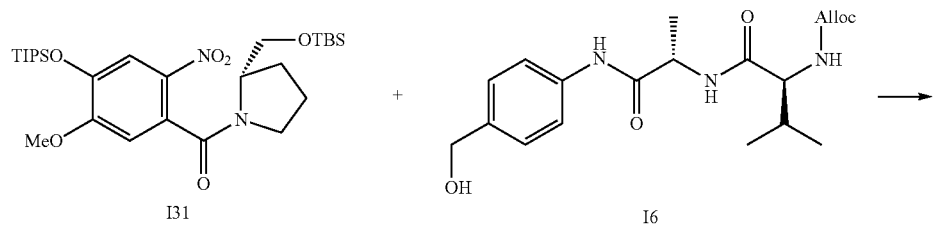

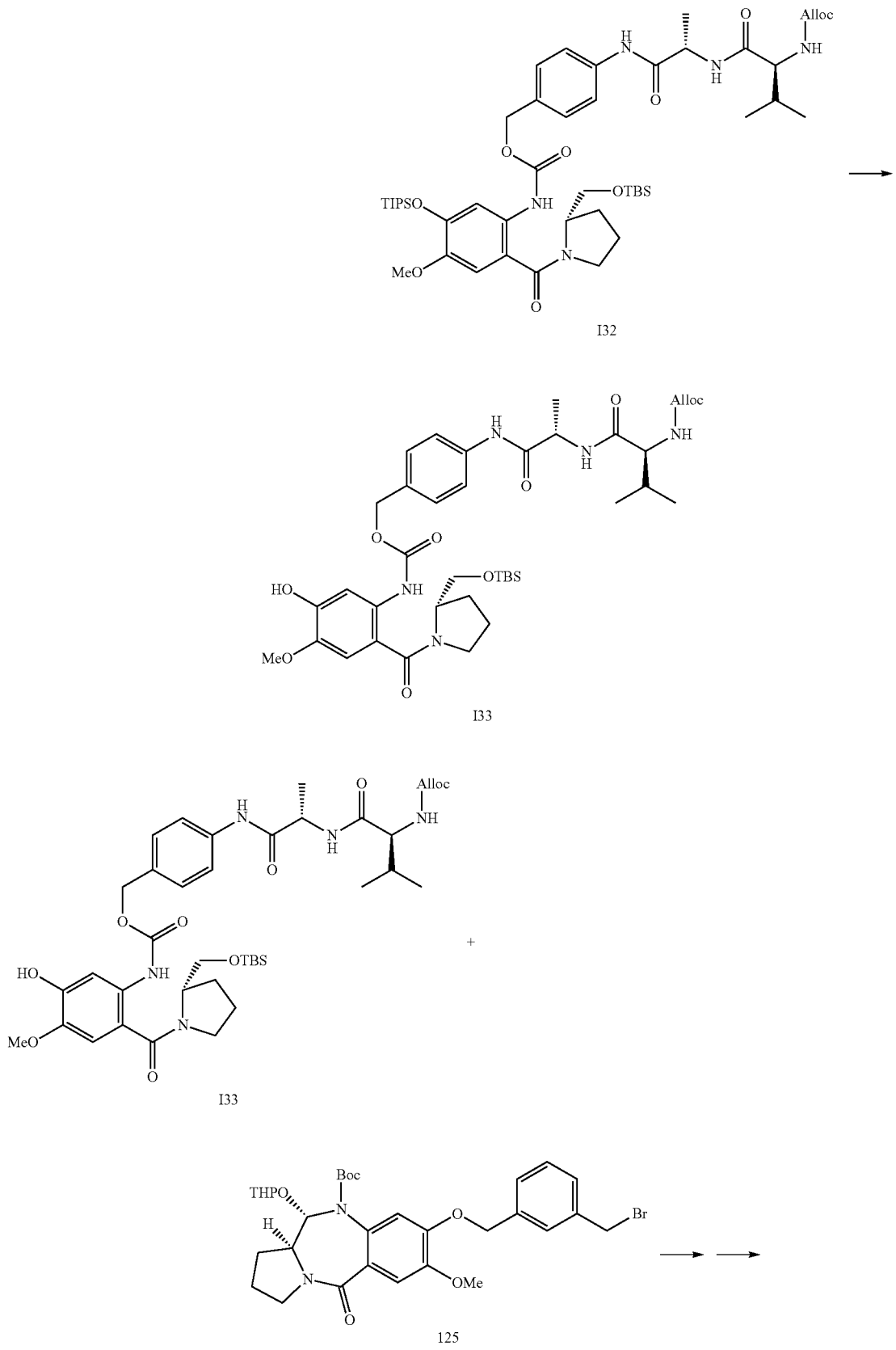

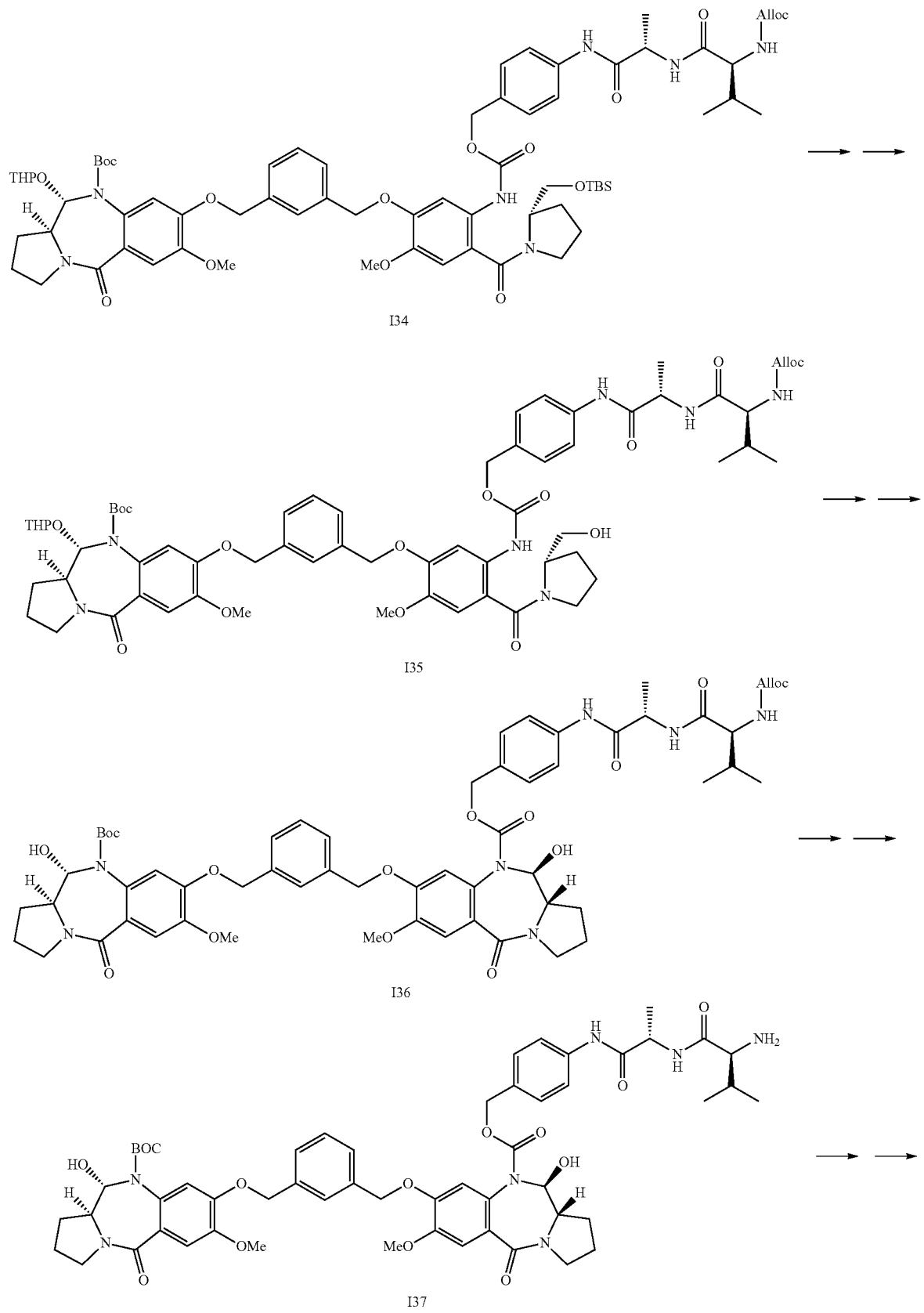

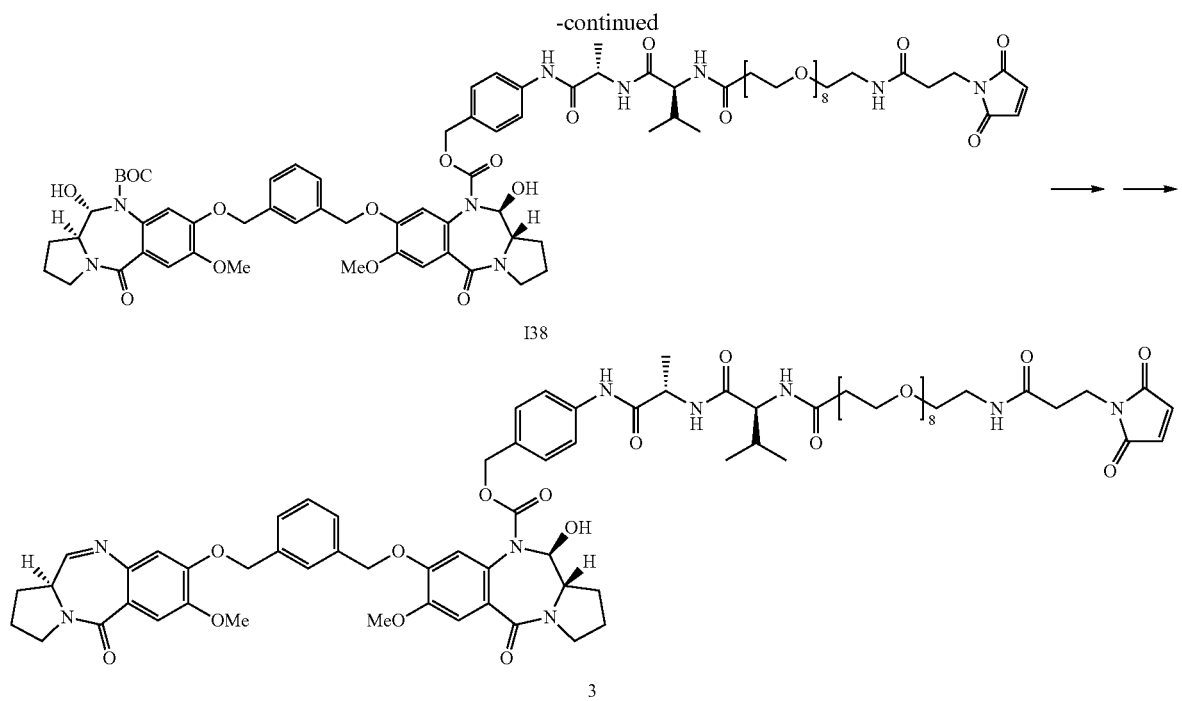

(a) I23

This step may be carried out as in the literature (see for example WO2005085259A2; or Wells, et al., *Bioorganic & Medicinal Chemistry Letters*, 18 (2008) 2147-2151). The method involves a Parr Hydrogenation at room temperature with 10% Pd/C in EtOH. The yield is quantitative. Ethanol is removed by two evaporations (EtOAc, followed by DCM).

(b) Tert-butyl (11S,11aS)-8-((3-(bromomethyl)benzyl)oxy)-7-methoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (I25)

A mixture of phenol I23 (4 g, 8.91 mmol, 1 eq), 1,3-bis(bromomethyl)benzene I24 (9.42 g, 35.7 mmol, 4 eq), potassium carbonate (1.23 g, 8.91 mmol, 1 eq), and acetone (40 mL) were heated at 60° C. for 5 hours. After completion was observed by LC/MS, the solids were removed by filtration and the filtrate was concentrated to dryness under vacuum. The residue was purified by chromatography (Biotage Isolera, 100 g Ultra, gradient EtOAc/Hexane 30/70 up to 80/20 in 12CV). Yield 4.25 g (75%). LC/MS, 3 min method, 1.82 min (ES+) m/z (relative intensity) 631.15 ([M+H]$^+$, 100), split peak: THP diastereoisomers. $^1$H NMR (400 MHz, DMSO-d$_6$) δ 7.67-7.27 (m, 4H), 7.20-6.57 (m, 2H), 5.72-5.57 (m, 1H), 5.24-4.84 (m, 3H), 4.72 (s, 2H), 3.91-3.73 (m, 4H), 3.61-3.33 (m, 4H), 2.20-1.75 (m, 4H), 1.74-1.57 (m, 2H), 1.55-1.01 (m, 13H).

I28 is known in the literature (see WO2013053872A1, Compound 2, page 60)

(c) (S)-(2-(hydroxymethyl)pyrrolidin-1-yl)(5-methoxy-2-nitro-4-((triisopropylsilyl)oxy)phenyl)methanone (I29)

EDCl (12.4 g, 65 mmol, 1.2 eq) was added to a solution of acid I28 (20 g, 54.1 mmol, 1 eq), and hydroxybenzotriazole hydrate (8.05 g, 59.5 mmol, 1.1 eq) in dichloromethane (200 mL) at 0° C. The cold bath was removed and the reaction was allowed to proceed for 30 mins at room temperature, at which time a solution of (S)-pyrrolidin-2-ylmethanol (5.87 mL, 59.5 mmol, 1.1 eq) and triethylamine (11.32 mL, 81.1 mmol, 1.5 eq) in dichloromethane (100 mL) was added rapidly at −10° C. under argon. The reaction mixture was allowed to stir at room temperature for 40 min to 1 h and monitored by LC/MS and TLC (EtOAc). The solids were removed by filtration over celite and the organic phase was washed with cold aqueous 0.1 M HCl until the pH was measured at 4 or 5. The organic phase was then washed with water, followed by saturated aqueous sodium bicarbonate and brine. The organic layer was dried over magnesium sulphate, filtered and excess solvent removed by rotary evaporation under reduced pressure. The residue was subjected to column flash chromatography (Isolera Biotage, 340 g Ultra; gradient 25/75 ethyl acetate/hexane to 100/0 ethyl acetate/hexane in 6 CV). Excess solvent was removed by rotary evaporation under reduced pressure afforded the pure product I29 as a pale yellow foam (15.7 g, 64%). LC/MS 1.92 min (ES+) m/z (relative intensity) 453.15 ([M+H]$^+$, 30%; 328.15, 100%); $^1$H NMR (400 MHz, Chloroform-d) δ 7.70 (s, 1H), 6.77 (s, 1H), 4.57-4.24 (m, 2H), 4.01-3.69 (m, 5H), 3.25-3.06 (m, 2H), 2.18 (dt, J=7.5, 5.6 Hz, 1H), 1.96-1.62 (m, 3H), 1.42-1.18 (m, 3H), 1.10 (d, J=7.4 Hz, 18H).

(d) (S)-(2-(((tert-butyldimethylsilyl)oxy)methyl)pyrrolidin-1-yl) (5-methoxy-2-nitro-4-((triisopropylsilyl)oxy)phenyl)methanone (I30)

t-Butyldimethylsilyl chloride (10.39 g, 68.9 mmol, 2 eq) was added to a solution of alcohol I29 (15.6 g, 34.5 mmol, 1 eq), and imidazole (5.87 g, 86.2 mmol, 2.5 eq) in DCM (100 mL). The reaction mixture stirred overnight at room temperature. The reaction mixture was sequentially washed with water (300 mL), 0.5 M citric acid (200 mL), brine (100 mL), and dried (MgSO4). Filtration and removal of excess solvent furnished the crude product, which was subjected to flash column chromatography (Biotage Isolera, KP-Sil 340 g; 10/90 v/v ethyl acetate/hexane up to 30/70 v/v ethyl acetate/hexane) to isolate the silyl ether I30 as a thick yellow oil. Yield: 18.9 g, 97%. LC/MS 2.32 min (ES+) m/z (relative intensity) 567.55 ([M+H]$^+$, 100%)

(e) (S)-(2-amino-5-methoxy-4-((triisopropylsilyl)oxy)phenyl) (2-(((tert-butyldimethylsilyl)oxy)methyl)pyrrolidin-1-yl)methanone (I31)

A solution of nitro compound I30 (18.9 g, 33.3 mmol, 1 eq) in ethyl acetate (200 mL) over 10% Pd/C (10% w/w, 1.89 g) was hydrogenated under pressure (45 psi) on a Parr apparatus for 6 h. The reaction mixture was filtered through celite to remove the Pd/C, and the filter pad was rinsed with ethyl acetate. Excess solvent was removed by rotary evaporation under reduced pressure, followed by drying under high vacuum to give amine I31 as a thick oil. LC/MS, 3 min method, 2.28 min (ES+) m/z (relative intensity) 537.30 ([M+H]$^+$, 100); $^1$H NMR (400 MHz, Chloroform-d) δ 6.73 (s, 1H), 6.24 (s, 1H), 4.54-4.13 (m, 3H), 4.07-3.80 (m, 1H), 3.79-3.61 (m, 4H), 3.50 (dd, J=9.2, 4.2 Hz, 2H), 2.10-1.97 (m, 2H), 1.92 (dt, J=11.7, 6.2 Hz, 1H), 1.80-1.65 (m, 1H), 1.24 (ddt, J=13.7, 9.9, 6.4 Hz, 3H), 1.09 (d, J=7.3 Hz, 18H), 0.90 (s, 9H), 0.04 (d, J=2.8 Hz, 6H).

(f) Allyl ((S)-1-(((S)-1-((4-((((2-((S)-2-(((tert-butyldimethylsilyl)oxy)methyl)pyrrolidine-1-carbonyl)-4-methoxy-5-((triisopropylsilyl)oxy)phenyl)carbamoyl)oxy)methyl)phenyl)amino)-1-oxopropan-2-yl)amino)-3-methyl-1-oxobutan-2-yl) carbamate (I32)

Triethylamine (10.1 mL, 72.4 mmol, 2.2 eq) was added to a stirred solution of the amine I31 (17.68 g, 32.9 mmol, 1 eq) and triphosgene (3.51 g, 11.8 mmol, 0.36 eq) in dry tetrahydrofuran (180 mL) at 5° C. (ice bath). The progress of the isocyanate reaction was monitored by periodically removing aliquots from the reaction mixture and quenching with methanol and performing LC/MS analysis. Once the isocyanate formation was complete a suspension of the alloc-Val-Ala-PABOH 16 (18.6 g, 49.4 mmol, 1.5 eq) and triethylamine (6.88 mL, 49.4 mmol, 1.5 eq) in dry tetrahydrofuran (70 mL) was rapidly added to the freshly prepared isocyanate. The reaction mixture was allowed to stir at 40° C. for 4 hours. The solids were removed by filtration. Excess solvent was removed by rotary evaporation under reduced pressure. The resulting residue was dry loaded on silica gel and subjected to manual flash column chromatography; 40/60 v/v ethyl acetate/hexane up to 70/30 v/v ethyl acetate/hexane. Pure fractions were collected and combined and excess eluent was removed by rotary evaporation under reduced pressure to give the product I32 8.17 g (26.4%). LC/MS, 3 min method, 2.29 min (ES+) m/z (relative intensity) 962.45 ([M+Na]$^+$, 100; 940.40 ([M+H]$^+$, 30); $^1$H NMR (400 MHz, Chloroform-d) δ 8.95 (s, 1H), 8.53 (s, 1H), 7.78 (s, 1H), 7.53 (d, J=8.1 Hz, 2H), 7.32 (d, J=8.3 Hz, 2H), 6.80 (s, 1H), 6.71 (d, J=7.5 Hz, 1H), 5.89 (tt, J=10.8, 5.3 Hz, 1H), 5.44-5.15 (m, 3H), 5.10 (s, 2H), 4.66 (p, J=7.2 Hz, 1H), 4.62-4.53 (m, 2H), 4.32 (s, 1H), 4.08-3.86 (m, 2H), 3.74 (s, 4H), 3.52 (dd, J=27.4, 7.6 Hz, 2H), 2.15 (h, J=6.8 Hz, 1H), 2.09-1.85 (m, 3H), 1.71 (s, 1H), 1.46 (d, J=7.0 Hz, 3H), 1.29 (dq, J=15.0, 7.4 Hz, 3H), 1.11 (d, J=7.4 Hz, 18H), 0.95 (dd, J=14.1, 6.8 Hz, 6H), 0.89 (s, 9H), 0.02 (d, J=13.1 Hz, 6H).

(g) Allyl ((S)-1-(((S)-1-((4-((((2-((S)-2-(((tert-butyldimethylsilyl)oxy)methyl)pyrrolidine-1-carbonyl)-5-hydroxy-4-methoxyphenyl)carbamoyl)oxy)methyl)phenyl)amino)-1-oxopropan-2-yl)amino)-3-methyl-1-oxobutan-2-yl) carbamate (I33)

Lithium acetate (50 mg, 0.49 mmol) was added to a solution of compound I32 (7 g, 7.44 mmol, 1 eq) in wet dimethylformamide (61.2 mL, 50:1 DMF/water). After 4 hours, the reaction was complete. Excess DMF was removed under vacuum and the residue was diluted with ethyl acetate (300 mL) and washed with 0.5M aqueous citric acid (100 mL), water (300 mL) and brine (100 mL). The organic layer was dried over magnesium sulphate filtered and excess ethyl acetate was removed by rotary evaporation under reduced pressure. The resulting residue was subjected to column flash chromatography (Biotage Isolera 100 g Ultra; gradient, 40/60 to 80/20 v/v ethyl acetate/hexane in 8 CV). Pure fractions were collected and combined and excess eluent was removed by rotary evaporation under reduced pressure to give the product I33 (5.13 g, 88%). LC/MS, 3 min method, 1.82 min (ES+) m/z (relative intensity) 784.40 ([M+H]$^+$, 100). $^1$H NMR (400 MHz, Chloroform-d) δ 9.06 (s, 1H), 8.62 (s, 1H), 7.78 (s, 1H), 7.45 (d, J=8.2 Hz, 2H), 7.35-7.18 (m, 2H), 6.92 (d, J=7.5 Hz, 1H), 6.80 (s, 1H), 6.50 (s, 1H), 5.89 (ddd, J=16.2, 10.7, 5.4 Hz, 1H), 5.44 (d, J=8.1 Hz, 1H), 5.37-5.15 (m, 2H), 5.14-5.01 (m, 2H), 4.67 (p, J=7.1 Hz, 1H), 4.63-4.50 (m, 2H), 4.33 (s, 1H), 4.13-3.89 (m, 2H), 3.81 (s, 3H), 3.74-3.33 (m, 3H), 2.24-1.84 (m, 4H), 1.69 (d, J=21.2 Hz, 1H), 1.43 (d, J=7.0 Hz, 3H), 1.07-0.71 (m, 15H), 0.23--0.20 (m, 6H).

(h) Tert-butyl (11S,11aS)-8-((3-((5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)pyrrolidine-1-carbonyl)-2-methoxyphenoxy)methyl)benzyl)oxy)-7-methoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (I34)

Potassium carbonate (582 mg, 4.21 mmol, 1.1 eq) was added to a solution of I25 (2.66 g, 4.21 mmol, 1.1 eq) and phenol I33 (3 g, 3.82 mmol, 1 eq) in acetone (18 mL). The reaction was stirred for 4 hours at 63° C. The solids were removed by filtration over cotton wool. Acetone was removed by rotary evaporation under reduced pressure. The resulting residue was subjected to flash column chromatography (Biotage isolera, 100 g Ultra, silica gel; gradient; 50/50 to 100/0 v/v ethyl acetate/hexane in 8 CV, elution from 83%). Pure fractions were collected and combined and excess eluent was removed by rotary evaporation under reduced pressure to give the product I34 (4.71 g, 92%). LC/MS, 3 min method, 2.08 min (ES+) m/z (relative intensity) 1335.15 ([M+H]$^+$, 50). $^1$H NMR (400 MHz, DMSO-d$_6$) δ 9.98 (s, 1H), 9.20 (s, 1H), 8.13 (d, J=7.0 Hz, 1H), 7.68-7.50 (m, 3H), 7.50-7.37 (m, 3H), 7.32 (d, J=8.2 Hz, 2H), 7.28-7.01 (m, 2H), 6.86 (s, 2H), 5.90 (ddd, J=16.0, 10.7, 5.2 Hz, 1H), 5.64 (t, J=9.8 Hz, 1H), 5.30 (d, J=17.2 Hz, 1H), 5.23-4.84 (m, 8H), 4.57-4.36 (m, 3H), 4.11 (s, 1H), 3.95-3.59 (m, 9H), 3.56-3.34 (m, 4H), 1.94 (d, J=34.0 Hz, 10H), 1.74-1.06 (m, 21H), 1.01-0.59 (m, 15H), 0.03 (s, 6H).

(i) Tert-butyl (11S,11aS)-8-((3-((5-((((4-((S)-2-((S)-2-(((allyloxy)carbonyl)amino)-3-methylbutanamido)propanamido)benzyl)oxy)carbonyl)amino)-4-((S)-2-(hydroxymethyl)pyrrolidine-1-carbonyl)-2-methoxyphenoxy)methyl)benzyl)oxy)-7-methoxy-5-oxo-11-((tetrahydro-2H-pyran-2-yl)oxy)-2,3,11,11a-tetrahydro-1H-benzo[e]pyrrolo[1,2-a][1,4]diazepine-10 (5H)-carboxylate (I35)

Tetra-n-butylammonium fluoride (1M, 6.94 mL, 6.94 mmol, 2 eq) was added to a solution of I34 (4.63 g, 3.47 mmol, 1 eq) in tetrahydrofuran (28 mL). The starting material was totally consumed after 1 h. The reaction mixture was diluted with ethyl acetate (30 mL) and washed sequentially with water and brine. The organic phase was dried over magnesium sulphate filtered and excess ethyl acetate removed by rotary evaporation under reduced pressure. The resulting residue was subjected to flash column chromatography (Biotage isolera, 50 g Ultra; gradient, 98/2 to 90/10 v/v ethyl acetate/methanol in 4 CV, elution from 10% methanol). Pure fractions were collected and combined and excess eluent was removed by rotary evaporation under reduced pressure to give the product I35 (4.23 g, quantitative). LC/MS, 3 min, 1.75 min (ES+) m/z (relative intensity) 1220.30 ([M+H]$^+$, 100). $^1$H NMR (400 MHz, DMSO-d$_6$) δ 9.98 (s, 1H), 9.17 (s, 1H), 8.13 (d, J=7.0 Hz, 1H), 7.70-7.49 (m, 3H), 7.51-7.27 (m, 6H), 7.21 (d, J=8.8 Hz, 1H), 7.15-6.58 (m, 3H), 5.90 (dt, J=10.9, 5.5 Hz, 1H), 5.66 (d, J=9.3 Hz, 1H), 5.38-4.82 (m, 9H), 4.73 (t, J=5.8 Hz, 1H), 4.59-4.34 (m, 3H), 4.05 (dd, J=15.4, 8.3 Hz, 1H), 3.96-3.68 (m, 8H), 3.66-3.32 (m, 6H), 2.16-1.72 (m, 8H), 1.63 (d, J=9.8 Hz, 3H), 1.54-1.02 (m, 18H), 0.86 (dd, J=18.2, 6.7 Hz, 6H).

(j) 4-((S)-2-((S)-2-(((allyloxy)carbonyl)amino)-3-methylbutanamido)propanamido)benzyl (11S,11aS)-8-((3-((((11S,11aS)-10-(tert-butoxycarbonyl)-7-methoxy-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)methyl)benzyl)oxy)-11-hydroxy-7-methoxy-5-oxo-2,3,11,11a-tetrahydro-1H-benzo[e]pyrrolo[1,2-a][1,4]diazepine-10(5H)-carboxylate (I36)

Stabilised IBX 45% (2.72 g, 4.36 mmol, 1.2 eq) was added to a solution of I35 (4.44 g, 3.64 mmol, 1 eq) in DMSO (2.6 mL). The reaction mixture was allowed to stir overnight. Another 0.2 eq of IBX (450 mg, 0.73 mmol, 0.2 eq) was added and the solution allowed to stir for another 18 h until reaction completion was observed by LC/MS. The solution was precipitated in water (250 mL) and filtered. The product was dissolved in DCM and the residual white solid removed by filtration. The organic phase was washed with aqueous NaHCO$_3$, water, brine, and dried over magnesium sulphate. The dichloromethane was removed by rotary evaporation under reduced pressure. The resulting residue was subjected to column flash chromatography (Biotage Isolera 100 g Ultra; gradient, 99/1 to 92/8 v/v DCM/methanol in 10 CV). Pure fractions were collected and combined and removal of excess eluent by rotary evaporation under reduced pressure afforded the product I36 (3.04 g, 69%). LC/MS, 15 min method Ace Excel 2, 7.89 and 7.97 min (THP diastereoisomers) (ES+) m/z (relative intensity) 1218.30 ([M]$^+$, 100). $^1$H NMR (400 MHz, DMSO-d$_6$) δ 9.93 (s, 1H), 8.11 (d, J=6.9 Hz, 1H), 7.68-7.27 (m, 6H), 7.27-7.01 (m, 4H), 7.01-6.32 (m, 3H), 6.02-5.81 (m, 1H), 5.71-5.57 (m, 1H), 5.57-5.40 (m, 1H), 5.29 (d, J=17.2 Hz, 1H), 5.21-4.78 (m, 8H), 4.58-4.32 (m, 3H), 3.99-3.68 (m, 8H), 3.58-3.31 (m, 8H), 2.23-1.72 (m, 9H), 1.72-1.04 (m, 18H), 0.85 (dd, J=18.0, 6.7 Hz, 6H).

(k) 4-((S)-2-((S)-2-amino-3-methylbutanamido)propanamido)benzyl (11S,11aS)-8-((3-((((11S,11aS)-10-(tert-butoxycarbonyl)-7-methoxy-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)methyl)benzyl)oxy)-11-hydroxy-7-methoxy-5-oxo-2,3,11,11a-tetrahydro-1H-benzo[e]pyrrolo[1,2-a][1,4]diazepine-10(5H)-carboxylate (I37)

Tetrakis(triphenylphosphine)palladium(0) (11 mg, 0.01 mmol, 0.02 eq) was added to a solution of I36 (600 mg, 0.49 mmol, 1 eq) and pyrrolidine (51 μL, 0.62 mmol, 1.25 eq) in dry dichloromethane (10 mL). The reaction was flushed with argon three times and stirred 20 minutes at room temperature. Then the reaction was diluted with dichloromethane (50 mL) and washed sequentially with saturated aqueous ammonium chloride (50 mL) and brine (30 mL). The organic phase was dried over magnesium sulphate filtered and excess dichloromethane removed by rotary evaporation under reduced pressure. The resulting residue I37 was used as a crude mixture for the next reaction. LC/MS, 3 min method, 1.29 min (ES+) m/z (relative intensity) 1134.35 ([M+H]$^+$, 80).

(l) tert-butyl (11S,11aS)-8-((3-((((11S,11aS)-10-(((4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl)oxy)carbonyl)-11-hydroxy-7-methoxy-5-oxo-2,3,5,10,11,11a-hexahydro-1H-benzo[e]pyrrolo[1,2-a][1,4]diazepin-8-yl)oxy)methyl)benzyl)oxy)-7-methoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (I38)

1-ethyl-3-(3'-dimethylaminopropyl)carbodiimide (94 mg, 0.79 mmol, 1 eq) was added to a solution of crude I37 (558 mg, 0.49 mmol, 1 eq) and Mal-(PEG)$_8$-acid (292 mg, 0.49 mmol, 1 eq) in chloroform (12 mL). The reaction was degassed three times with Argon and stirred for 2 hours and the presence of starting material was no longer observed by LC/MS. The reaction was diluted with dichloromethane and washed sequentially with water and brine. The organic phase was dried over magnesium sulphate filtered and excess dichloromethane removed by rotary evaporation under reduced pressure. The resulting residue was subjected to flash column chromatography (Biotage Isolera 50 g Ultra; 98/2 to 90/10 v/v DCM/methanol in 10 CV). Pure fractions were collected and combined and excess eluent was removed by rotary evaporation under reduced pressure to give I38 (485 mg, 58%). LC/MS, 3 min method, 1.58 min (ES+) m/z (relative intensity) 1709.30 ([M+H]$^+$, 100). $^1$H NMR (400 MHz, DMSO-d$_6$) δ 9.88 (s, 1H), 8.13 (d, J=7.0 Hz, 1H), 8.06-7.92 (m, 1H), 7.85 (d, J=8.6 Hz, 1H), 7.68-7.04 (m, 9H), 6.99 (s, 2H), 6.89 (d, J=15.0 Hz, 2H), 6.52 (s, 1H), 5.66 (d, J=9.4 Hz, 1H), 5.47 (d, J=8.0 Hz, 1H), 5.26-4.75 (m, 6H), 4.49-4.31 (m, 1H), 4.20 (t, J=7.6 Hz, 1H), 3.80 (d, J=11.9 Hz, 6H), 3.59 (t, J=7.2 Hz, 4H), 3.55-3.41 (m, 32H), 3.41-3.30 (m, 11H), 3.21-3.09 (m, 3H), 2.48-2.28 (m, 4H), 2.18-1.08 (m, 24H), 0.84 (dd, J=15.0, 6.7 Hz, 5H).

(m) 4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl (11S,11aS)-11-hydroxy-7-methoxy-8-((3-((((S)-7-methoxy-5-oxo-2,3,5,11a-tetrahydro-1H-benzo[e]pyrrolo[1,2-a][1,4]diazepin-8-yl)oxy)methyl)benzyl)oxy)-5-oxo-2,3,11,11a-tetrahydro-1H-benzo[e]pyrrolo[1,2-a][1,4]diazepine-10(5H)-carboxylate (3)

A cold mixture of TFA/water (6 mL) was added to I38 (460 mg, 0.27 mmol, 1 eq) and the resulting solution was allowed to stir at 0° C. for 2 hours. The reaction was neutralised with saturated aqueous NaHCO$_3$ (200 mL) and dichloromethane (50 mL). The DCM layer was washed sequentially with water and brine. The organic phase was dried over magnesium sulphate filtered and excess dichloromethane removed by rotary evaporation under reduced pressure. The resulting residue was subjected to flash column chromatography (Biotage Isolera 50 g Ultra; 98/2 to 88/12 v/v DCM/methanol in 10 CV). The pure fractions were collected, combined (154 mg, 38%), and further purified by reverse phase preparative HPLC (Method C) (gradient up to 75/25 acetonitrile/water, 0.02% formic) to give pure 3 (78 mg, 19%). LC/MS, 15 min method, Ace-Excel2, 6.18 min (ES+) m/z (relative intensity) 1506.70 ([M+H]$^+$, 100). $^1$H NMR (400 MHz, DMSO-d$_6$) δ 10.07-9.79 (m, 1H), 8.14 (d, J=7.2 Hz, 1H), 7.98 (t, J=5.6 Hz, 1H), 7.85 (d, J=8.6 Hz, 1H), 7.78 (d, J=4.4 Hz, 1H), 7.67-7.30 (m, 7H), 7.28-7.05 (m, 3H), 6.99 (s, 2H), 6.98-6.85 (m, 2H), 6.58-6.47 (m, 1H), 5.59-5.34 (m, 1H), 5.32-4.77 (m, 6H), 4.48-4.30 (m, 1H), 4.28-4.08 (m, 1H), 3.88-3.75 (m, 5H), 3.75-3.55 (m, 6H), 3.55-3.42 (m, 28H), 3.42-3.32 (m, 6H), 3.14 (q, J=5.8 Hz, 2H), 2.48-2.16 (m, 6H), 2.08-1.77 (m, 6H), 1.36-1.17 (m, 4H), 0.84 (dd, J=15.4, 6.7 Hz, 6H).

Example 4

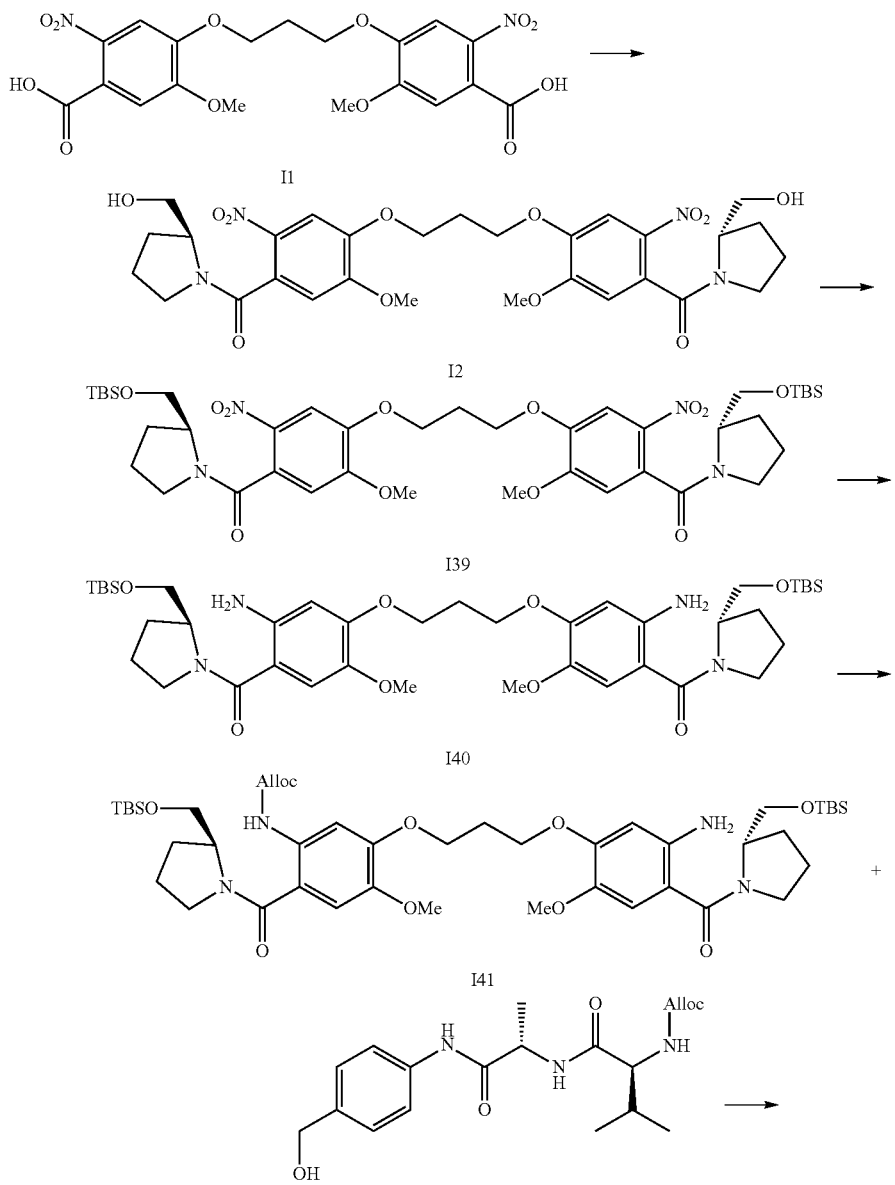

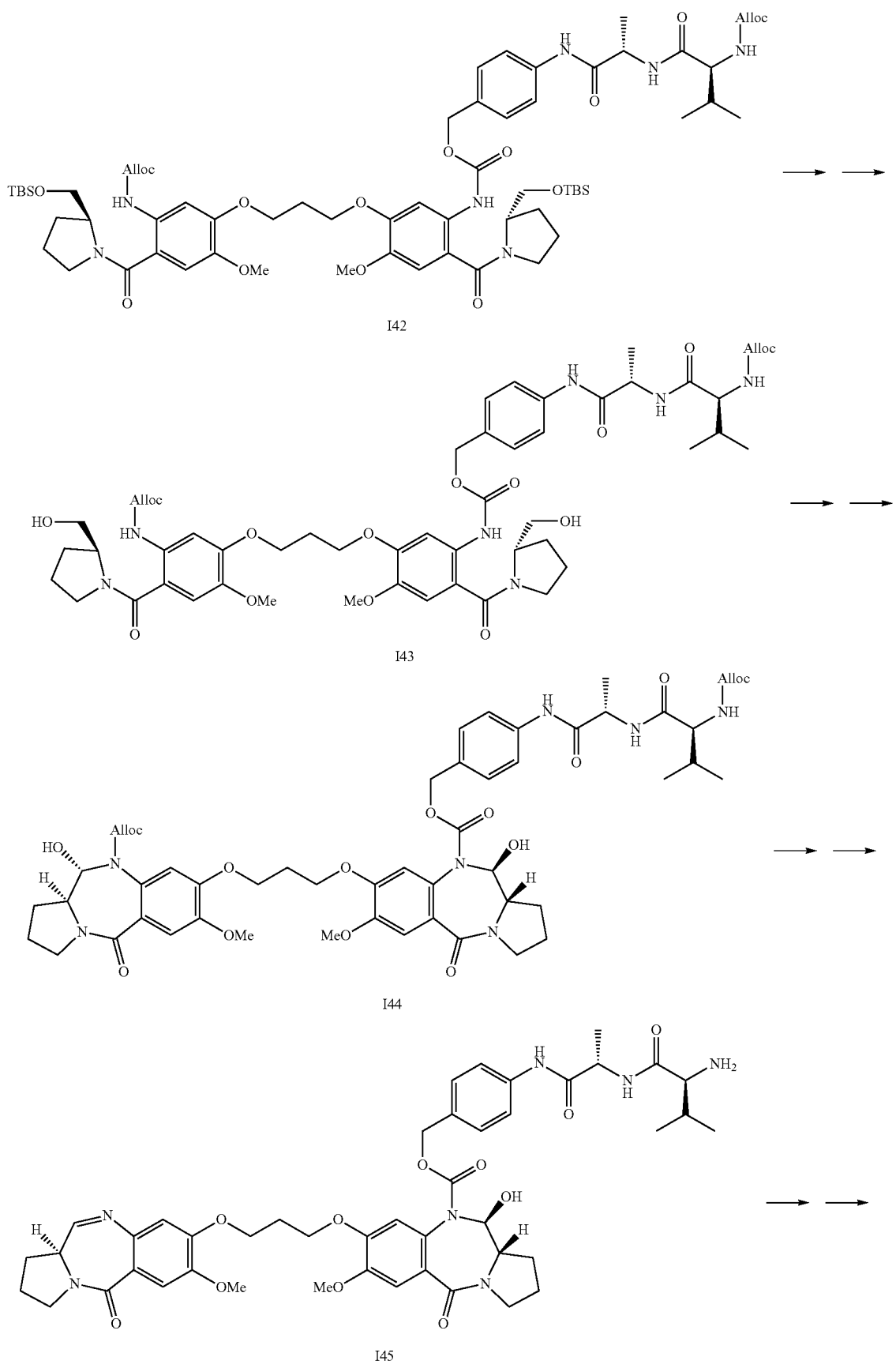

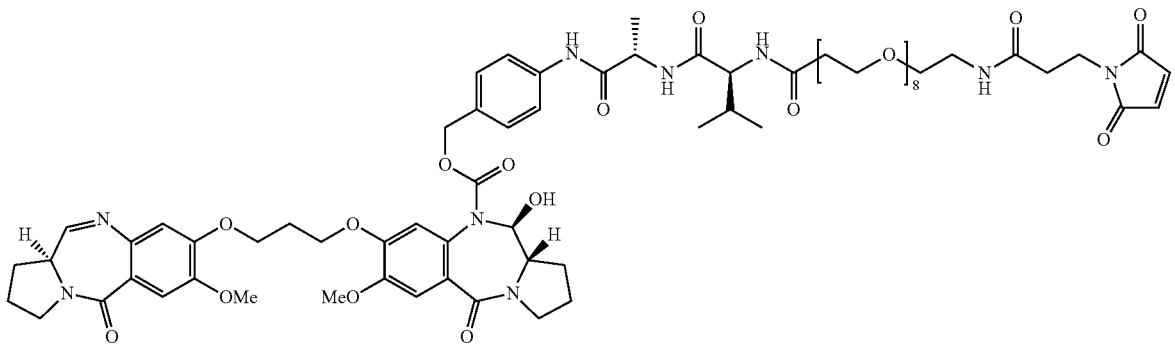

(a) ((Propane-1,3-diylbis(oxy))bis(5-methoxy-2-nitro-4,1-phenylene))bis(((S)-2-(hydroxymethyl) pyrrolidin-1-yl)methanone) (I2)

DMF (12 drops) was added to a stirred suspension of 11 (10 g, 21.5 mmol) and oxalyl chloride (5.6 mL, 8.2 g, 64.5 mmol) in anhydrous DCM (150 mL). Following initial effervescence the reaction suspension became a solution and the mixture was allowed to stir at room temperature for 16 hr. Majority of solvent was removed by evaporation under reduced pressure. The resulting concentrated solution was re-dissolved in a minimum amount of dry DCM and triturated with diethyl ether. The yellow precipitate was collected by vacuum filtration, washed with cold diethyl ether and dried for 1 hr in a vacuum oven at 40° C. The acid chloride was added, in portions, to a stirred suspension of (S)-(+)-2-pyrrolidinemethanol (5.0 g, 4.9 mL, 49.5 mmol) and TEA (15.0 mL, 10.9 g, 108 mmol) in anhydrous DCM (100 mL) at −40° C. (dry ice/CH$_3$CN). The resulting solution was stirred for a further 60 mins, diluted with DCM (100 mL) and washed with 1N HCl (2×50 mL), saturated NaHCO$_3$ (3×40 mL), brine (50 mL), dried (MgSO$_4$) and the solvent evaporated under vacuum to give the pure product I2 as a yellow solid (13.6 g, 100% yield). LC/MS (method A): retention time 1.33 mins (ES+) m/z 655 [M+Na]$^+$, 633 [M+H]$^+$ (see appendix). $^1$H NMR (400 MHz, DMSO-d$_6$) δ 1.68-1.80 (m, 2H), 1.80-2.00 (m, 6H), 2.27 (d, 2H), 3.05-3.25 (m, 4H), 3.37-3.48 (m, 2H), 3.56-3.76 (m, 2H), 3.92 (s, 6H), 4.09 (dd, 2H), 4.25-4.31 (m, 4H), 4.82 (t, 2H), 7.08 (s, 2H), 7.73 (s, 2H).

(b) ((propane-1,3-diylbis(oxy))bis(5-methoxy-2-nitro-4,1-phenylene))bis(((S)-2-(((tert-butyldimethylsilyl)oxy)methyl)pyrrolidin-1-yl)methanone) (I39)

TBS-Cl (8.12 g, 53.90 mmol) was added to a solution of 12 (15.5 g, 24.50 mmol) and imidazole (4.17 g, 61.25 mmol) in DCM (300 mL) at room temperature under nitrogen. The resulting mixture was stirred at room temperature for 12 hr. Water (200 mL) was added, the organic layer removed, and the aqueous phase extracted with DCM (2×300 mL). The combined organic phases were dried (Na$_2$SO$_4$) and evaporated under vacuum to afford dark residue which was purified by column chromatography (0 to 2% methanol/DCM). Pure fractions were evaporated under vacuum to afford I39 as a brown solid (17.0 g, 81% yield). LC/MS (method A): retention time 1.83 mins (ES+) m/z 861 [M+H]$^+$. $^1$H NMR (400 MHz, DMSO-d$_6$) δ 0.09 (s, 12H), 0.91 (s, 18H), 1.70-1.81 (m, 2H), 1.87-1.99 (m, 6H), 2.22-2.30 (m, 2H), 3.10 (t, 4H), 3.40-3.51 (m, 2H), 3.59-3.67 (m, 2H), 3.88-3.95 (m, 2H), 3.91 (s, 6H), 4.28 (t, 6H), 6.96 (s, 2H), 7.72 (s, 2H).

(c) ((propane-1,3-diylbis(oxy))bis(2-amino-5-methoxy-4, 1-phenylene))bis(((S)-2-(((tert-butyldimethylsilyl)oxy)methyl)pyrrolidin-1-yl)methanone) (I40)

Zinc (25.8 g, 394.8 mmol) and saturated NH$_4$Cl (150 mL) were added to a solution of I39 (17 g, 19.74 mmol) in EtOH (300 mL) at room temperature. The resulting mixture was stirred at 50° C. for 3 hr, cooled and filtered through a bed of celite which was then washed with EtOAc (300 mL) and water (300 mL). The organic layer was removed and the aqueous layer extracted with EtOAc (3×400 mL). The combined organic phases were dried (MgSO$_4$) and evaporated under vacuum to afford a yellow residue which was purified by column chromatography (0 to 5% methanol/DCM). Pure fractions were evaporated to dryness to give I40 as a yellow solid (13.00 g, 82% yield). LC/MS (method A): retention time 2.30 mins (ES+) m/z 802.2 [M+H]$^+$ 1H NMR (400 MHz, DMSO-d$_6$) δ 0.06 (s, 12H), 0.85 (s, 18H), 1.52-1.78 (m, 2H), 1.81-2.00 (m, 6H), 2.14-2.22 (m, 2H), 3.41 (d, 4H), 3.61-3.75 (m, 4H), 3.63 (s, 6H), 4.01-4.16 (m, 6H), 4.98-5.22 (m, 4H), 6.40 (s, 2H), 6.66 (s, 2H).

(d) allyl (5-(3-(5-amino-4-((S)-2-(((t-butyldimethylsilyl)oxy)methyl)pyrrolidine-1-carbonyl)-2-methoxyphenoxy)propoxy)-2-((S)-2-(((t-butyldimethylsilyl)oxy)methyl)pyrrolidine-1-carbonyl)-4-methoxyphenyl) carbamate (I41)

Allyl chloroformate (784 µL, 0.9 g, 7.36 mmol) was added dropwise to a solution of I40 (5.9 g, 7.36 mmol) and pyridine (715 µL, 0.7 g, 8.84 mmol) in DCM (100 mL) at 00° C. The reaction mixture was warmed to room temperature and stirred for a further 2 hr. The reaction mixture was washed with 0.5M HCl (50 mL), saturated sodium hydrogen carbonate (50 mL) and brine (50 mL). The solvent was removed under reduced pressure and the resulting oil purified by column chromatography; (initial elution with 50% ethyl acetate/heptane removed the bis-alloc protected amine, this was followed by elution with ethyl acetate to remove the desired mono-alloc protected product (141). Finally, any unreacted starting material was removed with 5% methanol/DCM). Pure fractions were evaporated under reduced pressure to leave I41 as a yellow solid (3.5 g, 54% yield). LC/MS (method B): retention time 2.41 mins (ES+) m/z 886.5 [M+H]+

(e) allyl (5-(3-(5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)pyrrolidine-1-carbonyl)-2-methoxyphenoxy)propoxy)-2-((S)-2-(((tert-butyldimethylsilyl)oxy)methyl)pyrrolidine-1-carbonyl)-4-methoxyphenyl)carbamate (I42)

Triphosgene (0.41 g, 1.4 mmol) was added to a stirred solution of I41 (3.5 g, 3.95 mmol) in dry THF (70 mL) at room temperature under Argon. Triethylamine (1.2 mL, 0.87 g, 8.6 mmol) was added, and the resulting mixture stirred for 10 mins. Analysis by LC/MS revealed complete conversion to isocyanate (sampled in MeOH to give methyl carbamate, retention time 2.48 mins, (ES+) m/z 944.4 [M+H]+). A mixture of 16 (1.64 g, 4.35 mmol) and triethylamine (0.83 mL, 0.6 g, 5.9 mmol) in dry THF (30 mL) was added. The reaction mixture was stirred under argon for 2 hr at 40° C. The solvent was removed under vacuum and the residue purified by column chromatography (0.5 to 2.5% methanol/DCM) to leave I42 as a white solid (3.58 g, 70% yield). LC/MS (method B): retention time 2.45 mins, (ES+) m/z 1290.0 [M+H]+.

(f) allyl (5-(3-(5-((((4-((S)-2-((S)-2-(((allyloxy)carbonyl)amino)-3-methylbutanamido)propanamido)benzyl)oxy)carbonyl)amino)-4-((S)-2-(hydroxymethyl)pyrrolidine-1-carbonyl)-2-methoxyphenoxy)propoxy)-2-((S)-2-(hydroxymethyl)pyrrolidine-1-carbonyl)-4-methoxyphenyl)carbamate (I43)

1M tetrabutylammonium fluoride (6.1 mL, 6.1 mmol) was added to a solution of I42 (3.58 g, 2.78 mmol) in THF (35 mL) at room temperature. The resulting solution was stirred for 60 mins, then evaporated to dryness under reduced pressure. The residue was purified by column chromatography (2 to 5% methanol/DCM) to leave I43 as a white foam (2.95 g, 98% yield). LC/MS (method B): retention time 1.70 mins, (ES+) m/z 1061.3 [M+H]+

(g) allyl (11S,11aS)-8-(3-(((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-5-oxo-2,3,5,10,11,11a-hexahydro-1H-benzo[e]pyrrolo[1,2-a][1,4]diazepin-8-yl)oxy)propoxy)-11-hydroxy-7-methoxy-5-oxo-2,3,11,11a-tetrahydro-1H-benzo[e]pyrrolo[1,2-a][1,4]diazepine-10(5H)-carboxylate (I44)

Stahl aerobic oxidation TEMPO solution 0.2M in MeCN (5.47 mL, 1.1 mmol) followed by tetrakisacetonitrile copper (I) triflate (0.41 g, 1.1 mmol) was added to a solution of I43 (2.9 g, 2.74 mmol) in DCM (30 mL) and acetonitrile (6 mL) and stirred at 35° C. for 36 hr under an atmosphere of air. The reaction mixture was washed with water (25 mL), dried (biotage phase separator) and evaporated to dryness under reduced pressure. The residue was purified by column chromatography (3 to 6% methanol/DCM) to leave the oxidised product I44 as a white solid (2.46 g, 85% yield). LC/MS (method B): retention time 1.60 mins, (ES+) m/z 1057.1 [M+H]+.

(h) 4-((S)-2-((S)-2-amino-3-methylbutanamido)propanamido)benzyl (11S,11aS)-11-hydroxy-7-methoxy-8-(3-(((S)-7-methoxy-5-oxo-2,3,5,11a-tetrahydro-1H-benzo[e]pyrrolo[1,2-a][1,4]diazepin-8-yl)oxy)propoxy)-5-oxo-2,3,11,11a-tetrahydro-1H-benzo[e]pyrrolo[1,2-a][1,4]diazepine-10(5H)-carboxylate (I45)

Pd(Ph3P)4 (10 mg, 5 mol %) was added to a solution of I44 (200 mg, 0.19 mmol) and pyrrolidine (40 μL, 0.34 g, 0.48 mmol) in DCM (10 mL) at room temperature. The resulting solution was stirred for 30 mins. The reaction mixture was washed with saturated ammonium chloride (10 mL), dried (biotage phase separator) and evaporated to dryness under reduced pressure. The residue was then placed on a high vacuum line for 4 hr to remove traces of pyrrolidine. The resulting off-white solid was used in the next step without further purification (160 mg, 97% yield). LC/MS (method B): retention time 1.17 mins, (ES+) m/z 871.1 [M+H]+.

(i) 4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl (11S,11aS)-11-hydroxy-7-methoxy-8-(3-(((S)-7-methoxy-5-oxo-2,3,5,11a-tetrahydro-1H-benzo[e]pyrrolo[1,2-a][1,4]diazepin-8-yl)oxy)propoxy)-5-oxo-2,3,11,11a-tetrahydro-1H-benzo[e]pyrrolo[1,2-a][1,4]diazepine-10(5H)-carboxylate (1)

EDCl.HCl (46 mg, 0.24 mmol) was added to a solution of I45 and Mal-PEG8-acid (130 mg, 0.22 mmol) in CHCl3 (10 mL) and stirred at room temperature for 2 hr. LC/MS shows 78% starting material present. A further 2 eq EDCl.HCl was added in portions to push the reaction to completion. The reaction mixture was washed with water (10 mL), dried (Biotage PS) and evaporated to dryness, under reduced pressure, to leave a yellow solid which was purified by prep HPLC to leave the product 1 as an off-white solid (90 mg, 34% yield). LC/MS (method B): retention time 1.47 mins, (ES+) m/z 1445.9 [M+H]+.

Example 5

(i) 4-((29S,32S)-1-azido-29-isopropyl-32-methyl-27,30-dioxo-3,6,9,12,15,18,21,24-octaoxa-28,31-diaza-tritriacontan-33-amido)benzyl (11S,11aS)-11-hydroxy-7-methoxy-8-(3-(((S)-7-methoxy-5-oxo-2,3,5,11a-tetrahydro-1H-benzo[e]pyrrolo[1,2-a][1,4]diazepin-8-yl)oxy)propoxy)-5-oxo-2,3,11,11a-tetrahydro-1H-benzo[e]pyrrolo[1,2-a][1,4]diazepine-10(5H)-carboxylate (4)

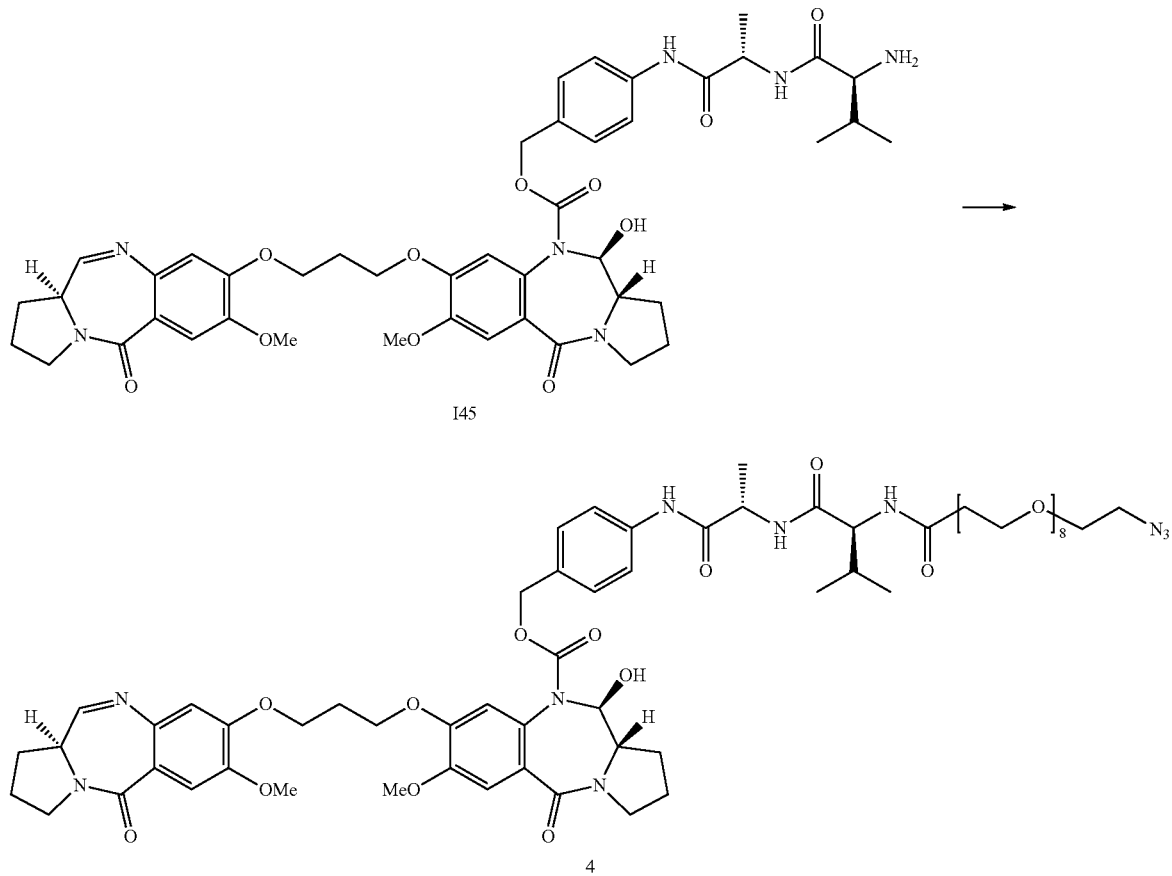

EDCl.HCl (27 mg, 0.14 mmol) was added to a solution of I45 and Azido-PEG$_8$-acid (49 mg, 0.10 mmol) in CHCl$_3$ (6 mL) and stirred at room temperature for 1 hr. The solvent was evaporated under reduced pressure, to leave a yellow foam. Purification by prep HPLC gave the product 4 as an off-white solid (20 mg, 17% yield). LC/MS (method B): retention time 6.01 min, (ES+) m/z 1320 [M+H]$^+$.

(ii) (R)-2-((3-nitropyridin-2-yl)disulfaneyl)propyl (11S,11aS)-11-hydroxy-7-methoxy-8-(3-(((S)-7-methoxy-5-oxo-2,3,5,11a-tetrahydro-1H-benzo[e]pyrrolo[1,2-a][1,4]diazepin-8-yl)oxy)propoxy)-5-oxo-2,3,11,11a-tetrahydro-1H-benzo[e]pyrrolo[1,2-a][1,4]diazepine-10(5H)-carboxylate (5)

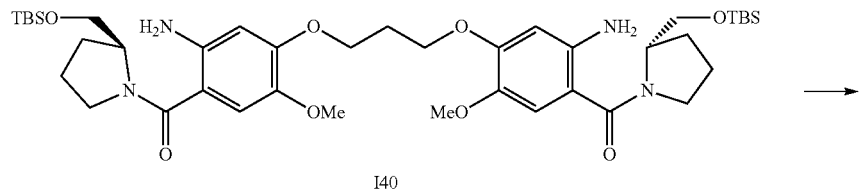

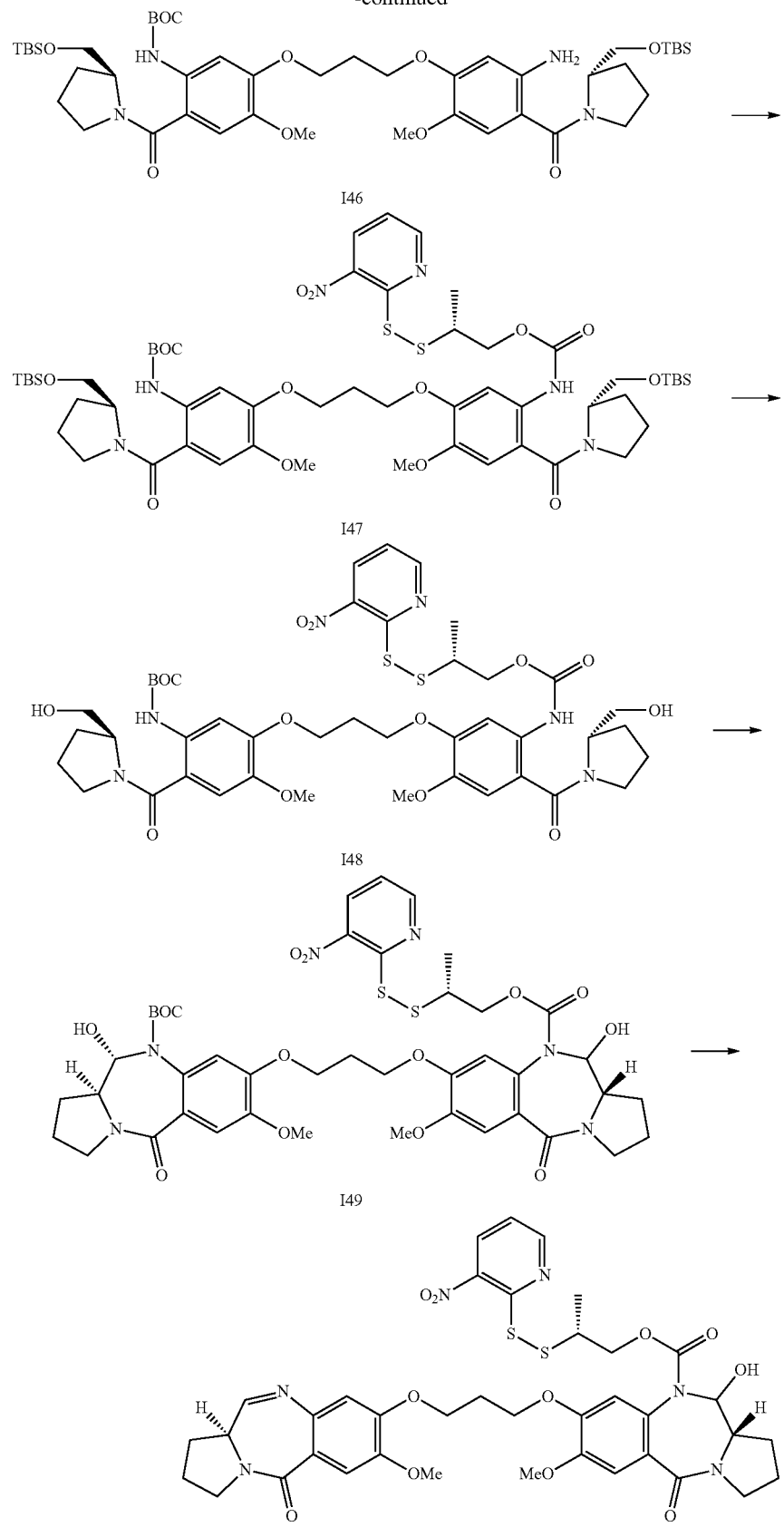

(a) tert-butyl (5-(3-(5-amino-4-((S)-2-(((tert-butyldimethylsilyl)oxy)methyl)pyrrolidine-1-carbonyl)-2-methoxyphenoxy)propoxy)-2-((S)-2-(((tert-butyldimethylsilyl)oxy)methyl)pyrrolidine-1-carbonyl)-4-methoxyphenyl)carbamate (I46)

Boc anhydride (0.5 g, 2.3 mmol, 1.0 eq) was added to a solution of I40 (1.9 g, 2.3 mmol, 1.0 eq) in THF (50 mL) and stirred at 55° C. for 5 hr. The solvent was removed by evaporation under reduced pressure and the residue purified by column chromatography (50-100% ethyl acetate/hexane) to leave the product as a yellow solid, 1.7 g (80%). LC/MS (method 1): rt 2.48 min, m/z (902.5) M+H.

(b) tert-butyl (2-((S)-2-(((tert-butyldimethylsilyl)oxy)methyl)pyrrolidine-1-carbonyl)-5-(3-(4-((S)-2-(((tert-butyldimethylsilyl)oxy)methyl)pyrrolidine-1-carbonyl)-2-methoxy-5-((((R)-2-((3-nitropyridin-2-yl)disulfaneyl)propoxy)carbonyl)amino)phenoxy)propoxy)-4-methoxyphenyl)carbamate (I47)

Triphosgene (0.135 g, 0.455 mmol, 0.35 eq) was added to a solution of (2R)-2-[(3-nitro-2-pyridyl)disulfanyl]propan-1-ol (0.316 g, 1.28 mmol, 1.05 eq) and pyridine (111 mg, 1.4 mmol, 1.15 eq) in anhydrous dichloromethane (5 mL) and stirred at room temperature for 30 min. The resulting solution was then added to a solution of I46 (1.10 g, 1.22 mmol, 1.0 eq) and pyridine (106 mg, 1.34 mmol, 1.1 eq) in anhydrous dichloromethane (10 mL) and stirred at room temperature for 60 min. The solvent was removed by evaporation under reduced pressure and the residue purified by column chromatography (40-50% ethyl acetate/hexane) to leave the product as a yellow foam, 1.21 g (85%). LC/MS (method 1): rt 2.53 min, m/z (1174.5) M+H.

(c) tert-butyl (2-((S)-2-(hydroxymethyl)pyrrolidine-1-carbonyl)-5-(3-(4-((S)-2-(hydroxymethyl)pyrrolidine-1-carbonyl)-2-methoxy-5-((((R)-2-((3-nitropyridin-2-yl)disulfaneyl)propoxy)carbonyl)amino)phenoxy)propoxy)-4-methoxyphenyl)carbamate (I48)

I47 (1.21 g, 1.03 mmol) was dissolved in a mixture of acetic acid (5 mL), THF (1 mL), methanol (1 mL) and water (2 mL). The resulting solution was stirred at room temperature for 90 mins then evaporated to dryness. The residue was taken up in ethyl acetate (50 mL), washed with water (50 mL), then sat NaHCO₃ (50 mL), dried (MgSO₄) and evaporated under reduced pressure. The residue was purified by column (4% methanol/DCM) to leave the product as a yellow solid, 0.97 g (100%). LC/MS (method 1): rt 1.87 min, m/z (946.0) M+H.

(d) tert-butyl (11S,11aS)-11-hydroxy-8-(3-(((11S,11aS)-11-hydroxy-7-methoxy-10-(((R)-2-((3-nitropyridin-2-yl)disulfaneyl)propoxy)carbonyl)-5-oxo-2,3,5,10,11,11a-hexahydro-1H-benzo[e]pyrrolo[1,2-a][1,4]diazepin-8-yl)oxy)propoxy)-7-methoxy-5-oxo-2,3,11,11a-tetrahydro-1H-benzo[e]pyrrolo[1,2-a][1,4]diazepine-10(5H)-carboxylate (I49)

Stahl Aerobic Oxidation TEMPO solution (2.05 mL, 0.4 mmol, 0.2 mol/L) followed by Tetrakisacetonitrile copper(I) triflate (0.15 g, 0.40 mmol) was added to a solution of 148 (0.97 g, 1.0 mmol) in DCM (20 mL, 312.0 mmol). The resulting mixture was heated at 35° C. for 15 hrs. The organic phase was washed with water (25 mL), dried (biotage) and evaporated to dryness under reduced pressure and purified by column chromatography (3-6% methanol/DCM) to leave the product as a white solid, 0.77 g (79%). LC/MS (method 1): rt 1.70 min, m/z (941.9) M+H.

(e) (R)-2-((3-nitropyridin-2-yl)disulfaneyl)propyl (11S,11aS)-11-hydroxy-7-methoxy-8-(3-(((S)-7-methoxy-5-oxo-2,3,5,11a-tetrahydro-1H-benzo[e]pyrrolo[1,2-a][1,4]diazepin-8-yl)oxy)propoxy)-5-oxo-2,3,11,11a-tetrahydro-1H-benzo[e]pyrrolo[1,2-a][1,4]diazepine-10(5H)-carboxylate (5)

Trifluoroacetic acid (4.5 mL) was added to water (0.5 mL) and cooled to 0° C. This solution was then added to I49 (0.75 g, 0.80 mmol) and the resulting mixture stirred at 0° C. for 2 hrs. The solvent was removed under reduced pressure, the residue taken up in DCM (10 mL) and the reaction mixture neutralised by the addition of sat NaHCO₃. After drying (biotage) and evaporation under reduced pressure, the residue was purified by column (4-6% methanol/DCM) to leave the product as a bright yellow solid, 0.6 g (91%). LC/MS (method 2): rt 6.04 min, m/z (824.0) M+H.

Analytical LC/MS Conditions for Example 5(ii)

Positive mode electrospray mass spectrometry was performed using a Waters Aquity H-class SQD2. Mobile phases used were solvent A (water with 0.1% formic acid) and solvent B (acetonitrile with 0.1% formic acid).

Method 1:

Gradient for routine 3-minute run: Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes. Flow rate was 0.8 mL/minute. Detection was at 254 nm. Column: Waters Acquity UPLC® BEH Shield RP18 1.7 µm 2.1×50 mm at 50° C. fitted with Waters Acquity UPLC® BEH Shield RP18 VanGuard Pre-column, 130A, 1.7 µm, 2.1 mm×5 mm.

Method 2:

Gradient for 15-minute run: Initial composition 5% B held over 1 minute, then increased from 5% B to 100% B over a 9 minute period. The composition was held for 2 minutes at 100% B, then returned to 5% B in 10 seconds and held there for 2 minutes 50 seconds. The total duration of the gradient run was 15.0 minutes. Flow rate was 0.8 mL/minute (for 3-minute run) and 0.6 mL/minute (for 15-minute run). Detection was at 254 nm. Column: ACE Excel 2 C18-AR, 2µ, 3.0×100 mm fitted with Waters Acquity UPLC® BEH Shield RP18 VanGuard Pre-column, 130A, 1.7 µm, 2.1 mm×5 mm.

Example 6—Conjugation

Conj-HER-1

A 50 mM solution of Dithiothreitol (DTT) in phosphate-buffered saline pH 7.4 (PBS) was added (80 molar equivalent/antibody, 16 micromoles, 0.32 mL at 50 mM) to a 12 mL solution of antibody Herceptin (30 mg, 0.2 micromoles) in reduction buffer containing PBS and 1 mM ethylenediaminetetraacetic acid (EDTA) and a final antibody concentration of 2.5 mg/mL. The reduction mixture was heated at +25° C. for 4 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 15 molar equivalent/antibody, 3 micromoles, 0.08 mL at 50 mM) in DMSO was added and the reoxidation mixture was allowed to react for 16 hours at room temperature with gentle (60 rpm) shaking at an antibody concentration of 1.5 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 µm membrane filter. Compound 1 was added as a DMSO solution (10 molar equivalent/antibody, 1.0 micromoles, in 1.5 mL DMSO) to 13.5 mL of this reoxidised antibody solution (15 mg, 0.1 micromoles) for a 10% (v/v) final DMSO concentration. The solution was shaken for 3 hours at +25° C. and then the conjugation was quenched with N-acetyl cysteine (15 micromoles, 0.150 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, the ADC was filtered using 0.22 µm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conj-HER-1 at 214 nm and 330 nm (Compound 1 specific) shows a mixture of light and heavy chains attached to several molecules of Compound 1, consistent with a drug-per-antibody ratio (DAR) of 1.74 molecules of Compound 1 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-HER-1 at 280 nm shows a monomer purity of greater than 99%. UHPLC SEC analysis gives a concentration of final ADC at 1.39 mg/mL in 7.8 mL, obtained mass of ADC is 10.8 mg (72% yield).

Conj-HER-2

A 50 mM solution of Dithiothreitol (DTT) in phosphate-buffered saline pH 7.4 (PBS) was added (80 molar equivalent/antibody, 55.5 micromoles, 1.11 mL at 50 mM) to a 11.8 mL solution of antibody Herceptin (104 mg, 0.69 micromoles) in reduction buffer containing PBS and 1 mM ethylenediaminetetraacetic acid (EDTA) and a final antibody concentration of 4.0 mg/mL. The reduction mixture was heated at +25° C. for 3.5 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 20 molar equivalent/antibody, 12.4 micromoles, 0.25 mL at 50 mM) in DMSO was added and the reoxidation mixture was allowed to react for 16 hours at room temperature with gentle (60 rpm) shaking at an antibody concentration of 2.4 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 µm membrane filter. Compound 2 was added as a DMSO solution (10 molar equivalent/antibody, 1.03 micromoles, in 1.40 mL DMSO) to 14 mL of this reoxidised antibody solution (15.5 mg, 0.103 micromoles) for a 10% (v/v) final DMSO concentration. The solution was shaken for 1.5 hours at +25° C. and then the conjugation was quenched with N-acetyl cysteine (5.15 micromoles, 0.051 mL at 100 mM).

Excess free drug was removed via Tangential Flow Filtration unit (TFF) using mPES, MidiKros® 30 kDa fiber filter with 115 cm² surface area, into buffer containing PBS pH 7.4. Extent of free drug removal was monitored by UHPLC-RP using neat conjugate. After complete removal of free drug, ADC was filtered using 0.22 µm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conj-HER-2 at 214 nm and 330 nm (Compound 2 specific) shows a mixture of light and heavy chains attached to several molecules of Compound 2, consistent with a drug-per-antibody ratio (DAR) of 1.85 molecules of Compound 2 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-HER-2 at 280 nm shows a monomer purity of greater than 98%. UHPLC SEC analysis gives a concentration of final ADC at 0.88 mg/mL in 8.5 mL, obtained mass of ADC is 7.5 mg (48% yield).

Conj-HER-3

A 50 mM solution of tris(2-carboxyethyl)phosphine (TCEP) in phosphate-buffered saline pH 7.4 (PBS) was added (40 molar equivalent/antibody, 40 micromoles, 0.08 mL at 50 mM) to a 1.39 mL solution of antibody Herceptin (15 mg, 0.1 micromoles) in reduction buffer containing PBS and 1 mM ethylenediaminetetraacetic acid (EDTA) and a final antibody concentration of 4.0 mg/mL. The reduction mixture was heated at +37° C. for 2 hours (or until full reduction observed by UHPLC) in an orbital shaker with gentle (60 rpm) shaking. After cooling down to room temperature, the reduced antibody was buffer exchanged, via Dialysis using 50 KDa MWCO cassette, into a reoxidation buffer containing PBS pH 7.4 and 1 mM EDTA to remove all the excess reducing agent for 16 hours at RT. A 50 mM solution of dehydroascorbic acid (DHAA, 25 molar equivalent/antibody, 2.5 micromoles, 0.04 mL at 50 mM) in DMSO was added and the reoxidation mixture was allowed to react for 2 hours at room temperature with gentle (60 rpm) shaking at an antibody concentration of ~1.5 mg/mL. Due to incomplete oxidation another 0.04 mL of 50 mM DHAA added and further shaken at room temperature for 2 h. After that full reoxidation of the cysteine thiols to reform the inter-chain cysteine disulfides is observed by UHPLC. The reoxidation mixture was centrifuged for 3 min at 4000 rpm and then sterile-filtered using 0.22 µm membrane filter. Compound 3 was added as a DMSO solution (10 molar equivalent/antibody, 0.8 micromoles, in 1.1 mL DMSO) to 11 mL of this reoxidised antibody solution (12 mg, 0.08 micromoles) for a 10% (v/v) final DMSO concentration. The solution was shaken for 1 hours at +25° C. and then the conjugation was quenched with N-acetyl cysteine (3.2 micromoles, 0.032 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 µm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conj-HER-3 at 214 nm and 330 nm (Compound 3 specific) shows a mixture of light and heavy chains attached to several molecules of Compound 3, consistent with a drug-per-antibody ratio (DAR) of 1.78 molecules of Compound 3 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-HER-3 at 280 nm shows a monomer purity of greater than 94%. UHPLC SEC analysis gives a concentration of final ADC at 1.14 mg/mL in 8.2 mL, obtained mass of ADC is 9.3 mg (62% yield).

Conj-R347-1

A 50 mM solution of Dithiothreitol (DTT) in phosphate-buffered saline pH 7.4 (PBS) was added (80 molar equivalent/antibody, 697 micromoles, 13.87 mL at 50 mM) to a 44.36 mL solution of antibody $R^{347}$ (1300 mg, 8.67 micromoles) in reduction buffer containing PBS and 1 mM ethylenediaminetetraacetic acid (EDTA) and a final antibody concentration of 5.0 mg/mL. The reduction mixture was heated at +25° C. for 3.5 hours (or until full reduction observed by UHPLC) in an orbital shaker with gentle (60 rpm) shaking. After cooling down to room temperature, the reduced antibody was buffer exchanged, via Tangential Flow Filtration unit (TFF) using mPES, MidiKros® 30 kDa fiber filter with 235 $cm^2$ surface area, into a reoxidation buffer containing PBS pH 7.4 and 1 mM EDTA to remove all the excess reducing agent. The reduced antibody was centrifuged for 3 min at 4000 rpm and then filtered using 0.22 µm membrane filter. A 50 mM solution of dehydroascorbic acid (DHAA, 15 molar equivalent/antibody, 130 micromoles, 2.6 mL at 50 mM) in DMSO was added and the reoxidation mixture was allowed to react for 16 hours at room temperature with gentle (60 rpm) shaking at an antibody concentration of 5.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 µm membrane filter. Compound 1 was added as a DMSO solution (10 molar equivalent/antibody, 86.7 micromoles, in 23.4 mL DMSO) to 330 mL of this reoxidised antibody solution (1300 mg, 8.67 micromoles) for a 10% (v/v) final DMSO concentration. The solution was shaken for 3 hours at +25° C. and then the conjugation was quenched with N-acetyl cysteine (433 micromoles, 4.33 mL at 100 mM).

Excess free drug was removed via Tangential Flow Filtration unit (TFF) using mPES, MidiKros® 30 kDa fiber filter with 235 $cm^2$ surface area, into buffer containing PBS pH 7.4. Extent of free drug removal was monitored by UHPLC-RP using neat conjugate. After complete removal of free drug, ADC was formulated onto 25 mM Histidine, 200 mM Sucrose, pH 6.0. ADC was filtered using 0.22 µm, Mustang filter under sterile atmosphere and then stored at −78° C.

UHPLC analysis on a Shimadzu Prominence system using a Phenomenex Aeris 3.6u XB-C18 150×2.1 mm column eluting with a gradient of water and acetonitrile on a reduced sample of Conj-R347-1 at 214 nm and 330 nm (Compound 1 specific) shows a mixture of light and heavy chains attached to several molecules of Compound 1, consistent with a drug-per-antibody ratio (DAR) of 1.82 molecules of Compound 1 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of greater than 99%. UHPLC SEC analysis gives a concentration of final Conj-R347-1 at 10.11 mg/mL in 113 mL, obtained mass of ADC is 1141 mg (88% yield).

Conj-R347-2

A 50 mM solution of Dithiothreitol (DTT) in phosphate-buffered saline pH 7.4 (PBS) was added (80 molar equivalent/antibody, 213 micromoles, 4.3 mL at 50 mM) to a 13.7 mL solution of antibody R347 (400 mg, 2.67 micromoles) in reduction buffer containing PBS and 1 mM ethylenediaminetetraacetic acid (EDTA) and a final antibody concentration of 5.0 mg/mL. The reduction mixture was heated at +25° C. for 3.5 hours (or until full reduction observed by UHPLC) in an orbital shaker with gentle (60 rpm) shaking. After cooling down to room temperature, the reduced antibody was buffer exchanged, via Tangential Flow Filtration unit (TFF) using mPES, MidiKros® 30 kDa fiber filter with 115 $cm^2$ surface area, into a reoxidation buffer containing PBS pH 7.4 and 1 mM EDTA to remove all the excess reducing agent. The reduced antibody was centrifuged for 3 min at 4000 rpm and then filtered using 0.22 µm membrane filter. A 50 mM solution of dehydroascorbic acid (DHAA, 15 molar equivalent/antibody, 40 micromoles, 0.8 mL at 50 mM) in DMSO was added and the reoxidation mixture was allowed to react for 16 hours at room temperature with gentle (60 rpm) shaking at an antibody concentration of 3.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 µm membrane filter. Compound 2 was added as a DMSO solution (10 molar equivalent/antibody, 26.7 micromoles, in 15.5 mL DMSO) to 330 mL of this reoxidised antibody solution (400 mg, 2.67 micromoles) for a 10% (v/v) final DMSO concentration. The solution was shaken for 1.5 hours at +25° C. and then the conjugation was quenched with N-acetyl cysteine (125 micromoles, 1.25 mL at 100 mM).

Excess free drug was removed via Tangential Flow Filtration unit (TFF) using mPES, MidiKros® 30 kDa fiber filter with 115 $cm^2$ surface area, into buffer containing PBS pH 7.4. Extent of free drug removal was monitored by UHPLC-RP using neat conjugate. After complete removal of free drug, ADC was formulated onto 25 mM Histidine, 200 mM Sucrose, pH 6.0. ADC was filtered using 0.22 µm, Mustang filter under sterile atmosphere and then stored at −78° C.

UHPLC analysis on a Shimadzu Prominence system using a Phenomenex Aeris 3.6u XB-C18 150×2.1 mm column eluting with a gradient of water and acetonitrile on a reduced sample of Conj-R347-2 at 214 nm and 330 nm (Compound 2 specific) shows a mixture of light and heavy chains attached to several molecules of Compound 2, consistent with a drug-per-antibody ratio (DAR) of 1.8 molecules of Compound 2 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-R347-2 at 280 nm shows a monomer purity of greater than 99%. UHPLC SEC analysis gives a concentration of final ADC at 3.06 mg/mL in 93 mL, obtained mass of ADC is 284 mg (71% yield).

Conj-R347-3

A 50 mM solution of Dithiothreitol (DTT) in phosphate-buffered saline pH 7.4 (PBS) was added (80 molar equivalent/antibody, 240 micromoles, 4.8 mL at 50 mM) to a 15.36 mL solution of antibody R347 (450 mg, 3.0 micromoles) in reduction buffer containing PBS and 1 mM ethylenediaminetetraacetic acid (EDTA) and a final antibody concentration of 5.0 mg/mL. The reduction mixture was heated at +25° C. for 3.5 hours (or until full reduction observed by UHPLC) in an orbital shaker with gentle (60 rpm) shaking. After cooling down to room temperature, the reduced antibody was buffer exchanged, via Tangential Flow Filtration unit (TFF) using mPES, MidiKros® 30 kDa fiber filter with 235 cm$^2$ surface area, into a reoxidation buffer containing PBS pH 7.4 and 1 mM EDTA to remove all the excess reducing agent. The reduced antibody was centrifuged for 3 min at 4000 rpm and then filtered using 0.22 µm membrane filter. A 50 mM solution of dehydroascorbic acid (DHAA, 15 molar equivalent/antibody, 45 micromoles, 0.9 mL at 50 mM) in DMSO was added and the reoxidation mixture was allowed to react for 16 hours at room temperature with gentle (60 rpm) shaking at an antibody concentration of 3.5 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 µm membrane filter. Compound 3 was added as a DMSO solution (10 molar equivalent/antibody, 30.0 micromoles, in 13.0 mL DMSO) to 330 mL of this reoxidised antibody solution (450 mg, 3.0 micromoles) for a 10% (v/v) final DMSO concentration. The solution was shaken for 3 hours at +25° C. and then the conjugation was quenched with N-acetyl cysteine (150 micromoles, 1.5 mL at 100 mM).

Excess free drug was removed via Tangential Flow Filtration unit (TFF) using mPES, MidiKros® 30 kDa fiber filter with 235 cm$^2$ surface area, into buffer containing PBS pH 7.4. Extent of free drug removal was monitored by UHPLC-RP using neat conjugate. After complete removal of free drug, ADC was formulated onto 25 mM Histidine, 200 mM Sucrose, pH 6.0. ADC was filtered using 0.22 µm, Mustang filter under sterile atmosphere and then stored at −78° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 3 specific) shows a mixture of light and heavy chains attached to several molecules of Compound 3, consistent with a drug-per-antibody ratio (DAR) of 1.82 molecules of Compound 3 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-R347-3 at 280 nm shows a monomer purity of greater than 99%. UHPLC SEC analysis gives a concentration of final ADC at 2.35 mg/mL in 174 mL, obtained mass of Conj-R347-3 is 409 mg (91% yield).

Conj-HLL2-1

A 50 mM solution of Dithiothreitol (DTT) in phosphate-buffered saline pH 7.4 (PBS) was added (80 molar equivalent/antibody, 53.3 micromoles, 1.07 mL at 50 mM) to a 11.8 mL solution of antibody HLL2 (100 mg, 0.6 micromoles) in reduction buffer containing PBS and 1 mM ethylenediaminetetraacetic acid (EDTA) and a final antibody concentration of 5.0 mg/mL. The reduction mixture was heated at +25° C. for 3.5 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 15 molar equivalent/antibody, 9 micromoles, 0.18 mL at 50 mM) in DMSO was added and the reoxidation mixture was allowed to react for 16 hours at room temperature with gentle (60 rpm) shaking at an antibody concentration of 3.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 µm membrane filter. Compound 1 was added as a DMSO solution (10 molar equivalent/antibody, 1.2 micromoles, in 0.58 mL DMSO) to 7 mL of this reoxidised antibody solution (18 mg, 0.12 micromoles) for a 10% (v/v) final DMSO concentration. The solution was shaken for 3 hours at +25° C. and then the conjugation was quenched with N-acetyl cysteine (6 micromoles, 0.06 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 µm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conj-HLL2-1 at 214 nm and 330 nm (Compound 1 specific) shows a mixture of light and heavy chains attached to several molecules of Compound 1, consistent with a drug-per-antibody ratio (DAR) of 1.74 molecules of Compound 1 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-HLL2-1 at 280 nm shows a monomer purity of greater than 98%. UHPLC SEC analysis gives a concentration of final ADC at 1.6 mg/mL in 7.5 mL, obtained mass of ADC is 12 mg (67% yield).

Conj-HLL2-2

A 50 mM solution of Dithiothreitol (DTT) in phosphate-buffered saline pH 7.4 (PBS) was added (80 molar equivalent/antibody, 53.3 micromoles, 1.07 mL at 50 mM) to a 11.8 mL solution of antibody HLL2 (100 mg, 0.6 micromoles) in reduction buffer containing PBS and 1 mM ethylenediaminetetraacetic acid (EDTA) and a final antibody concentration of 5.0 mg/mL. The reduction mixture was heated at +25° C. for 3.5 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 15 molar equivalent/antibody, 9 micromoles, 0.18 mL at 50 mM) in DMSO was added and the reoxidation mixture was allowed to react for 16 hours at room temperature with gentle (60 rpm) shaking at an antibody concentration of 3.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 μm membrane filter. Compound 2 was added as a DMSO solution (10 molar equivalent/antibody, 1.2 micromoles, in 0.58 mL DMSO) to 7 mL of this reoxidised antibody solution (18 mg, 0.12 micromoles) for a 10% (v/v) final DMSO concentration. The solution was shaken for 3 hours at +25° C. and then the conjugation was quenched with N-acetyl cysteine (6 micromoles, 0.06 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 2 specific) shows a mixture of light and heavy chains attached to several molecules of Compound 2, consistent with a drug-per-antibody ratio (DAR) of 1.78 molecules of Compound 2 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-HLL2-2 at 280 nm shows a monomer purity of greater than 98%. UHPLC SEC analysis gives a concentration of final ADC at 1.56 mg/mL in 8.0 mL, obtained mass of Conj-HLL2-2 is 12.5 mg (69% yield).

Conj-HLL2-3

A 50 mM solution of Dithiothreitol (DTT) in phosphate-buffered saline pH 7.4 (PBS) was added (80 molar equivalent/antibody, 53.3 micromoles, 1.07 mL at 50 mM) to a 11.8 mL solution of antibody HLL2 (100 mg, 0.6 micromoles) in reduction buffer containing PBS and 1 mM ethylenediaminetetraacetic acid (EDTA) and a final antibody concentration of 5.0 mg/mL. The reduction mixture was heated at +25° C. for 3.5 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 15 molar equivalent/antibody, 9 micromoles, 0.18 mL at 50 mM) in DMSO was added and the reoxidation mixture was allowed to react for 16 hours at room temperature with gentle (60 rpm) shaking at an antibody concentration of 3.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 μm membrane filter. Compound 3 was added as a DMSO solution (10 molar equivalent/antibody, 1.2 micromoles, in 0.58 mL DMSO) to 7 mL of this reoxidised antibody solution (18 mg, 0.12 micromoles) for a 10% (v/v) final DMSO concentration. The solution was shaken for 3 hours at +25° C. and then the conjugation was quenched with N-acetyl cysteine (6 micromoles, 0.06 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 3 specific) shows a mixture of light and heavy chains attached to several molecules of Compound 3, consistent with a drug-per-antibody ratio (DAR) of 1.79 molecules of Compound 3 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-HLL2-3 at 280 nm shows a monomer purity of greater than 98%. UHPLC SEC analysis gives a concentration of final ADC at 1.73 mg/mL in 8.2 mL, obtained mass of Conj-HLL2-3 is 14.2 mg (79% yield).

Conj-CD79b-1

A 50 mM solution of Dithiothreitol (DTT) in phosphate-buffered saline pH 7.4 (PBS) was added (80 molar equivalent/antibody, 53.6 micromoles, 1.07 mL at 50 mM) to a 13.9 mL solution of antibody CD79b (100 mg, 0.67 micromoles) in reduction buffer containing PBS and 1 mM ethylenediaminetetraacetic acid (EDTA) and a final antibody concentration of 4.0 mg/mL. The reduction mixture was heated at +25° C. for 4 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 15 molar equivalent/antibody, 9 micromoles, 0.18 mL at 50 mM) in DMSO was added and the reoxidation mixture was allowed to react for 16 hours at room temperature with gentle (60 rpm) shaking at an antibody concentration of 2.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 μm membrane filter. Compound 1 was added as a DMSO solution (10 molar equivalent/antibody, 1.2 micromoles, in 1.0 mL DMSO) to 9.0 mL of this reoxidised antibody solution (18 mg, 0.12 micromoles) for a 10% (v/v) final DMSO concentration. The solution was shaken for 2 hours at +25° C. and then the conjugation was quenched with N-acetyl cysteine (4.8 micromoles, 0.048 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 1 specific) shows a mixture of light and heavy chains attached to several molecules of Compound 1, consistent with a drug-per-antibody ratio (DAR) of 1.90 molecules of Compound 1 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-CD79b-1 at 280 nm shows a monomer purity of greater than 98%. UHPLC SEC analysis gives a concentration of final ADC at 2.00 mg/mL in 7.85 mL, obtained mass of Conj-CD79b-1 is 15.7 mg (79% yield).

Conj-CD79b-2

A 50 mM solution of Dithiothreitol (DTT) in phosphate-buffered saline pH 7.4 (PBS) was added (80 molar equivalent/antibody, 53.6 micromoles, 1.07 mL at 50 mM) to a 13.9 mL solution of antibody CD79b (100 mg, 0.67 micromoles) in reduction buffer containing PBS and 1 mM ethylenediaminetetraacetic acid (EDTA) and a final antibody concentration of 4.0 mg/mL. The reduction mixture was heated at +25° C. for 4 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 15 molar equivalent/antibody, 9 micromoles, 0.18 mL at 50 mM) in DMSO was added and the reoxidation mixture was allowed to react for 16 hours at room temperature with gentle (60 rpm) shaking at an antibody concentration of 2.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 μm membrane filter. Compound 2 was added as a DMSO solution (10 molar equivalent/antibody, 1.2 micromoles, in 1.0 mL DMSO) to 9.0 mL of this reoxidised antibody solution (18 mg, 0.12 micromoles) for a 10% (v/v) final DMSO concentration. The solution was shaken for 2 hours at +25° C. and then the conjugation was quenched with N-acetyl cysteine (4.8 micromoles, 0.048 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 2 specific) shows a mixture of light and heavy chains attached to several molecules of Compound 2, consistent with a drug-per-antibody ratio (DAR) of 1.87 molecules of Compound 2 per antibody. UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of Conj-CD79b-2 at 280 nm shows a monomer purity of greater than 98%. UHPLC SEC analysis gives a concentration of final ADC at 2.25 mg/mL in 5.9 mL, obtained mass of Conj-CD79b-2 is 13.3 mg (66% yield).

Conj-1C1-1

A 50 mM solution of Dithiothreitol (DTT) in phosphate-buffered saline pH 7.4 (PBS) was added (80 molar equivalent/antibody, 75 micromoles, 1.5 mL at 50 mM) to a 26.4 mL solution of antibody 1C1 (140 mg, 0.93 micromoles) in reduction buffer containing PBS and 1 mM ethylenediaminetetraacetic acid (EDTA) and a final antibody concentration of 5.0 mg/mL. The reduction mixture was heated at +25° C. for 3.5 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 15 molar equivalent/antibody, 14 micromoles, 0.28 mL at 50 mM) in DMSO was added and the reoxidation mixture was allowed to react for 16 hours at room temperature with gentle (60 rpm) shaking at an antibody concentration of 3.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 μm membrane filter. Compound 1 was added as a DMSO solution (10 molar equivalent/antibody, 1.3 micromoles, in 0.6 mL DMSO) to 6 mL of this reoxidised antibody solution (20 mg, 0.133 micromoles) for a 10% (v/v) final DMSO concentration. The solution was shaken for 4 hours at +25° C. and then the conjugation was quenched with N-acetyl cysteine (6.65 micromoles, 0.067 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, buffer exchanged onto 25 mM Histidine, 200 mM Sucrose, pH 6.0. ADC was filtered using 0.22 μm, Mustang filter under sterile atmosphere and then stored at −78° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 1 specific) shows a mixture of light and heavy chains attached to several molecules of Compound 1, consistent with a drug-per-antibody ratio (DAR) of 1.86 molecules of Compound 1 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of greater than 98%. UHPLC SEC analysis gives a concentration of final ADC at 1.49 mg/mL in 8.0 mL, obtained mass of ADC is 11.9 mg (60% yield).

Conj-HER-1++ (High DAR)

A 50 mM solution of Dithiothreitol (DTT) in phosphate-buffered saline pH 7.4 (PBS) was added (100 molar equivalent/antibody, 6.7 micromoles, 0.13 mL at 50 mM) to a 5 mL solution of antibody (10 mg, 67 nanomoles) in reduction buffer containing PBS and 1 mM ethylenediaminetetraacetic acid (EDTA) and a final antibody concentration of 2.0 mg/mL. The resultant mixture was incubated at +25° C. for overnight (or until full reduction observed by UHPLC) in an orbital shaker with gentle (60 rpm) shaking. After cooling down to room temperature, the reduced antibody was buffer exchanged, via spin filter using 50 KDa MWCO vivaspin, into conjugation buffer containing PBS pH 7.4 and 1 mM EDTA to remove all the excess reducing agent. Compound 1 was added as a DMSO solution (20 molar equivalent/antibody, 1.34 micromoles, in 0.4 mL DMSO) to 4.0 mL of this reduced antibody solution (10 mg, 67 nanomoles) for a 10% (v/v) final DMSO concentration. The solution was shaken for 1 hour at +25° C. and then conjugation was quenched with excess N-acetyl cysteine (6.7 micromoles, 67 μL at 100 mM).

Resultant ADC was purified via preparative size exclusion column (GE Sephadex 26/60) fitted to an AKTA Start instrument using PBS, pH 7.4 buffer. Fractions were collected and analysed for the monomeric content using Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) at 280 nm. Fractions with monomer content >92% were pooled and then concentrated using 50 kDa MWCO vivaspin into buffer containing PBS pH 7.4. Extent of free drug removal was monitored by UHPLC-RP using neat conjugate and after complete removal of free drug, ADC was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 1 specific) shows a mixture of light and heavy chains attached to several molecules of Compound 1, consistent with a drug-per-antibody ratio (DAR) of 7.41 molecules of Compound 1 per antibody.

UHPLC analysis on a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of 95%. UHPLC SEC analysis gives a concentration of final ADC at 1.44 mg/mL in 4.5 mL, obtained mass of ADC is 6.5 mg (65% yield).

Conj-HER-1+ (Medium DAR)

A 10 mM solution of tris(2-carboxyethyl)phosphine (TCEP) in phosphate-buffered saline pH 7.4 (PBS) was added (2 molar equivalent/antibody, 0.134 micromoles, 13.3 μL at 10 mM) to a 4 mL solution of antibody (10 mg, 67 nanomoles) in reduction buffer containing PBS and 1 mM ethylenediaminetetraacetic acid (EDTA) and a final antibody concentration of 2.5 mg/mL. The reduction mixture was heated at +37° C. for 2 hours in an orbital shaker with gentle (60 rpm) shaking. Compound 1 was added as a DMSO solution (15 molar equivalent/antibody, 1.0 micromoles, 0.1 mL of 10 mM in 0.3 mL DMSO) and the resultant mixture was shaken for 1.5 hours at +25° C. and then the conjugation was quenched with N-acetyl cysteine (5 micromoles, 50 μL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 1 specific) shows a mixture of light and heavy chains attached to several molecules of Compound 1, consistent with a drug-per-antibody ratio (DAR) of 4.2 molecules of Compound 1 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ADC at 280 nm shows a monomer purity of greater than 99%. UHPLC SEC analysis gives a concentration of final ADC at 2.05 mg/mL in 3.6 mL, obtained mass of ADC is 7.36 mg (74% yield).

Example 7—In Vitro Testing

MTS Cytotoxicity Method

The concentration and viability of cells from a sub-confluent (80-90% confluency) T75 flask are measured by trypan blue staining, and counted using the LUNA-II™ Automated Cell Counter. Cells were diluted to $2 \times 10^5$/ml, dispensed (50 μl per well) into 96-well flat-bottom plates.

A stock solution (1 ml) of the antibody drug conjugate (ADC) to be tested (20 μg/ml) was made by dilution of filter-sterilised ADC into cell culture medium. A set of 8×10-fold dilutions of stock ADC were made in a 24-well plate by serial transfer of 100 μl into 900 μl of cell culture medium. ADC dilution was dispensed (50 μl per well) into 4 replicate wells of the 96-well plate, containing 50 μl cell suspension seeded the previously. Control wells received 50 μl cell culture medium. The 96-well plate containing cells and ADCs was incubated at 37° C. in a $CO_2$-gassed incubator for the exposure time.

At the end of the incubation period, cell viability was measured by MTS assay. MTS (Promega) was dispensed (20 μl per well) into each well and incubated for 4 hours at 37° C. in the $CO_2$-gassed incubator. Well absorbance was measured at 490 nm. Percentage cell survival was calculated from the mean absorbance in the 4 ADC-treated wells compared to the mean absorbance in the 4 control untreated wells (100%). $IC_{50}$ was determined from the dose-response data using GraphPad Prism using the non-linear curve fit algorithm: sigmoidal dose-response curve with variable slope.

ADC incubation times were 4 days with SK-BR-3, MDA-MB-468, WSU-DLCL2, and SU-DHL-4, 5 days for Granta-519, 6 days for BJAB and 7 days for NCI-N87. MDA-MB-468, NCI-N87, WSU-DLCL2 and SU-DHL-4 were cultured in RPMI 1640 with Glutamax+10% (v/v) HyClone™ Fetal Bovine Serum, Granta-519 in DMEM+Glutamax with 10% (v/v) HyClone™ Fetal Bovine Serum, SK-BR-3 in McCoys 5A with 10% (v/v) HyClone™ Fetal Bovine Serum and BJAB in RPMI 1640+Glutamax with 20% (v/v) HyClone™ Fetal Bovine Serum.

CellTiter-Glo Cytotoxicity Method

The concentration and viability of cells from a sub-confluent (80-90% confluency) T75 flask are measured by trypan blue staining, and counted using the LUNA-II™ Automated Cell Counter. Cells were diluted and plated at 1500 cells per well (50 μl suspension per well) into white 96-well flat-bottom plates.

A stock solution (1 ml) of antibody drug conjugate (ADC) to be tested (20 μg per ml) was made by dilution of filter-sterilised ADC into cell culture medium. A set of 8×10-fold dilutions of stock ADC were made in a 24-well plate by serial transfer of 100 μl into 900 μl of cell culture medium. ADC dilution was dispensed (50 μl per well) into 4 replicate wells of the 96-well plate, containing 50 μl cell suspension seeded the previously. Control wells received 50 μl cell culture medium. The 96-well plate containing cells and ADCs was incubated at 37° C. in a $CO_2$-gassed incubator for the exposure time.

At the end of the incubation period, cell viability was measured by CellTiter-Glo assay. CellTiter-Glo (Promega) was dispensed at 100 μl per well and shaken for 2 min before 10 min stabilisation at room temperature. Luminescence of each well was read. Percentage cell survival was calculated from the mean absorbance in the 4 ADC-treated wells compared to the mean absorbance in the 4 control untreated wells (100%). $IC_{50}$ was determined from the dose-response data using GraphPad Prism using the non-linear curve fit algorithm: sigmoidal dose-response curve with variable slope.

ADC incubation time for PC-3 is 6 days. PC-3 were cultured in RPMI 1640 with Glutamax+10% (v/v) HyClone™ Fetal Bovine Serum.

Results

| $EC_{50}$ (μg/mL) | SU-DHL-4 | GRANTA-519 | BJAB | WSU-DLCL2 |
| --- | --- | --- | --- | --- |
| Conj-CD79b-1 | 1.216 | 49.69 | 0.2211 | >100 |
| Conj-CD79b-2 | 0.4781 | 0.1124 | 0.005712 | 0.7559 |
| Conj-R347-2 | >10 | | | |

The cell lines SU-DHL-4, GRANTA519, BJAB and WSU-DL-CL2 all express CD79b.

| $EC_{50}$ (μg/mL) | SK-BR-3 | NCI-N87 | MDA-MB-468 |
| --- | --- | --- | --- |
| Conj-Her-1 | 0.06953 | 0.9677 | 3.492 |
| Conj-Her-3 | 0.0175 | 0.02502 | 2.322 |
| Conj-Her-2 | 0.07427 | 0.08078 | 0.9533 |
| Conj-HER-1++ | | 0.1108 | 12.18 |
| Conj-HER-1+ | | 0.3226 | >10 |

The cell lines SK-BR-3 and NCI-N87 express Her2. The cell line MDA-MB-468 does not express HER2.

| $EC_{50}$ (μg/mL) | PC-3 |
| --- | --- |
| Conj-1C1-1 | 0.5408 |
| Conj-R347-1 | >100 |

Example 8—In Vivo Assays (i) Daudi

Conjugates tested: Conj-HLL2-1; Conj-HLL2-2; Conj-HLL2-3

Female CB.17 SCID mice, aged ten weeks, were injected with 0.1 ml of $1\times10^7$ Daudi cells subcutaneously in the right flank. When tumours reached an average size of 100-150 $mm^3$, treatment began. Mice were weighed twice a week. Tumour size was measured twice a week. Animals were monitored individually. The endpoint of the experiment was a tumour volume of 1500 $mm^3$ or 60 days, whichever came first.

Groups of 10 xenografted mice were injected i.v. with 0.2 ml per 20 g of body weight of antibody drug conjugate (ADC) in phosphate buffered saline (vehicle) or with 0.2 ml per 20 g of body weight of vehicle alone.

The concentration of ADC was adjusted to give the following doses:

| Conjuagte | Doses (mg ADC/kg body eight) |
| --- | --- |
| Conj-HLL2-1 | 0.6 or 1.8 |
| Conj-HLL2-2 | 0.3 or 1 |
| Conj-HLL2-3 | 0.1 or 0.3 |

All regimens were acceptably tolerated with little body weight loss.

Conj-HLL2-1:

The median time to end point (TTE) for vehicle-treated controls was 27.8 days, establishing a maximum possible tumour growth delay (TGD) of 32.2 days (116%) for the 60-day study. One non-treatment related death was recorded on day 28, and this animal was excluded from the analysis.

The 0.6 mg/kg regimen resulted in a TGD of 48.1 days (73%), which was statistically significant from controls ($p<0.001$). Furthermore, this regimen had five of nine 59-regression responses consisting of two partial and three complete regressions. Six animals attained the 1500 mm3 endpoint, leaving 3 survivors after 60 days. The three survivors had a mean tumour volume of 221 $mm^3$. There was one non-treatment related death and this animal was excluded from the analysis.

The 1.8 mg/kg regimen resulted in the maximum possible, significant TGD (vs controls, $p<0.001$), had eight of ten 60-day survivors and produced a survival benefit that was statistically significantly different from vehicle-treated controls ($p<0.001$). Eight animals showed complete regression responses. Five of these animals were tumour free after 60 days.

Both treatment regimens produced statistically significant survival benefits compared to control ($p<0.001$ for both 0.6 and 1.8 mg/ml).

Conj-HLL2-2:

The median time to end point (TTE) for vehicle-treated controls was 27.8 days, establishing a maximum possible tumour growth delay (TGD) of 32.2 days (116%) for the 60-day study.

The 0.3 and 1 mg/kg regimens both resulted in maximum achievable TGDs (32.2 days, 116%). Both of these results were statistically significant from controls ($p<0.001$ for each regimen).

Eighty percent of 0.3 mg/kg treated animals evinced regression responses consisting of two partial responses and six complete responses, four of which remained tumour free at the study end. Four 0.3 mg/kg treated animals reached the tumour volume endpoint leaving six study survivors tumour free at the end of the study.

One hundred percent of 1 mg/kg treated animals showed regression responses and all animals were tumour free on day 60.

Both treatment regimens resulted in significant overall survival differences versus controls (controls versus either 0.3 or 1 mg/kg, $p<0.0001$).

Conj-HLL2-3:

The median time to end point (TTE) for vehicle-treated controls was 27.8 days, establishing a maximum possible tumour growth delay (TGD) of 32.2 days (116%) for the 60-day study.

The 0.1 and 0.3 mg/kg regimens resulted in TGDs of 12.9 days (46%) and 24.6 days (88%). Both of these results were statistically significant from controls (p<0.001 for each regimen).

Thirty percent regression responses were observed in animals treated with the 0.1 mg/ml regimen with three partial responses. All the animals in this group reached the tumour volume endpoint by day 60.

Seventy percent of 0.3 mg/kg treated animals evinced regression responses consisting of three partial responses and four complete responses, one of which remained tumour free at the study end. Four 0.3 mg/kg treated animals reached the tumour volume endpoint leaving six study survivors tumour free at the end of the study. Seven animals in this group reached the tumour volume endpoint leaving three 60 day survivors with an MTV of 750 mm$^3$ at study end.

Both treatment regimens resulted in significant overall survival differences versus controls (controls versus either 0.1 or 0.13 mg/kg, p<0.0001).

(ii) JIMT-1

Conjugate tested: Conj-Her-3

Female CB.17 SCID mice, aged 10 weeks, were injected with 0.1 ml of 1×10$^7$ JIMT-1 cells in 50% Matrigel subcutaneously in the right flank. When tumours reached an average size of 100-150 mm$^3$, treatment began. Mice were weighed twice a week. Tumour size was measured twice a week. Animals were monitored individually. The endpoint of the experiment was a tumour volume of 1000 mm$^3$ or 59 days, whichever came first.

Groups of 10 xenografted mice were injected i.v. with 0.2 ml per 20 g of body weight of antibody drug conjugate (ADC) in phosphate buffered saline (vehicle) or with 0.2 ml per 20 g of body weight of vehicle alone. The concentration of ADC was adjusted to give 1 or 3 mg ADC/kg body weight in a single dose.

All regimens were acceptably tolerated with little body weight loss. The median time to end point (TTE) for vehicle-treated controls was 48.4 days, establishing a maximum possible tumour growth delay (TGD) of 10.6 days (22%) for the 59-day study.

A dose dependent effect was observed where in animals that received the 1 mg/kg dose the median tumour volume remained static until day 34, then progressed thereafter, while for animals treated with 3 mg/kg there was a small reduction in tumour size to an MTV of 81 mm$^3$. Both dosing regimens resulted in a maximal TGD of 10.6 days (22%) versus the control group (p<0.001 for both treated groups).

The 1 mg/kg regimen resulted in nine study survivors with an MTV of 650 mm$^3$ and no objective regression responses.

The 3 mg/kg regimen resulted in nine study survivors with 20% objective regression responses consisting of two partial responses. The MTV of the study survivors was 108 mm$^3$. The treatment regimens were not significantly different from each other (p>0.05).

Both treatment regimens resulted in significant overall survival differences versus controls (controls versus either 1 or 3 mg/kg, p<0.0001).

(iii) NCI-N87

Conjugate tested: Conj-Her-3

Female CB.17 SCID mice, aged ten weeks, were injected with 0.1 ml of 1×10$^7$ NCI-N87 cells in 50% Matrigel subcutaneously in the right flank. When tumours reached an average size of 100-150 mm$^3$, treatment began. Mice were weighed twice a week. Tumour size was measured twice a week. Animals were monitored individually. The endpoint of the experiment was a tumour volume of 800 mm$^3$ or 81 days, whichever came first.

Groups of 10 xenografted mice were injected i.v. with 0.2 ml per 20 g of body weight of antibody drug conjugate (ADC) in phosphate buffered saline (vehicle) or with 0.2 ml per 20 g of body weight of vehicle alone. The concentration of ADC was adjusted to give 0.3 or 1 mg ADC/kg body weight in a single dose.

All regimens were acceptably tolerated with little body weight loss. Six of ten control tumours reached the 800 mm$^3$, with time to endpoints (TTE) ranging 36.8 to 81.0 days. The median time to end point (TTE) for vehicle-treated controls was 77 days, establishing a maximum possible tumour growth delay (TGD) of 4 days (5%) for the 81-day study. Four control animals survived with a median tumour volume (MTV) of 696 mm$^3$.

The 0.3 and 1 mg/kg regimens resulted in TGDs of 0.5 (1%) and 4.0 days (5%) respectively. Both of these results were not statistically significant from controls, not each other (p>0.05). There were no objective regressions recorded in either group. Five 0.3 mg/kg and seven 1 mg/kg treated animals survived with MTVs of 550 mm$^3$ in both groups.

Neither treatment regimen resulted in statistically significant survival benefits compared to control (p>0.05 for both treatment groups), and there was no significant difference between the treatment groups (p>0.05).

(iv) NCI-N87

Conjugates tested: Conj-Her-1, Conj-Her-3

Female CB.17 SCID mice, aged eight weeks, were injected with 0.1 ml of 1×10$^7$ NCI-N87 in 50% Matrigel cells subcutaneously in the right flank. When tumours reached an average size of 100-150 mm$^3$, treatment began. Mice were weighed twice a week. Tumour size was measured twice a week. Animals were monitored individually. The endpoint of the experiment was a tumour volume of 800 mm$^3$ or 78 days, whichever came first.

Groups of 10 xenografted mice were injected i.v. with 0.2 ml per 20 g of body weight of antibody drug conjugate (ADC) in phosphate buffered saline (vehicle) or with 0.2 ml per 20 g of body weight of vehicle alone.

The concentration of ADC was adjusted to give the following doses:

| Conjugate | Doses (mg ADC/kg body eight) |
|---|---|
| Conj-Her-1 | 1, 3, or 6 |
| Conj-Her-3 | 0.3, 1 and 3 |

All regimens were acceptably tolerated with little body weight loss.

Conj-Her-1:

The median time to end point (TTE) for vehicle-treated controls was 42 days, establishing a maximum possible tumour growth delay (TGD) of 36 days (86%) for the 60-day study.

The 0.6 and 1 mg/kg regimens resulted in TGDs of 9.9 (24%) and 11.6 days (28%) respectively. Neither of these results were statistically significant from controls (p>0.05). All animals in both groups attained the 800 mm$^3$ endpoint.

The 6 mg/kg regimen resulted in the maximum possible, significant TGD (vs controls, p<0.001), had eight of ten 60-day survivors and produced a survival benefit that was statistically significantly different from vehicle-treated controls (p<0.0001). One animal reached the 800 mm$^3$ endpoint at day 78, leaving nine survivors with mean tumour volumes of 550 mm$^3$.

There were no observable regression responses with 1, 3, or 6 mg/kg regimens.

Conj-Her-3:

The median time to end point (TTE) for vehicle-treated controls was 42.0 days, establishing a maximum possible tumour growth delay (TGD) of 36.0 days (86%) for the 78-day study.

The TGDs for 0.3, 1 and 3 mg/kg were 15.1 (36%), 30.6 (73%) and 36.0 (86%) days respectively. There were significant differences for 1 and 3 mg/kg versus controls (p<0.001 for both treatment groups, but not 0.3 mg/kg (p>0.05). No regression responses were observed in animals treated with 0.3 and 1 mg/kg ADC. Ninety percent regression responses were observed in 3 mg/kg treated animals. This consisted of eight partial responses and one complete response, which remained tumour free at study end. All animals treated with 0.3 mg/kg reached the 800 mm$^3$ endpoint. Five 1 mg/kg treated animals attained endpoint leaving five 78 day survivors. These had an MTV of 486 mm$^3$. All ten 3 mg/kg treated animals survived the study with an MTV of 63 mm$^3$.

The 1 and 3 mg/kg regimens resulted in significant survival differences versus controls (p<0.001 for both treatment groups). The 0.3 mg/kg treatment group was not statistically significant from control (p>0.05). Both 1 and 3 mg/kg treatment were significantly different from the 0.3 mg/kg group (p<0.001 and p<0.0001 respectively).

(v) NCI-N87

Conjugate tested: Conj-Her-2

Female CB.17 SCID mice, aged eight weeks, were injected with 0.1 ml of 1×10$^7$ NCI-N87 cells in 50% Matrigel subcutaneously in the right flank. When tumours reached an average size of 100-150 mm$^3$, treatment began. Mice were weighed twice a week. Tumour size was measured twice a week. Animals were monitored individually. The endpoint of the experiment was a tumour volume of 800 mm$^3$ or 79 days, whichever came first.

Groups of 10 xenografted mice were injected i.v. with 0.2 ml per 20 g of body weight of antibody drug conjugate (ADC) in phosphate buffered saline (vehicle) or with 0.2 ml per 20 g of body weight of vehicle alone. The concentration of ADC was adjusted to give 1 or 2 mg ADC/kg body weight in a single dose.

All regimens were acceptably tolerated with little body weight loss. The median time to end point (TTE) for vehicle-treated controls was 49.6 days, establishing a maximum possible tumour growth delay (TGD) of 29.4 days (59%) for the 79-day study.

The 1 and 2 mg/kg regimens resulted in TGDs of 7.6 (15%) and 23.6 days (48%) respectively. Both of these results were statistically significant from controls (p<0.05 and p<0.001 respectively).

Eight animals treated with the 1 mg/kg regimen attained the 800 mm$^3$ endpoint leaving two 79-day survivors with an MTV of 694 mm$^3$. Seven animals in the 2 mg/ml treated group reached the tumour volume endpoint by day 79 leaving three end of study survivors with an MTV of 600 mm$^3$.

Both treatment regimens resulted in significant overall survival differences versus controls (controls versus 1 mg/kg, p<0.05; controls versus 2 mg/kg, p<0.001).

Regression responses were not recorded with either regimen.

(vi) NCI-N87

Conjugates tested: Conj-Her-1, Conj-Her-1++

Female CB.17 SCID mice, aged eight weeks, were injected with 0.1 ml of 1×10$^7$ NCI-N87 in 50% Matrigel cells subcutaneously in the right flank. When tumours reached an average size of 100-150 mm$^3$, treatment began. Mice were weighed twice a week. Tumour size was measured twice a week. Animals were monitored individually. The endpoint of the experiment was a tumour volume of 800 mm$^3$ or 81 days, whichever came first.

Groups of 10 xenografted mice were injected i.v. with 0.2 ml per 20 g of body weight of antibody drug conjugate (ADC) in phosphate buffered saline (vehicle) or with 0.2 ml per 20 g of body weight of vehicle alone.

The concentration of ADC was adjusted to give the following doses:

| Conjugate | Doses (mg ADC/kg body weight) |
| --- | --- |
| Conj-Her-1 | 6, 18, 6 (qwk × 3), 8 (qwk × 3) |
| Conj-Her-1++ | 6 |

All regimens were acceptably tolerated with little body weight loss.

The median time to end point (TTE) for vehicle-treated controls was 40.2 days, establishing a maximum possible tumour growth delay (TGD) of 40 days (86%) for the 80-day study.

Conj-Her-1:

The 6 and 18 mg/kg single-dose regimens resulted in the maximum possible tumor growth delays. In the 6 mg/kg single-dose regimen the mean tumour volume for 5 mice was 600 mm$^3$, with no observable regression responses. In the 18 mg/kg single-dose regimen there were ten survivors with a mean tumour volume of 36 mm$^3$. There were 4 partial regressions and 6 complete regressions.

The 6 and 8 mg/kg three weekly dose regimens also resulted in the in the maximum possible tumor growth delays. In the 6 mg/kg three weekly dose regimen the mean tumour volume for 9 mice at the end of the study was 245 mm$^3$, with two partial regressions. In the 8 mg/kg three weekly dose regimen there were ten survivors with a mean tumour volume of 92 mm$^3$. There were 7 partial regressions, 3 complete regressions and 2 tumour free survivors.

Conj-Her-1++:

The 6 mg/kg single-dose regimen resulted in the maximum possible tumour growth delays. There were ten survivors with a mean tumour volume of 161 mm$^3$. There were 5 partial regressions, 5 complete regressions and 2 tumour free survivors.

(vii) NCI-N87

Conjugates tested: Conj-Her-1, Conj-Her1+, Conj-Her-1++

Female CB.17 SCID mice, aged eight weeks, were injected with 0.1 ml of 1×10$^7$ NCI-N87 in 50% Matrigel cells subcutaneously in the right flank. When tumours reached an average size of 100-150 mm$^3$, treatment began. Mice were weighed twice a week. Tumour size was measured twice a week. Animals were monitored individually. The endpoint of the experiment was a tumour volume of 800 mm$^3$ or 83 days, whichever came first.

Groups of 10 xenografted mice were injected i.v. with 0.2 ml per 20 g of body weight of antibody drug conjugate (ADC) in phosphate buffered saline (vehicle) or with 0.2 ml per 20 g of body weight of vehicle alone.

The concentration of ADC was adjusted to give the following doses:

| Conjugate | Doses (mg ADC/kg body weight) |
|---|---|
| Conj-Her-1 | 6, 18 |
| Conj-Her-1+ | 3, 6 |
| Conj-Her-1++ | 1.5, 3 |

All regimens were acceptably tolerated with little body weight loss.

The median time to end point (TTE) for vehicle-treated controls was 36.8 days, establishing a maximum possible tumour growth delay (TGD) of 46.2 days (126%) for the 80-day study.

Conj-Her-1:

The 6 and 18 mg/kg regimens resulted in tumor growth delays of 45.9 days (125%) and 46.2 days (126%). In the 6 mg/kg regimen the mean tumour volume for 4 mice was 564 mm$^3$, with no observable regression responses. In the 18 mg/kg regimen there were nine survivors with a mean tumour volume of 108 mm$^3$. There were 9 partial regressions and 1 complete regressions.

Conj-Her-1++:

The 1.5 and 3 mg/kg regimen resulted in tumor growth delays of 45.9 days (125%) and 46.2 days (126%). In the 1.5 mg/kg regimen there were two survivors with a mean tumour volume of 634 mm$^3$. In the 3 mg/kg regimen there were ten survivors with a mean tumour volume of 451 mm$^3$.

Conj-Her-1+:

The 3 and 6 mg/kg regimens resulted in maximum tumor growth delays of 46.2 days (126%). In the 3 mg/kg regimen there were seven survivors with a mean tumour volume of 600 mm$^3$. In the 6 mg/kg regimen there were ten survivors with a mean tumour volume of 256 mm$^3$. There were two partial regressions.

(viii) JIMT1

Conjugates tested: Conj-Her-1, Conj-Her-1++

Female CB.17 SCID mice, aged eight weeks, were injected with 0.1 ml of 1×10$^7$ JIMT1 in 50% Matrigel cells subcutaneously in the right flank. When tumours reached an average size of 100-150 mm$^3$, treatment began. Mice were weighed twice a week. Tumour size was measured twice a week. Animals were monitored individually. The endpoint of the experiment was a tumour volume of 1000 mm$^3$ or 60 days, whichever came first.

Groups of 10 xenografted mice were injected i.v. with 0.2 ml per 20 g of body weight of antibody drug conjugate (ADC) in phosphate buffered saline (vehicle) or with 0.2 ml per 20 g of body weight of vehicle alone.

The concentration of ADC was adjusted to give the following doses:

| Conjugate | Doses (mg ADC/kg body weight) |
|---|---|
| Conj-Her-1 | 18, 24 |
| Conj-Her-1++ | 4, 6, 8 |

All regimens were acceptably tolerated with little body weight loss.

The median time to end point (TTE) for vehicle-treated controls was 37.5 days, establishing a maximum possible tumour growth delay (TGD) of 22.5 days (60%) for the 60-day study.

Conj-Her-1:

The 18 and 24 mg/kg regimens resulted in tumor growth delays of 5.3 days (14%) and 3.2 days (9%). In the 18 mg/kg regimen all animals reached the 1000 mm$^3$ endpoint. In the 24 mg/kg regimen there was a single survivor with a tumour volume of 968 mm$^3$. Both regimens resulted in a significant overall survival difference versus controls (P<0.01).

Conj-Her-1++:

The 4, 6 and 8 mg/kg regimen resulted in tumor growth delays of 4.4 days (12%). 6.9 days (18%) and 17.7 days (47%). In the 4 mg/kg regimen all animals reached the 1000 mm$^3$ endpoint. In the 6 mg/kg regimen there was a single survivor with a tumour volume of 650 mm$^3$. In the 8 mg/kg regimen there was a single survivor with a tumour volume of 847 mm$^3$. All regimens resulted in a significant overall survival difference versus controls (P<0.01).

Example 9—Toxicology Assay

A single dose nonGLP toxicity study was used to determine the maximum tolerated dose (MTD) and safety profile of the ADCs tested, which were: Conj-R347-1; Conj-R347-2; Conj-R347-3.

Male Sprague Dawley rats (Envigo, Inc) were dosed once by slow bolus intravenous injection via the tail vein with ADC. The vehicle for dilution used was 25 mM Histidine-HCl, 7% sucrose, 0.02% Polysorbate 80, pH 6.0. Parameters evaluated during the study included mortality, physical examinations, cageside observations, body weights, body weight changes, clinical pathology (clinical chemistry, hematology, and coagulation), and gross pathology findings. All animals were terminated on Study Day (SD) 29.

Conj-R347-1

| Group | Dose (mg/kg) | N |
|---|---|---|
| 2 | 5 | 5 |
| 4 | 7 | 5 |
| 6 | 10 | 5 |
| 8 | 16 | 5 |
| 10 | 20 | 5 |
| 12 | 25 | 5 |

Tolerability was determined based on toxicity end points, including mild decreases in hematological parameters, microscopic evaluations and bone marrow suppression. Based on microscopic changes in animals receiving the highest dose, the maximum tolerated dose (MTD) in the rat after a single dose was determined to be 25 mg/kg.

Conj-R347-2

| Group | Dose(mg/kg) | N |
|---|---|---|
| 2 | 2 | 5 |
| 3 | 5 | 5 |
| 4 | 8 | 5 |

Tolerability was determined based on toxicity end points. The ADC was tolerated up to 8 mg/kg in the rat after a single dose. Findings included dose dependent body weight decrease and bone marrow suppression.

Conj-R347-3

| Group | Dose (mg/kg) | N |
|---|---|---|
| 5 | 1 | 5 |
| 9 | 2.5 | 5 |
| 11 | 4 | 5 |

Tolerability was determined based on toxicity end points. The ADC was tolerated up to 4 mg/kg in the rat after a single dose. Findings included dose-dependent body weight loss and bone marrow suppression.

Therapeutic Index

The therapeutic index of each ADC/drug linker was calculated using the following equation:

$$TI = \text{MTD in rat (mg/kg)} / \text{MED in mouse efficacy model (mg/kg)}$$

| Drug Linker | MTD (mg/kg) | NCI-N87 MED (mg/kg) | TI |
|---|---|---|---|
| 1 | 25 | 6 | 4.2 |
| 2 | 8 | 2 | 4 |
| 3 | 4 | 1 | 4 |

The invention claimed is:

1. A compound of formula I:

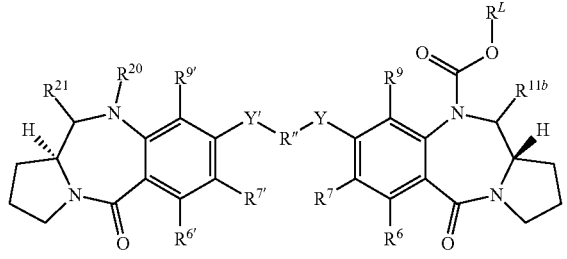

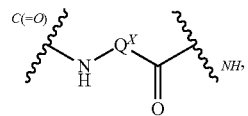

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NRR', nitro, $Me_3Sn$ and halo;

R" is a $C_{3-12}$ alkylene group, which chain may be interrupted by one or more heteroatoms selected from O, S, $NR^{N2}$ (where $R^{N2}$ is H or $C_{1-4}$ alkyl), and/or aromatic rings selected from benzene or pyridine;

Y and Y' are selected from O, S, or NH;

$R^{6'}$, $R^{7'}$, $R^{9'}$ are selected from the same groups as $R^6$, $R^7$ and $R^9$ respectively;

$R^{11b}$ is selected from OH, $OR^A$, where $R^A$ is $C_{1-4}$ alkyl; and $R^L$ is a linker for connection to a cell binding agent, which has the formula IIIa:

wherein

Q is:

where $Q^X$ is such that Q is an amino-acid residue, a dipeptide residue or a tripeptide residue;

X is:

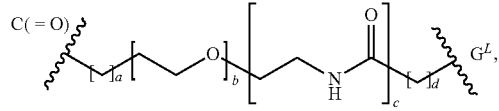

where a=0 to 5, b=0 to 16, c=0 or 1, d=0 to 5;

$G^L$ is a linker for connecting to a Ligand Unit; and either (a) $R^{20}$ is H, and $R^{21}$ is OH or $OR^A$, where $R^A$ is $C_{1-4}$ alkyl; or (b) $R^{20}$ and $R^{21}$ form a nitrogen-carbon double bond between the nitrogen and carbon atoms to which they are bound; or (c) $R^{20}$ is H and $R^{21}$ is $SO_zM$, where z is 2 or 3 and M is a monovalent pharmaceutically acceptable cation; or (d) $R^{20}$ is H and $R^{21}$ is H; or (e) $R^{21}$ is OH or $OR^A$, where $R^A$ is $C_{1-4}$ alkyl and $R^{20}$ is selected from:

(d-i)

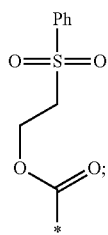

(d-ii)

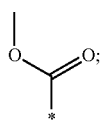

(d-iii)

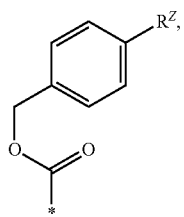

where $R^Z$ is selected from:

(z-i)

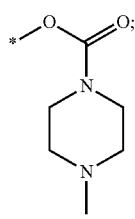 [SMILES: *OC(=O)N1CCN(C)CC1]

(z-ii) $OC(=O)CH_3$;

(z-iii) $NO_2$;

(z-iv) OMe; and (z-v) —C(=)—$X_1$—NHC(=O)$X_2$—NH—$R^{ZC}$, where —C(=O)—$X_1$—NH— and —C(=O)—$X_2$—NH— represent natural amino acid residues and $R^{ZC}$ is selected from Me, OMe, $OCH_2CH_2OMe$.

2. The compound according to claim 1, wherein both and Y' are O and R" is:

(a) $C_{3-7}$ alkylene; or (b) a group of formula:

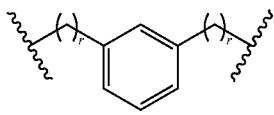

where r is 1 or 2.

3. The compound according to claim 1, wherein $R^9$ is H and $R^6$ is H.

4. The compound according to claim 1, wherein $R^7$ is a $C_{1-4}$ alkyloxy group.

5. The compound according to claim 1, wherein RU is the same group as $R^6$, $R^{7'}$ is the same group as $R^7$, $R^{9'}$ is the same group as $R^9$ and Y' is the same group as Y.

6. The compound according to claim 1, wherein $R^{20}$ and $R^{21}$ form a nitrogen-carbon double bond between the nitrogen and carbon atoms to which they are bound.

7. The compound according to claim 1, which is of formula Ia, Ib or Ic:

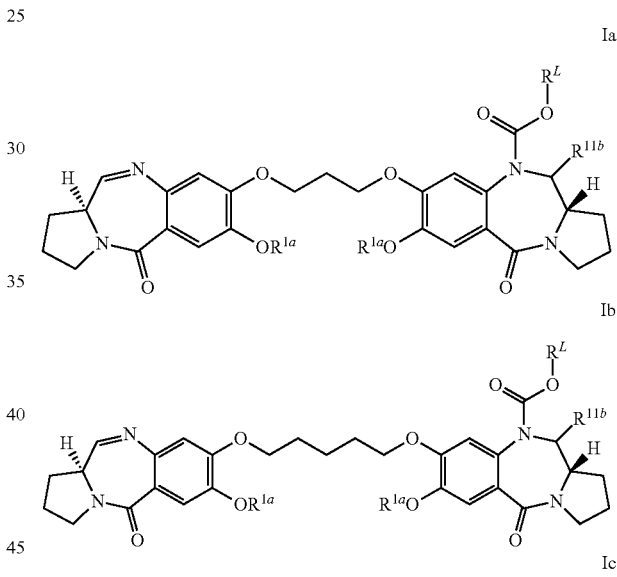

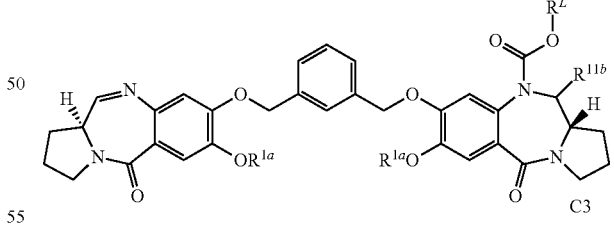

where $R^{1a}$ is selected from methyl and benzyl;
$R^L$ and $R^{11b}$ are as defined in claim 1.

8. The compound according to claim 1, wherein $R^{11b}$ is OH.

9. The compound according to claim 1, wherein Q is a dipeptide residue selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$, $^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$.

10. The compound according to claim 1, wherein a is 0.

11. The compound according to claim 1, wherein b is 0 to 8.

12. The compound according to claim 1, wherein d is 2.

13. The compound according to claim 1, wherein $G^L$ is selected from:

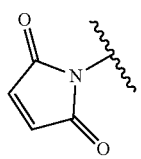
($G^{L1-1}$)

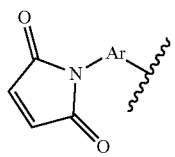
($G^{L1-2}$)

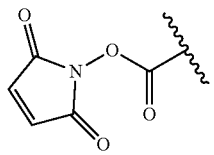
($G^{L2}$)

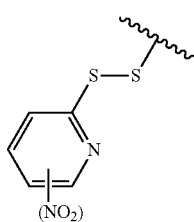
($G^{L3-1}$)

where the NO$_2$ group is optional

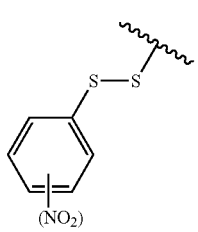
($G^{L3-2}$)

where the NO$_2$ group is optional

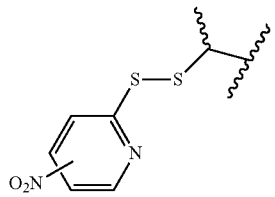
($G^{L3-3}$)

where the NO$_2$ group is optional

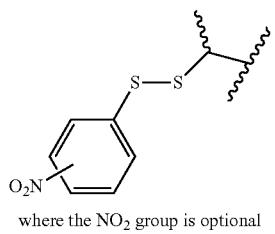
($G^{L3-4}$)

where the NO$_2$ group is optional

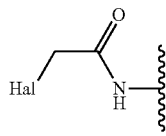
($G^{L4}$)

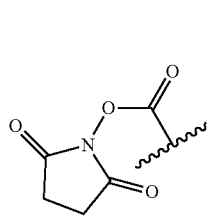
($G^{L5}$)

($G^{L6}$)

($G^{L7}$)

($G^{L8}$)

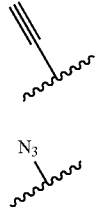
($G^{L9}$)

where Ar represents a $C_{5-6}$ arylene group, and Hal represents I, Br or Cl.

14. The compound according to claim 13, wherein $G^L$ is $G^{L1-1}$.

15. The compound according to claim 1, wherein the compound is of formula Id:

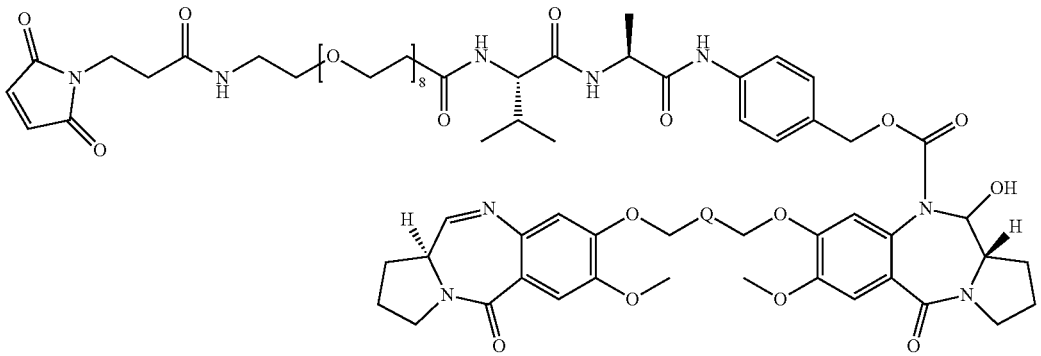
(Id)

where Q' is selected from:
(a) —CH₂—;
(b) —C₃H₆—; and
(c)

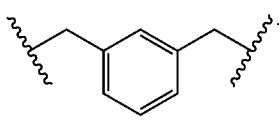

16. A conjugate of formula II:

L-(D^L)_p    (II)

wherein L is a Ligand unit, D^L is a Drug Linker unit of formula I':

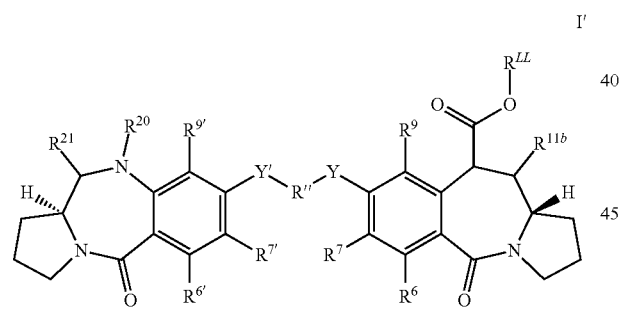

I' wherein $R^6$, $R^7$, $R^9$, $R^{11b}$, Y, R", Y', $R^{6'}$, $R^{7'}$, $R^{9'}$, $R^{20}$ and $R^{21}$, are as defined in claim 1;
$R^{LL}$ is a linker for connection to the ligand unit, which has the formula IIIa':

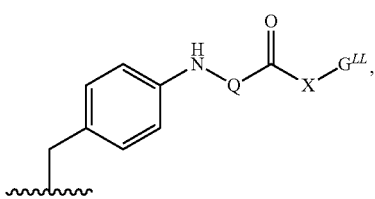

IIIa' where Q and X are as defined in claim 1 and $G^{LL}$ is a linker connected to a Ligand Unit;

and
wherein p is an integer of from 1 to 20.

17. The conjugate according to claim 16, wherein is selected from:

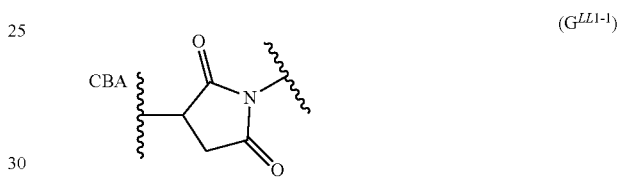
($G^{LL1-1}$)
($G^{LL6}$)

($G^{LL1-2}$)

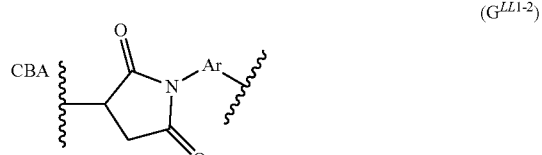
($G^{LL2}$)

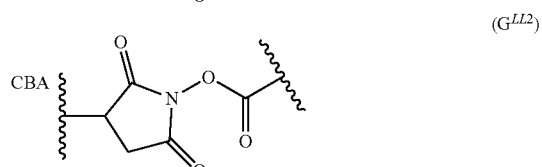
($G^{LL3-1}$)

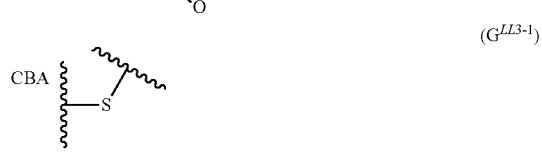
($G^{LL3-2}$)

($G^{LL4}$)

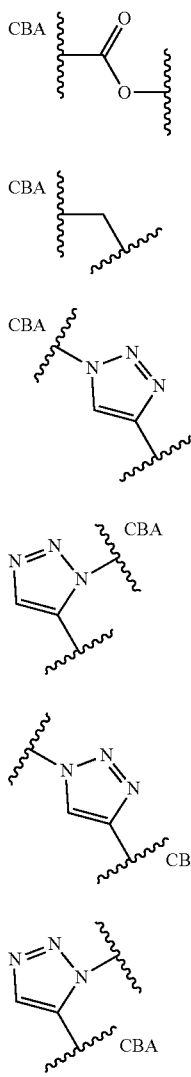

(G^LL5)

(G^LL7)

(G^LL8-1)

(G^LL8-2)

(G^LL9-1)

(G^LL9-2)

where Ar represents a $C_{5-6}$ arylene group.

18. The conjugate according to claim 17, wherein $G^{LL}$ is $G^{LL1-1}$.

19. The conjugate according to claim 16, wherein $D^L$ is of formula (Id'):

where Q' is selected from:
(a) —$CH_2$—;
(b) —$C_3H_6$—; and
(c)

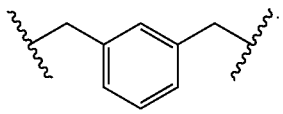 [SMILES: *Cc1cccc(C*)c1]

20. The conjugate according to claim 16, wherein the Ligand Unit is an antibody or an active fragment thereof which binds to one or more tumor-associated antigens or cell-surface receptors selected from:
(1) BMPR1B;
(2) E16;
(3) STEAP1;
(4) 0772P;
(5) MPF;
(6) Napi3b;
(7) Sema 5b;
(8) PSCA hlg;
(9) ETBR;
(10) MSG783;
(11) STEAP2;
(12) TrpM4;
(13) CRIPTO;
(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;
(32) CD72;

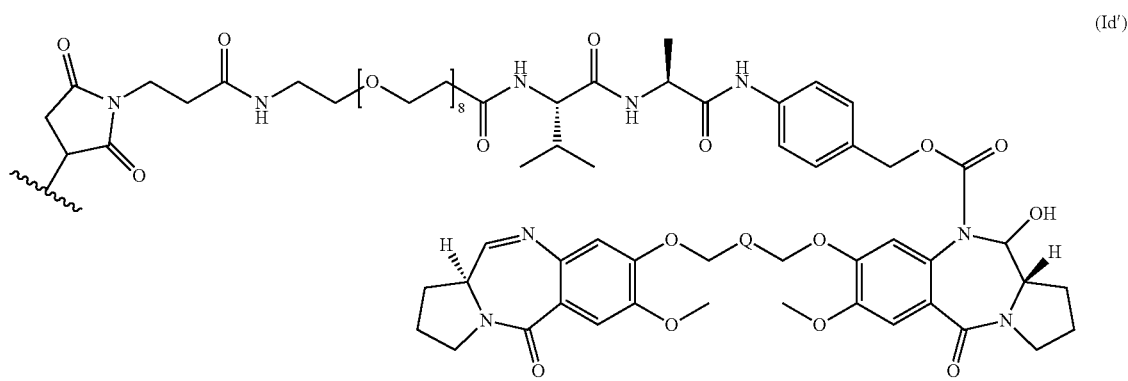

(Id')

(33) LY64;
(34) FcRH1;
(35) IRTA2;
(36) TENB2;
(37) PSMA—FOLH1;
(38) SST;
(38.1) SSTR2;
(38.2) SSTR5;
(38.3) SSTR1;
(38.4) SSTR3;
(38.5) SSTR4;
(39) ITGAV;
(40) ITGB6;
(41) CEACAM5;
(42) MET;
(43) MUC1;
(44) CA9;
(45) EGFRvIII;
(46) CD33;
(47) CD19;
(48) IL2RA;
(49) AXL;
(50) CD30—TNFRS8;
(51) BCMA—TNFRSF17;
(52) CT Ags—CTA;
(53) CD174 (Lewis Y)—FUT3;
(54) CLEC14A;
(55) GRP78—HSPA5;
(56) CD70;
(57) Stem Cell specific antigens;
(58) ASG-5;
(59) ENPP3;
(60) PRR4;
(61) GCC—GUCY2C;
(62) Liv-1—SLC39A6;
(63) 5T4;
(64) CD56—NCMA1;
(65) CanAg;
(66) FOLR1;
(67) GPNMB;
(68) TIM-1—HAVCR1;
(69) RG-1/Prostate tumor target Mindin—Mindin/RG-1;
(70) B7-H4—VTCN1;
(71) PTK7;
(72) CD37;
(73) CD138—SDC1;
(74) CD74;
(75) Claudins—CLs;
(76) EGFR;
(77) Her3;
(78) RON—MST1R;
(79) EPHA2;
(80) CD20—MS4A1;
(81) Tenascin C—TNC;
(82) FAP;
(83) DKK-1;
(84) CD52;
(85) CS1-SLAMF7;
(86) Endoglin—ENG;
(87) Annexin A1—ANXA1; and
(88) V-CAM (CD106)—VCAM1.

21. The conjugate according to claim 16 wherein p is an integer from 1 to 8.

22. A pharmaceutical composition comprising the conjugate of claim 16, and a pharmaceutically acceptable diluent, carrier or excipient.

23. A method of treating a mammal having ovarian cancer, comprising administering to the mammal an effective amount of a conjugate according to claim 16.

* * * * *